United States Patent
Erickson et al.

(10) Patent No.: US 10,428,330 B2
(45) Date of Patent: Oct. 1, 2019

(54) STEM-LOOP COMPOSITIONS AND METHODS FOR INHIBITING FACTOR D

(71) Applicants: Vitrisa Therapeutics, Inc., Larkspur, CA (US); Albert Einstein College of Medicine, Inc., Bronx, NY (US)

(72) Inventors: Carl Erickson, Corte Madera, CA (US); Christopher P. Rusconi, Durham, NC (US); Kevin G. McLure, Oakland, CA (US); Matthew Levy, Cary, NC (US); Arijit Bhowmick, Durham, NC (US)

(73) Assignees: Vitrisa Therapeutics, Inc., San Jose, CA (US); Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/990,547

(22) Filed: May 25, 2018

(65) Prior Publication Data
US 2019/0032056 A1 Jan. 31, 2019

Related U.S. Application Data

(63) Continuation of application No. PCT/US2018/014573, filed on Jan. 19, 2018.

(60) Provisional application No. 62/536,387, filed on Jul. 24, 2017, provisional application No. 62/448,872, filed on Jan. 20, 2017.

(51) Int. Cl.
*C12N 15/115* (2010.01)
*A61K 31/7088* (2006.01)

(52) U.S. Cl.
CPC ........ *C12N 15/115* (2013.01); *A61K 31/7088* (2013.01); *C12N 2310/16* (2013.01); *C12N 2310/317* (2013.01); *C12N 2310/321* (2013.01); *C12N 2310/322* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 5,270,163 A | 12/1993 | Gold et al. | |
| 5,475,096 A | 12/1995 | Gold et al. | |
| 6,140,490 A | 10/2000 | Biesecker et al. | |
| 6,333,034 B1 | 12/2001 | Gupta-Bansal et al. | |
| 6,653,340 B1 | 11/2003 | Babu et al. | |
| 6,956,107 B2 | 10/2005 | Fung et al. | |
| 7,112,327 B2 | 9/2006 | Fung et al. | |
| 7,927,592 B2 | 4/2011 | Fung et al. | |
| 7,943,135 B2 | 5/2011 | Fung et al. | |
| 7,999,082 B2 | 8/2011 | Holers et al. | |
| 8,007,791 B2 | 8/2011 | Hass et al. | |
| 8,067,002 B2 | 11/2011 | An et al. | |
| 8,124,090 B2 | 2/2012 | Fung et al. | |
| 8,273,352 B2 | 9/2012 | Huang et al. | |
| 8,435,512 B2 | 5/2013 | Bansal et al. | |
| 8,492,082 B2 | 7/2013 | De Franciscis et al. | |
| 8,580,735 B2 | 11/2013 | Francois et al. | |
| 8,664,362 B2 | 3/2014 | Bansal | |
| 8,703,136 B2 | 4/2014 | Baas et al. | |
| 8,753,625 B2 | 6/2014 | Fung et al. | |
| 8,858,943 B2 | 10/2014 | Burbidge et al. | |
| 8,911,733 B2 | 12/2014 | Holers et al. | |
| 8,921,523 B2 | 12/2014 | Alard et al. | |
| 8,940,299 B2 | 1/2015 | Medof et al. | |
| 8,981,060 B2 | 3/2015 | Bansal | |
| 9,066,925 B2 | 6/2015 | Tomlinson et al. | |
| 9,085,555 B2 | 7/2015 | Altmann et al. | |
| 9,278,108 B2 | 3/2016 | Takenaka et al. | |
| 9,803,194 B2 | 10/2017 | May et al. | |
| 9,873,727 B2 | 1/2018 | Sullenger et al. | |
| 10,174,325 B2 | 1/2019 | Erickson et al. | |
| 2004/0038869 A1 | 2/2004 | Finney et al. | |
| 2007/0065433 A1 | 3/2007 | Mollnes et al. | |
| 2007/0093443 A1 | 4/2007 | Madison et al. | |
| 2007/0149616 A1 | 6/2007 | Clark et al. | |
| 2007/0178068 A1 | 8/2007 | Reich et al. | |
| 2007/0196367 A1 | 8/2007 | Dinu | |
| 2008/0269318 A1 | 10/2008 | Romano | |
| 2009/0092980 A1 | 4/2009 | Arenz et al. | |

(Continued)

FOREIGN PATENT DOCUMENTS

| JP | 5825673 B2 | 12/2015 |
|---|---|---|
| WO | WO-9119813 A1 | 12/1991 |

(Continued)

OTHER PUBLICATIONS

Altschul, et al. Basic local alignment search tool. J Mol Biol. Oct. 5, 1990;215(3):403-10.
Altschul, et al. Gapped BLAST and PSI-BLAST: a new generation of protein database search programs. Nucleic Acids Res. Sep. 1, 1997;25(17):3389-402.
Berchuck, et al. All-trans-retinal sensitizes human RPE cells to alternative complement pathway-induced cell death. Invest Ophthalmol Vis Sci. Apr. 12, 2013;54(4):2669-77.
Forneris, et al. Structures of C3b in complex with factors B and D give insight into complement convertase formation. Science. Dec. 24, 2010;330(6012):1816-20. doi: 10.1126/science.1195821.
Gold, et al. Aptamer-based multiplexed proteomic technology for biomarker discovery. PLoS One. Dec. 7, 2010;5(12):e15004. doi: 10.1371/journal.pone.0015004.

(Continued)

*Primary Examiner* — Tracy Vivlemore
(74) *Attorney, Agent, or Firm* — Wilson Sonsini Goodrich & Rosati

(57) ABSTRACT

The application discloses methods and compositions for the inhibition of the alternative complement pathway. The methods and compositions involve the use of aptamers for inhibiting complement Factor D. The application further provides anti-Factor D aptamers for the treatment of dry age-related macular degeneration, geographic atrophy, wet age-related macular degeneration or Stargardt disease. In some cases, stem-loop aptamers are provided for the inhibition of Factor D.

28 Claims, 28 Drawing Sheets
Specification includes a Sequence Listing.

(56) References Cited

U.S. PATENT DOCUMENTS

| | | |
|---|---|---|
| 2009/0269356 A1 | 10/2009 | Epstein et al. |
| 2011/0044983 A1 | 2/2011 | Lambris et al. |
| 2011/0060027 A1 | 3/2011 | Benedict et al. |
| 2011/0160636 A1 | 6/2011 | Bansal |
| 2011/0165648 A1 | 7/2011 | Campagne et al. |
| 2011/0190221 A1 | 8/2011 | Francois et al. |
| 2012/0087905 A1 | 4/2012 | Lachmann |
| 2012/0107315 A1 | 5/2012 | Behrens et al. |
| 2012/0190578 A1 | 7/2012 | Seddon et al. |
| 2013/0035388 A1 | 2/2013 | McGeer et al. |
| 2014/0235701 A1* | 8/2014 | Jin ............... C12N 15/115 514/44 R |
| 2014/0371133 A1 | 12/2014 | Francois et al. |
| 2015/0044205 A1 | 2/2015 | Yaspan et al. |
| 2015/0104445 A1 | 4/2015 | Uknis et al. |
| 2015/0239837 A1 | 8/2015 | Wiles et al. |
| 2016/0061840 A1* | 3/2016 | Lee ............... C12N 15/115 435/6.14 |
| 2017/0328909 A1 | 11/2017 | Bock et al. |
| 2018/0030446 A1 | 2/2018 | Benedict et al. |
| 2018/0051287 A1 | 2/2018 | Erickson et al. |
| 2019/0010499 A1 | 1/2019 | Erickson et al. |

FOREIGN PATENT DOCUMENTS

| | | |
|---|---|---|
| WO | WO-9927133 A1 | 6/1999 |
| WO | WO-2007103549 A2 | 9/2007 |
| WO | WO-2012178083 A1 | 12/2012 |
| WO | WO-2015168468 A1 | 11/2015 |
| WO | WO-2017087919 A1 | 5/2017 |
| WO | WO-2017127761 A1 | 7/2017 |
| WO | WO-2018136827 A1 | 7/2018 |
| WO | WO-2018136831 A1 | 7/2018 |
| WO | WO-2019022986 A1 | 1/2019 |

OTHER PUBLICATIONS

Harper et al. Reaction of serine proteases with substituted isocoumarins: discovery of 3,4-dichloroisocoumarin, a new general mechanism based serine protease inhibitor.Biochemistry 24(8):1831-1841 (Apr. 1985).

Hedstrom, Lizbeth. Serine protease mechanism and specificity. Chem Rev. Dec. 2002;102(12):4501-24.

Jing, et al. Structural basis of profactor D activation: from a highly flexible zymogen to a novel self-inhibited serine protease, complement factor D. EMBO J. Feb. 15, 1999;18(4):804-14.

Jing, et al. Structures of native and complexed complement factor D: implications of the atypical His57 conformation and self-inhibitory loop in the regulation of specific serine protease activity. J Mol Biol. Oct. 9, 1998;282(5):1061-81.

Kam, et al. Human complement proteins D, C2, and B. Active site mapping with peptide thioester substrates. J Biol Chem. Mar. 15, 1987;262(8):3444-51.

Karlin, et al. Applications and statistics for multiple high-scoring segments in molecular sequences. Proc Natl Acad Sci U S A. Jun. 15, 1993;90(12):5873-7.

Karlin, et al. Methods for assessing the statistical significance of molecular sequence features by using general scoring schemes. Proc Natl Acad Sci U S A. Mar. 1990;87(6):2264-8.

Katschke, et al. Inhibiting alternative pathway complement activation by targeting the factor D exosite. J Biol Chem. Apr. 13, 2012;287(16):12886-92. doi: 10.1074/jbc.M112.345082. Epub Feb. 23, 2012.

Katschke, et al. Structural and functional analysis of a C3b-specific antibody that selectively inhibits the alternative pathway of complement. J Biol Chem. Apr. 17, 2009;284(16):10473-9.

Lao et al. Selection of Aptamers Targeting the Sialic Acid Receptor of Hemagglutinin by Epitope-Specific SELEX. Chemical Communications 50(63):8719-8722 (2014).

Loyet, et al. Complement inhibition in cynomolgus monkeys by anti-factor d antigen-binding fragment for the treatment of an advanced form of dry age-related macular degeneration. J Pharmacol Exp Ther. Dec. 2014;351(3):527-37.

Loyet et al. Activation of the Alternative Complement Pathway in Vitreous is Controlled by Genetics in Age-Related Macular Degeneration. 53(10):6628-6637 (Sep. 2012).

Macugen®. Drugs at FDA. Revised Jul. 2011. URL:< https://www.accessdata.fda.gov/drugsatfda_docs/label/2011/021756s018lbl.pdf>.

McHarg, et al. Age-related macular degeneration and the role of the complement system. Mol Immunol. Sep. 2015 ;67(1):43-50. doi: 10.1016/j.molimm.2015.02.032. Epub Mar. 21, 2015.

Molday, et al. ATP-binding cassette transporter ABCA4: molecular properties and role in vision and macular degeneration. J Bioenerg Biomembr. Dec. 2007;39(5-6):507-17.

Narayana, et al. Structure of human factor D. A complement system protein at 2.0 A resolution. J Mol Biol. Jan. 14, 1994;235(2):695-708.

Ouellet, et al. Hi-Fi SELEX: A High-Fidelity Digital-PCR Based Therapeutic Aptamer Discovery Platform. Biotechnol Bioeng. Aug. 2015;112(8):1506-22.

Ouellet, et al. Hi-Fi SELEX: A High-Fidelity Digital-Pcr Based Therapeutic Aptamer Discovery Platform. Supporting Information. Biotechnol Bioeng. Aug. 2015;112(8):1506-22.

Pangburn, MK. Alternative pathway of complement. Methods Enzymol. 1988;162:639-53.

PCT/US2017/014458 International Search Report dated Apr. 19, 2017.

Preclinical and Phase 1A Clinical Evaluation of an Anti-VEGF Pegylated Aptamer (EYE001) for the Treatment of Exudative Age-Related Macular Degeneration. The Eyetech Study Group. Retina 22(2):143-152 (2002).

Shukla et al. Pegaptanib sodium for ocular vascular disease. Indian J Ophthalmol. 55(6):427-30 (Nov.-Dec. 2007).

PCT/US2018/014573 International Search Report dated May 7, 2018.

U.S. Appl. No. 15/693,361 Notice of Allowance dated Aug. 30, 2018.

U.S. Appl. No. 15/693,361 Office Action dated May 25, 2018.

PCT/US2017/014458 Written Opinion dated Apr. 19, 2017.

Volanakis, et al. Complement factor D, a novel serine protease. Protein Sci. Apr. 1996; 5(4): 553-564. doi: 10.1002/pro.5560050401.

Wiles et al. Preclinical Evaluation of Orally Bioavailable Small-Molecule Inhibitors of Complement Factor D as a Potential Treatment for Paroxysmal Nocturnal Hemoglobinuria. Achillion Pharmaceuticals Inc. Abstract ID: 4819. Presented at the 56th Annual Meeting of the American Society of Hematology, San Francisco, California, USA, Dec. 6-9, 2014. One page.

Wootton, et al. Statistics of local complexity in amino acid sequences and sequence databases. Computers & Chemistry. vol. 17, Issue 2, Jun. 1993, pp. 149-163.

Yang, et al. Buried Hydrogen Bond Interactions Contribute to the High Potency of Complement Factor D Inhibitors. ACS Med. Chem. Lett., 2016, 7 (12), pp. 1092-1096. DOI: 10.1021/acsmedchemlett.6b00299.

Co-pending U.S. Appl. No. 16/121,458, filed Sep. 4, 2018.

PCT Application PCT/US2018/042317 as filed Jul. 16, 2018.

PCT/US2018/042317 International Search Report and Written Opinion dated Oct. 29, 2018.

\* cited by examiner

```
  16                                          46                                 56
ILGGREAEAHARPYMASVQLN----GAHLCGGVLVAEQWVLSAAHCIEDA
1         10          20          30          40

66                        76          86                              106
ADGKVQVLLGAHSLSQ-PEPSKRLYDVLRAVPHPDSQPDTI---DHDILII
          50          60          70          80          90

116                         126                 136                  146
QLSEKATIG---PAVRPIPWQRVDRDVAPGTICDVAGWGIVNHA---GRRPDS
          100         110         120         130         140

166                         176                    186                  196
LQHVLLPVLDRATCNRRTHHDGAITERLMCAES---NRRPDSCKGDSGGPL
          150         160         170         180

206                         216                     226                    236
VCG----GVLEGVVTSGSRV-CGNRKKPGIYTRVASYAAWIDSVLA---
          190         200         210         220
```

FIG. 6

SEQ ID NO: 9

FIG. 7A GGGAGUGUGUACGAGGCAUU-AGGCCCGCC-N30-GGCGGGCUU-UGAUACUUGAUCGCCCUAGAAGC

Apt 38

Apt 35

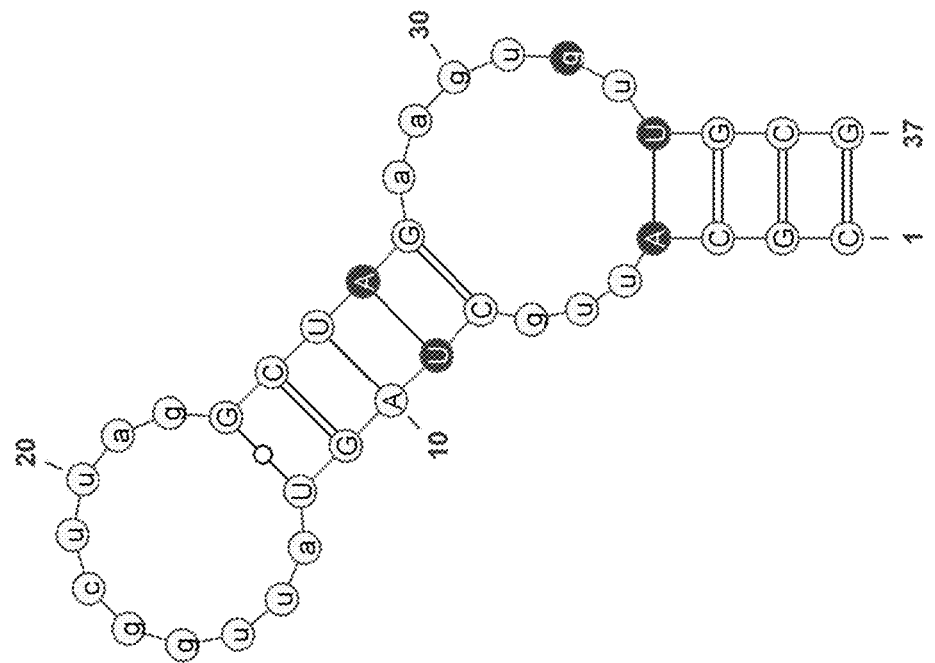
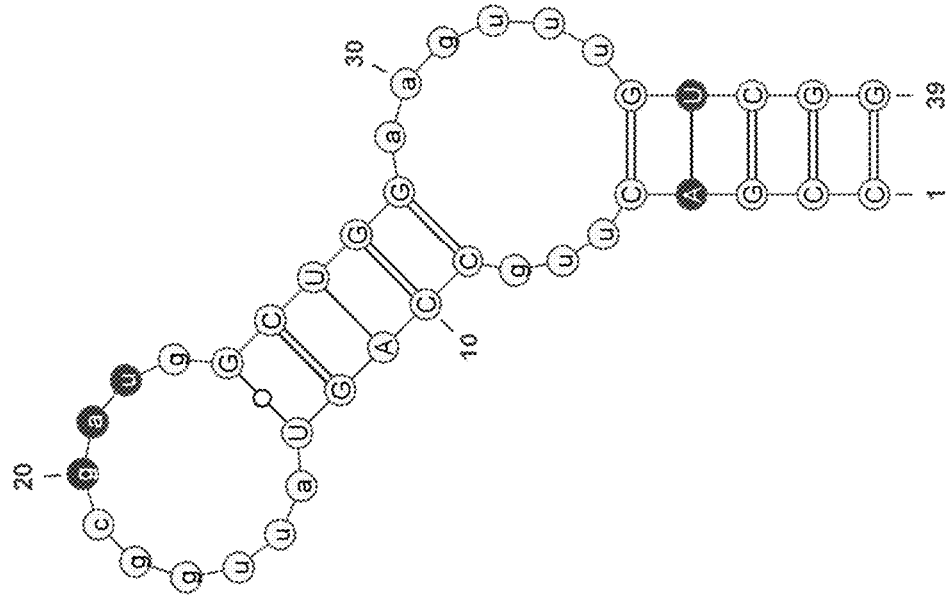
Apt 40
FIG. 20D
Apt 39
FIG. 20C

SEQUENCE LISTING

<160> NUMBER OF SEQ ID NOS: 324

<210> SEQ ID NO 1
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggagugugu acgaggcauu aggccgccac ccaaacugca guccucguaa gucugccugg      60
cggcuuugau acuugaucgc ccuagaagc                                       89

<210> SEQ ID NO 2
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 2
gggagugugu acgaggcauu aguccgccga agucuuuugg cucgguuuuu ucaaggucgg    60
cggcuuugau acuugaucgc ccuagaagc                                     89

<210> SEQ ID NO 3
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggagugugu acgaggcauu aggccgccac cucguuugau ugcgguuguu cggccgcggg    60
cggcuuugau acuugaucgc ccuagaagc                                     89

<210> SEQ ID NO 4
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(58)
<223> OTHER INFORMATION: a, c, t, g, unknown or other

<400> SEQUENCE: 4
gggagtgtgt acgaggcatt aggccgccnn nnnnnnnnnn nnnnnnnnnn nnnnnnnngg    60
cggctttgat acttgatcgc cctagaagc                                     89

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcttaatacg actcactata gggagtgtgt acgaggcatt a                       41

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcttctaggg cgatcaagta tca                                           23

<210> SEQ ID NO 7
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Gln Ser Gly Pro Glu Leu Lys Lys Pro Gly Ala
1               5                   10                  15
```

```
Ser Val Lys Val Ser Cys Lys Ala Ser Gly Tyr Thr Phe Thr Asn Tyr
             20                  25                  30

Gly Met Asn Trp Val Arg Gln Ala Pro Gly Gln Gly Leu Glu Trp Met
         35                  40                  45

Gly Trp Ile Asn Thr Tyr Thr Gly Glu Thr Thr Tyr Ala Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Glu Arg Gly Gly Val Asn Asn Trp Gly Gln Gly Thr Leu Val Thr Val
             100                 105                 110

Ser Ser Ala Ser Thr Lys Gly Pro Ser Val Phe Pro Leu Ala Pro Ser
         115                 120                 125

Ser Lys Ser Thr Ser Gly Gly Thr Ala Ala Leu Gly Cys Leu Val Lys
 130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                 165                 170                 175

Tyr Ser Leu Ser Ser Val Val Thr Val Pro Ser Ser Ser Leu Gly Thr
             180                 185                 190

Gln Thr Tyr Ile Cys Asn Val Asn His Lys Pro Ser Asn Thr Lys Val
         195                 200                 205

Asp Lys Lys Val Glu Pro Lys Ser Cys Asp Lys Thr His Thr
 210                 215                 220

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
             20                  25                  30

Met Asn Trp Tyr Gln Lys Pro Gly Lys Val Pro Lys Leu Leu Ile
         35                  40                  45

Ser Gly Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Ser Asp Ser Leu Pro Tyr
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 228
<212> TYPE: PRT
<213> ORGANISM: Homo sapiens

<400> SEQUENCE: 9

Ile Leu Gly Gly Arg Glu Ala Glu Ala His Ala Arg Pro Tyr Met Ala
1               5                   10                  15

Ser Val Gln Leu Asn Gly Ala His Leu Cys Gly Gly Val Leu Val Ala
            20                  25                  30

Glu Gln Trp Val Leu Ser Ala Ala His Cys Leu Glu Asp Ala Ala Asp
        35                  40                  45

Gly Lys Val Gln Val Leu Leu Gly Ala His Ser Leu Ser Gln Pro Glu
    50                  55                  60

Pro Ser Lys Arg Leu Tyr Asp Val Leu Arg Ala Val Pro His Pro Asp
65                  70                  75                  80

Ser Gln Pro Asp Thr Ile Asp His Asp Leu Leu Leu Leu Gln Leu Ser
                85                  90                  95

Glu Lys Ala Thr Leu Gly Pro Ala Val Arg Pro Leu Pro Trp Gln Arg
            100                 105                 110

Val Asp Arg Asp Val Ala Pro Gly Thr Leu Cys Asp Val Ala Gly Trp
        115                 120                 125

Gly Ile Val Asn His Ala Gly Arg Arg Pro Asp Ser Leu Gln His Val
    130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
        195                 200                 205

Lys Pro Gly Ile Tyr Thr Arg Val Ala Ser Tyr Ala Ala Trp Ile Asp
    210                 215                 220

Ser Val Leu Ala
225

<210> SEQ ID NO 10
<211> LENGTH: 88
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gggagugugu acgaggcauu aggccgccuu gccaguauug gcuuaggcug gaaguuuggc      60
```
ggcuuugaua cuugaucgcc cuagaagc                                           88

<210> SEQ ID NO 11
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
aggccgccuu gccaguauug gcuuaggcug gaaguuuggc ggcuu                        45

<210> SEQ ID NO 12
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ccgccuugcc aguauuggcu uaggcuggaa guuuggcgg                               39

<210> SEQ ID NO 13
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgccuugcc aguauuggcu uaggcuggaa guuuggcgg                               39

<210> SEQ ID NO 14
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cgccuugcaa guauuggcuu uggcuugaag uuuggcgg                                38

<210> SEQ ID NO 15
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ccgccuugca aguauuggcu uaggcuugaa guuuggcgg                               39

<210> SEQ ID NO 16
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cugccuugcg gguauuggcg uuggcccgaa guuuggcug                    39

```
<210> SEQ ID NO 17
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
```
cagucuugcg aguuuggcua agcuucgaag uuuggcug                     38

```
<210> SEQ ID NO 18
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
```
ccgccuugcg aguaauggcg uaggcucgaa guuggggcgg                    39

```
<210> SEQ ID NO 19
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
```
ccgccuugcg aguauuggcu uaggcucgaa guuuggcgg                     39

```
<210> SEQ ID NO 20
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
```
ccggcuugcg aguauuggcu uaggcucgaa guuugccgg                     39

```
<210> SEQ ID NO 21
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
```
ccgccuugcg aguauuggcu uuggcucgaa guuugucug                     39

```
<210> SEQ ID NO 22
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
```
ccgccuugcg aguauuggcg uuggcucgaa guuuucgg                      39

<210> SEQ ID NO 23
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ucaccuugcc auuauuggcu uaggauggaa guuuggugg                                39

<210> SEQ ID NO 24
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ccaccuugcc aguauuggcu uuggccggaa guuuggugg                                39

<210> SEQ ID NO 25
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ccaccuugcc aguauuggcu uaggcuggaa guuuggugg                                39

<210> SEQ ID NO 26
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ccgccuugcc aguauuggu uuggcuggaa guuuggcgg                                 39

<210> SEQ ID NO 27
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ccgcauugcc aguauuggcu ucggcuggaa guuugccgg                                39

<210> SEQ ID NO 28
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ccgcauugcc aguauaggcu uaugcuggaa guuugcgg                                 39

<210> SEQ ID NO 29
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccgcguugcc aguauaggcu uaggcuggaa guuucgcgg                              39

<210> SEQ ID NO 30
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cgcauugcua guauuggcuu aggcuagaag uguugcg                                37

<210> SEQ ID NO 31
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cugccuugcc aguauuggcu uaggcuggaa guuuugcgg                              39

<210> SEQ ID NO 32
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ccggguugcc aguauuggcu uaggcuggaa guuucgcgg                              39

<210> SEQ ID NO 33
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ccgacuugcc aguauuggcg uaggcuggaa guuugucgg                              39

<210> SEQ ID NO 34
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ccgacuugcc aguauuggcg uaggcuggaa guuugccgg                              39

```
<210> SEQ ID NO 35
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ccgacuugcc aguauuggcc uaggcuggaa guuugucgg                              39

<210> SEQ ID NO 36
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ucgacuugcc aguauuggcu uaggcuggaa guuugucgg                              39

<210> SEQ ID NO 37
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
cgacuugcca guauuggcuu agucuggaag uuugucg                                37

<210> SEQ ID NO 38
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccgacuugcc aguguuggcu uuggcuggaa guuugucgg                              39

<210> SEQ ID NO 39
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ccgacuugcc aguauuggcu uuggcuggaa guuugccgg                              39

<210> SEQ ID NO 40
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ccgacuugcc aguauuggcu uaggcuggaa guuugccgg                              39

<210> SEQ ID NO 41
```

```
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cggccuugcc aguauuggcu uuggcuggaa guuuggccg                              39

<210> SEQ ID NO 42
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cggccuugca uguauuggcu caggcaugaa guuuguccg                              39

<210> SEQ ID NO 43
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cgugcuuguc aguauuggcg uuggcugaaa guuugcacg                              39

<210> SEQ ID NO 44
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cguacuugcc aguauuggcg uaggcuggaa guuugugcg                              39

<210> SEQ ID NO 45
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cgggcuugcc aguauuaggg uaggcuggaa guuuggccg                              39

<210> SEQ ID NO 46
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cgggcuugcc aguauuggcu uaggcuggaa guuuguccg                              39

<210> SEQ ID NO 47
<211> LENGTH: 39
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gagacucgcc aguauaggcu aaggcuggaa guaugucug                              39

<210> SEQ ID NO 48
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cugacuugcc aguauuggcu uaggcuggaa guuugucgg                              39

<210> SEQ ID NO 49
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cugacuugcc aguauuggcu uaggcuggaa guuugucag                              39

<210> SEQ ID NO 50
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cugacuugcc aguauuagcu uaggcuggaa guuuggcgg                              39

<210> SEQ ID NO 51
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ccggcuugcc aguauuggcu uaggcuggaa guuugccgg                              39

<210> SEQ ID NO 52
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ccgccuugcc aguauuggcu uaggcuggaa guuugucgg                              39

<210> SEQ ID NO 53
<211> LENGTH: 39
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 53
ccggcuugcc aguauuggcu caggcuggaa guuugccgg                              39

<210> SEQ ID NO 54
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ccggcuugcc aguauaggcu caggcuggaa guuugccgg                              39

<210> SEQ ID NO 55
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ucggcuugcc aguauuggcu uaggcuggaa guuugccgg                              39

<210> SEQ ID NO 56
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
ccggcuugcc aguauuggcu uuggcuggaa guuugccgg                              39

<210> SEQ ID NO 57
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ccggcuugcc aguauuggcg uaggcuggaa guuugccgg                              39

<210> SEQ ID NO 58
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ccgacuugcc aguauucgcu uaggcgggaa guuugccgg                              39

<210> SEQ ID NO 59
<211> LENGTH: 39
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 59
ccgacuugcc aguauuggcu uaggcuggaa guuugucgg                              39

<210> SEQ ID NO 60
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cgacuugcca guauuggcuu aggcuggaag uuugucg                                37

<210> SEQ ID NO 61
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ccgacuugcc aguaauggcu uaggcuggaa guuugucgg                              39

<210> SEQ ID NO 62
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ccgacuugcc aguauuggcg auggcuggaa guuugucgg                              39

<210> SEQ ID NO 63
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ccgacuugcc aguauuggcu uuggcuggaa guuugucgg                              39

<210> SEQ ID NO 64
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ccgccuugcc aguauuggcu uaggcuggaa guauggcgg                              39

<210> SEQ ID NO 65
<211> LENGTH: 39
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 65
ccaccuugcc aguauuggcu uaggcuggaa guguggugg                              39

<210> SEQ ID NO 66
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
acaccuugcg aguauuggcu uaggcucgaa guuuggcgu                              39

<210> SEQ ID NO 67
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acgcuuugcc aguauuggcu uaggcuggaa guuucgcgu                              39

<210> SEQ ID NO 68
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ccgcguugcc aguauuggcu uuggcuggaa guuucgcgg                              39

<210> SEQ ID NO 69
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ccgccuugcc aguauuggcu uaggcuggaa guuuugcgg                              39

<210> SEQ ID NO 70
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
ccgccuugcc aguauuggcu caggcuggaa guuuggcgg                              39

<210> SEQ ID NO 71
<211> LENGTH: 39
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 71
ccgccuugcc aguauuagcg uaggcuggaa guuuggcgg                    39

<210> SEQ ID NO 72
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ccgccuugca aguauuggcg uuggcuugaa guuuggcgg                    39

<210> SEQ ID NO 73
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
ucgccuugca uguaugggu uuggcaugaa guuuggcgg                     39

<210> SEQ ID NO 74
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ccgccuugca aguauaggcu uaggcuuaag uuuggggg                     38

<210> SEQ ID NO 75
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
cagccaugca aguauuggcu uaggcuugaa guucggcug                    39

<210> SEQ ID NO 76
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
cagccgugcu aguauuggca uuggcuagaa guuaggcug                    39

<210> SEQ ID NO 77
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
cgggcuugcc aguauuggcg uuggcuggaa guuugcccg    39

<210> SEQ ID NO 78
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ugggcuugcc aguauuggcu uaggcuggaa guuugcccg    39

<210> SEQ ID NO 79
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gggcuugcca guauuggcuu aggcuggaag uuuqucc    37

<210> SEQ ID NO 80
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gggagauggc gcugaucagg ccgccuugcc aguauuggcu uaggcuggaa guuuggcggc    60
uuugauacuu gaucgcccua gaagca    86

<210> SEQ ID NO 81
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gggagauggc gcugaucagg ucgccuugca aguauuggcu uuggcuugaa guuuggcggc    60
cuugauacuu gaucgcccua gaagca    86

<210> SEQ ID NO 82
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gggagauggc gcugaucagg ccgccuugca aguauuggcu uaggcuugaa guuuggcggc    60
uuugauacuu gaucgcccua gaagca    86

<210> SEQ ID NO 83
<211> LENGTH: 86

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
gggagauggc gcugaucagg cugccuugcg gguauggcg uuggcccgaa guuggcugc      60 uuugauacuu gaucgcccua gaagca                                         86

<210> SEQ ID NO 84
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gggagauggc gcugaucagg cagucuugcg aguuuggcua agcuucgaag uuuggcugcu     60
uugauacuug aucgcccuag aagca                                          85

<210> SEQ ID NO 85
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gggagauggc gcugaucagg ccgccuugcg aguaauggcg uaggcucgaa guugggcggc     60
uuugauacuu gaucgcccua gaagca                                         86

<210> SEQ ID NO 86
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gggagauggc gcugaucagg ccgccuugcg aguauuggcu uaggcucgaa guuggcggc     60 uuugauacuu gaucgcccua gaagca                                         86

<210> SEQ ID NO 87
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gggagauggc gcugaucagg ccggcuugcg aguauuggcu uaggcucgaa guuugccggc     60
uuugauacuu gaucgcccua gaagca                                         86

<210> SEQ ID NO 88
<211> LENGTH: 85
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 88
gggagauggc gcugaucagg ccgccuugcg aguauuggcu uggcucgaa guuugucugg    60 uugauacuug aucgcccuag aagca    85

<210> SEQ ID NO 89
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
gggagauggc gcugaucagg ccgccuugcg aguauuggcg uggcucgaa guuuucggc    60 uuugauacuu gaucgcccua gaagca    86

<210> SEQ ID NO 90
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
gggagauggc gcugaucagg ucaccuugcc auuauggcu uaggauggaa guuuggugc    60 uugauacuug aucgcccuag aagca    85

<210> SEQ ID NO 91
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gggagauggc gcugaucagg ccaccuugcc aguauuggcu uggccggaa guuuggugc    60 uuugauacuu gaucgcccua gaagca    86

<210> SEQ ID NO 92
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
gggagauggc gcugaucagg ccaccuugcc aguauuggcu uaggcuggaa guuuggugc    60 uugugauacu ugaucgcccu agaagca    87

<210> SEQ ID NO 93
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93

```
gggagauggc gcugaucagg ccgccuugcc aguauggggu uuggcuggaa guuggcggc    60 uuugauacuu gaucgcccua gaagca                                        86
```

<210> SEQ ID NO 94
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94

```
gggagauggc gcugaucagg ccgcauugcc aguauggcu ucggcuggaa guugccggc     60 uuugauacuu gaucgcccua gaagca                                        86
```

<210> SEQ ID NO 95
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95

```
gggagauggc gcugaucagg ccgcauugcc aguauaggcu uaugcuggaa guuugcggc    60 uuugauacuu gaucgcccua gaagca                                        86
```

<210> SEQ ID NO 96
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96

```
gggagauggc gcugaucagg ccgcguugcc aguauaggcu uaggcuggaa guucgcggc    60 uuugauacuu gaucgcccua gaagca                                        86
```

<210> SEQ ID NO 97
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97

```
gggagauggc gcugaucagg acgcauugcu aguauuggcu uaggcuagaa guguugcggc   60
uuugauacuu gaucgcccua gaagca                                        86
```

<210> SEQ ID NO 98
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98

```
gggagauggc gcugaucagg cugccuugcc aguauuggcu uaggcuggaa guuugcggc    60 uuugauacuu gaucgcccua gaagca                                        86
```

<210> SEQ ID NO 99
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gggagauggc gcugaucagg ccggguugcc aguauuggcu uaggcuggaa guuucgcggu      60
uuugauacuu gaucgcccua gaagca                                          86

<210> SEQ ID NO 100
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gggagauggc gcugaucagg ccgacuugcc aguauuggcg uaggcuggaa guuugucggc      60
uuugauacuu gaucgcccua gaagca                                          86

<210> SEQ ID NO 101
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gggagauggc gcugaucagg ccgacuugcc aguauuggcg uaggcuggaa guuugccggc      60
uuugauacuu gaucgcccua gaagca                                          86

<210> SEQ ID NO 102
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gggagauggc gcugaucagg ccgacuugcc aguauuggcc uaggcuggaa guuugucggc      60
uuugauacuu gaucgcccua gaagca                                          86

<210> SEQ ID NO 103
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gggagauggc gcugaucaag ucgacuugcc aguauuggcu uaggcuggaa guuugucggc      60
uuugauacuu gaucgcccua gaagca                                          86

<210> SEQ ID NO 104
<211> LENGTH: 86
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 104
gggagauggc gcugaucagg acgacuugcc aguauuggcu uagucuggaa guuugucggc    60
uuugauacuu gaucgcccua gaagca                                         86

<210> SEQ ID NO 105
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gggagauggc gcugaucagg ccgacuugcc aguguuggcu uuggcuggaa guuugucggc    60
uuugauacuu gaucgcccua gaagca                                         86

<210> SEQ ID NO 106
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gggagauggc gcugaucagg ccgacuugcc aguauuggcu uuggcuggaa guuugccggc    60
uuugauacuu gaucgcccua gaagca                                         86

<210> SEQ ID NO 107
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gggagauggc gcugaucagg ccgacuugcc aguauuggcu uaggcuggaa guuugccggc    60
uuugauacuu gaucgcccua gaagca                                         86

<210> SEQ ID NO 108
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gggagauggc gcugaucagg cggccuugcc aguauuggcu uuggcuggaa guuuggccgc    60
uuugauacuu gaucgcccua gaagca                                         86

<210> SEQ ID NO 109
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 109
gggagauggc gcugaucagg cggccuugca uguauuggcu caggcaugaa guugguccgc    60
uuugauacuu gaucgcccua gaagca                                        86

<210> SEQ ID NO 110
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gggagauggc gcugaucagg cgucuuguc aguauuggcg uuggcugaaa guuugcacgc     60
uuugauacuu gaucgcccua gaagca                                        86

<210> SEQ ID NO 111
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
gggagauggc gcugaucagg cguacuugcc aguauuggcg uaggcuggaa guuugugcgc    60
uuugauacuu gaucgcccua gaagca                                        86

<210> SEQ ID NO 112
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gggagauggc gcugaucagg cgggcuugcc aguauuaggg uaggcuggaa guuuggccgc    60
uuugauacuu gaucgcccua gaagca                                        86

<210> SEQ ID NO 113
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gggagauggc gcugaucagg cgggcuugcc aguauuggcu uaggcuggaa guuuggccgc    60
uuugauacuu gaucgcccua gaaca                                         85

<210> SEQ ID NO 114
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gggagauggc gcugaucagg gagacucgcc aguauaggcu aaggcuggaa guaugucugc    60
uugauacuug aucgcccuag aagca               85

<210> SEQ ID NO 115
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gggagauggc gcugaucagg cugacuugcc aguauuggcu uaggcuggaa guuugucggc     60
uuugauacuu gaucgcccua gaagca          86

<210> SEQ ID NO 116
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gggagauggc gcugaucagg cugacuugcc aguauuggcu uaggcuggaa guuugucagc     60
uuugauacuu gaucgcccua gaagca          86

<210> SEQ ID NO 117
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
gggagauggc gcugaucagg cugacuugcc aguauuagcu uaggcuggaa guuugcggc     60 uuugauacuu gaucgcccua gaagca          86

<210> SEQ ID NO 118
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gggagauggc gcugaucagg ccggcuugcc aguauuggcu uaggcuggaa guuugccggc     60
uuugauacuu gaucgcccua gaagca          86

<210> SEQ ID NO 119
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gggagauggc gcugaucagg ccgccuugcc aguauuggcu uaggcuggaa guuugucggc     60
uuugauacuu gaucgcccua gaagca          86

```
<210> SEQ ID NO 120
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gggagauggc gcugaucagg ccggcuugcc aguauuggcu caggcuggaa guuugccggc    60
uuugauacuu gaucgcccua gaagca                                        86

<210> SEQ ID NO 121
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gggagauggc gcugaucagg ccggcuugcc aguauaggcu caggcuggaa guuugccggc    60
uuugauacuu gaucgcccua gaagca                                        86

<210> SEQ ID NO 122
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gggagauggc gcugaucagg ucggcuugcc aguauuggcu uaggcuggaa guuugccggc    60
uuugauacuu gaucgcccua gaagca                                        86

<210> SEQ ID NO 123
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gggagauggc gcugaucagg ccggcuugcc aguauuggcu uaggcuggaa guuugccggc    60
uuugauacuu gaucgcccua gaagca                                        86

<210> SEQ ID NO 124
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gggagauggc gcugaucagg ccggcuugcc aguauggcg uaggcuggaa guuugccggc    60
uuugauacuu gaucgcccua gaagca                                        86

<210> SEQ ID NO 125
<211> LENGTH: 86
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 125
gggagauggc gcugaucagg ccgacuugcc aguauucgcu uaggcgggaa guuugccggc      60
uuugauacuu gaucgcccua gaagca                                          86

<210> SEQ ID NO 126
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gggagauggc gcugaucagg ccgacuugcc aguauuggcu uaggcuggaa guuugucggc      60
uuugauacuu gaucgcccua gaagca                                          86

<210> SEQ ID NO 127
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gggagauggc gcugaucagg ccgacuugcc aguauuggcu uaggcuggaa guuugucgcu      60
uugauacuug aucgcccuag aagca                                           85

<210> SEQ ID NO 128
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gggagauggc gcugaucagg ccgacuugcc aguaauggcu uaggcuggaa guuugucggc      60
uuugauacuu gaucgcccua gaagca                                          86

<210> SEQ ID NO 129
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gggagauggc gcugaucagg ccgacuugcc aguauggcg auggcuggaa guuugucggc      60
uuugauacuu gaucgcccua gaagca                                          86

<210> SEQ ID NO 130
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 130
gggagauggc gcugaucagg ccgacuugcc aguauuggcu uuggcuggaa guuugucggc    60
uuugauacuu gaucgcccua gaagca                                        86

<210> SEQ ID NO 131
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gggagauggc gcugaucagg ccgccuugcc aguauuggcu uaggcuggaa guauggcggc    60
uuugauacuu gaucgcccua gaagca                                        86

<210> SEQ ID NO 132
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ggagauggcg cugaucaggc caccuugcca guauuggcuu aggcuggaag ugugguggcu    60
uugauacuug aucgcccuag aagca                                         85

<210> SEQ ID NO 133
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gggagauggc gcugaucagg acaccuugcg aguauuggcu uaggcucgaa guuggcguc    60 uuugauacuu gaucgcccua gaagca                                        86

<210> SEQ ID NO 134
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
gggagauggc gcugaucagg acgcuugcc aguauuggcu uaggcuggaa guuucgcguc    60
uuugauacuu gaucgcccua gaagca                                        86

<210> SEQ ID NO 135
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gggagauggc gcugaucagg ccgcguugcc aguauuggcu uuggcuggaa guuucgcggc    60
```

```
uuugauacuu gaucgcccua gaagca                                              86

<210> SEQ ID NO 136
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gggagauggc gcugaucagg ccgccuugcc aguauggcu uaggcuggaa guuugcggc           60 uuugauacuu gaucgcccua gaagca                                              86

<210> SEQ ID NO 137
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gggagauggc gcugaucagg ccgccuugcc aguauggcu caggcuggaa guuggcggc           60 uuugauacuu gaucgcccua gaagca                                              86

<210> SEQ ID NO 138
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gggagauggc gcugaucagg ccgccuugcc aguauuagcg uaggcuggaa guuggcggc           60 uuugauacuu gaucgcccua gaagca                                              86

<210> SEQ ID NO 139
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gggagauggc gcugaucagg ccgccuugca aguauggcg uuggcuugaa guuggcggc           60 uuugauacuu gaucgcccua gaagca                                              86

<210> SEQ ID NO 140
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gggagauggc gcugaucagg ucgccuugca uguauggu uuggcaugaa guuuggcggc           60
uuugauacuu gaucgcccua gaagca                                              86

<210> SEQ ID NO 141
```

```
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gggagauggc gcugaucagg ccgccuugca aguauaggcu uaggcuuaag uuuggggcu      60 uugauacuug aucgcccuag aagca                                          85

<210> SEQ ID NO 142
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
gggagauggc gcugaucagg cagccaugca aguauuggcu uaggcuugaa guucggcugc     60
uuugauacuu gaucgcccua gaagca                                         86

<210> SEQ ID NO 143
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
gggagauggc gcugaucagg cagccgugcu aguauuggca uggcuagaa guuaggcugc      60 uuugauacuu gaucgcccua gaagca                                         86

<210> SEQ ID NO 144
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
gggagauggc gcugaucagg cgggcuugcc aguauuggcg uggcuggaa guuugcccgc      60 uuugauacuu gaucgcccua gaagca                                         86

<210> SEQ ID NO 145
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
gggagauggc gcugaucagg ugggcuugcc aguauuggcu uaggcuggaa guuugcccgc     60
uuugauacuu gaucgcccua gaagca                                         86

<210> SEQ ID NO 146
<211> LENGTH: 85
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 146
gggagauggc gcugaucagg gggcuugcca guauuggcuu aggcuggaag uuuguccgcu    60
uugauacuug aucgcccuag aagca                                          85

<210> SEQ ID NO 147
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
cgccuugcca guauuggcuu aggcuggaag uuuggcg                              37

<210> SEQ ID NO 148
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gccuugccag uauuggcuua ggcuggaagu uuggc                                35

<210> SEQ ID NO 149
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ccgccuugca guauuggcuu aggcugaagu uuggcgg                              37

<210> SEQ ID NO 150
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ccgccuugcc agauuggcuu agcuggaagu uuggcgg                              37

<210> SEQ ID NO 151
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ccgccuugaa guauuggcuu aggcuuaagu uuggcgg                              37

<210> SEQ ID NO 152
<211> LENGTH: 34
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 152
ccgccuugcc aguauugggc uggaaguuug gcgg                                    34

<210> SEQ ID NO 153
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
ccgccuugcc aguauuggcg gcuggaaguu uggcgg                                  36

<210> SEQ ID NO 154
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ccgccuugcc aguauug                                                       17

<210> SEQ ID NO 155
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ccgccuugcc aguauug                                                       17

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ccgccuugcc aguauuggc                                                     19

<210> SEQ ID NO 157
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ccgccuugcc aguauuggcu uaggcuggaa guggcgg                                 37

<210> SEQ ID NO 158
<211> LENGTH: 38
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 158
ccgccuugcc aguauuggcu uaggcuggaa guuggcgg                              38

<210> SEQ ID NO 159
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ccgccuugcc aguauuggcu uaggcuggaa gu                                    32

<210> SEQ ID NO 160
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cagccaugca aguauuggcu uaggcuugaa guucggcug                             39

<210> SEQ ID NO 161
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
cagccgugcu aguauuggca uuggcuagaa guuaggcug                             39

<210> SEQ ID NO 162
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ccgccuugcg aguaauggcg uaggcucgaa guugggcgg                             39

<210> SEQ ID NO 163
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ccgacuugcc aguguuggcu uuggcuggaa guuugucgg                             39

<210> SEQ ID NO 164
<211> LENGTH: 38
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 164
cagucuugcg aguuggcua agcuucgaag uuuggcug                     38

<210> SEQ ID NO 165
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
cugccuugcg gguauuggcg uuggcccgaa guuuggcug                   39

<210> SEQ ID NO 166
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ccgacuugcc aguauuggcg auggcuggaa guuugucgg                   39

<210> SEQ ID NO 167
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
cgcauugcua guauuggcuu aggcuagaag uguugcg                     37

<210> SEQ ID NO 168
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gtgacgactg acatatctgc tccgaggtta ttggggttgg ggcctgggcg attggggcct    60
cgtagttgag tctgagtgct                                        80

<210> SEQ ID NO 169
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gtgacgactg acatatctgc gtttggggtt ggggcctggg agtttgggga gcagaaagga    60
cgtagttgag tctgagtgct                                        80

<210> SEQ ID NO 170
<211> LENGTH: 80
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 170
gtgacgactg acatatctgc tgtgggtgtt gtggggtgg gtggtgggcc cttcgccatg    60
cgtagttgag tctgagtgct                                               80

<210> SEQ ID NO 171
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gtgacgactg acatatctgc ggcggttggg gtcgaagggc gaggggtggg aggtcgccgt    60
agttgagtct gagtgct                                                  77

<210> SEQ ID NO 172
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gtgacgactg acatatctgc tattttgggg cctgggtgtt ggggattggg gactatgtgt    60
cgtagttgag tctgagtgct                                               80

<210> SEQ ID NO 173
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gtgacgactg acatatctgc tgtggatggt gggggtggt gtgggagggc tggtcggtcg    60
cgtagttgag tctgagtgct                                               80

<210> SEQ ID NO 174
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gtgacgactg acatatctgc cctataggg tgtgggcgag gggtgggtgg tagggcggct    60
cgtagttgag tctgagtgct                                               80

<210> SEQ ID NO 175
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 175
gtgacgactg acatatctgc ggaggtgggt gggtgggtgc gtgcgagggc ggtgtaggtc    60
cgtagttgag tctgagtgct                                                80

<210> SEQ ID NO 176
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gtgacgactg acatatctgc aaaagttaga ttgacatggt atgcaccgtc tgaggttggt    60
cgtagttgag tctgagtgct                                                80

<210> SEQ ID NO 177
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gtgacgactg acatatctgc accacgctag gggtgagggc gaggggtggg tagcgcgtgg    60
cgtagttgag tctgagtgct                                                80

<210> SEQ ID NO 178
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gtgacgactg acatatctgc tgtgggtgtt gtggggcgg gtggtgggtg cgtcggtggt    60
cgtagttgag tctgagtgct                                                80

<210> SEQ ID NO 179
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gtgacgactg acatatctgc tgcttccagc ggtcatgata tgcactgtct gaagctcggt    60
cgtagttgag tctgagtgct                                                80

<210> SEQ ID NO 180
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gtgacgactg acatatctgc tgtgttatga tatgcaccgt ctgagggtag tcgcggggtg    60
cgtagttgag tctgagtgct                                               80

<210> SEQ ID NO 181
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gtgacgactg acatatctgc tgcttgttta gtgggtgggt gggtggtgtg gtggtgatgc    60
gtagttgagt ctgagtgct                                                79

<210> SEQ ID NO 182
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gtgacgactg acatatctgc cttggggttg gggcctgggt gtttggggtg gcctagaagt    60
cgtagttgag tctgagtgct                                               80

<210> SEQ ID NO 183
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gtgacgactg acatatctgc gctaggggtg ggttggggtt ggtggtgtgc gtgtgggttg    60
cgtagttgag tctgagtgct                                               80

<210> SEQ ID NO 184
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gtgacgactg acatatctgc tgttgaggtt ggtgggggggt gggcggtggg atggttgtgc    60
cgtagttgag tctgagtgct                                               80

<210> SEQ ID NO 185
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gtgacgactg acatatctgc ttgacagtct gctttgcagg ggccgagagc gccattgcgt    60
cgtagttgag tctgagtgct                                               80

```
<210> SEQ ID NO 186
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gtgacgactg acatatctgc tgtggttggt gggggtgga gggtgggagg ccgtgtgtcc    60
cgtagttgag tctgagtgct                                               80

<210> SEQ ID NO 187
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gtgacgactg acatatctgc tgtggtggtg gggagggtg gtggggtggc cggcgctcgt    60
cgtagttgag tctgagtgct                                               80

<210> SEQ ID NO 188
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gtgacgactg acatatctgc tgggttacgt ggttcggggc tagggggtg gggtgtgttt    60 cgtagttgag tctgagtgct                                               80

<210> SEQ ID NO 189
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
gtgacgactg acatatctgc tggtggtgtg cggtgggttc ttgggtggga tgggtggtac    60
cgtagttgag tctgagtgct                                               80

<210> SEQ ID NO 190
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gtgacgactg acatatctgc tattagatcc tcggtgggtg ggtgggtgtg tggtggtgtg    60
cgtagttgag tctgagtgct                                               80

<210> SEQ ID NO 191
<211> LENGTH: 80
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 191
gtgacgactg acatatctgc gggcgtctga gcgcatggat gacccaccga cagattgcgg    60
cgtagttgag tctgagtgct                                                80

<210> SEQ ID NO 192
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gtgacgactg acatatctgc gctttgggtg ggctcggtgt gcggtgtgcg ggtgggtttg    60
cgtagttgag tctgagtgct                                                80

<210> SEQ ID NO 193
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gtgacgactg acatatctgc gtttggggtt ggggcctggg agtttgggga gcagaaaggg    60
cgtagttgag tctgagtgct                                                80

<210> SEQ ID NO 194
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gtgacgactg acatatctgc gggtgggttg ggttgggttt ggtggtggtg cctgttagtt    60
cgtagttgag tctgagtgct                                                80

<210> SEQ ID NO 195
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gtgacgactg acatatctgc aggtgggtgg gtgggtgtgt gtgcggtggt gtgatttggc    60
cgtagttgag tctgagtgct                                                80

<210> SEQ ID NO 196
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 196
gtgacgactg acatatctgc tgtggttggt gggggcggc gggtggggag cctggtgttc    60
cgtagttgag tctgagtgct                                              80

<210> SEQ ID NO 197
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gtgacgactg acatatctgc tcccgtttga gggcttgtcg acagattgc tggcacgtca    60 cgtagttgag tctgagtgct                                              80

<210> SEQ ID NO 198
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gtgacgactg acatatctgc tcttggtggt ggtggtgggt tgggatgggt cttgggctgc    60
cgtagttgag tctgagtgct                                              80

<210> SEQ ID NO 199
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gtgacgactg acatatctgc ctgtgagggg agggagggtg ggtttggcgg tggcgcaggc    60
cgtagttgag tctgagtgct                                              80

<210> SEQ ID NO 200
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
gtgacgactg acatatctgc gtggtggtgc gtgggtggtg ggggggggag ctgggtgccc    60
cgtagttgag tctgagtgct                                              80

<210> SEQ ID NO 201
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gtgacgactg acatatctgc tgtgggtgtt gtggggtgg gtggtgggcc cttcgccgtg    60

```
cgtagttgag tctgagtgct                                                 80

<210> SEQ ID NO 202
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gtgacgactg acatatctgc ttccggtatg tgtgggtggg tggtggtgt ggtggtgttg      60 cgtagttgag tctgagtgct                                                 80

<210> SEQ ID NO 203
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gtgacgactg acatatctgc tctcttctgt tgtgggtggg tgggtggtgt ggtgcgtgtg     60
cgtagttgag tctgagtgct                                                 80

<210> SEQ ID NO 204
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gtgacgactg acatatctgc ggctgggtgg gttgggttag ggtggtgtgc ggtgggttgc     60
cgtagttgag tctgagtgct                                                 80

<210> SEQ ID NO 205
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gtgacgactg acatatctgc gtttaggtgg gcgggtgggt gtgcggtggg cggtgttgaa     60
cgtagttgag tctgagtgct                                                 80

<210> SEQ ID NO 206
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gtgacgactg acatatctgc ggtgattggg gttggggcct gggcgtttgg ggaccgcatg     60
cgtagttgag tctgagtgct                                                 80

<210> SEQ ID NO 207
```

```
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gtgacgactg acatatctgc gtttggggtt ggggcctggg agtttgggga gcagagagga    60
cgtagttgag tctgagtgct                                                80

<210> SEQ ID NO 208
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gtgacgactg acatatctgc taacttgttg gggtttgggg cctgggtgtt ggggttgttt    60
cgtagttgag tctgagtgct                                                80

<210> SEQ ID NO 209
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gtgacgactg acatatctgc tggggttggt gggggaggt gggtgggtta tgtgcgctgg     60
cgtagttgag tctgagtgct                                                80

<210> SEQ ID NO 210
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gtgacgactg acatatctgc tgtgggtgtt gtggggtgg gttggtgggc attgcgtgtg     60
cgtagttgag tctgagtgct                                                80

<210> SEQ ID NO 211
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
gtgacgactg acatatctgc gagtgggttc ggtggtggtg tgtgggaggg ttgggtacgt    60
cgtagttgag tctgagtgct                                                80

<210> SEQ ID NO 212
<211> LENGTH: 80
<212> TYPE: DNA
<213> ORGANISM: Artificial Sequence
<220> FEATURE:
```

<223> OTHER INFORMATION: Description of Artificial Sequence: Synthetic
    oligonucleotide

<400> SEQUENCE: 212
gtgacgactg acatatctgc tggacatgat tgcaccgtat gaggtttagt cgttaatgtg    60
cgtagttgag tctgagtgct                                                80

<210> SEQ ID NO 213
<211> LENGTH: 80
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 213
gtgacgactg acatatctgc agtggggcct gggcgttggg gtttggggtg cctcgtcagt    60
cgtagttgag tctgagtgct                                                80

<210> SEQ ID NO 214
<211> LENGTH: 80
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 214
gtgacgactg acatatctgc atggattttc ggtgggtggg tgggttggtg tggtggtgtg    60
cgtagttgag tctgagtgct                                                80

<210> SEQ ID NO 215
<211> LENGTH: 80
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 215
gtgacgactg acatatctgc tgtggttggt ggggggtggg tggtgggaag gttccggtgc    60
cgtagttgag tctgagtgct                                                80

<210> SEQ ID NO 216
<211> LENGTH: 80
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 216
gtgacgactg acatatctgc ggttggggtt ggggcctggg tgttggggag caggtagcac    60
cgtagttgag tctgagtgct                                                80

<210> SEQ ID NO 217
<211> LENGTH: 80
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 217

```
gtgacgactg acatatctgc ggcctgggag ggttcggtgg tggtgcgagg gtgggcaagc    60
cgtagttgag tctgagtgct                                               80
```

<210> SEQ ID NO 218
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(18)
<223> OTHER INFORMATION: 5-(amino-1-propenyl)-2'-deoxyuridine
<220> FEATURE:
<221> NAME/KEY: modified_base
<222> LOCATION: (26)..(26)
<223> OTHER INFORMATION: 5-(4-pivaloylbenzamido-1-propenyl)-2'-
      deoxyuridine

<400> SEQUENCE: 218

```
acctagtttg gcttgcanaa gtaacnagca cgtgggctag                         40
```

<210> SEQ ID NO 219
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (17)..(17)
<223> OTHER INFORMATION: 5-(indole-3-acetamido-1-propenyl)-2'-
      deoxyuridine
<220> FEATURE:
<221> NAME/KEY: modified_base
<222> LOCATION: (23)..(23)
<223> OTHER INFORMATION: 5-(amino-1-propenyl)-2'-deoxyuridine

<400> SEQUENCE: 219

```
acgatcgccc cngtctntaa gancgaatac tatgggctag                         40
```

<210> SEQ ID NO 220
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: 5-(indole-3-acetamido-1-propenyl)-2'-
      deoxyuridine

<400> SEQUENCE: 220

```
acctagaaag gcttagtgaa gtaangatca gggcgggatc                         40
```

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (12)..(12)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (18)..(18)
<223> OTHER INFORMATION: 5-(amino-1-propenyl)-2'-deoxyuridine
<220> FEATURE:
<221> NAME/KEY: modified_base
<222> LOCATION: (19)..(19)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (23)..(23)
<223> OTHER INFORMATION: 5-(amino-1-propenyl)-2'-deoxyuridine
<220> FEATURE:
<221> NAME/KEY: modified_base
<222> LOCATION: (29)..(29)
<223> OTHER INFORMATION: 5-(amino-1-propenyl)-2'-deoxyuridine

<400> SEQUENCE: 221
acctagttcc cngtctanna ganccgagng tatgccgatc                              40

<210> SEQ ID NO 222
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: 5-(amino-1-propenyl)-2'-deoxyuridine

<400> SEQUENCE: 222
acctaggcag tcttgccgaa tttacgagng gggagggatc                              40

<210> SEQ ID NO 223
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(12)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (17)..(17)
<223> OTHER INFORMATION: 5-(indole-3-acetamido-1-propenyl)-2'-
      deoxyuridine
<220> FEATURE:
<221> NAME/KEY: modified_base
<222> LOCATION: (19)..(19)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (26)..(26)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (30)..(30)
<223> OTHER INFORMATION: 5-(4-pivaloylbenzamido-1-propenyl)-2'-
      deoxyuridine
```

<400> SEQUENCE: 223
acgatcactg cncagcntna ttaacnagcn tcgaccctag          40

<210> SEQ ID NO 224
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (23)..(23)
<223> OTHER INFORMATION: 5-(amino-1-propenyl)-2'-deoxyuridine
<220> FEATURE:
<221> NAME/KEY: modified_base
<222> LOCATION: (29)..(29)
<223> OTHER INFORMATION: 5-(amino-1-propenyl)-2'-deoxyuridine

<400> SEQUENCE: 224
acgatcttcc gccagctgna ttncgaagng cgtgaggatc          40

<210> SEQ ID NO 225
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 5-(amino-1-propenyl)-2'-deoxyuridine
<220> FEATURE:
<221> NAME/KEY: modified_base
<222> LOCATION: (30)..(30)
<223> OTHER INFORMATION: 5-(4-pivaloylbenzamido-1-propenyl)-2'-
      deoxyuridine

<400> SEQUENCE: 225
acctaggcgg tcttnccgtc gttacgtccn cggccctag          40

<210> SEQ ID NO 226
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 5-(4-pivaloylbenzamido-1-propenyl)-2'-
      deoxyuridine
<220> FEATURE:
<221> NAME/KEY: modified_base
<222> LOCATION: (25)..(25)
<223> OTHER INFORMATION: 5-(indole-3-acetamido-1-propenyl)-2'-
      deoxyuridine
<220> FEATURE:
<221> NAME/KEY: modified_base
<222> LOCATION: (29)..(29)
<223> OTHER INFORMATION: 5-(amino-1-propenyl)-2'-deoxyuridine

<400> SEQUENCE: 226
acctagtttg gcgtagcgna ttaangggng cggcagctag          40

<210> SEQ ID NO 227
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 5-(amino-1-propenyl)-2'-deoxyuridine
<220> FEATURE:
<221> NAME/KEY: modified_base
<222> LOCATION: (18)..(18)
<223> OTHER INFORMATION: 5-(amino-1-propenyl)-2'-deoxyuridine
<220> FEATURE:
<221> NAME/KEY: modified_base
<222> LOCATION: (19)..(19)
<223> OTHER INFORMATION: 5-(4-pivaloylbenzamido-1-propenyl)-2'-
      deoxyuridine

<400> SEQUENCE: 227
acgatcgctg acgtncanna gtatgaggca cgtgggctag                              40

<210> SEQ ID NO 228
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
acggagaaag agagagtgta attgctagca taaccgctgc                              40

<210> SEQ ID NO 229
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gtaaccacgt tgccagaccg agtctaccag cgatcctcag                              40

<210> SEQ ID NO 230
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tatgcccaaa tccctcaagt cggccaggat acaccaccgt                              40

<210> SEQ ID NO 231
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
aatcaaaagg ctcacgcgcg gattggtcaa ccttacaacc                              40

```
<210> SEQ ID NO 232
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tcggccttcc cagaccaccg caatccccag ggaacaggca                40

<210> SEQ ID NO 233
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
catcacactg tcaacatacc cagcctgggg aaagacgaac                40

<210> SEQ ID NO 234
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
aacccgcatg ccgatcgatg tcgtgcctcg ctccacgctc                40

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
accaggcacc cgacggacta actcatcact caggcgaggg                40

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
aatgcctcgt acacactccc                                     20

<210> SEQ ID NO 237
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
cgacuugcca guauuggcga uggcuggaag uuugucg                   37

<210> SEQ ID NO 238
```

```
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
ccgacuugcg gguauuggcg auggcccgaa guuugucgg                              39

<210> SEQ ID NO 239
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
cgacuugcgg guauuggcga uggcccgaag uuugucg                                37

<210> SEQ ID NO 240
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
cugccuugcc aguauuggcg auggcuggaa guuuggcug                              39

<210> SEQ ID NO 241
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cugccuugcg gguauuggcg auggcccgaa guuuggcug                              39

<210> SEQ ID NO 242
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gccuugccag uauuggcgau ggcuggaagu uuggc                                  35

<210> SEQ ID NO 243
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ccgacuugcg gguauuggcg uuggcccgaa guuugucgg                              39

<210> SEQ ID NO 244
<211> LENGTH: 37
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
cgccuugcca guauuggcga uggcuggaag uuuggcg                               37

<210> SEQ ID NO 245
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
ccgacuugcc aguauaggcu caggcuggaa guuugucgg                             39

<210> SEQ ID NO 246
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
ccgacuugcc aguauuagcu uaggcuggaa guuugucgg                             39

<210> SEQ ID NO 247
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ccgacuugcc aguauuggcc uaggcuggaa guuugucgg                             39

<210> SEQ ID NO 248
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
ccgacuugcc aguauaggcu uaugcuggaa guuugucgg                             39

<210> SEQ ID NO 249
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
ccgacuugcc aguauuggcg cuggcuggaa guuugucgg                             39

<210> SEQ ID NO 250
<211> LENGTH: 39
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 250
ccgacuugcc aguauuggcg caggcuggaa guuugucgg                    39

<210> SEQ ID NO 251
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ccgacuugcc aguauuggcg aaggcuggaa guuugucgg                    39

<210> SEQ ID NO 252
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ccgacuugcc aguauuggcu cuggcuggaa guuugucgg                    39

<210> SEQ ID NO 253
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ccgacuugcc aguauuggcu uaggcuggaa guuugucgg                    39

<210> SEQ ID NO 254
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ccguuguggg uauuggcuua ggcccaaagu uucgg                        35

<210> SEQ ID NO 255
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
gccuugcggg uauuggcguu ggcccgaagu uuggc                        35

<210> SEQ ID NO 256
<211> LENGTH: 35
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 256
gccuugcggg uauuggcgau ggcccgaagu uuggc                                    35

<210> SEQ ID NO 257
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
gccuugaggg uauuggcgau ggcccuaagu uuggc                                    35

<210> SEQ ID NO 258
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gcccuugucc guauuggcuu aggcggaaag uuugggc                                  37

<210> SEQ ID NO 259
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
gcgguugcgg guauuggcga uggcccgaag uuuccgc                                  37

<210> SEQ ID NO 260
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
cccuugcccg uauuggcuua ggcgggaagu uggg                                     35

<210> SEQ ID NO 261
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
ggccuugccc guauuggcuu aggcgggaag uuuggcc                                  37

<210> SEQ ID NO 262
<211> LENGTH: 37
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 262
ggccuugccc guauuggcga uggcgggaag uuuggcc                                37

<210> SEQ ID NO 263
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
cgacuugcca guauuggcga uggcuggaag uuugucg                                37

<210> SEQ ID NO 264
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
cgccuugcca guauuggcuu aggcuggaag uuuggcg                                37

<210> SEQ ID NO 265
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
cgacuugcca guauuggcuu aggcuggaag uuugucg                                37

<210> SEQ ID NO 266
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ccgccuugcc aguauuggcg auggcuggaa guuuggcgg                              39

<210> SEQ ID NO 267
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
aggccgccuu gccaguauug gcuuaggcug gaaguuuggc ggcuut                      46

<210> SEQ ID NO 268
<211> LENGTH: 40
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
ccgccuugcc aguauuggcu uaggcuggaa guuuggcggt                              40

<210> SEQ ID NO 269
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
ccgccuugcc aguauuggcu uaggcuggaa guuuggcggt                              40

<210> SEQ ID NO 270
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
cgccuugcca guauuggcuu aggcuggaag uuuggcgt                                38

<210> SEQ ID NO 271
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
gccuugccag uauuggcuua ggcuggaagu uuggct                                  36

<210> SEQ ID NO 272
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
ccgccuugca guauuggcuu aggcugaagu uuggcggt                                38

<210> SEQ ID NO 273
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
ccgccuugcc agauuggcuu agcuggaagu uuggcggt                                38

<210> SEQ ID NO 274
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
ccgccuugaa guauuggcuu aggcuuaagu uuggcggt                                38

<210> SEQ ID NO 275
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
ccgccuugcc aguauugggc uggaaguuug gcggt                                   35

<210> SEQ ID NO 276
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
ccgccuugcc aguauuggcg gcuggaaguu uggcggt                                 37

<210> SEQ ID NO 277
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
ccgccuugcc aguauuggcu uaggcuggaa guggcggt                                38

<210> SEQ ID NO 278
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
ccgccuugcc aguauuggcu uaggcuggaa guuggcggt                              39

<210> SEQ ID NO 279
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
cagccaugca aguauuggcu uaggcuugaa guucggcugt                             40

<210> SEQ ID NO 280
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
cagccgugcu aguauuggca uuggcuagaa guuaggcugt                             40

<210> SEQ ID NO 281
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
ccgccuugcg aguaauggcg uaggcucgaa guugggcggt                             40

<210> SEQ ID NO 282
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
ccgacuugcc aguguuggcu uuggcuggaa guuugucggt                             40
```

```
<210> SEQ ID NO 283
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
cagucuugcg aguuuggcua agcuucgaag uuuggcugt                              39

<210> SEQ ID NO 284
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
cugccuugcg gguauuggcg uuggcccgaa guuuggcugt                             40

<210> SEQ ID NO 285
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
ccgacuugcc aguauuggcg auggcuggaa guuugucggt                             40

<210> SEQ ID NO 286
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
cgcauugcua guauuggcuu aggcuagaag uguugcgt                               38

<210> SEQ ID NO 287
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
cgacuugcca guauuggcga uggcuggaag uuugucgt                               38
```

<210> SEQ ID NO 288
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
ccgacuugcg gguauuggcg auggcccgaa guuugucggt                              40

<210> SEQ ID NO 289
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
cgacuugcgg guauuggcga uggcccgaag uuugucgt                                38

<210> SEQ ID NO 290
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
cugccuugcc aguauuggcg auggcuggaa guuuggcugt                              40

<210> SEQ ID NO 291
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
cugccuugcg gguauuggcg auggcccgaa guuuggcugt                              40

<210> SEQ ID NO 292
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
gccuugccag uauuggcgau ggcuggaagu uuggct                                  36

<210> SEQ ID NO 293
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
ccgacuugcg gguauuggcg uuggcccgaa guuugucggt                              40

<210> SEQ ID NO 294
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
cgccuugcca guauuggcga uggcuggaag uuuggcgt                                38

<210> SEQ ID NO 295
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
ccgacuugcc aguauaggcu caggcuggaa guuugucggt                              40

<210> SEQ ID NO 296
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
ccgacuugcc aguauuagcu uaggcuggaa guuugucggt                              40

<210> SEQ ID NO 297
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
ccgacuugcc aguauuggcc uaggcuggaa guuugucggt                                40

<210> SEQ ID NO 298
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
ccgacuugcc aguauaggcu uaugcuggaa guuugucggt                                40

<210> SEQ ID NO 299
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
ccgacuugcc aguauuggcg cuggcuggaa guuugucggt                                40

<210> SEQ ID NO 300
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
ccgacuugcc aguauuggcg caggcuggaa guuugucggt                                40

<210> SEQ ID NO 301
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
ccgacuugcc aguauuggcg aaggcuggaa guuugucggt                                40

<210> SEQ ID NO 302
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
ccgacuugcc aguauuggcu cuggcuggaa guuugucggt      40

<210> SEQ ID NO 303
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
ccgacuugcc aguauuggcu uaggcuggaa guuugucggt      40

<210> SEQ ID NO 304
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
ccguuguggg uauuggcuua ggcccaaagu uucggt      36

<210> SEQ ID NO 305
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
gccuugcggg uauuggcguu ggcccgaagu uuggct      36

<210> SEQ ID NO 306
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
gccuugcggg uauuggcgau ggcccgaagu uuggct      36

<210> SEQ ID NO 307
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 307
gccuugaggg uauuggcgau ggcccuaagu uuggct                                36

<210> SEQ ID NO 308
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
gcccuugucc guauuggcuu aggcggaaag uuugggct                              38

<210> SEQ ID NO 309
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
gcgguugcgg guauuggcga uggcccgaag uuuccgct                              38

<210> SEQ ID NO 310
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 310
cccuugcccg uauuggcuua ggcgggaagu uuggt                                 36

<210> SEQ ID NO 311
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
ggccuugccc guauuggcuu aggcgggaag uuuggcct                              38

<210> SEQ ID NO 312
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 312
ggccuugccc guauuggcga uggcgggaag uuuggcct        38

<210> SEQ ID NO 313
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
cgacuugcca guauuggcga uggcuggaag uuugucgt        38

<210> SEQ ID NO 314
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
cgccuugcca guauuggcuu aggcuggaag uuuggcgt        38

<210> SEQ ID NO 315
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
cgacuugcca guauuggcuu aggcuggaag uuugucgt        38

<210> SEQ ID NO 316
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
ccgccuugcc aguauuggcg auggcuggaa guuuggcggt        40

<210> SEQ ID NO 317
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317

```
ggcuggaagu uuggcgg                                                    17

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
ggcuggaagu uuggcggt                                                   18

<210> SEQ ID NO 319
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319 hwwvgcbhwg                                                            10

<210> SEQ ID NO 320
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, u, g, unknown or other
<220> FEATURE:
<221> NAME/KEY: modified_base
<222> LOCATION: (9)..(12)
<223> OTHER INFORMATION: a, c, u, g, unknown or other
<220> FEATURE:
<221> NAME/KEY: modified_base
<222> LOCATION: (25)..(28)
<223> OTHER INFORMATION: a, c, u, g, unknown or other
<220> FEATURE:
<221> NAME/KEY: modified_base
<222> LOCATION: (34)..(39)
<223> OTHER INFORMATION: a, c, u, g, unknown or other

<400> SEQUENCE: 320
nnnnndugnn nnudwwvgcb hwggnnnnaa guknnnnnn                            39

<210> SEQ ID NO 321
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, u, g, unknown or other
<220> FEATURE:
<221> NAME/KEY: modified_base
<222> LOCATION: (9)..(12)
<223> OTHER INFORMATION: a, c, u, g, unknown or other

<400> SEQUENCE: 321
```

```
nnnaaguknn nn                                                          12

<210> SEQ ID NO 322
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(58)
<223> OTHER INFORMATION: a, c, u, g, unknown or other

<400> SEQUENCE: 322
gggagugugu acgaggcauu aggccgccnn nnnnnnnnnn nnnnnnnnnn nnnnnnnngg      60
cggcuuugau acuugaucgc ccuagaagc                                       89

<210> SEQ ID NO 323
<211> LENGTH: 89
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(58)
<223> OTHER INFORMATION: a, c, u, g, unknown or other

<400> SEQUENCE: 323
gggagugugu acgaggcauu aggccgccnn nnnnnnnnnn nnnnnnnnnn nnnnnnnngg      60
cggcuuugau acuugaucgc ccuagaagc                                       89

<210> SEQ ID NO 324
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 324

His His His His His His
1               5
```

STEM-LOOP COMPOSITIONS AND METHODS FOR INHIBITING FACTOR D

CROSS-REFERENCE

This application is a continuation application of International Patent Application No. PCT/US2018/014573, filed Jan. 19, 2018, which claims the benefit of U.S. Provisional Application Nos. 62/448,872, filed Jan. 20, 2017, and 62/536,387, filed Jul. 24, 2017, which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 6, 2018, is named 49644-716_601_SL.txt and is 100,140 bytes in size.

BACKGROUND OF THE INVENTION

Visual impairment is a national and global health concern that has a negative impact on physical and mental health. The number of people with visual impairment and blindness is increasing due to an overall aging population. Visual impairment and blindness can be caused by any one of a large number of eye diseases and disorders affecting people of all ages. In one example, age-related macular degeneration (AMD) is an eye disorder that is currently the leading cause of vision loss in people fifty years of age or older in industrialized countries. It is estimated that by 2020, the number of people with AMD could exceed 196 million and by 2040, that number is expected to rise to 288 million. AMD is a degenerative eye disease that progresses from early stages to advanced stages of the disease. Risk factors for the disease include aging, lifestyle factors such as smoking, and genetics. The clearest indicator of progression to AMD is the appearance of drusen, yellow-white deposits under the retina, and it is an important component of both forms of AMD: exudative ("wet") and non-exudative ("dry"). Wet AMD causes vision loss due to abnormal blood vessel growth in the choriocapillaris through Bruch's membrane. The most advanced form of dry AMD, known as geographic atrophy, is generally more gradual and occurs when light-sensitive cells in the macula atrophy, blurring and eliminating vision in the affected eye. While there are currently some promising treatments for wet AMD, no FDA-approved treatment exists for dry AMD or geographic atrophy.

A second example is childhood-onset Stargardt Disease ("STGD"), also known as Stargardt 1, a genetic, rare juvenile macular dystrophy generally associated with loss of central vision in the first two decades of life. STGD has a prevalence of approximately 1/20,000 affecting approximately 30,000 people in the US. STGD affects many ages, with the childhood-onset population at highest risk and most need. Patients with childhood-onset STGD tend to develop early severe visual acuity loss, significantly compromised retinal function, and rapid retinal pigment epithelial (RPE) cell atrophy with accompanying loss of retinal function. The median ages of onset and the median age at baseline examination are 8.5 (range, 3-16) and 12 years (range, 7-16), respectively. Patients with adult-onset disease are more likely to preserve visual acuity for a longer time and show slighter retinal dysfunction. STGD is an autosomal recessive genetic disease or complex heterozygous disease, caused by mutations in the ABCA4 gene. The ABCA4 gene encodes the photoreceptor protein ABCA4 Transporter, which is responsible for removal of bisretinoid fluorophores, which can include N-retinylidene-N-retinyethanolamine (A2E), all-trans-retinal and related photo-oxidation products of vitamin A aldehyde which together constitute lipofuscin from photoreceptor cells. Accumulation of all-trans-retinal in photoreceptor cells is believed to damage RPE cells via oxidative stress, and trigger or promote complement-mediated damage to RPE cells, leading to retinal atrophy. A related disease termed Stargardt-like macular dystrophy, also known as STGD3, is inherited in a dominant autosomal manner and is due to mutations in the ELOVL4 gene. ELOVL4 encodes the ELOVL4 protein, ELOVL fatty acid elongase 4. Mutations in ELOVL4 protein associated with STGD lead to mis-folding and accumulation of ELOVL4 protein aggregates in retinal cells, which impact retinal cell function, eventually leading to cell death and retinal atrophy. No treatments exist for STGD or Stargardt-like disease.

SUMMARY OF THE INVENTION

In one aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the third loop comprises 6 or more nucleotides, non-nucleotidyl spacers, or a combination thereof, and wherein the first loop has fewer nucleotides than the second loop.

In another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the third loop comprises 6 or more nucleotides, non-nucleotidyl spacers, or a combination thereof, and wherein the second loop comprises more than 5 nucleotides, non-nucleotidyl spacers, or a combination thereof.

In another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the third loop comprises 6 or more nucleotides, non-nucleotidyl spacers, or a combination thereof, and wherein the third loop is adjacent to the first stem.

In yet another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the third loop comprises 6 or more nucleotides, non-nucleotidyl spacers, or a combination thereof, and wherein the first base-paired stem has no more than 5 base pairs.

In some cases, the third loop is connected to the first base-paired stem. In some cases, the first loop has from 1 to 10 nucleotides, non-nucleotidyl spacers, or a combination thereof. In some cases, the first loop has from 3 to 5 nucleotides, non-nucleotidyl spacers, or a combination thereof. In some cases, first loop comprises a nucleic acid sequence of 5'-DUG-3', where D is A, G, or U. In some cases, the second loop comprises at least 6 nucleotides, non-nucleotidyl spacers, or a combination thereof. In some cases, the second loop comprises at least 7 nucleotides, non-nucleotidyl spacers, or a combination thereof. In some cases, the second loop comprises 10 or 11 nucleotides, non-nucleotidyl spacers, or a combination thereof. In some cases, the second loop comprises a nucleic acid sequence of 5'-DWWVGCBHWG-3' (SEQ ID NO:319), where D is A, G, or U; W is A or U; V is A, C, or G; B is C, G, or U; and H is A, C, or U. In some cases, the second loop comprises a nucleic acid sequence having a U at nucleotide position 2, nucleotide position 3, or both. In some cases, the third loop has from 6 to 8 nucleotides, non-nucleotidyl spacers, or a combination thereof. In some cases, the third loop comprises a nucleic acid sequence comprising 5'-AAGUKN-3', where K is G or U; and N is A, G, C, or U. In some cases, the first base-paired stem has from 2 to 10 base pairs. In some cases, the first base-paired stem has from 3 to 8 base pairs. In some cases, the second base-paired stem has from 2 to 10 base pairs. In some cases, the second base-paired stem comprises 4 or 5 base pairs. In some cases, the second base-paired stem comprises a terminal U-G base pair adjacent to the second loop. In some cases, the second base-paired stem comprises a terminal C-G base pair adjacent to the second loop. In some cases, the nucleic acid sequence comprises nucleotides having ribose in a β-D-ribofuranose configuration. In some cases, at least 50% of the nucleic acid sequence comprises nucleotides having ribose in a β-D-ribofuranose configuration. In some cases, the third loop comprises at least 4 nucleotides and up to 2 non-nucleotidyl spacers. In some cases, the third loop comprises at least 6 nucleotides. In some cases, the non-nucleotidyl spacers comprise 3 carbons, 6 carbons, or 9 carbons. In some cases, the non-nucleotidyl spacers comprise an 18-atom spacer. In one example, the 18-atom spacer comprises hexaethylene glycol. In some cases, a) the first base-paired stem is adjacent to said first loop; b) the second base-paired stem is adjacent to the first loop, the second loop, and the third loop; or c) the first base-paired stem is adjacent to the first loop and the second base-paired stem is adjacent to the first loop, the second loop, and the third loop.

In another aspect, an aptamer is provided comprising a nucleic acid sequence that selectively binds to complement factor D (fD) and having a stem-loop secondary structure comprising a base-paired terminal stem; an asymmetric internal loop; an internal base-paired stem; and exactly one terminal loop, wherein the terminal loop comprises more than 4 nucleotides, non-nucleotidyl spacers, or a combination thereof, and wherein the asymmetric internal loop is adjacent to exactly 2 base-paired stems.

In another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the second loop comprises 7 or more nucleotides, non-nucleotidyl spacers, or a combination thereof, wherein the first base-paired stem has no more than 5 base pairs, and wherein the second base-paired stem comprises more than 2 base pairs.

In another aspect, an aptamer is provided comprising a nucleic acid sequence that selectively binds to complement factor D (fD) and having a stem-loop secondary structure comprising exactly one terminal base-paired stem; exactly one asymmetric internal loop comprising, from a 5' to 3' direction, a first loop and a second loop; exactly one internal base-paired stem; and exactly one terminal loop, wherein the first loop of the asymmetric internal loop has fewer nucleotides than the terminal loop.

In another aspect, an aptamer is provided comprising a nucleic acid sequence that selectively binds to complement factor D (fD) and having a stem-loop secondary structure comprising exactly one terminal base-paired stem; exactly one asymmetric internal loop; exactly one internal base-paired stem; and exactly one terminal loop, wherein the exactly one terminal loop comprises more than 4 nucleotides, non-nucleotidyl spacers, or a combination thereof. In some cases, the exactly one terminal loop comprises 10 or more nucleotides, non-nucleotidyl spacers, or a combination thereof.

In another aspect, an aptamer is provided comprising a nucleic acid sequence that selectively binds to complement factor D (fD) and having a stem-loop secondary structure comprising exactly one terminal base-paired stem; exactly one asymmetric internal loop comprising, from a 5' to 3' direction, a first loop and a second loop; exactly one internal base-paired stem; and exactly one terminal loop, wherein the second loop comprises 6 or more nucleotides, non-nucleotidyl spacers, or a combination thereof.

In another aspect, an aptamer is provided comprising a nucleic acid sequence that selectively binds to complement factor D (fD) and having a stem-loop secondary structure comprising exactly one terminal base-paired stem; exactly one asymmetric internal loop; exactly one internal base-paired stem; and exactly one terminal loop, wherein the exactly one terminal loop comprises 7 or more nucleotides, non-nucleotidyl spacers, or a combination thereof.

In some cases, the exactly one terminal base-paired stem comprises a tail at a 5' end, at a 3' end, or at both a 5' end and a 3' end, and the tail comprises at least one unpaired nucleotide.

In another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the second base-paired stem comprises a terminal U-G base pair adjacent to the second loop.

In yet another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the first loop comprises a nucleic acid sequence of 5'-DUG-3', where D is A, G, or U.

In yet another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the third loop comprises a nucleic acid sequence comprising 5'-AAGUKN-3', where K is G or U; and N is A, G, C, or U.

In yet another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the second loop comprises a nucleic acid sequence of 5'-DWWVGCBHWG-3' (SEQ ID NO:319), where D is A, G, or U; W is A or U; V is A, C, or G; B is C, G, or U; and H is A, C, or U.

In yet another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the second loop comprises a nucleic acid sequence having a U at nucleotide position 2, nucleotide position 3, or both.

In yet another aspect, an aptamer is provided comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein the second base-paired stem comprises a terminal C-G base pair adjacent to the second loop.

In some cases, any aptamer of the preceding is an RNA aptamer or a modified RNA aptamer. In other cases, any aptamer of the preceding is a DNA aptamer or a modified DNA aptamer. In some cases, any aptamer of the preceding comprises one or more modified nucleotides. In some instances, at least 50% of the nucleic acid sequence comprises the one or more modified nucleotides. In some instances, the one or more modified nucleotides comprises a 2'F-modified nucleotide, a 2'OMe-modified nucleotide, or a combination thereof. In some instances, the one or more modified nucleotides are selected from the group consisting of: 2'F-G, 2'OMe-G, 2'OMe-U, 2'OMe-A, 2'OMe-C, a 3' terminal inverted deoxythymidine, and any combination thereof. In some cases, an aptamer of any of the preceding comprises a nuclease-stabilized nucleic acid backbone. In some cases, the stem-loop structure of any aptamer of the preceding has exactly two base-paired stems. In some cases, any aptamer of the preceding is an RNA aptamer comprising nucleotides having ribose in a β-D-ribofuranose configuration. In some cases, any aptamer of the preceding selectively binds to an active site of fD. In some cases, any aptamer of the preceding selectively binds to a substrate-binding exosite of fD. In some cases, any aptamer of the preceding selectively binds to both an active site of fD and a substrate-binding exosite of fD. In some cases, any aptamer of the preceding blocks an active site of fD. In some cases, any aptamer of the preceding blocks a substrate-binding exosite of fD. In some cases, any aptamer of the preceding blocks both an active site and a substrate-binding exosite of fD. In some cases, any aptamer of the preceding inhibits a function associated with fD. In some cases, any aptamer of the preceding prevents association of fD with pre-formed C3bB complex. In some cases, any aptamer of the preceding has no more than one nucleic acid strand. In other cases, any aptamer of the preceding comprises more than one nucleic acid strand. In some cases, the nucleic acid sequence of any aptamer of the preceding has from 30-90 nucleotides, non-nucleotidyl spacers, or a combination thereof. In some cases, any aptamer of the preceding selectively binds to an active site of fD with a $K_d$ of less than about 50 nM. In some cases, any aptamer of the preceding inhibits fD in an alternative complement dependent hemolysis assay with an $IC_{50}$ of less than about 50 nM. In some cases, any aptamer of the preceding inhibits fD in a fD convertase assay with an $IC_{50}$ of less than about 50 nM. In some cases, any aptamer of the preceding inhibits at least 85% of fD activity in an alternative complement dependent hemolysis assay. In some cases, any aptamer of the preceding inhibits at least 85% of fD activity in a fD convertase assay. In some cases, any aptamer of the preceding inhibits fD activity in an esterase activity assay. In some cases, any aptamer of the preceding binds to fD with a $K_d$ of less than about 50 nM and inhibits fD in an alternative complement dependent hemolysis assay with an $IC_{90}$ of less than about 500 nM. In some cases, any aptamer of the preceding binds to fD with a $K_d$ of less than about 50 nM and inhibits fD in an alternative complement dependent hemolysis assay with an $IC_{50}$ of less than about 100 nM. In some cases, any aptamer of the preceding is conjugated to a polyethylene glycol (PEG) molecule. In some cases, the PEG molecule has a molecular weight of 80 kDa or less. In some cases, any aptamer of the preceding does not contain a pseudoknot structure. In some cases, any aptamer of the preceding has less than 3 unpaired nucleotide residues at a 5' terminus, a 3' terminus, or both.

In another aspect, an aptamer is provided comprising a nucleic acid sequence comprising any one of SEQ ID NOs:13, 165, 166, 244, 253, 256, 262, 269, 284, 285, 294, 303, 306, and 312, or comprising at least 80% sequence identity to any one of SEQ ID NOs:13, 165, 166, 244, 253, 256, 262, 269, 284, 285, 294, 303, 306, and 312. In some cases, the nucleic acid sequence comprises one or more modified nucleotides. In some instances, at least 50% of said nucleic acid sequence comprises the one or more modified nucleotides. In some cases, the one or more modified nucleotides comprises a 2'F-modified nucleotide, a 2'OMe-modified nucleotide, or a combination thereof. In some cases, the one or more modified nucleotides are selected from the group consisting of: 2'F-G, 2'OMe-G, 2'OMe-U, 2'OMe-A, 2'OMe-C, a 3' terminal inverted deoxythymidine, and any combination thereof. In some cases, the aptamer is selected from the group consisting of: Aptamer 76 as described in Table 2, Aptamer 116 as described in Table 2, Aptamer 102 as described in Table 2, Aptamer 104 as described in Table 2, Aptamer 106 as described in Table 2, Aptamer 108 as described in Table 2, Aptamer 107 as described in Table 2, Aptamer 109 as described in Table 2, and Aptamer 99 as described in Table 2. In some cases, the aptamer is conjugated to a polyethylene glycol (PEG) molecule. In some cases, the PEG molecule has a molecular weight of 80 kDa or less. In some cases, the PEG molecule is conjugated to the aptamer using a pegylation reagent, wherein the pegylation reagent comprises 2,3-Bis(methyl-polyoxyethylene-oxy)-1-{3-[(1,5-dioxo-5-succinimidyloxy, pentyl)amino]propyloxy} propane.

In another aspect, an aptamer is provided comprising a nucleic acid sequence that selectively blocks the active site of complement factor D (fD) and having a stem-loop secondary structure comprising at least one stem and at least one loop.

In another aspect, an aptamer is provided comprising a nucleic acid sequence that selectively binds to complement factor D (fD) and having a stem-loop secondary structure comprising at least one stem and at least one loop, wherein the aptamer comprises at least one modified nucleotide. In some cases, the aptamer comprises a nuclease-stabilized nucleic acid backbone.

In another aspect, an aptamer is provided comprising a nucleic acid sequence that selectively binds to complement factor D (fD) and having a stem-loop secondary structure comprising at least one stem and at least one loop, wherein the nucleic acid sequence does not include any one of SEQ ID NOs:228-235.

In yet another aspect, an aptamer is provided comprising a nucleic acid sequence that selectively blocks an active site of complement factor D (fD) and having a secondary structure having exactly three loops. In some cases, the secondary structure further has exactly two base-paired stems.

In some cases, an aptamer of any of the preceding has a nucleic acid sequence that does not include any one of SEQ ID NOs:1-3, 168-227.

In yet another aspect, an aptamer is provided comprising a nucleic acid sequence that selectively binds to complement factor D and having a stem-loop secondary structure comprising at least one stem and at least one loop, wherein said aptamer is an RNA aptamer or a modified RNA aptamer.

In some cases, an aptamer of any of the preceding further comprises up to two stems. In some cases, an aptamer of any of the preceding further comprises up to three loops. In some cases, an aptamer of any of the preceding is an RNA aptamer or a modified RNA aptamer. In some cases, an aptamer of any of the preceding is a DNA aptamer or a modified DNA aptamer. In some cases, an aptamer of any of the preceding selectively binds to an active site of fD. In some cases, an aptamer of the preceding has at least one loop, wherein each of the at least one loop has up to 25 nucleotides. In some cases, an aptamer of any of the preceding has no more than one nucleic acid strand. In some cases, an aptamer of any of the preceding has at least one stem, wherein no more than one of the at least one stem has more than 20 base pairs. In some cases, an aptamer of any of the preceding has a nucleic acid sequence comprising from 30-90 nucleotides.

In some cases, an aptamer of any of the preceding has a stem-loop secondary structure comprising, in a 5' to 3' direction, a first stem, a first loop, a second stem, a second loop, and a third loop. In some cases, the first loop comprises fewer nucleotides than the second loop. In some cases, the third loop is connected to the first stem. In some cases, the first loop has from 1 to 10 nucleotides. In some cases, the first loop has from 3 to 5 nucleotides. In some cases, the first loop comprises a nucleic acid sequence of 5'-DUG-3', where D is A, G, or U. In some cases, the second loop has from 2 to 15 nucleotides. In some cases, the second loop has at least 8 nucleotides. In some cases, the second loop has exactly 10 nucleotides. In some cases, the second loop has 10 or 11 nucleotides. In some cases, the second loop comprises a nucleic acid sequence of 5'-DWWVGCBHWG-3' (SEQ ID NO:319), where D is A, G, or U; W is A or U; V is A, C, or G; B is C, G, or U; and H is A, C, or U. In some cases, the second loop comprises a nucleic acid sequence having a U at nucleotide position 2, position 3, or both. In some cases, the third loop has from 2 to 10 nucleotides. In some cases, the third loop has at least 6 nucleotides. In some cases, the third loop has exactly 6 nucleotides. In some cases, the third loop has from 6 to 8 nucleotides. In some cases, the third loop has a nucleic acid sequence comprising 5'-AAGUKN-3', where K is G or U; and N is A, G, C, or U. In some cases, the first stem has from 2 to 10 base pairs. In some cases, the first stem has from 3 to 8 base pairs. In some cases, the second stem has from 2 to 10 base pairs. In some cases, the second stem has 4 or 5 base pairs. In some cases, the second stem comprises a terminal U-G base pair adjacent to the second loop. In some cases, the second stem comprises a terminal C-G base pair adjacent to the second loop.

In some cases, an aptamer of any of the preceding selectively binds to an active site of fD with a $K_d$ of less than about 50 nM. In some cases, an aptamer of any of the preceding inhibits fD in an alternative complement dependent hemolysis assay with an $IC_{50}$ of less than about 50 nM. In some cases, an aptamer of any of the preceding inhibits fD in a fD convertase assay with an $IC_{50}$ of less than about 50 nM. In some cases, an aptamer of any of the preceding inhibits at least 85% of fD activity in an alternative complement dependent hemolysis assay. In some cases, an aptamer of any of the preceding inhibits at least 85% of fD activity in a fD convertase assay. In some cases, an aptamer of any of the preceding inhibits fD activity in an esterase activity assay. In some cases, an aptamer of any of the preceding binds to fD with a IQ of less than about 50 nM and inhibits fD in an alternative complement dependent hemolysis assay with an $IC_{90}$ of less than about 500 nM. In some cases, an aptamer of any of the preceding binds to fD with a $K_d$ of less than about 50 nM and inhibits fD in an alternative complement dependent hemolysis assay with an $IC_{50}$ of less than about 100 nM. In some cases, an aptamer of any of the preceding has a nucleic acid sequence comprising at least one modified nucleotide. In some cases, an aptamer of any of the preceding is conjugated to a polyethylene glycol (PEG) molecule. In some cases, the PEG molecule has a molecular weight of 80 kDa or less.

In another aspect, an aptamer is provided having a nucleic acid sequence comprising any one of SEQ ID NOs:1-3, 10-167, 267-286, 317, and 318, or any nucleic acid sequence described in Table 2 or having at least 80% sequence identity to any one of SEQ ID NOs:1-3, 10-167, 267-286, 317, and 318, or any nucleic acid sequence described in Table 2.

In yet another aspect, an aptamer is provided comprising a nucleic acid sequence that selectively binds to complement factor D (fD) and having a stem-loop secondary structure comprising a terminal stem, an asymmetric internal loop, an internal stem, and a terminal loop.

In some cases, an aptamer of any of the preceding does not contain a pseudoknot structure. In some cases, an aptamer of any of the preceding has less than 3 unpaired nucleotide residues at a 5' terminus, a 3' terminus, or both.

In another aspect, an aptamer according to any of the preceding is provided for use in a method of therapy; for use in a method of treatment that benefits from modulating fD; for use in a method of treatment that benefits from inhibiting a function associated with fD; or for use in a method for the treatment of ocular diseases.

In another aspect, an aptamer according to any of the preceding is provided and a pharmaceutically acceptable carrier, excipient, or diluent. In some cases, a pharmaceutical composition or medicament is provided comprising a plurality of aptamers according to any of the preceding. In some cases, greater than 90% of the plurality of aptamers comprise nucleotides having ribose in a β-D-ribofuranose configuration.

In yet another aspect, a method is provided for modulating complement factor D (fD) in a biological system, the method comprising: administering to the biological system, an aptamer according to any one of the preceding, thereby modulating fD in the biological system. In some cases, the modulating comprises inhibiting a function associated with fD. In some cases, the modulating comprises preventing association of fD with pre-formed C3bB complex. In some cases, the biological system is a subject. In some cases, the subject is a human.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 further depicts a non-limiting illustration of numbering of stem and loop sequences according to an embodiment of the disclosure.

FIG. 6 depicts the amino acid sequence of human complement Factor D, chymotrypsin numbering scheme, and fD numbering scheme.

FIG. 7A, FIG. 7B, and FIG. 7C depict a non-limiting example of an aptamer library sequence that may be utilized to generate anti-Factor D aptamers according to an embodiment of the disclosure (SEQ ID NOs: 322, 323, and 6, in order of appearance).

FIG. 20A, FIG. 20B, FIG. 20C, and FIG. 20D depict non-limiting examples of secondary structures of several active-site directed inhibitors of fD according to an embodiment of the disclosure (SEQ ID NOs: 162, and 165-167, in order of appearance).

DETAILED DESCRIPTION OF THE INVENTION

Figure 1:
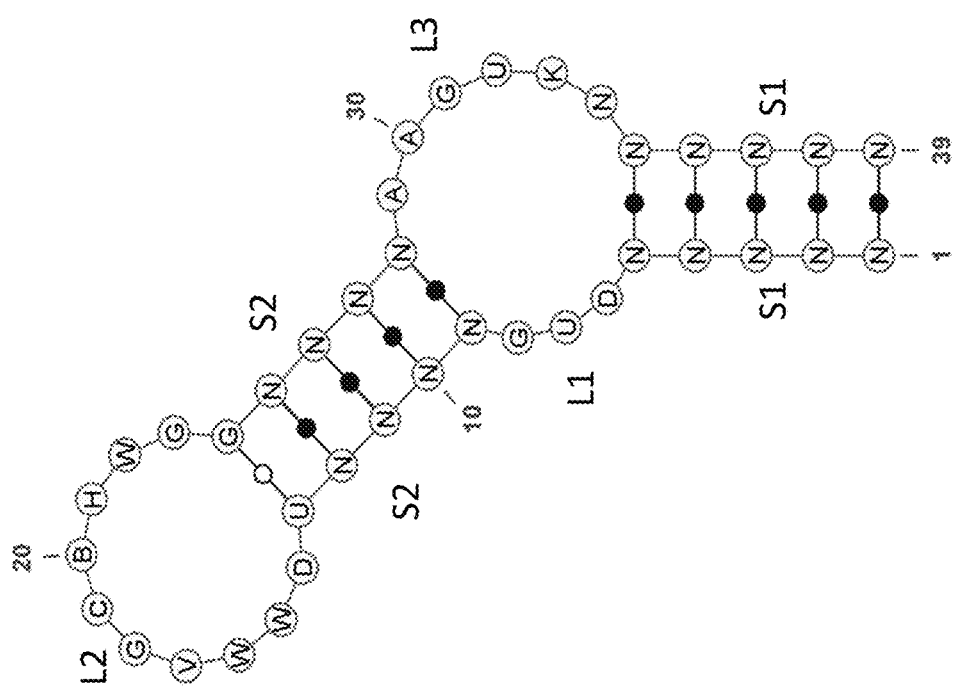
FIG. 1 depicts a non-limiting example of a consensus secondary structure of a family of stem-loop anti-fD aptamers according to an embodiment of the disclosure (SEQ ID NO:320).

The disclosure herein provides aptamer compositions that selectively bind to and inhibit a function associated with complement factor D (fD) and methods of using such aptamer compositions. Specifically, the aptamer compositions described herein have unique stem-loop secondary structures. In some cases, the aptamers of the disclosure have, in a 5' to 3' direction, a first base paired stem, a first loop, a second base paired stem, a second loop, and a third loop. The aptamers may also include one or more further elements (e.g., additional stem(s) or loop(s)). In some cases, such further elements are located before the first base paired stem and/or after the third loop. In some cases, such further elements are located interspersed between other elements of the aptamer (e.g., between the first loop and the second base paired stem, etc.). In other embodiments, each element is adjacent to each other. For example, the aptamers may have, in a 5' to 3' direction, a first base paired stem adjacent to a first loop, which is adjacent to a second base paired stem, which is adjacent to a second loop. A third loop may be present, and may, in some cases be adjacent to the first and/or second base paired stems. In some cases, the aptamers of the disclosure have a terminal base paired stem, an asymmetric internal loop, an internal base paired stem, and/or a terminal loop. Non-limiting examples of stem-loop aptamers that may be used to inhibit fD are described throughout.

The disclosure herein provides methods and compositions for the treatment of ocular diseases or disorders. In some cases, the methods and compositions include the use of an anti-fD stem-loop aptamer for, e.g., the treatment of ocular diseases or disorders. In some cases, the ocular disease is macular degeneration. In some cases, macular degeneration is age-related macular degeneration. In some cases, age-related macular degeneration is dry age-related macular degeneration. In some cases, dry age-related macular degeneration is advanced dry age-related macular degeneration (i.e., geographic atrophy). In some cases, the ocular disease is wet age-related macular degeneration. In some cases, the ocular disease is Stargardt disease. In some cases, the methods and compositions involve the inhibition of the alternative complement pathway. In some cases, the methods and compositions involve the inhibition of a function associated with Factor D (fD). In some cases, the methods and compositions involve the inhibition of a function associated with fD for the treatment of ocular diseases. In some cases, the methods and compositions involve the inhibition of a function associated with fD for the treatment of dry age-related macular degeneration or geographic atrophy. In some cases, the methods and compositions involve the inhibition of a function associated with fD for the treatment of wet age-related macular degeneration. In some cases, the methods and compositions involve the inhibition of a function associated with fD for the treatment of Stargardt disease.

In various aspects, the compositions may include oligonucleotides (e.g., aptamers) that selectively bind to and modulate an activity associated with fD. In some instances, the oligonucleotide compositions of the disclosure inhibit a function associated with fD. In some cases, the oligonucleotide compositions may bind directly to an active site of fD or to a region of fD that includes the active site, or the oligonucleotide compositions may bind to a region of fD such that the oligonucleotide occludes or blocks access to the active site. In some cases, the oligonucleotide compositions may bind directly to an exosite of fD or to a region of fD that includes the exosite, or the oligonucleotide compositions may bind to a region of fD such that the oligonucleotide occludes or blocks access of a substrate to the exosite. In some cases, the oligonucleotide compositions may bind to and/or block access to both the active site and the exosite of fD. In some cases, the oligonucleotide compositions may bind to the active site of fD and block access to the exosite of fD. In some cases, the oligonucleotide compositions may block access to the active site of fD and bind to the exosite of fD. In some cases, the oligonucleotides are aptamers, such as RNA aptamers, DNA aptamers, modified RNA aptamers, or modified DNA aptamers. In particular examples, the aptamers of the disclosure may have secondary structures. The secondary structures may include a stem-loop structure which may include one or more loops and one or more stems. Various examples of aptamers having stem-loop structures for modulating fD are described herein.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 80% to 100% and integer values therebetween. Typically, the percent identities between a disclosed sequence and a claimed sequence are at least 80%, at least 85%, at least 90%, at least 95%, or at least 98%.

The term "aptamer" as used herein refers to an oligonucleotide and/or nucleic acid analogues that can bind to a specific target molecule. Aptamers can include RNA, DNA, modified RNA, modified DNA, any nucleic acid analogue, and/or combinations thereof. Aptamers can be single-stranded oligonucleotides. In some cases, aptamers may comprise more than one nucleic acid strand (e.g., two or more nucleic acid strands). Without wishing to be bound by theory, aptamers are thought to bind to a three-dimensional structure of a target molecule. Aptamers may be monomeric (composed of a single unit) or multimeric (composed of multiple units). Multimeric aptamers can be homomeric (composed of multiple identical units) or heteromeric (composed of multiple non-identical units). Aptamers herein may be described by their primary structures, meaning the linear nucleotide sequence of the aptamer. Aptamer sequences herein are generally described from the 5' end to the 3' end, unless otherwise stated. Additionally or alternatively, aptamers herein may be described by their secondary structures which may refer to the combination of single-stranded regions and base-pairing interactions within the aptamer.

An aptamer may have a secondary structure having at least two complementary regions of the same nucleic acid strand that base-pair to form a double helix (referred to herein as a "stem"). Generally, these complementary regions are complementary when read in the opposite direction. The term "stem" as used herein may refer to either of the complementary nucleotide regions individually or may encompass a base-paired region containing both complementary regions, or a portion thereof. For example, the term "stem" may refer to the 5' side of the stem, that is, the stem sequence that is closer to the 5' end of the aptamer; additionally or alternatively, the term "stem" may refer to the 3' side of the stem, that is, the stem sequence that is closer to the 3' end of the aptamer. In some cases, the term "stem" may refer to the 5' side of the stem and the 3' side of the stem, collectively. The term "base-paired stem" is generally used herein to refer to both complementary stem regions collectively. A base-paired stem may be perfectly complementary meaning that 100% of its base pairs are Watson-Crick base pairs. A base-paired stem may also be "partially complementary." As used herein, the term "partially complementary stem" refers to a base-paired stem that is not entirely made up of Watson-Crick base pairs but does contain base pairs (either Watson-Crick base pairs or G-U/U-G wobble base pairs) at each terminus. In some cases, a partially complementary stem contains both Watson-Crick base-pairs and G-U/U-G wobble base pairs. In other cases, a partially complementary stem is exclusively made up of G-U/U-G wobble base pairs. A partially complementary stem may contain mis-matched base pairs and/or unpaired bases in the region between the base pairs at each terminus of the stem; but in such cases, the mis-matched base pairs and/or unpaired bases make up at most 50% of the positions between the base pairs at each terminus of the stem.

A stem as described herein may be referred to by the position, in a 5' to 3' direction on the aptamer, of the 5' side of the stem (i.e., the stem sequence closer to the 5' terminus of the aptamer), relative to the 5' side of additional stems present on the aptamer. For example, as depicted in FIG. 1, stem 1 (S1) may refer to the stem sequence that is closest to the 5' terminus of the aptamer, its complementary stem sequence, or both stem sequences collectively. Similarly, stem 2 (S2) may refer to the next stem sequence that is positioned 3' relative to S1, its complementary stem sequence, or both stem sequences collectively. In some cases, the aptamers of the disclosure have exactly two stems (e.g., S1 and S2). In other cases, the aptamers of the disclosure may have more than two stems (e.g., S1, S2, S3, etc.). Each additional stem may be referred to by its position, in a 5' to 3' direction, on the aptamer, as described above. For example, S3 may be positioned 3' relative to S2 on the aptamer, S4 may be positioned 3' relative to S3 on the aptamer, and so on. In some cases, the term "first stem" is used to refer to a stem in the aptamer, irrespective of its location. For example, a first stem may be S1, S2, S3, S4 or any other stem in the aptamer.

A stem may be adjacent to an unpaired region. An unpaired region may be present at a terminus of the aptamer or at an internal region of the aptamer.

Figure 2:
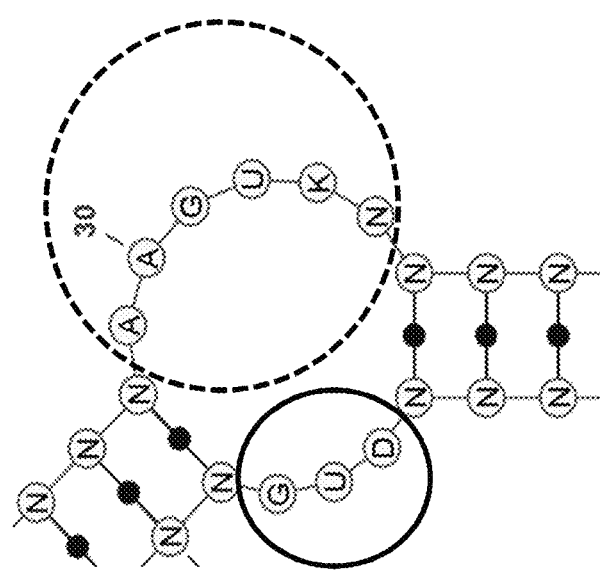
FIG. 2 depicts a non-limiting example of an asymmetric loop according to an embodiment of the disclosure (SEQ ID NO:321).

As used herein, the term "loop" generally refers to an internal unpaired region of an aptamer. The term "loop" generally refers to any unpaired region of an aptamer that is flanked on both the 5' end and the 3' end by a stem region. In some cases, a loop sequence may be adjacent to a single base-paired stem, such that the loop and stem structure together resemble a hairpin. In such cases, generally the primary sequence of the aptamer contains a first stem sequence adjacent to the 5' end of the loop sequence and a second stem sequence adjacent to the 3' end of the loop sequence; and the first and second stem sequences are complementary to each other. In some cases, each terminus of a loop is adjacent to first and second stem sequences that are not complementary. In such cases, the primary sequence of the aptamer may contain an additional loop sequence that is bordered at one or both ends by stem sequences that are complementary to the first and/or second stem sequences. In cases where the two loops have different number of nucleotides, the two loops are referred to jointly herein as an "asymmetric loop" or "asymmetric loop pair," terms that are used herein interchangeably. In cases where the two loops have the same number of nucleotides, they are referred to jointly as a "symmetric loop" or "symmetric loop pair," terms that are used interchangeably herein. FIG. 2 depicts an example of an "asymmetric loop", composed of two loops that each contain different numbers of nucleotides and that border the same two stems. In this example, the first loop sequence has 3 nucleotides, and the second loop sequence has 6 nucleotides. An "asymmetric loop" is bordered by exactly two base-paired stems, as depicted in the example shown in FIG. 2. Similarly, a "symmetric loop" is bordered by exactly two base-paired stems.

A loop as described herein may be referred to by its position, in a 5' to 3' direction, on the aptamer. For example, as depicted in FIG. 1, loop 1 (L1) may refer to a loop sequence that is positioned most 5' on the aptamer. Similarly, loop 2 (L2) may refer to a loop sequence that is positioned 3' relative to L1, and loop 3 (L3) may refer to a loop sequence that is positioned 3' relative to L2. In some cases, the aptamers of the disclosure have exactly three loops (e.g., L1, L2, and L3). In other cases, the aptamers of the disclosure may have more than three loops (e.g., L1, L2, L3, L4, etc.). Each additional loop may be referred to by its position, in a 5' to 3' direction, on the aptamer, as described above. For example, L4 may be positioned 3' relative to L3 on the aptamer, L5 may be positioned 3' relative to L4 on the aptamer, and so on. In some cases, the term "first loop" is used to refer to a loop in the aptamer, irrespective of its location. For example, a first loop may be L1, L2, L3, L4 or any other loop in the aptamer.

The term "stem-loop" as used herein generally refers to the secondary structure of an aptamer of the disclosure having at least one stem and at least one loop. In some cases, a stem-loop secondary structure may include a terminal stem and a terminal loop. In some cases, a stem-loop secondary structure includes structures having two stems, which may include a terminal stem, an internal loop, an internal stem, and a terminal loop. A "terminal stem" as used herein generally refers to a stem that encompasses both the 5' and/or 3' terminus of the aptamer. In some cases, a "terminal stem" is bordered at one or both termini by a "tail" comprising one or more unpaired nucleotides. For example, a terminal stem present in the aptamer may be bordered by a tail of one or more unpaired nucleotides (or other structures) at its 5' end. Similarly, a terminal stem present in the aptamer may be bordered by a tail of one or more unpaired nucleotides (or other structures) at its 3' end. In some cases, a terminal stem present in the aptamer may be bordered by a tail of one or more unpaired nucleotides (or other structures) at both its 5' end and its 3' end. A terminal stem is generally adjacent to a loop; for example, the 5' side of a terminal stem (i.e., the terminal stem sequence closest to the 5' end of the molecule) may be bordered at its 3' terminus by the 5' terminus of a loop. Similarly, the 3' side of a terminal stem (i.e., the terminal stem sequence closest to the 3' end of the molecule) may be bordered at its 5' terminus by the 3' terminus of a loop. An "internal stem" as used herein generally refers to a stem that is bordered at both termini by a loop sequence. A "terminal loop" as used herein generally refers to a loop that is bordered by the same stem at both termini of the loop. For example, a terminal loop may be bordered at its 5' end by a stem sequence, and may be bordered at its 3' end by the complementary stem sequence. An "internal loop" as used herein generally refers to a loop that is bordered at both termini by different stems. For example, an internal loop may be bordered at its 5' end by a first stem sequence, and may be bordered at its 3' end by a second stem sequence that is not complementary to the first stem sequence. In some cases, a stem-loop secondary structure includes structures having more than two stems. Unless otherwise stated, when an aptamer includes more than one stem and/or more than one loop, the stems and loops are numbered consecutively in ascending order from the 5' end to the 3' end of the primary nucleotide sequence.

In some cases, an aptamer of the disclosure may have a terminal stem, an asymmetric internal loop, an internal stem, and a terminal loop, such as depicted in FIG. 1. In some cases, an aptamer of the disclosure may have exactly one terminal stem, exactly one asymmetric internal loop, exactly one internal stem, and exactly one terminal loop. In some cases, an aptamer of the disclosure may have, in a 5' to 3' direction, a first stem, a first loop, a second stem, a second loop, and a third loop. In some cases, an aptamer of the disclosure may have the general structure, in a 5' to 3' direction, S1-L1-S2-L2-S2-L3-S1 (FIG. 1).

The term "exosite" as used herein generally refers to a protein domain or region of a protein that is capable of binding to another protein. The exosite may also be referred to herein as a "secondary binding site", for example, a binding site that is remote from or separate from a primary binding site (e.g., an active site). In some cases, the primary and secondary binding sites may overlap. Binding of a molecule to an exosite may cause a physical change in the protein (e.g., a conformational change). In some cases, the activity of a protein may be dependent on occupation of the exosite. In some examples, the exosite may be distinct from an allosteric site. In some cases, the oligonucleotide compositions of the disclosure may bind to the exosite of fD or to part of the exosite of fD, or may bind to a region of fD that includes the exosite. In some cases, the oligonucleotide compositions of the disclosure may block or occlude the exosite such that the natural substrate of fD is prevented from accessing the exosite. In such cases, the oligonucleotide may block access to the exosite without directly binding the exosite (e.g., may bind to a region of fD other than the exosite in such a way that the exosite is sterically occluded).

The term "catalytic cleft" or "active site" as used herein refers to a domain of an enzyme in which a substrate molecule binds to and undergoes a chemical reaction. The active site may include amino acid residues that form temporary bonds with the substrate (e.g., a binding site) and amino acid residues that catalyze a reaction of that substrate (e.g., catalytic site). The active site may be a groove or pocket (e.g., a cleft) of the enzyme which can be located in a deep tunnel within the enzyme or between the interfaces of multimeric enzymes. In some cases, the oligonucleotide compositions of the disclosure may bind to the active site of fD or to part of the active site of fD, or may bind to a region of fD that includes the active site. In some cases, the oligonucleotide compositions of the disclosure may block or occlude the active site of fD such that the natural substrate of fD is prevented from accessing the active site. In such cases, the oligonucleotide may block access to the active site, without directly binding the active site (e.g., may bind to a region of fD other than the active site in such a way that the active site is sterically occluded). In some cases, the oligonucleotide compositions of the disclosure may include oligonucleotides that block or occlude the active site of fD, without directly binding the constituent amino acids comprising the active site of fD, such that the natural substrate of fD is prevented from accessing the active site.

In some cases, oligonucleotide compositions (e.g., aptamers) of the disclosure may block or occlude both the active site and the exosite. For example, oligonucleotide compositions (e.g., aptamers) of the disclosure may both block access to the active site and may block access to the substrate-binding exosite. In some cases, oligonucleotide compositions of the disclosure may bind to and/or block access to the active site of fD and prevent association of fD with pre-formed C3bB complex. In some cases, oligonucleotide compositions of the disclosure may bind to and/or block access to both the active site and the substrate-binding exosite of fD, and may prevent association of fD with pre-formed C3bB complex.

The term "epitope" as used herein refers to the part of an antigen (e.g., a substance that stimulates an immune system to generate an antibody against) that is specifically recognized by the antibody. In some cases, the antigen is a protein or peptide and the epitope is a specific region of the protein or peptide that is recognized and bound by an antibody. In some cases, the aptamers described herein bind to a region of fD that is an epitope for an anti-fD antibody or antibody fragment thereof, wherein the anti-fD antibody inhibits a function associated with fD. In some cases, the aptamer binding region of fD overlaps with at least 50%, at least 60%, at least 70%, at least 80%, at least 90%, at least 95%, or 100% of the epitope for an anti-fD antibody or the binding site of another fD-inhibiting molecule.

The terms "peptide" and "protein" are used interchangeably herein to refer to polymers of amino acids of any length. A polypeptide can be any protein, peptide, protein fragment or component thereof. A polypeptide can be a protein naturally occurring in nature or a protein that is ordinarily not found in nature. A polypeptide can consist largely of the standard twenty protein-building amino acids or it can be modified to incorporate non-standard amino acids. A polypeptide can be modified, typically by the host cell, by e.g., adding any number of biochemical functional groups, including phosphorylation, acetylation, acylation, formylation, alkylation, methylation, lipid addition (e.g. palmitoylation, myristoylation, prenylation, etc) and carbohydrate addition (e.g. N-linked and O-linked glycosylation, etc). Polypeptides can undergo structural changes in the host cell such as the formation of disulfide bridges or proteolytic cleavage. The peptides described herein may be therapeutic peptides utilized for e.g., the treatment of a disease.

The Complement System and the Alternative Complement Pathway

The complement system is a part of the innate immune system that enhances the ability of antibodies and phagocytic cells to clear pathogens from an organism. Although the system is not adaptable and does not change over the course of an individual's lifetime, it can be recruited and brought into action by the adaptive immune system.

The complement system consists of a number of small proteins found in the blood, in general synthesized by the liver, and normally circulating as inactive precursors (proproteins). When stimulated by one of several triggers, proteases in the system cleave specific proteins to release cytokines and initiate an amplifying cascade of further cleavages. The end result of this complement activation or complement fixation cascade is massive amplification of the response and activation of the cell-killing membrane attack complex. Over 30 proteins and protein fragments make up the complement system, including serum proteins, serosal proteins, and cell membrane receptors.

The alternative complement pathway is a rapid, antibody-independent route for complement system activation and amplification. The alternative pathway comprises several components: C3, Factor B (fB), and fD. Activation of the alternative pathway occurs when C3b, a proteolytic cleavage form of C3, is bound to an activating surface agent such as a bacterium. fB is then bound to C3b, and cleaved by fD to yield the C3 convertase C3bBb. Amplification of C3 convertase activity occurs as additional C3b is produced and deposited. The amplification response is further aided by the binding of the positive regulator protein properdin (Factor P), which stabilizes the active convertase against degradation, extending its half-life from 1-2 minutes to 18 minutes.

The C3 convertase further assembles into a C5 convertase (C3b3bBb). This complex subsequently cleaves complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The alternative complement pathway is believed to play a role in the pathogenesis of a variety of ischemic, inflammatory and autoimmune diseases including age-related macular degeneration, geographic atrophy, Stargardt disease, systemic lupus erythematosus, rheumatoid arthritis, and asthma. Thus, components of the alternative complement pathway may be important targets for the treatment of these diseases.

Age-Related Macular Degeneration

Age-related macular degeneration ("AMD") is a chronic and progressive eye disease that is the leading cause of irreparable vision loss in the United States, Europe, and Japan. AMD is characterized by the progressive deterioration of the central portion of the retina referred to as the macula. The clearest indicator of progression to AMD is the appearance of drusen, yellow-white deposits under the retina, which are plaques of material that are derived from the metabolic waste products of retinal cells. The appearance of drusen is an important component of both forms of AMD: exudative ("wet") and non-exudative ("dry"). The presence of numerous, intermediate-to-large drusen is associated with the greatest risk of progression to late-stage disease, characterized by geographic atrophy and/or neovascularization. The majority of patients with wet AMD experience severe vision loss in the affected eye within months to two years after diagnosis of the disease, although vision loss can occur within hours or days. Dry AMD is more gradual and occurs when light-sensitive cells in the macula slowly atrophy, gradually blurring central vision in the affected eye. Vision loss is exacerbated by the formation and accumulation of drusen and sometimes the deterioration of the retina, although without abnormal blood vessel growth and bleeding. Geographic atrophy is a term used to refer to advanced dry AMD. Geographic atrophy is characterized by an "island" of atrophied photoreceptors cells. It is believed that the alternative complement pathway may play a role in the pathogenesis of AMD.

Figure 3:
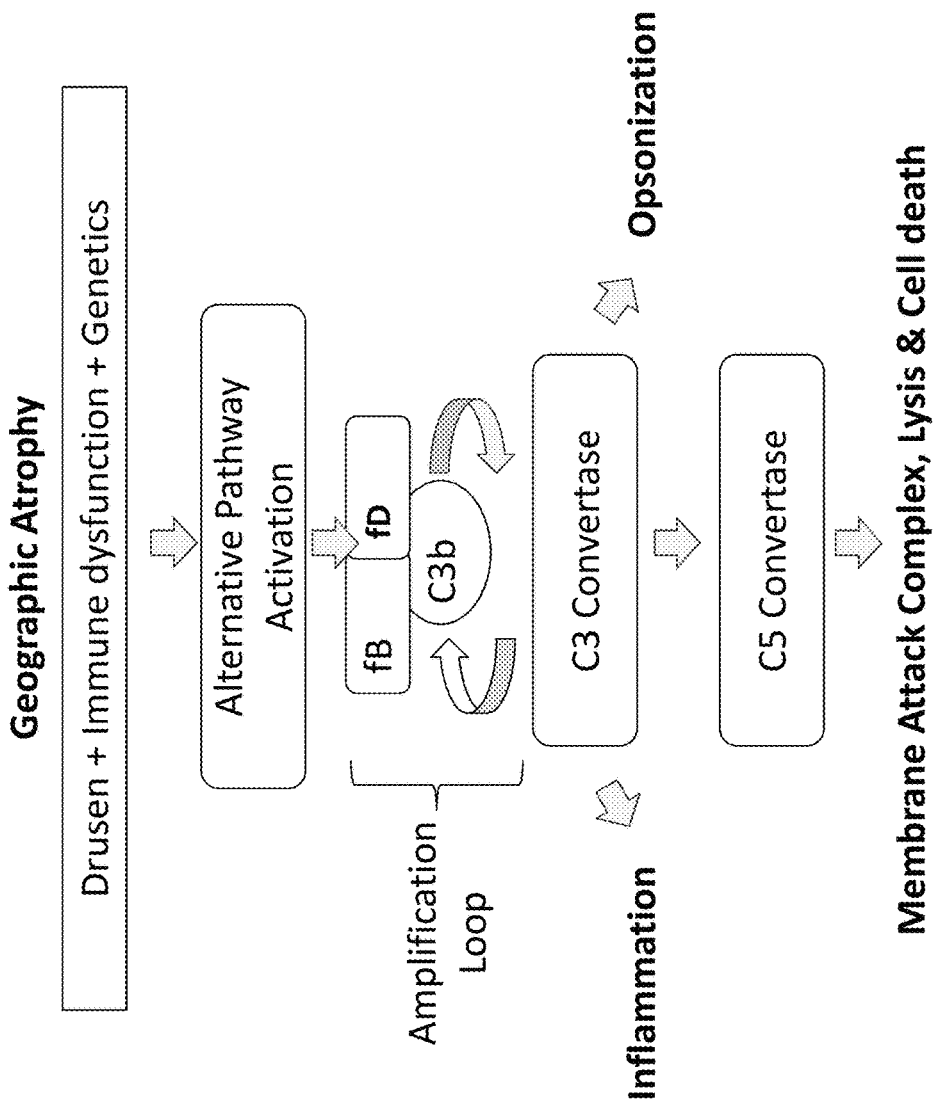
FIG. 3 depicts a non-limiting example of a role for the alternative complement pathway in the pathogenesis of geographic atrophy.

For example, FIG. 3 depicts a potential role for the alternative complement pathway in the pathogenesis of geographic atrophy. In this example, multiple factors may lead to activation of the alternative complement pathway, including the appearance of drusen in the eye, immune dysfunction, and genetic differences that predispose patients to activation of the complement pathway. As described above, amplification of C3 convertase activity may occur as additional C3b is produced and deposited. C3 convertase activity may lead to inflammation and opsonization. The C3 convertase may further assemble into a C5 convertase (C3b3bBb) which may lead to cell death through formation of the Membrane Attack Complex.

In some aspects, the oligonucleotide compositions of the disclosure may be used to treat AMD. In some cases, the oligonucleotide compositions of the disclosure may be used to treat wet AMD. In some cases, the oligonucleotide compositions of the disclosure may be used to treat geographic atrophy. In some cases, the oligonucleotide compositions of the disclosure may be used to stop, slow, or reverse the progression of wet AMD or geographic atrophy. In some cases, the oligonucleotide compositions of the disclosure may be used to treat symptoms associated with wet AMD or geographic atrophy.

Stargardt Disease

Stargardt Disease ("STGD") is a rare, genetic, macular dystrophy with an incidence of 1/20,000, affecting approximately 30,000 individuals in the United States. STGD is an autosomal recessive or complex heterozygous genetic disease caused by mutations in the ABCA4 gene. The ABCA4 gene encodes the photoreceptor protein ABCA4 Transporter, which is responsible for removal of bisretinoid fluorophores, which can include N-retinylidene-N-retinyethanolamine (A2E), all-trans-retinal and related photo-oxidation products of vitamin A aldehyde which together constitute lipofuscin from photoreceptor cells. Accumulation of all-trans-retinal in photoreceptor cells is believed to damage RPE cells via oxidative stress, and trigger or promote complement-mediated damage to RPE cells, leading to retinal atrophy. STGD is characterized by the progressive deterioration of the central portion of the retina referred to as the macula, generally beginning in the first two decades of life. The clearest indicator of progression of STGD is the appearance of drusen, yellow-white deposits under the retina, which are plaques of material that are derived from the metabolic waste products of retinal cells, including all-trans-retinal and other vitamin A-related metabolites. The onset of STGD is typically between the ages of 6-20 years, with early symptoms including difficulties in reading and adjusting to light. Patients with childhood-onset STGD tend to develop early severe visual acuity loss, significantly compromised retinal function, and rapid retinal pigment epithelial (RPE) cell atrophy with accompanying loss of retinal function. The median ages of onset and the median age at baseline examination are 8.5 (range, 3-16) and 12 years (range, 7-16), respectively. Patients with adult-onset disease are more likely to preserve visual acuity for a longer time and show slighter retinal dysfunction. Accumulation of all-trans-retinal in photoreceptor cells leads to inflammation, oxidative stress, deposition of auto-fluorescent lipofuscin pigments in the retinal pigment epithelium and retinal atrophy. Lipofuscin deposits (drusen), and oxidative products, trigger the alternative complement pathway into an inflammatory response leading to cell death. Data supporting the role of alternative complement in STGD include human cell models, genetic mouse models and the accumulation of complement factors in humans in drusen during disease progression. Therefore, inhibitors of complement, particularly complement factor D, are anticipated to stop or slow the progression of vision loss in individuals with STGD. A related disease termed Stargardt-like macular dystrophy, also known as STGD3, is inherited in a dominant autosomal manner and is due to mutations in the ELOVL4 gene. ELOVL4 encodes the ELOVL4 protein, ELOVL fatty acid elongase 4. Mutations in ELOVL4 protein associated with STGD lead to mis-folding and accumulation of ELOVL4 protein aggregates in retinal cells, which impact retinal cell function, eventually leading to cell death and retinal atrophy. Complement pathway activation is also thought to play a role in Stargardt-like disease, and therefore inhibitors of complement, particularly complement factor D, are anticipated to stop or slow the progression of vision loss in individuals with Stargardt-like disease.

In some aspects, the oligonucleotide compositions of the disclosure may be used to treat Stargardt and Stargardt-like disease. In some cases, the oligonucleotide compositions of the disclosure may be used to stop, slow, or reverse the progression of Stargardt and Stargardt-like disease. In some cases, the oligonucleotide compositions of the disclosure may be used to treat symptoms associated with Stargardt and Stargardt-like disease.

Aptamers

In some cases, the methods and compositions described herein use one or more aptamers for the treatment of an ocular disease. In some cases, the methods and compositions described herein utilize one or more aptamers for modulating an activity associated with fD. The term aptamer as used herein refers to oligonucleotide molecules that bind to a target (e.g., a protein) with high affinity and specificity through non-Watson-Crick base pairing interactions. Generally, the aptamers described herein are non-naturally occurring oligonucleotides (i.e., synthetically produced) that are isolated and used for the treatment of a disorder or a disease. Aptamers can bind to essentially any target molecule including, without limitation, proteins, oligonucleotides, carbohydrates, lipids, small molecules, and even bacterial cells. The aptamers described herein are oligonucleotides that bind to proteins of the alternative complement pathway. Whereas many naturally occurring oligonucleotides, such as mRNA, encode information in their linear base sequences, aptamers generally do not encode information in their linear base sequences. Further, aptamers can be distinguished from naturally occurring oligonucleotides in that binding of aptamers to target molecules is dependent upon secondary and tertiary structures of the aptamer.

Aptamers may be suitable as therapeutic agents and may be preferable to other therapeutic agents because: 1) aptamers may be fast and economical to produce because aptamers can be developed entirely by in vitro processes; 2) aptamers may have low toxicity and may lack an immunogenic response; 3) aptamers may have high specificity and affinity for their targets; 4) aptamers may have good solubility; 5) aptamers may have tunable pharmacokinetic properties; 6) aptamers may be amenable to site-specific conjugation of PEG and other carriers; and 7) aptamers may be stable at ambient temperatures.

Aptamers as described herein may include any number of modifications that can affect the function or affinity of the aptamer. For example, aptamers may be unmodified or they may contain modified nucleotides to improve stability, nuclease resistance or delivery characteristics. Examples of such modifications may include chemical substitutions at the sugar and/or phosphate and/or base positions, for example, at the 2' position of ribose, the 5 position of pyrimidines, and the 8 position of purines, various 2'-modified pyrimidines and modifications with 2'-amino (2'-NH$_2$), 2'-fluoro (2'-F), and/or 2'-O-methyl (2'-OMe) substituents. In some cases, aptamers described herein comprise a 2'-OMe and/or a 2'F modification to increase in vivo stability. In some cases, the aptamers described herein contain modified nucleotides to improve the affinity and specificity of the aptamers for a specific epitope, exosite or active site. Examples of modified nucleotides include those modified with guanidine, indole, amine, phenol, hydroxymethyl, or boronic acid. In other cases, pyrimidine nucleotide triphosphate analogs or CE-phosphoramidites may be modified at the 5 position to generate, for example, 5-benzylaminocarbonyl-2'-deoxyuridine (BndU); 5-[N-(phenyl-3-propyl)carboxamide]-2'-deoxyuridine (PPdU); 5-(N-thiophenylmethylcarboxyamide)-2'-deoxyuridine (ThdU); 5-(N-4-fluorobenzylcarboxyamide)-2'-deoxyuridine (FBndU); 5-(N-(1-naphthylmethyl)carboxamide)-2'-deoxyuridine (NapdU); 5-(N-2-naphthylmethylcarboxyamide)-2'-deoxyuridine (2NapdU); 5-(N-1-naphthylethylcarboxyamide)-2'-deoxyuridine (NEdU); 5-(N-2-naphthylethylcarboxyamide)-2'-deoxyuridine (2NEdU); 5-(N-tryptaminocarboxyamide)-2'-deoxyuridine (TrpdU); 5-isobutylaminocarbonyl-2'-deoxyuridine (IbdU); 5-(N-tyrosylcarboxyamide)-2'-deoxyuridine (TyrdU); 5-(N-isobutylaminocarbonyl-2'-deoxyuridine (iBudU); 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-3,4-methylenedioxybenzylcarboxyamide)-2'-deoxyuridine (MBndU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, 5-(N-3-benzothiophenylethylcarboxyamide)-2'-fluorouridine; 5-[N-(1-morpholino-2-ethyl)carboxamide]-2'-deoxyuridine (MOEdu); R-tetrahydrofiranylmethyl-2'-deoxyuridine (RTMdU); 3-methoxybenzyl-2'-deoxyuridine (3MBndU); 4-methoxybenzyl-2'-deoxyuridine (4MBndU); 3,4-dimethoxybenzyl-2'-deoxyuridine (3,4DMBndU); S-tetrahydrofuranylmethyl-2'-deoxyuridine (STMdU); 3,4-methylenedioxyphenyl-2-ethyl-2'-deoxyuridine (MPEdU); 4-pyridinylmethyl-2'-deoxyuridine (PyrdU); or 1-benzimidazol-2-ethyl-2'-deoxyuridine (BidU); 5-(amino-1-propenyl)-2'-deoxyuridine; 5-(indole-3-acetamido-1-propenyl)-2'-deoxyuridine; or 5-(4-pivaloylbenzamido-1-propenyl)-2'-deoxyuridine.

Modifications of the aptamers contemplated in this disclosure include, without limitation, those which provide other chemical groups that incorporate additional charge, polarizability, hydrophobicity, hydrogen bonding, electrostatic interaction, and functionality to the nucleic acid aptamer bases or to the nucleic acid aptamer as a whole. Modifications to generate oligonucleotide populations that are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate, phosphorodithioate, or alkyl phosphate modifications, methylations, and unusual base-pairing combinations such as the isobases isocytidine and isoguanosine. Modifications can also include 3' and 5' modifications such as capping, e.g., addition of a 3'-3'-dT cap to increase exonuclease resistance.

Aptamers of the disclosure may generally comprise nucleotides having ribose in the β-D-ribofuranose configuration. In some cases, 100% of the nucleotides present in the aptamer have ribose in the β-D-ribofuranose configuration. In some cases, at least 50% of the nucleotides present in the aptamer have ribose in the β-D-ribofuranose configuration. In some cases, at least 10%, at least 20%, at least 30%, at least 40%, at least 50%, at least 60%, at least 70%, at least 80%, at least 90%, or 100% of the nucleotides present in the aptamer have ribose in the β-D-ribofuranose configuration.

The length of the aptamer can be variable. In some cases, the length of the aptamer is less than 100 nucleotides. In some cases, the length of the aptamer is greater than 10 nucleotides. In some cases, the length of the aptamer is between 10 and 90 nucleotides. The aptamer can be, without limitation, about 10, about 15, about 20, about 25, about 30, about 35, about 40, about 45, about 50, about 55, about 60, about 65, about 70, about 75, about 80, about 85, or about 90 nucleotides in length.

In some instances, a polyethylene glycol (PEG) polymer chain is covalently bound to the aptamer, referred to herein as PEGylation. Without wishing to be bound by theory, PEGylation may increase the half-life and stability of the aptamer in physiological conditions. In some cases, the PEG polymer is covalently bound to the 5' end of the aptamer. In some cases, the PEG polymer is covalently bound to the 3' end of the aptamer. In some cases, the PEG polymer is covalently bound to specific site on a nucleobase within the aptamer, including the 5-position of a pyrimidine or 8-position of a purine. In some cases, the PEG polymer is covalently bound to an abasic site within the aptamer.

In some cases, an aptamer described herein may be conjugated to a PEG having the general formula, H—(O—CH$_2$—CH$_2$)$_n$—OH. In some cases, an aptamer described herein may be conjugated to a methoxy-PEG (mPEG) of the general formula, CH$_3$O—(CH$_2$—CH$_2$—O)$_n$—H. In some cases, the aptamer is conjugated to a linear chain PEG or mPEG. The linear chain PEG or mPEG may have an average molecular weight of up to about 30 kD. Multiple linear chain PEGs or mPEGs can be linked to a common reactive group to form multi-arm or branched PEGs or mPEGs. For example, more than one PEG or mPEG can be linked together through an amino acid linker (e.g., lysine) or another linker, such as glycerine. In some cases, the aptamer is conjugated to a branched PEG or branched mPEG. Branched PEGs or mPEGs may be referred to by their total mass (e.g., two linked 20 kD mPEGs have a total molecular weight of 40 kD). Branched PEGs or mPEGs may have more than two arms. Multi-arm branched PEGs or mPEGs may be referred to by their total mass (e.g. four linked 10 kD mPEGs have a total molecular weight of 40 kD). In some cases, an aptamer of the present disclosure is conjugated to a PEG polymer having a total molecular weight from about 5 kD to about 200 kD, for example, about 5 about 10 kD, about 20 kD, about 30 kD, about 40 kD, about 50 kD, about 60 kD, about 70 kD, about 80 kD, about 90 kD, about 100 kD, about 110 kD, about 120 kD, about 130 kD, about 140 kD, about 150 kD, about 160 kD, about 170 kD, about 180 kD, about 190 kD, or about 200 kD. In one non-limiting example, the aptamer is conjugated to a PEG having a total molecular weight of about 40 kD.

In some cases, the reagent that may be used to generate PEGylated aptamers is a branched PEG N-Hydroxysuccinimide (mPEG-NHS) having the general formula:

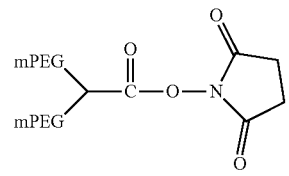

with a 20 kD, 40 kD or 60 kD total molecular weight (e.g., where each mPEG is about 10 kD, 20 kD or about 30 kD). As described above, the branched PEGs can be linked through any appropriate reagent, such as an amino acid (e.g., lysine or glycine residues).

In one non-limiting example, the reagent used to generate PEGylated aptamers is [N$^2$-(monomethoxy 20 K polyethylene glycol carbamoyl)-N$^6$-(monomethoxy 20 K polyethylene glycol carbamoyl)]-lysine N-hydroxysuccinimide having the formula:

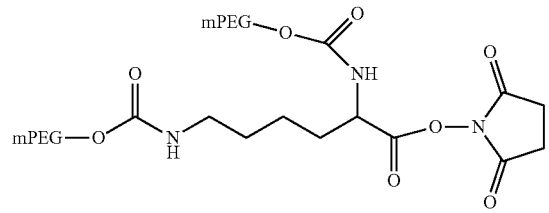

In yet another non-limiting example, the reagent used to generate PEGylated aptamers has the formula:

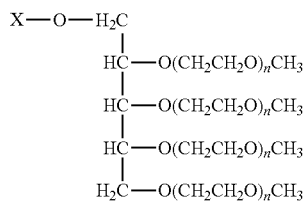

where X is N-hydroxysuccinimide and the PEG arms are of approximately equivalent molecular weight. Such PEG architecture may provide a compound with reduced viscosity compared to a similar aptamer conjugated to a two-armed or single-arm linear PEG.

In some examples, the reagent used to generate PEGylated aptamers has the formula:

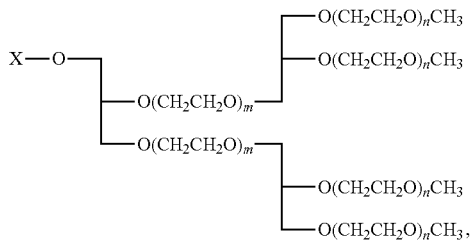

where X is N-hydroxysuccinimide and the PEG arms are of different molecular weights, for example, a 40 kD PEG of this architecture may be composed of 2 arms of 5 kD and 4 arms of 7.5 kD. Such PEG architecture may provide a compound with reduced viscosity compared to a similar aptamer conjugated to a two-armed PEG or a single-arm linear PEG.

In some cases, the reagent that may be used to generate PEGylated aptamers is a non-branched mPEG-Succinimidyl Propionate (mPEG-SPA), having the general formula:

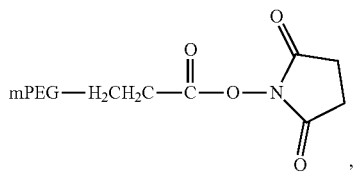

where mPEG is about 20 kD or about 30 kD. In one example, the reactive ester may be —O—CH$_2$—CH$_2$—CO$_2$—NHS.

In some instances, the reagent that may be used to generate PEGylated aptamers may include a branched PEG linked through glycerol, such as the Sunbright™ series from NOF Corporation, Japan. Non-limiting examples of these reagents include:

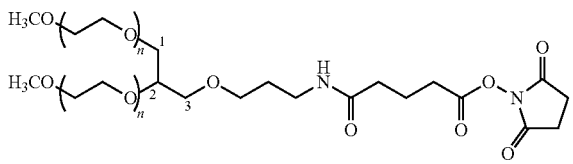

(SUNBRIGHT® GL2-400GS2);

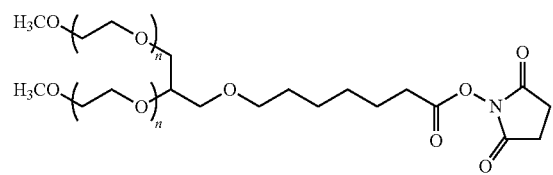

(SUNBRIGHT® GL2-400HS); and

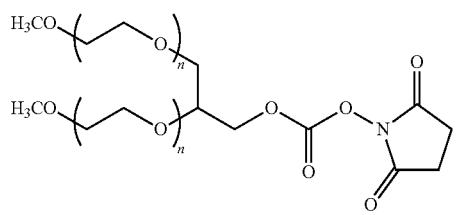

(SUNBRIGHT® GL2-400TS).

In another example, the reagents may include a non-branched mPEG Succinimidyl alpha-methylbutanoate (mPEG-SMB) having the general formula:

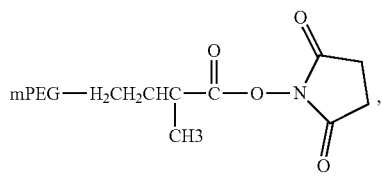

where mPEG is between 10 and 30 kD. In one example, the reactive ester may be —O—CH$_2$—CH$_2$—CH(CH$_3$)—CO$_2$—NHS.

In other instances, the PEG reagents may include nitrophenyl carbonate-linked PEGs, having the general formula:

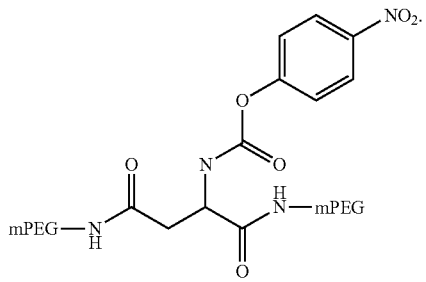

Compounds including nitrophenyl carbonate can be conjugated to primary amine containing linkers.

In some cases, the reagents used to generate PEGylated aptamers may include PEG with thiol-reactive groups that can be used with a thiol-modified linker. One non-limiting example may include reagents having the following general structure:

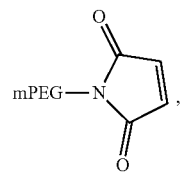

where mPEG is about 10 kD, about 20 kD or about 30 kD. Another non-limiting example may include reagents having the following general structure:

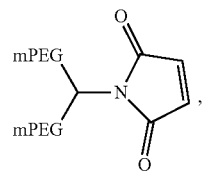

where each mPEG is about 10 kD, about 20 kD, or about 30 kD and the total molecular weight is about 20 kD, about 40 kD, or about 60 kD, respectively. Branched PEGs with thiol reactive groups that can be used with a thiol-modified linker, as described above, may include reagents in which the branched PEG has a total molecular weight of about 40 kD or about 60 kD (e.g., where each mPEG is about 20 kD or about 30 kD).

In some cases, the reagents used to generated PEGylated aptamers may include reagents having the following structure:

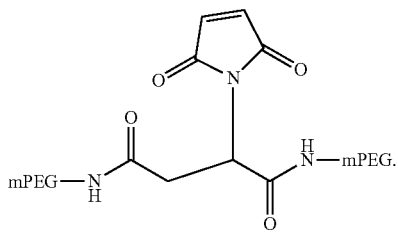

In some cases, the reaction is carried out between about pH 6 and about pH 10, or between about pH 7 and pH 9 or about pH 8.

In some cases, the reagents used to generate PEGylated aptamers may include reagents having the following structure:

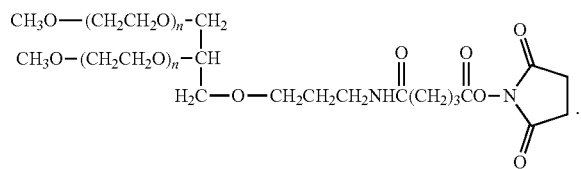

In some cases, the reagents used to generate PEGylated aptamers may include reagents having the following structure:

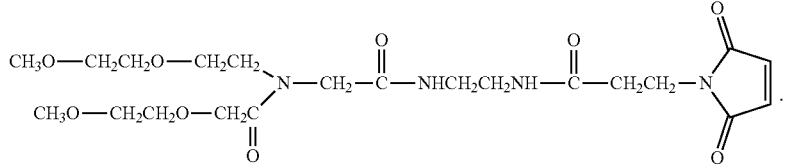

In some cases, the aptamer is associated with a single PEG molecule. In other cases, the aptamer is associated with two or more PEG molecules.

In some cases, the aptamers described herein may be bound or conjugated to one or more molecules having desired biological properties. Any number of molecules can be bound or conjugated to aptamers, non-limiting examples including antibodies, peptides, proteins, carbohydrates, enzymes, polymers, drugs, small molecules, gold nanoparticles, radiolabels, fluorescent labels, dyes, haptens (e.g., biotin), other aptamers, or nucleic acids (e.g., siRNA). In some cases, aptamers may be conjugated to molecules that increase the stability, the solubility or the bioavailability of the aptamer. Non-limiting examples include polyethylene glycol (PEG) polymers, carbohydrates and fatty acids. In some cases, molecules that improve the transport or delivery of the aptamer may be used, such as cell penetration peptides. Non-limiting examples of cell penetration peptides can include peptides derived from Tat, penetratin, polyarginine peptide Arg$_8$ sequence, Transportan, VP22 protein from Herpes Simplex Virus (HSV), antimicrobial peptides such as Buforin I and SynB, polyproline sweet arrow peptide molecules, Pep-1 and MPG. In some embodiments, the aptamer is conjugated to a lipophilic compound such as cholesterol, dialkyl glycerol, diacyl glycerol, or a non-immunogenic, high molecular weight compound or polymer such as polyethylene glycol (PEG) or other water-soluble pharmaceutically acceptable polymers including, but not limited to, polyaminoamines (PAMAM) and polysaccharides such as dextran, or polyoxazolines (POZ).

The molecule to be conjugated can be covalently bonded or can be associated through non-covalent interactions with the aptamer of interest. In one example, the molecule to be conjugated is covalently attached to the aptamer. The covalent attachment may occur at a variety of positions on the aptamer, for example, to the exocyclic amino group on the base, the 5-position of a pyrimidine nucleotide, the 8-position of a purine nucleotide, the hydroxyl group of the phosphate, or a hydroxyl group or other group at the 5' or 3' terminus. In one example, the covalent attachment is to the 5' or 3' hydroxyl group of the aptamer.

In some cases, the aptamer can be attached to another molecule directly or with the use of a spacer or linker. For example, a lipophilic compound or a non-immunogenic, high molecular weight compound can be attached to the aptamer using a linker or a spacer. Various linkers and attachment chemistries are known in the art. In a non-limiting example, 6-(trifluoroacetamido)hexanol (2-cyanoethyl-N,N-diisopropyl)phosphoramidite can be used to add a hexylamino linker to the 5' end of the synthesized aptamer. This linker, as with the other amino linkers provided herein, once the group protecting the amine has been removed, can be reacted with PEG-NHS esters to produce covalently linked PEG-aptamers. Other non-limiting examples of linker phosphoramidites may include: TFA-amino C4 CED phosphoramidite having the structure:

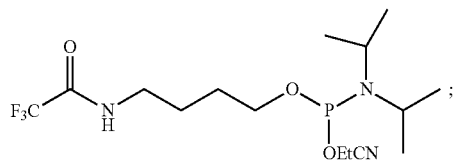

5'-amino modifier C3 TFA having the structure:

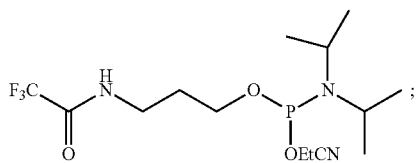

MT amino modifier C6 CED phosphoramidite having the structure:

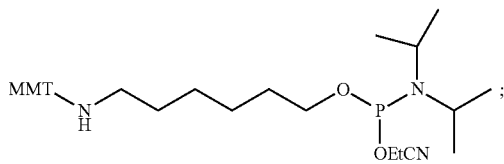

5'-amino modifier 5 having the structure:

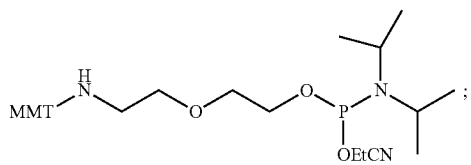

MMT: 4-Monomethoxytrityl

5'-amino modifier C12 having the structure:

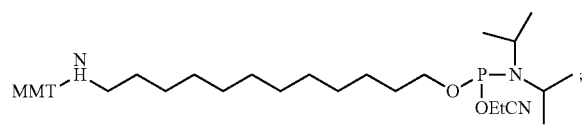

MMT: 4-Monomethoxytrityl

5' thiol-modifier C6 having the structure:

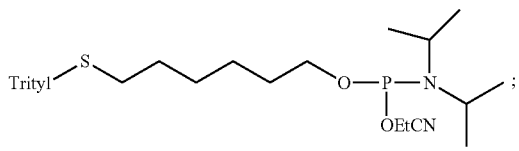

5' thiol-modifier C6 having the structure:

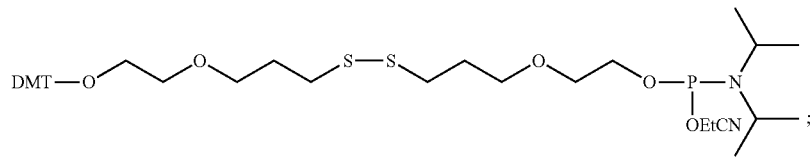

DMT: 4,4'–Dimethoxytrityl and 5' thiol-modifier C6 having the structure:

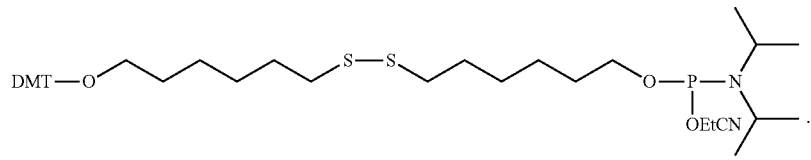

DMT: 4,4'–Dimethoxytrityl

The 5'-thiol modified linker may be used, for example, with PEG-maleimides, PEG-vinylsulfone, PEG-iodoacetamide and PEG-orthopyridyl-disulfide. In one example, the aptamer may be bonded to the 5'-thiol through a maleimide or vinyl sulfone functionality.

In some cases, the aptamer formulated according to the present disclosure may also be modified by encapsulation within a liposome. In other cases, the aptamer formulated according to the present disclosure may also be modified by encapsulation within a micelle. Liposomes and micelles may be comprised of any lipids, and in some cases the lipids may be phospholipids, including phosphatidylcholine.

In some cases, the aptamers described herein are designed to inhibit a function associated with an alternative complement pathway enzyme. In one example, an anti-fD aptamer is used to inhibit a function associated with fD (e.g., inhibit the catalytic activity of fD). In other cases, the aptamers described herein are designed to prevent an interaction or binding of two or more proteins of the alternative complement pathway. In one example, an aptamer binds to fD and prevents binding of the complex C3bBb to fD. In another example, an aptamer of the disclosure binds to fD and prevents binding of pre-formed C3bB complex. The aptamers described herein may bind to a region of fD that is recognized by an antibody or antibody fragment thereof that inhibits a function associated with fD. In some cases, the antibody or antibody fragment thereof that inhibits a function associated with fD has an amino acid sequence of heavy chain variable region of: EVQLVQSGPELKKPGASVK-VSCKASGYTFTNYGMNWVRQA PGQGLEWMGWIN-TYTGETTYADDFKGRFVFSLDTSVSTAYLQISSLKAE-DTAVYYCER GGVNNWGQGTLVTVSSASTKGPSVFPLAPSSKST-SGGTAALGCLVKDYFPEPVTVSWNS GALTSGVHTF-PAVLQSSGLYSLSSVVTVPSSSLGTQTYICNVNH-KPSNTKVDKKVEPKSC DKTHT (SEQ ID NO:7) and an amino acid sequence of light chain variable region of: DIQVTQSPSSLSASVGDRVTITCITSTDIDDDMNWY-QQKPGKVPKLLISGGNTLRPGVPS RFSGSGSGTD-FTLTISSLQPEDVATYYCLQSDSLPYTFGQGTK-VEIKRTVAAPSVFIFPP SDEQLKSGTASVVCLLNNFYPREAKVQWKVD-
NALQSGNSQESVTEQDSKDSTYSLSST LTL-
SKADYEKHKVYACEVTHQGLSSPVTKSFNRGEC
(SEQ ID NO:8).

Figure 4A:
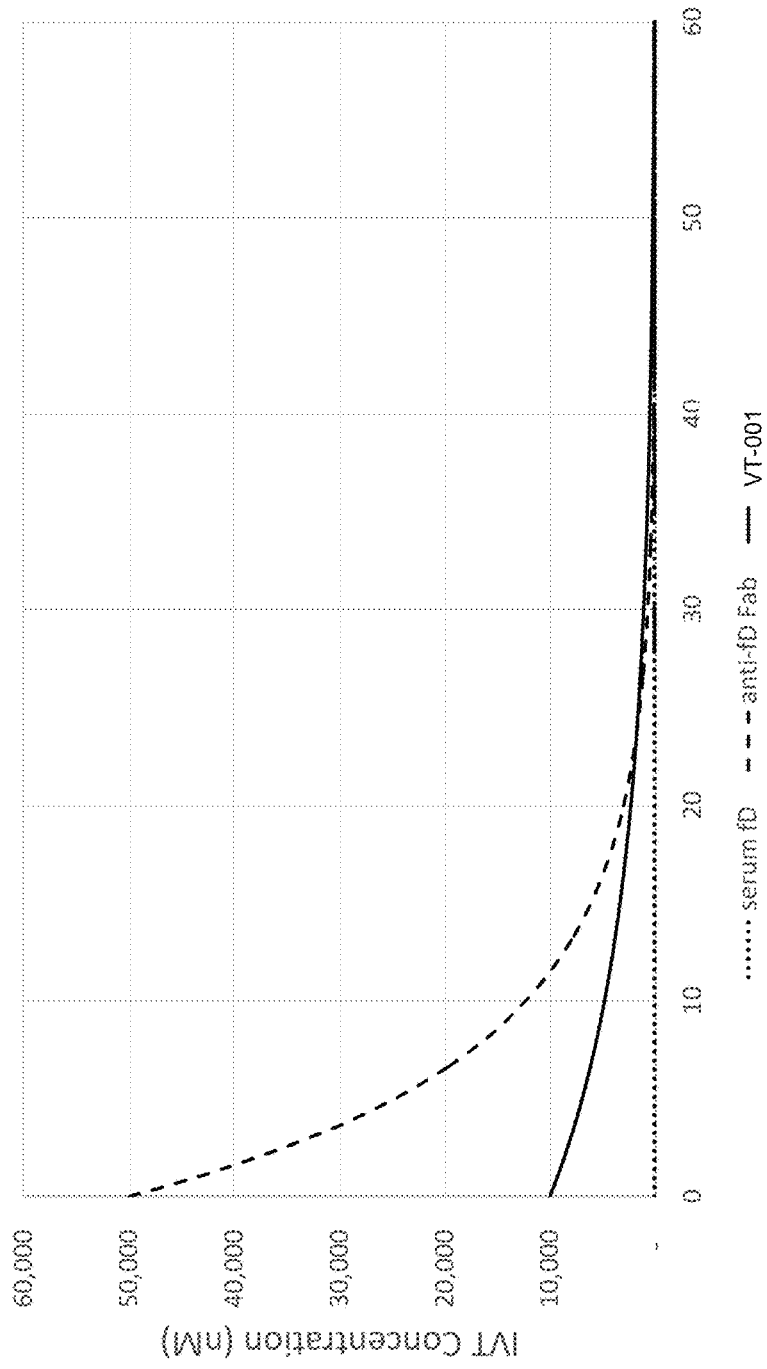
FIG. 4A and FIG. 4B depict modeling of the intravitreal (IVT) inhibition of Factor D by an anti-Factor D aptamer at various IVT concentrations over time.
Figure 4B:
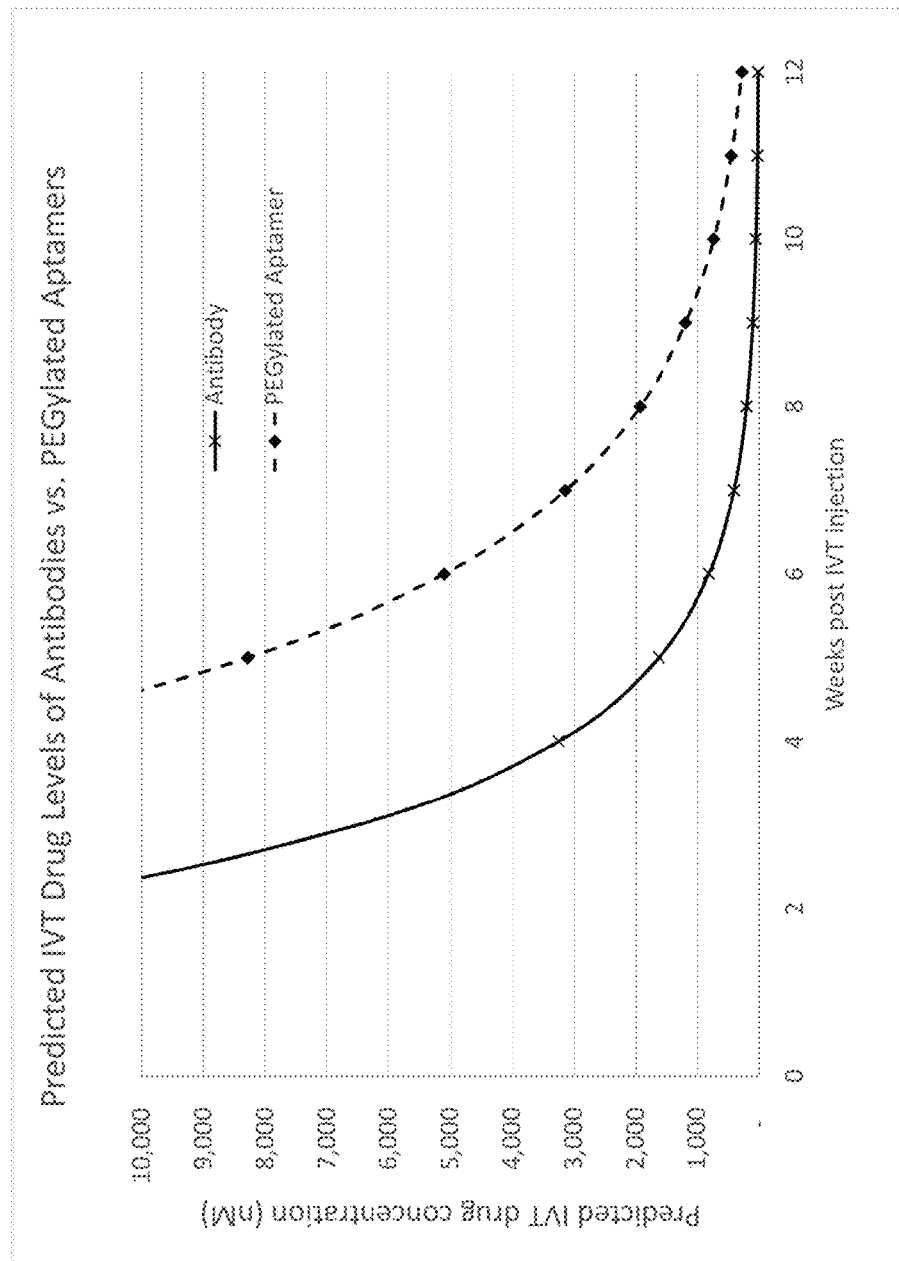
Figure 5B:
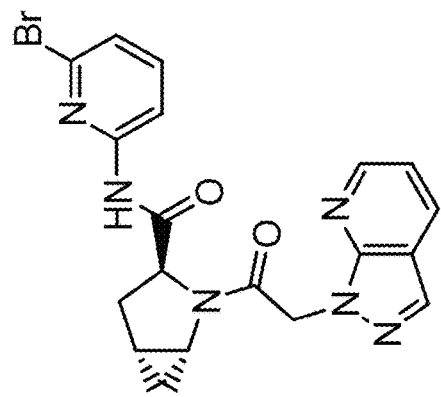
FIG. 5A, FIG. 5B, FIG. 5C, and FIG. 5D depict non-limiting examples of small molecule inhibitors of fD.
Figure 5D:
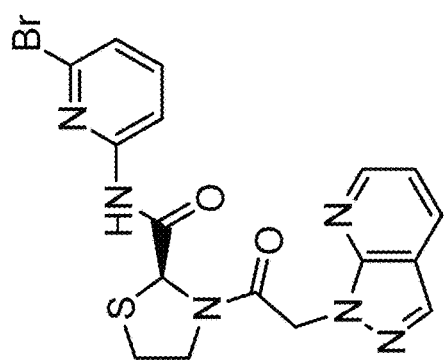
Figure 5A:
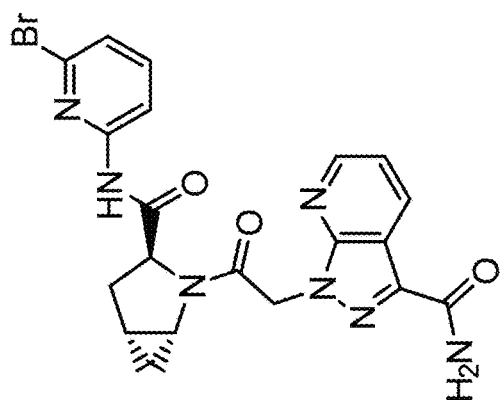
Figure 5C:
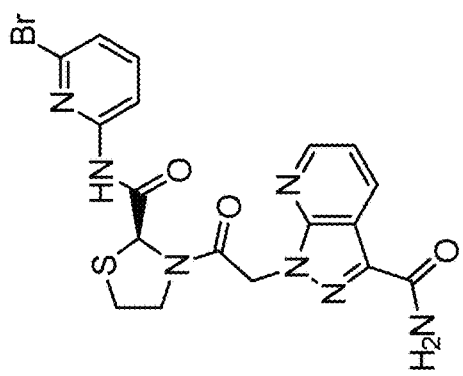

FIG. 4 depicts modeling of the intravitreal (IVT) inhibition of Factor D by an anti-Factor D aptamer at various IVT concentrations. FIG. 4A and FIG. 4B demonstrate IVT inhibition of Factor D at various IVT concentrations of an anti-Factor D aptamer. Effective inhibition of IVT Factor D inhibition was modeled using a standard 2 compartment model, assuming reported IVT half-lives for Fabs (7 days, LUCENTIS®) and PEGylated aptamers (10 days, MACUGEN®) and 1:1 inhibition of Factor D by each therapy at the relevant IVT concentrations ($IC_{50}$ data). As depicted in FIG. 4A, effective inhibition curves after IVT injection are shown for an anti-Factor D Fab (dashed line), an anti-Factor D aptamer VT-001 (solid line), and the intercept with the serum level of Factor D (dotted line) can be visualized as a surrogate for loss of clinically relevant Factor D inhibition. FIG. 4B depicts the predicted IVT drug concentration (nM) of a PEGylated aptamer (dotted line) and an anti-Factor D antibody (solid line) over the number of weeks post IVT injection.

The aptamers described herein may bind to a region of fD that is recognized by a small molecule inhibitor that inhibits a function associated with fD, non-limiting examples including dichloroisocoumarin or any one of the compounds depicted in FIG. 5A, FIG. 5B, FIG. 5C, and FIG. 5D. The aptamers described herein may bind to a region of fD that is recognized by a peptide inhibitor that inhibits a function associated with fD.

In some cases, an aptamer of the disclosure comprises one of the following sequences described in Table 1 or Table 2.

TABLE 1 fD Aptamer Sequences

| SEQ ID NO. | Backbone | Sequence 5' to 3' |
|---|---|---|
| SEQ ID NO: 1 | RNA | GGGAGUGUGUACGAGGCAUUAGGCCG CCACCCAAACUGCAGUCCUCGUAAGUC UGCCUGGCGGCUUUGAUACUUGAUCG CCCUAGAAGC |
| SEQ ID NO: 2 | RNA | GGGAGUGUGUACGAGGCAUUAGUCCG CCGAAGUCUUUUGGCUCGGUUUUUUC AAGGUCGGCGGCUUUGAUACUUGAUC GCCCUAGAAGC |
| SEQ ID NO: 3 | RNA | GGGAGUGUGUACGAGGCAUUAGGCCG CCACCUCGUUUGAUUGCGGUUGUUCG GCCGCGGGCGGCUUUGAUACUUGAUC GCCCUAGAAGC |
| SEQ ID NO: 10 | RNA | GGGAGUGUGUACGAGGCAUUAGGCCG CCUUGCCAGUAUUGGCUUAGGCUGGA AGUUUGGCGGCUUUGAUACUUGAUCG CCCUAGAAGC |
| SEQ ID NO: 11 | RNA | AGGCCGCCUUGCCAGUAUUGGCUUAG GCUGGAAGUUUGGCGGCUU |
| SEQ ID NO: 12 | RNA | CCGCCUUGCCAGUAUUGGCUUAGGCU GGAAGUUUGGCGG |
| SEQ ID NO: 13 | RNA | CCGCCUUGCCAGUAUUGGCUUAGGCU GGAAGUUUGGCGG |
| SEQ ID NO: 14 | RNA | CGCCUUGCAAGUAUUGGCUUUGGCUU GAAGUUUGGCGG |

TABLE 1-continued fD Aptamer Sequences

| SEQ ID NO. | Backbone | Sequence 5' to 3' |
|---|---|---|
| SEQ ID NO: 15 | RNA | CCGCCUUGCAAGUAUUGGCUUAGGCU UGAAGUUUGGCGG |
| SEQ ID NO: 16 | RNA | CUGCCUUGCGGGUAUUGGCGUUGGCC CGAAGUUUGGCUG |
| SEQ ID NO: 17 | RNA | CAGUCUUGCGAGUUUGGCUAAGCUUC GAAGUUUGGCUG |
| SEQ ID NO: 18 | RNA | CCGCCUUGCGAGUAAUGGCGUAGGCU CGAAGUUGGGCGG |
| SEQ ID NO: 19 | RNA | CCGCCUUGCGAGUAUUGGCUUAGGCU CGAAGUUUGGCGG |
| SEQ ID NO: 20 | RNA | CCGGCUUGCGAGUAUUGGCUUAGGCU CGAAGUUUGCCGG |
| SEQ ID NO: 21 | RNA | CCGCCUUGCGAGUAUUGGCUUUGGCU CGAAGUUUGUCUG |
| SEQ ID NO: 22 | RNA | CCGCCUUGCGAGUAUUGGCGUUGGCU CGAAGUUUUUCGG |
| SEQ ID NO: 23 | RNA | UCACCUUGCCAUUAUUGGCUUAGGAU GGAAGUUUGGUGG |
| SEQ ID NO: 24 | RNA | CCACCUUGCCAGUAUUGGCUUUGGCC GGAAGUUUGGUGG |
| SEQ ID NO: 25 | RNA | CCACCUUGCCAGUAUUGGCUUAGGCU GGAAGUUUGGUGG |
| SEQ ID NO: 26 | RNA | CCGCCUUGCCAGUAUUGGGUUUGGCU GGAAGUUUGGCGG |
| SEQ ID NO: 27 | RNA | CCGCAUUGCCAGUAUUGGCUUCGGCU GGAAGUUUGCCGG |
| SEQ ID NO: 28 | RNA | CCGCAUUGCCAGUAUAGGCUUAUGCU GGAAGUUUGCGG |
| SEQ ID NO: 29 | RNA | CCGCGUUGCCAGUAUAGGCUUAGGCU GGAAGUUUCGCGG |
| SEQ ID NO: 30 | RNA | CGCAUUGCUAGUAUUGGCUUAGGCUA GAAGUGUUGCG |
| SEQ ID NO: 31 | RNA | CUGCCUUGCCAGUAUUGGCUUAGGCU GGAAGUUUUUUUG |
| SEQ ID NO: 32 | RNA | CCGGGUUGCCAGUAUUGGCUUAGGCU GGAAGUUUCGCGG |
| SEQ ID NO: 33 | RNA | CCGACUUGCCAGUAUUGGCGUAGGCU GGAAGUUUGUCGG |
| SEQ ID NO: 34 | RNA | CCGACUUGCCAGUAUUGGCGUAGGCU GGAAGUUUGCCGG |
| SEQ ID NO: 35 | RNA | CCGACUUGCCAGUAUUGGCCUAGGCU GGAAGUUUGUCGG |
| SEQ ID NO: 36 | RNA | UCGACUUGCCAGUAUUGGCUUAGGCU GGAAGUUUGUCGG |
| SEQ ID NO: 37 | RNA | CGACUUGCCAGUAUUGGCUUAGUCUG GAAGUUUGUCG |
| SEQ ID NO: 38 | RNA | CCGACUUGCCAGUGUUGGCUUUGGCU GGAAGUUUGUCGG |
| SEQ ID NO: 39 | RNA | CCGACUUGCCAGUAUUGGCUUUGGCU GGAAGUUUGCCGG |

TABLE 1-continued fD Aptamer Sequences

| SEQ ID NO. | Backbone | Sequence 5' to 3' |
|---|---|---|
| SEQ ID NO: 40 | RNA | CCGACUUGCCAGUAUUGGCUUAGGCUGGAAGUUUGCCGG |
| SEQ ID NO: 41 | RNA | CGGCCUUGCCAGUAUUGGCUUUGGCUGGAAGUUUGGCCG |
| SEQ ID NO: 42 | RNA | CGGCCUUGCAUGUAUUGGCUCAGGCAUGAAGUUUGUCCG |
| SEQ ID NO: 43 | RNA | CGUGCUUGUCAGUAUUGGCGUUGGCUGAAAGUUUGCACG |
| SEQ ID NO: 44 | RNA | CGUACUUGCCAGUAUUGGCGUAGGCUGGAAGUUUGUGCG |
| SEQ ID NO: 45 | RNA | CGGGCUUGCCAGUAUUAGGGUAGGCUGGAAGUUUGGCCG |
| SEQ ID NO: 46 | RNA | CGGGCUUGCCAGUAUUGGCUUAGGCUGGAAGUUUGUCCG |
| SEQ ID NO: 47 | RNA | GAGACUCGCCAGUAUAGGCUAAGGCUGGAAGUAUGUCUG |
| SEQ ID NO: 48 | RNA | CUGACUUGCCAGUAUUGGCUUAGGCUGGAAGUUUGUCGG |
| SEQ ID NO: 49 | RNA | CUGACUUGCCAGUAUUGGCUUAGGCUGGAAGUUUGUCAG |
| SEQ ID NO: 50 | RNA | CUGACUUGCCAGUAUUAGCUUAGGCUGGAAGUUUGGCGG |
| SEQ ID NO: 51 | RNA | CCGGCUUGCCAGUAUUGGCUUAGGCUGGAAGUUUGCCGG |
| SEQ ID NO: 52 | RNA | CCGCCUUGCCAGUAUUGGCUUAGGCUGGAAGUUUGUCGG |
| SEQ ID NO: 53 | RNA | CCGGCUUGCCAGUAUUGGCUCAGGCUGGAAGUUUGCCGG |
| SEQ ID NO: 54 | RNA | CCGGCUUGCCAGUAUAGGCUCAGGCUGGAAGUUUGCCGG |
| SEQ ID NO: 55 | RNA | UCGGCUUGCCAGUAUUGGCUUAGGCUGGAAGUUUGCCGG |
| SEQ ID NO: 56 | RNA | CCGGCUUGCCAGUAUUGGCUUUGGCUGGAAGUUUGCCGG |
| SEQ ID NO: 57 | RNA | CCGGCUUGCCAGUAUUGGCGUAGGCUGGAAGUUUGCCGG |
| SEQ ID NO: 58 | RNA | CCGACUUGCCAGUAUUCGCUUAGGCGGGAAGUUUGCCGG |
| SEQ ID NO: 59 | RNA | CCGACUUGCCAGUAUUGGCUUAGGCUGGAAGUUUGUCGG |
| SEQ ID NO: 60 | RNA | CGACUUGCCAGUAUUGGCUUAGGCUGGAAGUUUGUCG |
| SEQ ID NO: 61 | RNA | CCGACUUGCCAGUAAUUGGCUUAGGCUGGAAGUUUGUCGG |
| SEQ ID NO: 62 | RNA | CCGACUUGCCAGUAUUGGCGAUGGCUGGAAGUUUGUCGG |
| SEQ ID NO: 63 | RNA | CCGACUUGCCAGUAUUGGCUUUGGCUGGAAGUUUGUCGG |
| SEQ ID NO: 64 | RNA | CCGCCUUGCCAGUAUUGGCUUAGGCUGGAAGUAUGGCGG |
| SEQ ID NO: 65 | RNA | CCACCUUGCCAGUAUUGGCUUAGGCUGGAAGUGUGGUGG |
| SEQ ID NO: 66 | RNA | ACACCUUGCGAGUAUUGGCUUAGGCUCGAAGUUUGGCGU |
| SEQ ID NO: 67 | RNA | ACGCUUUGCCAGUAUUGGCUUAGGCUGGAAGUUUCGCGU |
| SEQ ID NO: 68 | RNA | CCGCGUUGCCAGUAUUGGCUUUGGCUGGAAGUUUCGCGG |
| SEQ ID NO: 69 | RNA | CCGCCUUGCCAGUAUUGGCUUAGGCUGGAAGUUUUGCGG |
| SEQ ID NO: 70 | RNA | CCGCCUUGCCAGUAUUGGCUCAGGCUGGAAGUUUGGCGG |
| SEQ ID NO: 71 | RNA | CCGCCUUGCCAGUAUUAGCGUAGGCUGGAAGUUUGGCGG |
| SEQ ID NO: 72 | RNA | CCGCCUUGCAAGUAUUGGCGUUGGCUGAAGUUUGGCGG |
| SEQ ID NO: 73 | RNA | UCGCCUUGCAUGUAUUGGGUUUGGCAUGAAGUUUGGCGG |
| SEQ ID NO: 74 | RNA | CCGCCUUGCAAGUAUAGGCUUAGGCUUAAGUUUGGGGG |
| SEQ ID NO: 75 | RNA | CAGCCAUGCAAGUAUUGGCUUAGGCUUGAAGUUCGGCUG |
| SEQ ID NO: 76 | RNA | CAGCCGUGCUAGUAUUGGCAUUGGCUAGAAGUUAGGCUG |
| SEQ ID NO: 77 | RNA | CGGGCUUGCCAGUAUUGGCGUUGGCUGGAAGUUUGCCCG |
| SEQ ID NO: 78 | RNA | UGGGCUUGCCAGUAUUGGCUUAGGCUGGAAGUUUGCCCG |
| SEQ ID NO: 79 | RNA | GGGCUUGCCAGUAUUGGCUUAGGCUGGAAGUUUGUCC |
| SEQ ID NO: 80 | RNA | GGGAGAUGGCGCUGAUCAGGCCGCCUUGCCAGUAUUGGCUUAGGCUGGAAGUUUGGCGGCUUUGAUACUUGAUCGCCUAGAAGCA |
| SEQ ID NO: 81 | RNA | GGGAGAUGGCGCUGAUCAGGUCGCCUUGCAAGUAUUGGCUUUGGCUUGAAGUUUGGCGGCUUUGAUACUUGAUCGCCUAGAAGCA |
| SEQ ID NO: 82 | RNA | GGGAGAUGGCGCUGAUCAGGCCGCCUUGCAAGUAUUGGCUUAGGCUUGAAGUUUGGCGGCUUUGAUACUUGAUCGCCUAGAAGCA |
| SEQ ID NO: 83 | RNA | GGGAGAUGGCGCUGAUCAGGCUGCCUUGCGAGUAUUGGCGUUGCCCGGAAGUUUGGCUGCUUUGAUACUUGAUCGCCUAGAAGCA |
| SEQ ID NO: 84 | RNA | GGGAGAUGGCGCUGAUCAGGCAGUCUUGCGAGUUUGGCUAAGCUUCGAAGUUUGGCUGCUUUGAUACUUGAUCGCCCUAGAAGCA |
| SEQ ID NO: 85 | RNA | GGGAGAUGGCGCUGAUCAGGCCGCCUUGCGAGUAUUGGCUAGGCUCGAAGUUGGGCGGCUUUGAUACUUGAUCGCCUAGAAGCA |

TABLE 1-continued fD Aptamer Sequences

| SEQ ID NO. | Backbone | Sequence 5' to 3' |
|---|---|---|
| SEQ ID NO: 86 | RNA | GGGAGAUGGCGCUGAUCAGGCCGCCU UGCGAGUAUUGGCUUAGGCUCGAAGU UUGGCGGCUUUGAUACUUGAUCGCCC UAGAAGCA |
| SEQ ID NO: 87 | RNA | GGGAGAUGGCGCUGAUCAGGCCGGCU UGCGAGUAUUGGCUUAGGCUCGAAGU UUGCCGGCUUUGAUACUUGAUCGCCC UAGAAGCA |
| SEQ ID NO: 88 | RNA | GGGAGAUGGCGCUGAUCAGGCCGCCU UGCGAGUAUUGGCUUUGGCUCGAAGU UUGUCUGGUUGAUACUUGAUCGCCCU AGAAGCA |
| SEQ ID NO: 89 | RNA | GGGAGAUGGCGCUGAUCAGGCCGCCU UGCGAGUAUUGGCGUUGGCUCGAAGU UUUCGGCUUUGAUACUUGAUCGCCC UAGAAGCA |
| SEQ ID NO: 90 | RNA | GGGAGAUGGCGCUGAUCAGGUCACCU UGCCAUUAUUGGCUUAGGAUGGAAGU UUGGUGGCUUGAUACUUGAUCGCCCU AGAAGCA |
| SEQ ID NO: 91 | RNA | GGGAGAUGGCGCUGAUCAGGCCACCU UGCCAGUAUUGGCUUUGGCCGGAAGU UUGGUGGCUUUGAUACUUGAUCGCCC UAGAAGCA |
| SEQ ID NO: 92 | RNA | GGGAGAUGGCGCUGAUCAGGCCACCU UGCCAGUAUUGGCUUAGGCUGGAAGU UUGGUGGCUUGUGAUACUUGAUCGCC CUAGAAGCA |
| SEQ ID NO: 93 | RNA | GGGAGAUGGCGCUGAUCAGGCCGCCU UGCCAGUAUUGGGUUUGGCUGGAAGU UUGGCGGCUUUGAUACUUGAUCGCCC UAGAAGCA |
| SEQ ID NO: 94 | RNA | GGGAGAUGGCGCUGAUCAGGCCGCAU UGCCAGUAUUGGCUUCGGCUGGAAGU UUGCCGGCUUUGAUACUUGAUCGCCC UAGAAGCA |
| SEQ ID NO: 95 | RNA | GGGAGAUGGCGCUGAUCAGGCCGCAU UGCCAGUAUAGGCUUAUGCUGGAAGU UUUGCGGCUUUGAUACUUGAUCGCCC UAGAAGCA |
| SEQ ID NO: 96 | RNA | GGGAGAUGGCGCUGAUCAGGCCGCGU UGCCAGUAUAGGCUUAGGCUGGAAGU UUCGCGGCUUUGAUACUUGAUCGCCC UAGAAGCA |
| SEQ ID NO: 97 | RNA | GGGAGAUGGCGCUGAUCAGGACGCAU UGCUAGUAUUGGCUUAGGCUAGAAGU GUUGCGGCUUUGAUACUUGAUCGCCC UAGAAGCA |
| SEQ ID NO: 98 | RNA | GGGAGAUGGCGCUGAUCAGGCUGCCU UGCCAGUAUUGGCUUAGGCUGGAAGU UUUGCGGCUUUGAUACUUGAUCGCCC UAGAAGCA |
| SEQ ID NO: 99 | RNA | GGGAGAUGGCGCUGAUCAGGCCGGGU UGCCAGUAUUGGCUUAGGCUGGAAGU UUCGCGGUUUUGAUACUUGAUCGCCC UAGAAGCA |
| SEQ ID NO: 100 | RNA | GGGAGAUGGCGCUGAUCAGGCCGACU UGCCAGUAUUGGCUGUAGGCUGGAAGU UUGUCGGCUUUGAUACUUGAUCGCCC UAGAAGCA |
| SEQ ID NO: 101 | RNA | GGGAGAUGGCGCUGAUCAGGCCGACU UGCCAGUAUUGGCGUAGGCUGGAAGU UUGCCGGCUUUGAUACUUGAUCGCCC UAGAAGCA |
| SEQ ID NO: 102 | RNA | GGGAGAUGGCGCUGAUCAGGCCGACU UGCCAGUAUUGGCCUAGGCUGGAAGU UUGUCGGCUUUGAUACUUGAUCGCCC UAGAAGCA |
| SEQ ID NO: 103 | RNA | GGGAGAUGGCGCUGAUCAAGUCGACU UGCCAGUAUUGGCUUAGGCUGGAAGU UUGUCGGCUUUGAUACUUGAUCGCCC UAGAAGCA |
| SEQ ID NO: 104 | RNA | GGGAGAUGGCGCUGAUCAGGACGACU UGCCAGUAUUGGCUUAGUCUGGAAGU UUGUCGGCUUUGAUACUUGAUCGCCC UAGAAGCA |
| SEQ ID NO: 105 | RNA | GGGAGAUGGCGCUGAUCAGGCCGACU UGCCAGUGUUGGCUUUGGCUGGAAGU UUGUCGGCUUUGAUACUUGAUCGCCC UAGAAGCA |
| SEQ ID NO: 106 | RNA | GGGAGAUGGCGCUGAUCAGGCCGACU UGCCAGUAUUGGCUUUGGCUGGAAGU UUGCCGGCUUUGAUACUUGAUCGCCC UAGAAGCA |
| SEQ ID NO: 107 | RNA | GGGAGAUGGCGCUGAUCAGGCCGACU UGCCAGUAUUGGCUUAGGCUGGAAGU UUGCCGGCUUUGAUACUUGAUCGCCC UAGAAGCA |
| SEQ ID NO: 108 | RNA | GGGAGAUGGCGCUGAUCAGGCGGCCU UGCCAGUAUUGGCUUUGGCUGGAAGU UUGGCCGCUUUGAUACUUGAUCGCCC UAGAAGCA |
| SEQ ID NO: 109 | RNA | GGGAGAUGGCGCUGAUCAGGCGGCCU UGCAUGUAUUGGCUCAGGCAUGAAGU UUGUCCGCUUUGAUACUUGAUCGCCC UAGAAGCA |
| SEQ ID NO: 110 | RNA | GGGAGAUGGCGCUGAUCAGGCGUGCU UGUCAGUAUUGGCGUUGGCUGAAAGU UUGCACGCUUUGAUACUUGAUCGCCC UAGAAGCA |
| SEQ ID NO: 111 | RNA | GGGAGAUGGCGCUGAUCAGGCGUACU UGCCAGUAUUGGCGUAGGCUGGAAGU UUGUGCGCUUUGAUACUUGAUCGCCC UAGAAGCA |
| SEQ ID NO: 112 | RNA | GGGAGAUGGCGCUGAUCAGGCGGGCU UGCCAGUAUUAGGGUAGGCUGGAAGU UUGGCCGCUUUGAUACUUGAUCGCCC UAGAAGCA |
| SEQ ID NO: 113 | RNA | GGGAGAUGGCGCUGAUCAGGCGGGCU UGCCAGUAUUGGCUUAGGCUGGAAGU UUGGCCGCUUUGAUACUUGAUCGCCC UAGAACA |
| SEQ ID NO: 114 | RNA | GGGAGAUGGCGCUGAUCAGGGAGACU CGCCAGUAUAGGCUAAGGCUGGAAGU AUGUCUGCUUGAUACUUGAUCGCCCU AGAAGCA |
| SEQ ID NO: 115 | RNA | GGGAGAUGGCGCUGAUCAGGCUGACU UGCCAGUAUUGGCUUAGGCUGGAAGU UUGUCGGCUUUGAUACUUGAUCGCCC UAGAAGCA |

TABLE 1-continued fD Aptamer Sequences

| SEQ ID NO. | Backbone | Sequence 5' to 3' |
|---|---|---|
| SEQ ID NO: 116 | RNA | GGGAGAUGGCGCUGAUCAGGCUGACU UGCCAGUAUUGGCUUAGGCUGGAAGU UUGUCAGCUUUGAUACUUGAUCGCCC UAGAAGCA |
| SEQ ID NO: 117 | RNA | GGGAGAUGGCGCUGAUCAGGCUGACU UGCCAGUAUUAGCUUAGGCUGGAAGU UUGGCGCUUUGAUACUUGAUCGCCC UAGAAGCA |
| SEQ ID NO: 118 | RNA | GGGAGAUGGCGCUGAUCAGGCCGGCU UGCCAGUAUUGCUUAGGCUGGAAGU UUGCCGGCUUUGAUACUUGAUCGCCC UAGAAGCA |
| SEQ ID NO: 119 | RNA | GGGAGAUGGCGCUGAUCAGGCCGCCU UGCCAGUAUUGGCUUAGGCUGGAAGU UUGUCGGCUUUGAUACUUGAUCGCCC UAGAAGCA |
| SEQ ID NO: 120 | RNA | GGGAGAUGGCGCUGAUCAGGCCGGCU UGCCAGUAUUGGCUCAGGCUGGAAGU UUGCCGGCUUUGAUACUUGAUCGCCC UAGAAGCA |
| SEQ ID NO: 121 | RNA | GGGAGAUGGCGCUGAUCAGGCCGGCU UGCCAGUAUAGGCUCAGGCUGGAAGU UUGCCGGCUUUGAUACUUGAUCGCCC UAGAAGCA |
| SEQ ID NO: 122 | RNA | GGGAGAUGGCGCUGAUCAGGUCGGCU UGCCAGUAUUGGCUUAGGCUGGAAGU UUGCCGGCUUUGAUACUUGAUCGCCC UAGAAGCA |
| SEQ ID NO: 123 | RNA | GGGAGAUGGCGCUGAUCAGGCCGGCU UGCCAGUAUUGGCUUUGGCUGGAAGU UUGCCGGCUUUGAUACUUGAUCGCCC UAGAAGCA |
| SEQ ID NO: 124 | RNA | GGGAGAUGGCGCUGAUCAGGCCGGCU UGCCAGUAUUGGCGUAGGCUGGAAGU UUGCCGGCUUUGAUACUUGAUCGCCC UAGAAGCA |
| SEQ ID NO: 125 | RNA | GGGAGAUGGCGCUGAUCAGGCCGACU UGCCAGUAUUCGCUUAGGCGGGAAGU UUGCCGGCUUUGAUACUUGAUCGCCC UAGAAGCA |
| SEQ ID NO: 126 | RNA | GGGAGAUGGCGCUGAUCAGGCCGACU UGCCAGUAUUGGCUUAGGCUGGAAGU UUGUCGGCUUUGAUACUUGAUCGCCC UAGAAGCA |
| SEQ ID NO: 127 | RNA | GGGAGAUGGCGCUGAUCAGGCCGACU UGCCAGUAUUGGCUUAGGCUGGAAGU UUGUCGCUUUGAUACUUGAUCGCCCU AGAAGCA |
| SEQ ID NO: 128 | RNA | GGGAGAUGGCGCUGAUCAGGCCGACU UGCCAGUAAUGGCUUAGGCUGGAAGU UUGUCGGCUUUGAUACUUGAUCGCCC UAGAAGCA |
| SEQ ID NO: 129 | RNA | GGGAGAUGGCGCUGAUCAGGCCGACU UGCCAGUAUUGGCGAUGGCUGGAAGU UUGUCGGCUUUGAUACUUGAUCGCCC UAGAAGCA |
| SEQ ID NO: 130 | RNA | GGGAGAUGGCGCUGAUCAGGCCGACU UGCCAGUAUUGGCUUUGGCUGGAAGU UUGUCGGCUUUGAUACUUGAUCGCCC UAGAAGCA |
| SEQ ID NO: 131 | RNA | GGGAGAUGGCGCUGAUCAGGCCGCCU UGCCAGUAUUGGCUUAGGCUGGAAGU AUGGCGGCUUUGAUACUUGAUCGCCC UAGAAGCA |
| SEQ ID NO: 132 | RNA | GGAGAUGGCGCUGAUCAGGCCACCUU GCCAGUAUUGGCUUAGGCUGGAAGUG UGGUGGCUUUGAUACUUGAUCGCCCU AGAAGCA |
| SEQ ID NO: 133 | RNA | GGGAGAUGGCGCUGAUCAGGACACCU UGCGAGUAUUGGCUUAGGCUCGAAGU UUGGCGUCUUUGAUACUUGAUCGCCC UAGAAGCA |
| SEQ ID NO: 134 | RNA | GGGAGAUGGCGCUGAUCAGGACGCUU UGCCAGUAUUGGCUUAGGCUGGAAGU UUCGCGUCUUUGAUACUUGAUCGCCC UAGAAGCA |
| SEQ ID NO: 135 | RNA | GGGAGAUGGCGCUGAUCAGGCCGCGU UGCCAGUAUUGGCUUUGGCUGGAAGU UUCGCGGCUUUGAUACUUGAUCGCCC UAGAAGCA |
| SEQ ID NO: 136 | RNA | GGGAGAUGGCGCUGAUCAGGCCGCCU UGCCAGUAUUGGCUUAGGCUGGAAGU UUUGCGGCUUUGAUACUUGAUCGCCC UAGAAGCA |
| SEQ ID NO: 137 | RNA | GGGAGAUGGCGCUGAUCAGGCCGCCU UGCCAGUAUUGGCUCAGGCUGGAAGU UUGGCGGCUUUGAUACUUGAUCGCCC UAGAAGCA |
| SEQ ID NO: 138 | RNA | GGGAGAUGGCGCUGAUCAGGCCGCCU UGCCAGUAUUAGCGUAGGCUGGAAGU UUGGCGGCUUUGAUACUUGAUCGCCC UAGAAGCA |
| SEQ ID NO: 139 | RNA | GGGAGAUGGCGCUGAUCAGGCCGCCU UGCAAGUAUUGGCGUUGGCUUGAAGU UUGGCGGCUUUGAUACUUGAUCGCCC UAGAAGCA |
| SEQ ID NO: 140 | RNA | GGGAGAUGGCGCUGAUCAGGUCGCCU UGCAUGUAUUGGGUUUGGCAUGAAGU UUGGCGGCUUUGAUACUUGAUCGCCC UAGAAGCA |
| SEQ ID NO: 141 | RNA | GGGAGAUGGCGCUGAUCAGGCCGCCU UGCAAGUAUAGGCUUAGGCUUAAGUU UGGGGGCUUUGAUACUUGAUCGCCCU AGAAGCA |
| SEQ ID NO: 142 | RNA | GGGAGAUGGCGCUGAUCAGGCAGCCA UGCAAGUAUUGGCUUAGGCUUGAAGU UCGGCUGCUUUGAUACUUGAUCGCCC UAGAAGCA |
| SEQ ID NO: 143 | RNA | GGGAGAUGGCGCUGAUCAGGCAGCCG UGCUAGUAUUGGCAUUUGGCUAGAAGU UAGGCUGCUUUGAUACUUGAUCGCCC UAGAAGCA |
| SEQ ID NO: 144 | RNA | GGGAGAUGGCGCUGAUCAGGCGGGCU UGCCAGUAUUGGCGUUGGCUGGAAGU UUGCCCGCUUUGAUACUUGAUCGCCC UAGAAGCA |
| SEQ ID NO: 145 | RNA | GGGAGAUGGCGCUGAUCAGGUGGGCU UGCCAGUAUUGGCUUAGGCUGGAAGU UUGCCCGCUUUGAUACUUGAUCGCCC UAGAAGCA |

TABLE 1-continued fD Aptamer Sequences

| SEQ ID NO. | Backbone | Sequence 5' to 3' |
|---|---|---|
| SEQ ID NO: 146 | RNA | GGGAGAUGGCGCUGAUCAGGGGGCUUGCCAGUAUUGGCUUAGGCUGGAAGUUUGUCCGCUUUGAUACUUGAUCGCCCUAGAAGCA |
| SEQ ID NO: 147 | RNA | CGCCUUGCCAGUAUUGGCUUAGGCUGGAAGUUUGGCG |
| SEQ ID NO: 148 | RNA | GCCUUGCCAGUAUUGGCUUAGGCUGGAAGUUUGGC |
| SEQ ID NO: 149 | RNA | CCGCCUUGCAGUAUUGGCUUAGGCUGAAGUUUGGCGG |
| SEQ ID NO: 150 | RNA | CCGCCUUGCCAGAUUGGCUUAGCUGGAAGUUUGGCGG |
| SEQ ID NO: 151 | RNA | CCGCCUUGAAGUAUUGGCUUAGGCUUAAGUUUGGCGG |
| SEQ ID NO: 152 | RNA | CCGCCUUGCCAGUAUUGGGCUGGAAGUUUGGCGG |
| SEQ ID NO: 153 | RNA | CCGCCUUGCCAGUAUUGGCGGCUGGAAGUUUGGCGG |
| SEQ ID NOs: 154 and 317 | RNA | CCGCCUUGCCAGUAUUG[I-18]GGCUGGAAGUUUGGCGG |
| SEQ ID NOs: 155 and 317 | RNA | CCGCCUUGCCAGUAUUG[I-9]GGCUGGAAGUUUGGCGG |
| SEQ ID NOs: 156 and 317 | RNA | CCGCCUUGCCAGUAUUGGC[I-9]GGCUGGAAGUUUGGCGG |
| SEQ ID NO: 157 | RNA | CCGCCUUGCCAGUAUUGGCUUAGGCUGGAAGUGGCGG |
| SEQ ID NO: 158 | RNA | CCGCCUUGCCAGUAUUGGCUUAGGCUGGAAGUUGGCGG |
| SEQ ID NO: 159 | RNA | CCGCCUUGCCAGUAUUGGCUUAGGCUGGAAGU[I-6]GGCGG |
| SEQ ID NO: 160 | RNA | CAGCCAUGCAAGUAUUGGCUUAGGCUUGAAGUUCGGCUG |
| SEQ ID NO: 161 | RNA | CAGCCGUGCUAGUAUUGGCAUUGGCUAGAAGUUAGGCUG |
| SEQ ID NO: 162 | RNA | CCGCCUUGCGAGUAAUGGCGUAGGCUCGAAGUUGGGCGG |
| SEQ ID NO: 163 | RNA | CCGACUUGCCAGUGUUGGCUUUGGCUGGAAGUUUGUCGG |
| SEQ ID NO: 164 | RNA | CAGUCUUGCGAGUUUGGCUAAGCUUCGAAGUUUGGCUG |
| SEQ ID NO: 165 | RNA | CUGCCUUGCGGGUAUUGGCGUUGGCCCGAAGUUUGGCUG |
| SEQ ID NO: 166 | RNA | CCGACUUGCCAGUAUUGGCGAUGGCUGGAAGUUUGUCGG |
| SEQ ID NO: 167 | RNA | CGCAUUGCUAGUAUUGGCUUAGGCUAGAAGUGUUGCG |
| SEQ ID NO: 237 | RNA | CGACUUGCCAGUAUUGGCGAUGGCUGGAAGUUUGUCG |
| SEQ ID NO: 238 | RNA | CCGACUUGCGGGUAUUGGCGAUGGCCCGAAGUUUGUCGG |
| SEQ ID NO: 239 | RNA | CGACUUGCGGGUAUUGGCGAUGGCCCGAAGUUUGUCG |
| SEQ ID NO: 240 | RNA | CUGCCUUGCCAGUAUUGGCGAUGGCUGGAAGUUUGGCUG |
| SEQ ID NO: 241 | RNA | CUGCCUUGCGGGUAUUGGCGAUGGCCCGAAGUUUGGCUG |
| SEQ ID NO: 242 | RNA | GCCUUGCCAGUAUUGGCGAUGGCUGGAAGUUUGGC |
| SEQ ID NO: 243 | RNA | CCGACUUGCGGGUAUUGGCGUUGGCCCGAAGUUUGUCGG |
| SEQ ID NO: 244 | RNA | CGCCUUGCCAGUAUUGGCGAUGGCUGGAAGUUUGGCG |
| SEQ ID NO: 245 | RNA | CCGACUUGCCAGUAUAGGCUCAGGCUGGAAGUUUGUCGG |
| SEQ ID NO: 246 | RNA | CCGACUUGCCAGUAUUAGCUUAGGCUGGAAGUUUGUCGG |
| SEQ ID NO: 247 | RNA | CCGACUUGCCAGUAUUGGCCUAGGCUGGAAGUUUGUCGG |
| SEQ ID NO: 248 | RNA | CCGACUUGCCAGUAUAGGCUUAUGCUGGAAGUUUGUCGG |
| SEQ ID NO: 249 | RNA | CCGACUUGCCAGUAUUGGCGCUGGCUGGAAGUUUGUCGG |
| SEQ ID NO: 250 | RNA | CCGACUUGCCAGUAUUGGCGCAGGCUGGAAGUUUGUCGG |
| SEQ ID NO: 251 | RNA | CCGACUUGCCAGUAUUGGCGAAGGCUGGAAGUUUGUCGG |
| SEQ ID NO: 252 | RNA | CCGACUUGCCAGUAUUGGCUCUGGCUGGAAGUUUGUCGG |
| SEQ ID NO: 253 | RNA | CCGACUUGCCAGUAUUGGCUUAGGCUGGAAGUUUGUCGG |
| SEQ ID NO: 254 | RNA | CCGUUGUGGGUAUUGGCUUAGGCCCAAAGUUUCGG |
| SEQ ID NO: 255 | RNA | GCCUUGCGGGUAUUGGCGUUGGCCCGAAGUUUGGC |
| SEQ ID NO: 256 | RNA | GCCUUGCGGGUAUUGGCGAUGGCCCGAAGUUUGGC |
| SEQ ID NO: 257 | RNA | GCCUUGAGGGUAUUGGCGAUGGCCCUAAGUUUGGC |
| SEQ ID NO: 258 | RNA | GCCUUGUCCGUAUUGGCUUAGGCGGAAAGUUUGGC |
| SEQ ID NO: 259 | RNA | GCGGUUGCGGGUAUUGGCGAUGGCCCGAAGUUCCGC |
| SEQ ID NO: 260 | RNA | CCCUUGCCCGUAUUGGCUUAGGCGGGAAGUUUGGG |
| SEQ ID NO: 261 | RNA | GGCCUUGCCCGUAUUGGCUUAGGCGGGAAGUUUGGCC |
| SEQ ID NO: 262 | RNA | GGCCUUGCCCGUAUUGGCGAUGGCGGGAAGUUUGGCC |

TABLE 1-continued fD Aptamer Sequences

| SEQ ID NO. | Backbone | Sequence 5' to 3' |
|---|---|---|
| SEQ ID NO: 263 | RNA | CGACUUGCCAGUAUUGGCGAUGGCUG GAAGUUUGUCG |
| SEQ ID NO: 264 | RNA | CGCCUUGCCAGUAUUGGCUUAGGCUG GAAGUUUGGCG |
| SEQ ID NO: 265 | RNA | CGACUUGCCAGUAUUGGCUUAGGCUG GAAGUUUGUCG |
| SEQ ID NO: 266 | RNA | CCGCCUUGCCAGUAUUGGCGAUGGCU GGAAGUUUGGCGG |

TABLE 2 fD Aptamer Sequences

| SEQ ID NO. | Compound Name | Backbone | Sequence 5' to 3' |
|---|---|---|---|
| SEQ ID NO: 1 with modifications | C1 | RNA | GGGAGUGUGUACGAGGCAUUAGGCCG CCACCCAAACUGCAGUCCUCGUAAGUC UGCCUGGCGGCUUUGAUACUUGAUCG CCCUAGAAGC; where G is 2'F and A, C and U are 2'OMe modified RNA |
| SEQ ID NO: 2 with modifications | C2 | RNA | GGGAGUGUGUACGAGGCAUUAGUCCG CCGAAGUCUUUUGGCUCGGUUUUUUC AAGGUCGGCGGCUUUGAUACUUGAUC GCCCUAGAAGC; where G is 2'F and A, C and U are 2'OMe modified RNA |
| SEQ ID NO: 3 with modifications | C3 | RNA | GGGAGUGUGUACGAGGCAUUAGGCCG CCACCUCGUUUGAUUGCGGUUGUUCG GCCGCGGGCGGCUUUGAUACUUGAUC GCCCUAGAAGC; where G is 2'F and A, C and U are 2'OMe modified RNA |
| SEQ ID NO: 10 with modifications | 10FR14 | RNA | GGGAGUGUGUACGAGGCAUUAGGCCG CCUUGCCAGUAUUGGCUUAGGCUGGA AGUUUGGCGGCUUUGAUACUUGAUCG CCCUAGAAGC; where G is 2'F and A, C and U are 2'OMe modified RNA |
| SEQ ID NO: 267 with modifications | S31 | RNA | C6S-AGGCCGCCUUGCCAGUAUUGGCUUAG GCUGGAAGUUUGGCGGCUUidT; where G is 2'F and A, C and U are 2'OMe modified RNA, C6S represents a six-carbon disulfide linker, and idT represents a 3' inverted deoxythymidine residue. |
| SEQ ID NO: 268 with modifications | S32 | RNA | C6S-CCGCCUUGCCAGUAUUGGCUUAGGCU GGAAGUUUGGCGGidT; where G is 2'F and A, C and U are 2'OMe modified RNA, C6S represents a six-carbon disulfide linker, and idT represents a 3' inverted deoxythymidine residue. |
| SEQ ID NO: 269 with modifications | Aptamer 15 | RNA | C6NH$_2$-CCGCCUUGCCAGUAUUGGCUUAGGCU GGAAGUUUGGCGGidT; where G is 2'F and A, C and U are 2'OMe modified RNA, C6NH$_2$ represents a 6-carbon amino containing linker, and idT represents a 3' inverted deoxythymidine residue. |
| SEQ ID NO: 14 with modifications | Rd3-06 | RNA | CGCCUUGCAAGUAUUGGCUUUGGCUU GAAGUUUGGCGG; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 15 with modifications | Rd4-28 | RNA | CCGCCUUGCAAGUAUUGGCUUAGGCU UGAAGUUUGGCGG; where G is 2'F and A, C and U are 2'OMe modified RNA. |
| SEQ ID NO: 16 with modifications | Rd3-11 | RNA | CUGCCUUGCGGGUAUUGGCGUUGGCC CGAAGUUUGGCUG; where G is 2'F and A, C and U are 2'OMe modified RNA. |
| SEQ ID NO: 17 with modifications | Rd3-10 | RNA | CAGUCUUGCGAGUUUGGCUAAGCUUC GAAGUUUGGCUG; where G is 2'F and A, C and U are 2'OMe modified RNA. |
| SEQ ID NO: 18 with modifications | Rd4-42 | RNA | CCGCCUUGCGAGUAAUGGCGUAGGCU CGAAGUUGGGCGG; where G is 2'F and A, C and U are 2'OMe modified RNA. |
| SEQ ID NO: 19 with modifications | Rd3-18 | RNA | CCGCCUUGCGAGUAUUGGCUUAGGCU CGAAGUUUGGCGG; where G is 2'F and A, C and U are 2'OMe modified RNA. |
| SEQ ID NO: 20 with modifications | Rd4-02 | RNA | CCGGCUUGCGAGUAUUGGCUUAGGCU CGAAGUUUGCCGG; where G is 2'F and A, C and U are 2'OMe modified RNA. |
| SEQ ID NO: 21 with modifications | Rd4-46 | RNA | CCGCCUUGCGAGUAUUGGCUUUGGCU CGAAGUUUGUCUG; where G is 2'F and A, C and U are 2'OMe modified RNA. |
| SEQ ID NO: 22 with modifications | Rd3-21 | RNA | CCGCCUUGCGAGUAUUGGCGUUGGCU CGAAGUUUUCGG; where G is 2'F and A, C and U are 2'OMe modified RNA. |
| SEQ ID NO: 23 with modifications | Rd3-08 | RNA | UCACCUUGCCAUUAUUGGCUUAGGAU GGAAGUUUGGUGG; where G is 2'F and A, C and U are 2'OMe modified RNA. |
| SEQ ID NO: 24 with modifications | Rd3-22 | RNA | CCACCUUGCCAGUAUUGGCUUUGGCC GGAAGUUUGGUGG; where G is 2'F and A, C and U are 2'OMe modified RNA. |
| SEQ ID NO: 25 with modifications | Rd4-29 | RNA | CCACCUUGCCAGUAUUGGCUUAGGCU GGAAGUUUGGUGG; where G is 2'F and A, C and U are 2'OMe modified RNA. |
| SEQ ID NO: 26 with modifications | Rd3-35 | RNA | CCGCCUUGCCAGUAUUGGGUUUGGCU GGAAGUUUGGCGG; where G is 2'F and A, C and U are 2'OMe modified RNA. |
| SEQ ID NO: 27 with modifications | Rd3-24 | RNA | CCGCAUUGCCAGUAUUGGCUUCGGCU GGAAGUUUGCCGG; where G is 2'F and A, C and U are 2'OMe modified RNA. |
| SEQ ID NO: 28 with modifications | Rd3-01 | RNA | CCGCAUUGCCAGUAUAGGCUUAUGCU GGAAGUUUGCGG; where G is 2'F and A, C and U are 2'OMe modified RNA. |
| SEQ ID NO: 29 with modifications | Rd4-07 | RNA | CCGCGUUGCCAGUAUAGGCUUAGGCU GGAAGUUUCGCGG; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 30 with modifications | Rd3-47 | RNA | CGCAUUGCUAGUAUUGGCUUAGGCUAGAAGUGUUGCG; where G is 2'F and A, C and U are 2'OMe modified RNA. |
| SEQ ID NO: 31 with modifications | Rd3-31 | RNA | CUGCCUUGCCAGUAUUGGCUUAGGCUGGAAGUUUUGCGG; where G is 2'F and A, C and U are 2'OMe modified RNA. |
| SEQ ID NO: 32 with modifications | Rd4-18 | RNA | CCGGGUUGCCAGUAUUGGCUUAGGCUGGAAGUUUCGCGG; where G is 2'F and A, C and U are 2'OMe modified RNA. |
| SEQ ID NO: 33 with modifications | Rd4-03 | RNA | CCGACUUGCCAGUAUUGGCGUAGGCUGGAAGUUUGUCGG; where G is 2'F and A, C and U are 2'OMe modified RNA. |
| SEQ ID NO: 34 with modifications | Rd3-23 | RNA | CCGACUUGCCAGUAUUGGCGUAGGCUGGAAGUUUGCCGG; where G is 2'F and A, C and U are 2'OMe modified RNA. |
| SEQ ID NO: 35 with modifications | Rd4-24 | RNA | CCGACUUGCCAGUAUUGGCCUAGGCUGGAAGUUUGUCGG; where G is 2'F and A, C and U are 2'OMe modified RNA. |
| SEQ ID NO: 36 with modifications | Rd4-32 | RNA | UCGACUUGCCAGUAUUGGCUUAGGCUGGAAGUUUGUCGG; where G is 2'F and A, C and U are 2'OMe modified RNA. |
| SEQ ID NO: 37 with modifications | Rd3-39 | RNA | CGACUUGCCAGUAUUGGCUUAGUCUGGAAGUUUGUCG; where G is 2'F and A, C and U are 2'OMe modified RNA. |
| SEQ ID NO: 38 with modifications | Rd4-20 | RNA | CCGACUUGCCAGUGUUGGCUUUGGCUGGAAGUUUGUCGG; where G is 2'F and A, C and U are 2'OMe modified RNA. |
| SEQ ID NO: 39 with modifications | Rd4-38 | RNA | CCGACUUGCCAGUAUUGGCUUUGGCUGGAAGUUUGCCGG; where G is 2'F and A, C and U are 2'OMe modified RNA. |
| SEQ ID NO: 40 with modifications | Rd4-13 | RNA | CCGACUUGCCAGUAUUGGCUUAGGCUGGAAGUUUGCCGG; where G is 2'F and A, C and U are 2'OMe modified RNA. |
| SEQ ID NO: 41 with modifications | Rd4-37 | RNA | CGGCCUUGCCAGUAUUGGCUUUGGCUGGAAGUUUGGCCG; where G is 2'F and A, C and U are 2'OMe modified RNA. |
| SEQ ID NO: 42 with modifications | Rd3-03 | RNA | CGGCCUUGCAUGUAUUGGCUCAGGCAUGAAGUUUGUCCG; where G is 2'F and A, C and U are 2'OMe modified RNA. |
| SEQ ID NO: 43 with modifications | Rd4-25 | RNA | CGUGCUUGUCAGUAUUGGCGUUGGCUGAAAGUUUGCACG; where G is 2'F and A, C and U are 2'OMe modified RNA. |
| SEQ ID NO: 44 with modifications | Rd3-27 | RNA | CGUACUUGCCAGUAUUGGCGUAGGCUGGAAGUUUGUGCG; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 45 with modifications | Rd4-47 | RNA | CGGGCUUGCCAGUAUUAGGGUAGGCU GGAAGUUUGGCCG; where G is 2'F and A, C and U are 2'OMe modified RNA. |
| SEQ ID NO: 46 with modifications | Rd4-12 | RNA | CGGGCUUGCCAGUAUUGGCUUAGGCU GGAAGUUUGUCCG; where G is 2'F and A, C and U are 2'OMe modified RNA. |
| SEQ ID NO: 47 with modifications | Rd3-33 | RNA | GAGACUCGCCAGUAUAGGCUAAGGCU GGAAGUAUGUCUG; where G is 2'F and A, C and U are 2'OMe modified RNA. |
| SEQ ID NO: 48 with modifications | Rd4-39 | RNA | CUGACUUGCCAGUAUUGGCUUAGGCU GGAAGUUUGUCGG; where G is 2'F and A, C and U are 2'OMe modified RNA. |
| SEQ ID NO: 49 with modifications | Rd4-10 | RNA | CUGACUUGCCAGUAUUGGCUUAGGCU GGAAGUUUGUCAG; where G is 2'F and A, C and U are 2'OMe modified RNA. |
| SEQ ID NO: 50 with modifications | Rd3-25 | RNA | CUGACUUGCCAGUAUUAGCUUAGGCU GGAAGUUUGGCGG; where G is 2'F and A, C and U are 2'OMe modified RNA. |
| SEQ ID NO: 51 with modifications | Rd4-16 | RNA | CCGGCUUGCCAGUAUUGGCUUAGGCU GGAAGUUUGCCGG; where G is 2'F and A, C and U are 2'OMe modified RNA. |
| SEQ ID NO: 52 with modifications | Rd4-21 | RNA | CCGCCUUGCCAGUAUUGGCUUAGGCU GGAAGUUUGUCGG; where G is 2'F and A, C and U are 2'OMe modified RNA. |
| SEQ ID NO: 53 with modifications | Rd3-20 | RNA | CCGGCUUGCCAGUAUUGGCUCAGGCU GGAAGUUUGCCGG; where G is 2'F and A, C and U are 2'OMe modified RNA. |
| SEQ ID NO: 54 with modifications | Rd3-41 | RNA | CCGGCUUGCCAGUAUAGGCUCAGGCU GGAAGUUUGCCGG; where G is 2'F and A, C and U are 2'OMe modified RNA. |
| SEQ ID NO: 55 with modifications | Rd3-40 | RNA | UCGGCUUGCCAGUAUUGGCUUAGGCU GGAAGUUUGCCGG; where G is 2'F and A, C and U are 2'OMe modified RNA. |
| SEQ ID NO: 56 with modifications | Rd3-02 | RNA | CCGGCUUGCCAGUAUUGGCUUUGGCU GGAAGUUUGCCGG; where G is 2'F and A, C and U are 2'OMe modified RNA. |
| SEQ ID NO: 57 with modifications | Rd4-43 | RNA | CCGGCUUGCCAGUAUUGGCGUAGGCU GGAAGUUUGCCGG; where G is 2'F and A, C and U are 2'OMe modified RNA. |
| SEQ ID NO: 58 with modifications | Rd4-34 | RNA | CCGACUUGCCAGUAUUCGCUUAGGCG GGAAGUUUGCCGG; where G is 2'F and A, C and U are 2'OMe modified RNA. |
| SEQ ID NO: 59 with modifications | Rd4-04 | RNA | CCGACUUGCCAGUAUUGGCUUAGGCU GGAAGUUUGUCGG; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 60 with modifications | Rd3-36 | RNA | CGACUUGCCAGUAUUGGCUUAGGCUG GAAGUUUGUCG; where G is 2'F and A, C and U are 2'OMe modified RNA. |
| SEQ ID NO: 61 with modifications | Rd4-06 | RNA | CCGACUUGCCAGUAAUGGCUUAGGCU GGAAGUUUGUCGG; where G is 2'F and A, C and U are 2'OMe modified RNA. |
| SEQ ID NO: 62 with modifications | Rd3-13 | RNA | CCGACUUGCCAGUAUUGGCGAUGGCU GGAAGUUUGUCGG; where G is 2'F and A, C and U are 2'OMe modified RNA. |
| SEQ ID NO: 63 with modifications | Rd4-15 | RNA | CCGACUUGCCAGUAUUGGCUUUGGCU GGAAGUUUGUCGG; where G is 2'F and A, C and U are 2'OMe modified RNA. |
| SEQ ID NO: 64 with modifications | Rd3-16 | RNA | CCGCCUUGCCAGUAUUGGCUUAGGCU GGAAGUAUGGCGG; where G is 2'F and A, C and U are 2'OMe modified RNA. |
| SEQ ID NO: 65 with modifications | Rd4-01 | RNA | CCACCUUGCCAGUAUUGGCUUAGGCU GGAAGUGUGGUGG; where G is 2'F and A, C and U are 2'OMe modified RNA. |
| SEQ ID NO: 66 with modifications | Rd3-26 | RNA | ACACCUUGCGAGUAUUGGCUUAGGCU CGAAGUUUGGCGU; where G is 2'F and A, C and U are 2'OMe modified RNA. |
| SEQ ID NO: 67 with modifications | Rd3-07 | RNA | ACGCUUUGCCAGUAUUGGCUUAGGCU GGAAGUUUCGCGU; where G is 2'F and A, C and U are 2'OMe modified RNA. |
| SEQ ID NO: 68 with modifications | Rd4-23 | RNA | CCGCGUUGCCAGUAUUGGCUUUGGCU GGAAGUUUCGCGG; where G is 2'F and A, C and U are 2'OMe modified RNA. |
| SEQ ID NO: 69 with modifications | Rd4-26 | RNA | CCGCCUUGCCAGUAUUGGCUUAGGCU GGAAGUUUUGCGG; where G is 2'F and A, C and U are 2'OMe modified RNA. |
| SEQ ID NO: 70 with modifications | Rd4-30 | RNA | CCGCCUUGCCAGUAUUGGCUCAGGCU GGAAGUUUGGCGG; where G is 2'F and A, C and U are 2'OMe modified RNA. |
| SEQ ID NO: 71 with modifications | Rd4-41 | RNA | CCGCCUUGCCAGUAUUAGCGUAGGCU GGAAGUUUGGCGG; where G is 2'F and A, C and U are 2'OMe modified RNA. |
| SEQ ID NO: 72 with modifications | Rd4-11 | RNA | CCGCCUUGCAAGUAUUGGCGUUGGCU UGAAGUUUGGCGG; where G is 2'F and A, C and U are 2'OMe modified RNA. |
| SEQ ID NO: 73 with modifications | Rd3-43 | RNA | UCGCCUUGCAUGUAUUGGGUUUGGCA UGAAGUUUGGCGG; where G is 2'F and A, C and U are 2'OMe modified RNA. |
| SEQ ID NO: 74 with modifications | Rd3-28 | RNA | CCGCCUUGCAAGUAUAGGCUUAGGCU UAAGUUUGGGGG; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 75 with modifications | Rd3-34 | RNA | CAGCCAUGCAAGUAUUGGCUUAGGCUUGAAGUUCGGCUG; where G is 2'F and A, C and U are 2'OMe modified RNA. |
| SEQ ID NO: 76 with modifications | Rd4-19 | RNA | CAGCCGUGCUAGUAUUGGCAUUGGCUAGAAGUUAGGCUG; where G is 2'F and A, C and U are 2'OMe modified RNA. |
| SEQ ID NO: 77 with modifications | Rd3-44 | RNA | CGGGCUUGCCAGUAUUGGCGUUGGCUGGAAGUUUGCCCG; where G is 2'F and A, C and U are 2'OMe modified RNA. |
| SEQ ID NO: 78 with modifications | Rd3-14 | RNA | UGGGCUUGCCAGUAUUGGCUUAGGCUGGAAGUUUGCCCG; where G is 2'F and A, C and U are 2'OMe modified RNA. |
| SEQ ID NO: 79 with modifications | Rd3-15 | RNA | GGGCUUGCCAGUAUUGGCUUAGGCUGGAAGUUUGUCC; where G is 2'F and A, C and U are 2'OMe modified RNA. |
| SEQ ID NO: 80 with modifications | 10F/R-14 full length | RNA | GGGAGAUGGCGCUGAUCAGGCCGCCUUGCCAGUAUUGGCUUAGGCUGGAAGUUUGGCGGCUUUGAUACUUGAUCGCCCUAGAAGCA; where G is 2'F and A, C and U are 2'OMe modified RNA. |
| SEQ ID NO: 81 with modifications | Rd3-06 full length | RNA | GGGAGAUGGCGCUGAUCAGGUCGCCUUGCAAGUAUUGGCUUUGGCUUGAAGUUUGGCGGCCUUGAUACUUGAUCGCCCUAGAAGCA; where G is 2'F and A, C and U are 2'OMe modified RNA. |
| SEQ ID NO: 82 with modifications | Rd4-28 full length | RNA | GGGAGAUGGCGCUGAUCAGGCCGCCUUGCAAGUAUUGGCUUAGGCUUGAAGUUUGGCGGCUUUGAUACUUGAUCGCCCUAGAAGCA; where G is 2'F and A, C and U are 2'OMe modified RNA. |
| SEQ ID NO: 83 with modifications | Rd3-11 full length | RNA | GGGAGAUGGCGCUGAUCAGGCUGCCUUGCGGGUAUUGGCGUUGGCCCGAAGUUUGGCUGCUUUGAUACUUGAUCGCCCUAGAAGCA; where G is 2'F and A, C and U are 2'OMe modified RNA. |
| SEQ ID NO: 84 with modifications | Rd3-10 full length | RNA | GGGAGAUGGCGCUGAUCAGGCAGUCUUGCGAGUUUGGCUAAGCUUCGAAGUUUGGCUGCUUUGAUACUUGAUCGCCCUAGAAGCA; where G is 2'F and A, C and U are 2'OMe modified RNA. |
| SEQ ID NO: 85 with modifications | Rd4-42 full length | RNA | GGGAGAUGGCGCUGAUCAGGCCGCCUUGCGAGUAAUGGCGUAGGCUCGAAGUUUGGGCGGCUUUGAUACUUGAUCGCCCUAGAAGCA; where G is 2'F and A, C and U are 2'OMe modified RNA. |
| SEQ ID NO: 86 with modifications | Rd3-18 full length | RNA | GGGAGAUGGCGCUGAUCAGGCCGCCUUGCGAGUAUUGGCUUAGGCUCGAAGUUUUGGCGGCUUUGAUACUUGAUCGCCCUAGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 87 with modifications | Rd4-02 full length | RNA | GGGAGAUGGCGCUGAUCAGGCCGGCU UGCGAGUAUUGGCUUAGGCUCGAAGU UUGCCGGCUUUGAUACUUGAUCGCCC UAGAAGCA; where G is 2'F and A, C and U are 2'OMe modified RNA. |
| SEQ ID NO: 88 with modifications | Rd4-46 full length | RNA | GGGAGAUGGCGCUGAUCAGGCCGCCU UGCGAGUAUUGGCUUUGGCUCGAAGU UUGUCUGGUUGAUACUUGAUCGCCCU AGAAGCA; where G is 2'F and A, C and U are 2'OMe modified RNA. |
| SEQ ID NO: 89 with modifications | Rd3-21 full length | RNA | GGGAGAUGGCGCUGAUCAGGCCGCCU UGCGAGUAUUGGCGUUGGCUCGAAGU UUUUCGGCUUUGAUACUUGAUCGCCC UAGAAGCA; where G is 2'F and A, C and U are 2'OMe modified RNA. |
| SEQ ID NO: 90 with modifications | Rd3-08 full length | RNA | GGGAGAUGGCGCUGAUCAGGUCACCU UGCCAUUAUUGGCUUAGGAUGGAAGU UUGGUGGCUUGAUACUUGAUCGCCCU AGAAGCA; where G is 2'F and A, C and U are 2'OMe modified RNA. |
| SEQ ID NO: 91 with modifications | Rd3-22 full length | RNA | GGGAGAUGGCGCUGAUCAGGCCACCU UGCCAGUAUUGGCUUUGGCCGGAAGU UUGGUGGCUUUGAUACUUGAUCGCCC UAGAAGCA; where G is 2'F and A, C and U are 2'OMe modified RNA. |
| SEQ ID NO: 92 with modifications | Rd4-29 full length | RNA | GGGAGAUGGCGCUGAUCAGGCCACCU UGCCAGUAUUGGCUUAGGCUGGAAGU UUGGUGGCUUGUGAUACUUGAUCGCC CUAGAAGCA; where G is 2'F and A, C and U are 2'OMe modified RNA. |
| SEQ ID NO: 93 with modifications | Rd3-35 full length | RNA | GGGAGAUGGCGCUGAUCAGGCCGCCU UGCCAGUAUUGGGUUUGGCUGGAAGU UUGGCGGCUUUGAUACUUGAUCGCCC UAGAAGCA; where G is 2'F and A, C and U are 2'OMe modified RNA. |
| SEQ ID NO: 94 with modifications | Rd3-24 full length | RNA | GGGAGAUGGCGCUGAUCAGGCCGCAU UGCCAGUAUUGGCUUCGGCUGGAAGU UUGCCGGCUUUGAUACUUGAUCGCCC UAGAAGCA; where G is 2'F and A, C and U are 2'OMe modified RNA. |
| SEQ ID NO: 95 with modifications | Rd3-01 full length | RNA | GGGAGAUGGCGCUGAUCAGGCCGCAU UGCCAGUAUAGGCUUAUGCUGGAAGU UUUGCGGCUUUGAUACUUGAUCGCCC UAGAAGCA; where G is 2'F and A, C and U are 2'OMe modified RNA. |
| SEQ ID NO: 96 with modifications | Rd4-07 full length | RNA | GGGAGAUGGCGCUGAUCAGGCCGCGU UGCCAGUAUAGGCUUAGGCUGGAAGU UUCGCGGCUUUGAUACUUGAUCGCCC UAGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 97 with modifications | Rd3-47 full length | RNA | GGGAGAUGGCGCUGAUCAGGACGCAU UGCUAGUAUUGGCUUAGGCUAGAAGU GUUGCGGCUUUGAUACUUGAUCGCCC UAGAAGCA; where G is 2'F and A, C and U are 2'OMe modified RNA. |
| SEQ ID NO: 98 with modifications | Rd3-31 full length | RNA | GGGAGAUGGCGCUGAUCAGGCUGCCU UGCCAGUAUUGGCUUAGGCUGGAAGU UUUGCGGCUUUGAUACUUGAUCGCCC UAGAAGCA; where G is 2'F and A, C and U are 2'OMe modified RNA. |
| SEQ ID NO: 99 with modifications | Rd4-18 full length | RNA | GGGAGAUGGCGCUGAUCAGGCCGGGU UGCCAGUAUUGGCUUAGGCUGGAAGU UUCGCGGUUUUGAUACUUGAUCGCCC UAGAAGCA; where G is 2'F and A, C and U are 2'OMe modified RNA. |
| SEQ ID NO: 100 with modifications | Rd4-03 full length | RNA | GGGAGAUGGCGCUGAUCAGGCCGACU UGCCAGUAUUGGCGUAGGCUGGAAGU UUGUCGGCUUUGAUACUUGAUCGCCC UAGAAGCA; where G is 2'F and A, C and U are 2'OMe modified RNA. |
| SEQ ID NO: 101 with modifications | Rd3-23 full length | RNA | GGGAGAUGGCGCUGAUCAGGCCGACU UGCCAGUAUUGGCGUAGGCUGGAAGU UUGCCGGCUUUGAUACUUGAUCGCCC UAGAAGCA; where G is 2'F and A, C and U are 2'OMe modified RNA. |
| SEQ ID NO: 102 with modifications | Rd4-24 full length | RNA | GGGAGAUGGCGCUGAUCAGGCCGACU UGCCAGUAUUGGCCUAGGCUGGAAGU UUGUCGGCUUUGAUACUUGAUCGCCC UAGAAGCA; where G is 2'F and A, C and U are 2'OMe modified RNA. |
| SEQ ID NO: 103 with modifications | Rd4-32 full length | RNA | GGGAGAUGGCGCUGAUCAAGUCGACU UGCCAGUAUUGGCUUAGGCUGGAAGU UUGUCGGCUUUGAUACUUGAUCGCCC UAGAAGCA; where G is 2'F and A, C and U are 2'OMe modified RNA. |
| SEQ ID NO: 104 with modifications | Rd3-39 full length | RNA | GGGAGAUGGCGCUGAUCAGGACGACU UGCCAGUAUUGGCUUAGUCUGGAAGU UUGUCGGCUUUGAUACUUGAUCGCCC UAGAAGCA; where G is 2'F and A, C and U are 2'OMe modified RNA. |
| SEQ ID NO: 105 with modifications | Rd4-20 full length | RNA | GGGAGAUGGCGCUGAUCAGGCCGACU UGCCAGUGUUGGCUUUGGCUGGAAGU UUGUCGGCUUUGAUACUUGAUCGCCC UAGAAGCA; where G is 2'F and A, C and U are 2'OMe modified RNA. |
| SEQ ID NO: 106 with modifications | Rd4-38 full length | RNA | GGGAGAUGGCGCUGAUCAGGCCGACU UGCCAGUAUUGGCUUUGGCUGGAAGU UUGCCGGCUUUGAUACUUGAUCGCCC UAGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 107 with modifications | Rd4-13 full length | RNA | GGGAGAUGGCGCUGAUCAGGCCGACU UGCCAGUAUUGGCUUAGGCUGGAAGU UUGCCGGCUUUGAUACUUGAUCGCCC UAGAAGCA; where G is 2'F and A, C and U are 2'OMe modified RNA. |
| SEQ ID NO: 108 with modifications | Rd4-37 full length | RNA | GGGAGAUGGCGCUGAUCAGGCGGCCU UGCCAGUAUUGGCUUUGGCUGGAAGU UUGGCCGCUUUGAUACUUGAUCGCCC UAGAAGCA; where G is 2'F and A, C and U are 2'OMe modified RNA. |
| SEQ ID NO: 109 with modifications | Rd3-03 full length | RNA | GGGAGAUGGCGCUGAUCAGGCGGCCU UGCAUGUAUUGGCUCAGGCAUGAAGU UUGUCCGCUUUGAUACUUGAUCGCCC UAGAAGCA; where G is 2'F and A, C and U are 2'OMe modified RNA. |
| SEQ ID NO: 110 with modifications | Rd4-25 full length | RNA | GGGAGAUGGCGCUGAUCAGGCGUGCU UGUCAGUAUUGGCGUUGGCUGAAAGU UUGCACGCUUUGAUACUUGAUCGCCC UAGAAGCA; where G is 2'F and A, C and U are 2'OMe modified RNA. |
| SEQ ID NO: 111 with modifications | Rd3-27 full length | RNA | GGGAGAUGGCGCUGAUCAGGCGUACU UGCCAGUAUUGGCGUAGGCUGGAAGU UUGUGCGCUUUGAUACUUGAUCGCCC UAGAAGCA; where G is 2'F and A, C and U are 2'OMe modified RNA. |
| SEQ ID NO: 112 with modifications | Rd4-47 full length | RNA | GGGAGAUGGCGCUGAUCAGGCGGGCU UGCCAGUAUUAGGGUAGGCUGGAAGU UUGGCCGCUUUGAUACUUGAUCGCCC UAGAAGCA; where G is 2'F and A, C and U are 2'OMe modified RNA. |
| SEQ ID NO: 113 with modifications | Rd4-12 full length | RNA | GGGAGAUGGCGCUGAUCAGGCGGGCU UGCCAGUAUUGGCUUAGGCUGGAAGU UUGGCCGCUUUGAUACUUGAUCGCCC UAGAACA; where G is 2'F and A, C and U are 2'OMe modified RNA. |
| SEQ ID NO: 114 with modifications | Rd3-33 full length | RNA | GGGAGAUGGCGCUGAUCAGGGAGACU CGCCAGUAUAGGCUAAGGCUGGAAGU AUGUCUGCUUGAUACUUGAUCGCCCU AGAAGCA; where G is 2'F and A, C and U are 2'OMe modified RNA. |
| SEQ ID NO: 115 with modifications | Rd4-39 full length | RNA | GGGAGAUGGCGCUGAUCAGGCUGACU UGCCAGUAUUGGCUUAGGCUGGAAGU UUGUCGGCUUUGAUACUUGAUCGCCC UAGAAGCA; where G is 2'F and A, C and U are 2'OMe modified RNA. |
| SEQ ID NO: 116 with modifications | Rd4-10 full length | RNA | GGGAGAUGGCGCUGAUCAGGCUGACU UGCCAGUAUUGGCUUAGGCUGGAAGU UUGUCAGCUUUGAUACUUGAUCGCCC UAGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 117 with modifications | Rd3-25 full length | RNA | GGGAGAUGGCGCUGAUCAGGCUGACU UGCCAGUAUUAGCUUAGGCUGGAAGU UUGGCGGCUUUGAUACUUGAUCGCCC UAGAAGCA; where G is 2'F and A, C and U are 2'OMe modified RNA. |
| SEQ ID NO: 118 with modifications | Rd4-16 full length | RNA | GGGAGAUGGCGCUGAUCAGGCCGGCU UGCCAGUAUUGGCUUAGGCUGGAAGU UUGCCGGCUUUGAUACUUGAUCGCCC UAGAAGCA; where G is 2'F and A, C and U are 2'OMe modified RNA. |
| SEQ ID NO: 119 with modifications | Rd4-21 full length | RNA | GGGAGAUGGCGCUGAUCAGGCCGCCU UGCCAGUAUUGGCUUAGGCUGGAAGU UUGUCGGCUUUGAUACUUGAUCGCCC UAGAAGCA; where G is 2'F and A, C and U are 2'OMe modified RNA. |
| SEQ ID NO: 120 with modifications | Rd3-20 full length | RNA | GGGAGAUGGCGCUGAUCAGGCCGGCU UGCCAGUAUUGGCUCAGGCUGGAAGU UUGCCGGCUUUGAUACUUGAUCGCCC UAGAAGCA; where G is 2'F and A, C and U are 2'OMe modified RNA. |
| SEQ ID NO: 121 with modifications | Rd3-41 full length | RNA | GGGAGAUGGCGCUGAUCAGGCCGGCU UGCCAGUAUAGGCUCAGGCUGGAAGU UUGCCGGCUUUGAUACUUGAUCGCCC UAGAAGCA; where G is 2'F and A, C and U are 2'OMe modified RNA. |
| SEQ ID NO: 122 with modifications | Rd3-40 full length | RNA | GGGAGAUGGCGCUGAUCAGGUCGGCU UGCCAGUAUUGGCUUAGGCUGGAAGU UUGCCGGCUUUGAUACUUGAUCGCCC UAGAAGCA; where G is 2'F and A, C and U are 2'OMe modified RNA. |
| SEQ ID NO: 123 with modifications | Rd3-02 full length | RNA | GGGAGAUGGCGCUGAUCAGGCCGGCU UGCCAGUAUUGGCUUUGGCUGGAAGU UUGCCGGCUUUGAUACUUGAUCGCCC UAGAAGCA; where G is 2'F and A, C and U are 2'OMe modified RNA. |
| SEQ ID NO: 124 with modifications | Rd4-43 full length | RNA | GGGAGAUGGCGCUGAUCAGGCCGGCU UGCCAGUAUUGGCGUAGGCUGGAAGU UUGCCGGCUUUGAUACUUGAUCGCCC UAGAAGCA; where G is 2'F and A, C and U are 2'OMe modified RNA. |
| SEQ ID NO: 125 with modifications | Rd4-34 full length | RNA | GGGAGAUGGCGCUGAUCAGGCCGACU UGCCAGUAUUCGCUUAGGCGGGAAGU UUGCCGGCUUUGAUACUUGAUCGCCC UAGAAGCA; where G is 2'F and A, C and U are 2'OMe modified RNA. |
| SEQ ID NO: 126 with modifications | Rd4-04 full length | RNA | GGGAGAUGGCGCUGAUCAGGCCGACU UGCCAGUAUUGGCUUAGGCUGGAAGU UUGUCGGCUUUGAUACUUGAUCGCCC UAGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 127 with modifications | Rd3-36 full length | RNA | GGGAGAUGGCGCUGAUCAGGCCGACUUGCCAGUAUUGGCUUAGGCUGGAAGUUUGUCGCUUUGAUACUUGAUCGCCCUAGAAGCA; where G is 2'F and A, C and U are 2'OMe modified RNA. |
| SEQ ID NO: 128 with modifications | Rd4-06 full length | RNA | GGGAGAUGGCGCUGAUCAGGCCGACUUGCCAGUAAUGGCUUAGGCUGGAAGUUUGUCGGCUUUGAUACUUGAUCGCCCUAGAAGCA; where G is 2'F and A, C and U are 2'OMe modified RNA. |
| SEQ ID NO: 129 with modifications | Rd3-13 full length | RNA | GGGAGAUGGCGCUGAUCAGGCCGACUUGCCAGUAUUGGCGAUGGCUGGAAGUUUGUCGGCUUUGAUACUUGAUCGCCCUAGAAGCA; where G is 2'F and A, C and U are 2'OMe modified RNA. |
| SEQ ID NO: 130 with modifications | Rd4-15 full length | RNA | GGGAGAUGGCGCUGAUCAGGCCGACUUGCCAGUAUUGGCUUUGGCUGGAAGUUUGUCGGCUUUGAUACUUGAUCGCCCUAGAAGCA; where G is 2'F and A, C and U are 2'OMe modified RNA. |
| SEQ ID NO: 131 with modifications | Rd3-16 full length | RNA | GGGAGAUGGCGCUGAUCAGGCCGCCUUGCCAGUAUUGGCUUAGGCUGGAAGUAUGGCGGCUUUGAUACUUGAUCGCCCUAGAAGCA; where G is 2'F and A, C and U are 2'OMe modified RNA. |
| SEQ ID NO: 132 with modifications | Rd4-01 full length | RNA | GGAGAUGGCGCUGAUCAGGCCACCUUGCCAGUAUUGGCUUAGGCUGGAAGUGUGGUGGCUUUGAUACUUGAUCGCCCUAGAAGCA; where G is 2'F and A, C and U are 2'OMe modified RNA. |
| SEQ ID NO: 133 with modifications | Rd3-26 full length | RNA | GGGAGAUGGCGCUGAUCAGGACACCUUGCGAGUAUUGGCUUAGGCUCGAAGUUUGGCGUCUUUGAUACUUGAUCGCCCUAGAAGCA; where G is 2'F and A, C and U are 2'OMe modified RNA. |
| SEQ ID NO: 134 with modifications | Rd3-07 full length | RNA | GGGAGAUGGCGCUGAUCAGGACGCUUUGCCAGUAUUGGCUUAGGCUGGAAGUUUCGCGUCUUUGAUACUUGAUCGCCCUAGAAGCA; where G is 2'F and A, C and U are 2'OMe modified RNA. |
| SEQ ID NO: 135 with modifications | Rd4-23 full length | RNA | GGGAGAUGGCGCUGAUCAGGCCGCGUUGCCAGUAUUGGCUUUGGCUGGAAGUUUCGCGGCUUUGAUACUUGAUCGCCCUAGAAGCA; where G is 2'F and A, C and U are 2'OMe modified RNA. |
| SEQ ID NO: 136 with modifications | Rd4-26 full length | RNA | GGGAGAUGGCGCUGAUCAGGCCGCCUUGCCAGUAUUGGCUUAGGCUGGAAGUUUUGCGGCUUUGAUACUUGAUCGCCCUAGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 137 with modifications | Rd4-30 full length | RNA | GGGAGAUGGCGCUGAUCAGGCCGCCU UGCCAGUAUUGGCUCAGGCUGGAAGU UUGGCGGCUUUGAUACUUGAUCGCCC UAGAAGCA; where G is 2'F and A, C and U are 2'OMe modified RNA. |
| SEQ ID NO: 138 with modifications | Rd4-41 full length | RNA | GGGAGAUGGCGCUGAUCAGGCCGCCU UGCCAGUAUUAGCGUAGGCUGGAAGU UUGGCGGCUUUGAUACUUGAUCGCCC UAGAAGCA; where G is 2'F and A, C and U are 2'OMe modified RNA. |
| SEQ ID NO: 139 with modifications | Rd4-11 full length | RNA | GGGAGAUGGCGCUGAUCAGGCCGCCU UGCAAGUAUUGGCGUUGGCUUGAAGU UUGGCGGCUUUGAUACUUGAUCGCCC UAGAAGCA; where G is 2'F and A, C and U are 2'OMe modified RNA. |
| SEQ ID NO: 140 with modifications | Rd3-43 full length | RNA | GGGAGAUGGCGCUGAUCAGGUCGCCU UGCAUGUAUUGGGUUUGGCAUGAAGU UUGGCGGCUUUGAUACUUGAUCGCCC UAGAAGCA; where G is 2'F and A, C and U are 2'OMe modified RNA. |
| SEQ ID NO: 141 with modifications | Rd3-28 full length | RNA | GGGAGAUGGCGCUGAUCAGGCCGCCU UGCAAGUAUAGGCUUAGGCUUAAGUU UGGGGGCUUUGAUACUUGAUCGCCCU AGAAGCA; where G is 2'F and A, C and U are 2'OMe modified RNA. |
| SEQ ID NO: 142 with modifications | Rd3-34 full length | RNA | GGGAGAUGGCGCUGAUCAGGCAGCCA UGCAAGUAUUGGCUUAGGCUUGAAGU UCGGCUGCUUUGAUACUUGAUCGCCC UAGAAGCA; where G is 2'F and A, C and U are 2'OMe modified RNA. |
| SEQ ID NO: 143 with modifications | Rd4-19 full length | RNA | GGGAGAUGGCGCUGAUCAGGCAGCCG UGCUAGUAUUGGCAUUGGCUAGAAGU UAGGCUGCUUUGAUACUUGAUCGCCC UAGAAGCA; where G is 2'F and A, C and U are 2'OMe modified RNA. |
| SEQ ID NO: 144 with modifications | Rd3-44 full length | RNA | GGGAGAUGGCGCUGAUCAGGCGGGCU UGCCAGUAUUGGCGUUGGCUGGAAGU UUGCCCGCUUUGAUACUUGAUCGCCC UAGAAGCA; where G is 2'F and A, C and U are 2'OMe modified RNA. |
| SEQ ID NO: 145 with modifications | Rd3-14 full length | RNA | GGGAGAUGGCGCUGAUCAGGUGGGCU UGCCAGUAUUGGCUUAGGCUGGAAGU UUGCCCGCUUUGAUACUUGAUCGCCC UAGAAGCA; where G is 2'F and A, C and U are 2'OMe modified RNA. |
| SEQ ID NO: 146 with modifications | Rd3-15 full length | RNA | GGGAGAUGGCGCUGAUCAGGGGGCUU GCCAGUAUUGGCUUAGGCUGGAAGUU UGUCCGCUUUGAUACUUGAUCGCCCU AGAAGCA; where G is 2'F and A, C and U are 2'OMe modified RNA. |

TABLE 2-continued fD Aptamer Sequences

| SEQ ID NO. | Compound Name | Backbone | Sequence 5' to 3' |
|---|---|---|---|
| SEQ ID NO: 270 with modifications | Aptamer 16 | RNA | C6NH$_2$-CGCCUUGCCAGUAUUGGCUUAGGCUGGAAGUUUGGCG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 271 with modifications | Aptamer 17 | RNA | C6NH$_2$-GCCUUGCCAGUAUUGGCUUAGGCUGGAAGUUUGGC-idT; where G is 2'F and A, C and U are 2'OMe modified RNA, C6NH$_2$ represents a six-carbon amino containing linker, and idT represents a 3' inverted deoxythymidine residue. |
| SEQ ID NO: 272 with modifications | Aptamer 18 | RNA | C6NH$_2$-CCGCCUUGCAGUAUUGGCUUAGGCUGAAGUUUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 273 with modifications | Aptamer 19 | RNA | C6NH$_2$-CCGCCUUGCCAGAUUGGCUUAGCUGGAAGUUUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 274 with modifications | Aptamer 20 | RNA | C6NH$_2$-CCGCCUUGAAGUAUUGGCUUAGGCUUAAGUUUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 275 with modifications | Aptamer 21 | RNA | C6NH$_2$-CCGCCUUGCCAGUAUUGGGCUGGAAGUUUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 276 with modifications | Aptamer 22 | RNA | C6NH$_2$-CCGCCUUGCCAGUAUUGGCGGCUGGAAGUUUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NOs: 154 and 318 with modifications | Aptamer 23 | RNA | C6NH$_2$-CCGCCUUGCCAGUAUUG[I-18]GGCUGGAAGUUUGGCGG-idT; where G is 2'F and A, C and U are 2'OMe modified RNA, [I-18] represents a hexaethylene glycol spacer, C6NH$_2$ represents a six-carbon amino containing linker, and idT represents a 3' inverted deoxythymidine residue. |
| SEQ ID NOs: 155 and 318 with modifications | Aptamer 24 | RNA | C6NH$_2$-CCGCCUUGCCAGUAUUG[I-9]GGCUGGAAGUUUGGCGG-idT; where G is 2'F and A, C and U are 2'OMe modified RNA, [I-9] represents a 9-carbon spacer, C6NH$_2$ represents a six-carbon amino containing linker, and idT represents a 3' inverted deoxythymidine residue. |

TABLE 2-continued fD Aptamer Sequences

| SEQ ID NO. | Compound Name | Backbone | Sequence 5' to 3' |
|---|---|---|---|
| SEQ ID NOs: 156 and 318 with modifications | Aptamer 25 | RNA | C6NH$_2$-CCGCCUUGCCAGUAUUGGC[I-9]GGCUGGAAGUUUGGCGG-idT; where G is 2'F and A, C and U are 2'OMe modified RNA, [I-9] represents a 9-carbon spacer, C6NH$_2$ represents a six-carbon amino containing linker, and idT represents a 3' inverted deoxythymidine residue. |
| SEQ ID NO: 277 with modifications | Aptamer 26 | RNA | C6NH$_2$-CCGCCUUGCCAGUAUUGGCUUAGGCUGGAAGUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 278 with modifications | Aptamer 27 | RNA | C6NH$_2$-CCGCCUUGCCAGUAUUGGCUUAGGCUGGAAGUUGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 159 with modifications | Aptamer 28 | RNA | C6NH$_2$-CCGCCUUGCCAGUAUUGGCUUAGGCUGGAAGU[I-6]GGCGG-idT; where G is 2'F and A, C and U are 2'OMe modified RNA, [I-6] represents a 6-carbon spacer, C6NH$_2$ represents a six-carbon amino containing linker, and idT represents a 3' inverted deoxythymidine residue. |
| SEQ ID NO: 279 with modifications | Aptamer 33 | RNA | C6NH$_2$-CAGCCAUGCAAGUAUUGGCUUAGGCUUGAAGUUCGGCUG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 280 with modifications | Aptamer 34 | RNA | C6NH$_2$-CAGCCGUGCUAGUAUUGGCAUUGGCUAGAAGUUAGGCUG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 281 with modifications | Aptamer 35 | RNA | C6NH$_2$-CCGCCUUGCGAGUAAUGGCGUAGGCUCGAAGUUGGGCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 282 with modifications | Aptamer 36 | RNA | C6NH$_2$-CCGACUUGCCAGUGUUGGCUUUGGCUGGAAGUUUGUCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 283 with modifications | Aptamer 37 | RNA | C6NH$_2$-CAGUCUUGCGAGUUUGGCUAAGCUUCGAAGUUUGGCUG-idT; where G is 2'F and A, C and U are 2'OMe modified RNA, C6NH$_2$ represents a six-carbon amino containing linker, and idT represents a 3' inverted deoxythymidine residue. |

TABLE 2-continued fD Aptamer Sequences

| SEQ ID NO. | Compound Name | Backbone | Sequence 5' to 3' |
|---|---|---|---|
| SEQ ID NO: 284 with modifications | Aptamer 38 | RNA | C6NH$_2$-CUGCCUUGCGGGUAUUGGCGUUGGCCCGAAGUUUGGCUG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 285 with modifications | Aptamer 39 | RNA | C6NH$_2$-CCGACUUGCCAGUAUUGGCGAUGGCUGGAAGUUUGUCGG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 286 with modifications | Aptamer 40 | RNA | C6NH$_2$-CGCAUUGCUAGUAUUGGCUUAGGCUAGAAGUGUUGCG-idT; where G is 2'F and A, C and U are 2'OMe modified RNA, C6NH$_2$ represents a six-carbon amino containing linker, and idT represents a 3' inverted deoxythymidine residue. |
| SEQ ID NO: 287 with modifications | Aptamer 53 | RNA | C6NH$_2$-CGACUUGCCAGUAUUGGCGAUGGCUGGAAGUUUGUCG-idT; where G is 2'F and A, C and U are 2'OMe modified RNA; C6NH$_2$ represents a hexylamine linker; and idT represents a 3' inverted deoxythymidine residue. |
| SEQ ID NO: 288 with modifications | Aptamer 54 | RNA | C6NH$_2$-CCGACUUGCGGGUAUUGGCGAUGGCCCGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 289 with modifications | Aptamer 55 | RNA | C6NH$_2$-CGACUUGCGGGUAUUGGCGAUGGCCCGAAGUUUGUCG-idT; where G is 2'F and A, C and U are 2'OMe modified RNA; C6NH$_2$ represents a hexylamine linker; and idT represents a 3' inverted deoxythymidine residue. |
| SEQ ID NO: 290 with modifications | Aptamer 56 | RNA | C6NH$_2$-CUGCCUUGCCAGUAUUGGCGAUGGCUGGAAGUITUGGCUG-idT; where G is 2'F and A, C and U are 2'OMe modified RNA; C6NH$_2$ represents a hexylamine linker; and idT represents a 3' inverted deoxythymidine residue. |
| SEQ ID NO: 291 with modifications | Aptamer 57 | RNA | C6NH$_2$-CUGCCUUGCGGGUAUUGGCGAUGGCCCGAAGUUUGGCUG-idT; where G is 2'F and A, C and U are 2'OMe modified RNA; C6NH$_2$ represents a hexylamine linker; and idT represents a 3' inverted deoxythymidine residue. |
| SEQ ID NO: 292 with modifications | Aptamer 58 | RNA | C6NH$_2$-GCCUUGCCAGUAUUGGCGAUGGCUGGAAGUUUGGC-idT; where G is 2'F and A, C and U are 2'OMe modified RNA; C6NH$_2$ represents a hexylamine linker; and idT represents a 3' inverted deoxythymidine residue. |

TABLE 2-continued fD Aptamer Sequences

| SEQ ID NO. | Compound Name | Backbone | Sequence 5' to 3' |
|---|---|---|---|
| SEQ ID NO: 293 with modifications | Aptamer 59 | RNA | C6NH$_2$-CCGACUUGCGGGUAUUGGCGUUGGCCCGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 294 with modifications | Aptamer 60 | RNA | C6NH$_2$-CGCCUUGCCAGUAUUGGCGAUGGCUGGAAGUUUGGCG-idT; where G is 2'F and A, C and U are 2'OMe modified RNA; C6NH$_2$ represents a hexylamine linker; and idT represents a 3' inverted deoxythymidine residue. |
| SEQ ID NO: 295 with modifications | Aptamer 62 | RNA | C6NH$_2$-CCGACUUGCCAGUAUAGGCUCAGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 296 with modifications | Aptamer 64 | RNA | C6NH$_2$-CCGACUUGCCAGUAUUAGCUUAGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 297 with modifications | Aptamer 66 | RNA | C6NH$_2$-CCGACUUGCCAGUAUUGGCCUAGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 298 with modifications | Aptamer 67 | RNA | C6NH$_2$-CCGACUUGCCAGUAUAGGCUUAUGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 299 with modifications | Aptamer 68 | RNA | C6NH$_2$-CCGACUUGCCAGUAUUGGCGCUGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 300 with modifications | Aptamer 69 | RNA | C6NH$_2$-CCGACUUGCCAGUAUUGGCGCAGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 301 with modifications | Aptamer 71 | RNA | C6NH$_2$-CCGACUUGCCAGUAUUGGCGAAGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |

TABLE 2-continued fD Aptamer Sequences

| SEQ ID NO. | Compound Name | Backbone | Sequence 5' to 3' |
|---|---|---|---|
| SEQ ID NO: 302 with modifications | Aptamer 72 | RNA | C6NH$_2$-CCGACUUGCCAGUAUUGGCUCUGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 269 with modifications | Aptamer 74 | RNA | C6NH$_2$-CC<u>G</u>CCUUGCCAGUAUUGGCUUAGGCUGGAAGUUU<u>GGCG</u>G-idT; where G is 2'F, and <u>G</u>, A, C and U are 2'OMe modified RNA, C6NH$_2$ represents a six-carbon amino containing linker, and idT represents a 3' inverted deoxythymidine residue. |
| SEQ ID NO: 285 with modifications | Aptamer 76 | RNA | C6NH$_2$-CC<u>G</u>ACUUGCCAGUAUUGGC<u>G</u>AUGGCUGGAAGUUU<u>G</u>UC<u>G</u>G-idT; where G is 2'F, and <u>G</u>, A, C and U are 2'OMe modified RNA, C6NH$_2$ represents a six-carbon amino containing linker, and idT represents a 3' inverted deoxythymidine residue. |
| SEQ ID NO: 303 with modifications | Aptamer 88 | RNA | C6NH$_2$-CCGACUUGCCAGUAUUGGCUUAGGCUGGAAGUUUGUCGG-idT; where G is 2'F and A, C and U are 2'OMe modified RNA; C6NH$_2$ represents a hexylamine linker; and idT represents a 3' inverted deoxythymidine residue. |
| SEQ ID NO: 304 with modifications | Aptamer 90 | RNA | C6NH$_2$-CCGUUGUGGGUAUUGGCUUAGGCCCAAGUUUCGG-idT; where G is 2'F and A, C and U are 2'OMe modified RNA; C6NH$_2$ represents a hexylamine linker; and idT represents a 3' inverted deoxythymidine residue. |
| SEQ ID NO: 305 with modifications | Aptamer 91 | RNA | C6NH$_2$-GCCUUGCGGGUAUUGGCGUUGGCCCGAAGUUUGGC-idT; where G is 2'F and A, C and U are 2'OMe modified RNA; C6NH$_2$ represents a hexylamine linker; and idT represents a 3' inverted deoxythymidine residue. |
| SEQ ID NO: 306 with modifications | Aptamer 92 | RNA | C6NH$_2$-GCCUUGCGGGUAUUGGCGAUGGCCCGAAGUUUGGC-idT; where G is 2'F and A, C and U are 2'OMe modified RNA; C6NH$_2$ represents a hexylamine linker; and idT represents a 3' inverted deoxythymidine residue. |
| SEQ ID NO: 307 with modifications | Aptamer 93 | RNA | C6NH$_2$-GCCUUGAGGGUAUUGGCGAUGGCCCUAAGUUUGGC-idT; where G is 2'F and A, C and U are 2'OMe modified RNA; C6NH$_2$ represents a hexylamine linker; and idT represents a 3' inverted deoxythymidine residue. |
| SEQ ID NO: 308 with modifications | Aptamer 94 | RNA | C6NH$_2$-GCCCUUGUCCGUAUUGGCUUAGGCGGAAAGUUUGGGC-idT; where G is 2'F and A, C and U are 2'OMe modified RNA; C6NH$_2$ represents a hexylamine linker; and idT represents a 3' inverted deoxythymidine residue. |

TABLE 2-continued fD Aptamer Sequences

| SEQ ID NO. | Compound Name | Backbone | Sequence 5' to 3' |
|---|---|---|---|
| SEQ ID NO: 309 with modifications | Aptamer 95 | RNA | C6NH$_2$-GCGGUUGCGGGUAUUGGCGAUGGCCCGAAGUUUCCGC-idT; where G is 2'F and A, C and U are 2'OMe modified RNA; C6NH$_2$ represents a hexylamine linker; and idT represents a 3' inverted deoxythymidine residue. |
| SEQ ID NO: 310 with modifications | Aptamer 96 | RNA | C6NH$_2$-CCCUUGCCCGUAUUGGCUUAGGCGGGAAGUUUGGG-idT; where G is 2'F and A, C and U are 2'OMe modified RNA; C6NH$_2$ represents a hexylamine linker; and idT represents a 3' inverted deoxythymidine residue. |
| SEQ ID NO: 311 with modifications | Aptamer 97 | RNA | C6NH$_2$-GGCCUUGCCCGUAUUGGCUUAGGCGGGAAGUUUGGCC-idT; where G is 2'F and A, C and U are 2'OMe modified RNA; C6NH$_2$ represents a hexylamine linker; and idT represents a 3' inverted deoxythymidine residue. |
| SEQ ID NO: 312 with modifications | Aptamer 98 | RNA | C6NH$_2$-GGCCUUGCCCGUAUUGGCGAUGGCGGGAAGUUUGGCC-idT; where G is 2'F and A, C and U are 2'OMe modified RNA; C6NH$_2$ represents a hexylamine linker; and idT represents a 3' inverted deoxythymidine residue. |
| SEQ ID NO: 294 with modifications | Aptamer 99 | RNA | C6NH$_2$-CGCCUUGCCAGUAUUGGCGAUGGCUGGAAGUUUGGCG-idT; where G is 2'F, and G, A, C and U are 2'OMe modified RNA, C6NH$_2$ represents a six-carbon amino containing linker, and idT represents a 3' inverted deoxythymidine residue. |
| SEQ ID NO: 313 with modifications | Aptamer 102 | RNA | C6NH$_2$-CGACUUGCCAGUAUUGGCGAUGGCUGGAAGUUUGUCG-idT; where G is 2'F, and G, A, C and U are 2'OMe modified RNA, C6NH$_2$ represents a six-carbon amino containing linker, and idT represents a 3' inverted deoxythymidine residue. |
| SEQ ID NO: 314 with modifications | Aptamer 104 | RNA | C6NH$_2$-CGCCUUGCCAGUAUUGGCUUAGGCUGGAAGUUUGGCG-idT; where G is 2'F, and G, A, C and U are 2'OMe modified RNA, C6NH$_2$ represents a six-carbon amino containing linker, and idT represents a 3' inverted deoxythymidine residue. |
| SEQ ID NO: 303 with modifications | Aptamer 106 | RNA | C6NH$_2$-CCGACUUGCCAGUAUUGGCUUAGGCUGGAAGUUUGUCGG-idT; where G is 2'F, and G, A, C and U are 2'OMe modified RNA, C6NH$_2$ represents a six-carbon amino containing linker, and idT represents a 3' inverted deoxythymidine residue. |
| SEQ ID NO: 315 with modifications | Aptamer 107 | RNA | C6NH$_2$-CGACUUGCCAGUAUUGGCUUAGGCUGGAAGUUUGUCG-idT; where G is 2'F, and G, A, C and U are 2'OMe modified RNA, C6NH$_2$ represents a six-carbon amino containing linker, and idT represents a 3' inverted deoxythymidine residue. |

TABLE 2-continued fD Aptamer Sequences

| SEQ ID NO. | Compound Name | Backbone | Sequence 5' to 3' |
|---|---|---|---|
| SEQ ID NO: 306 with modifications | Aptamer 108 | RNA | C6NH₂-GCCUUGCGGGUAUUGGCGAUGGCCCGAAGUUUGGC-idT; where G is 2'F, and G, A, C and U are 2'OMe modified RNA, C6NH₂ represents a six-carbon amino containing linker, and idT represents a 3' inverted deoxythymidine residue. |
| SEQ ID NO: 312 with modifications | Aptamer 109 | RNA | C6NH₂-GGCCUUGCCCGUAUUGGCGAUGGCGGGAAGUUUGGCC-idT; where G is 2'F, and G, A, C and U are 2'OMe modified RNA, C6NH₂ represents a six-carbon amino containing linker, and idT represents a 3' inverted deoxythymidine residue. |
| SEQ ID NO: 316 with modifications | Aptamer 116 | RNA | C6NH₂-CCGCCUUGCCAGUAUUGGCGAUGGCUGGAAGUUUGGCGG-idT; where G is 2'F, and G, A, C and U are 2'OMe modified RNA, C6NH₂ represents a six-carbon amino containing linker, and idT represents a 3' inverted deoxythymidine residue. |
| SEQ ID NO: 269 with modifications | Aptamer 1721 | RNA | C6SH-CCGCCUUGCCAGUAUUGGCUUAGGCUGGAAGUHUGGCGG-idT; where G is 2'F, and G, A, C and U are 2'OMe modified RNA, C6SH represents a six-carbon thiol linker, and idT represents a 3' inverted deoxythymidine residue. |
| SEQ ID NO: 269 with modifications | Aptamer 1722 | RNA | C6SH-CCGCCUUGCCAGUAUUGGCUUAGGCUGGAAGUUUGGCGG-idT; where G is 2'F, and G, A, C and U are 2'OMe modified RNA, C6SH represents a six-carbon thiol linker, and idT represents a 3' inverted deoxythymidine residue. |
| SEQ ID NO: 269 with modifications | Aptamer 1723 | RNA | C6SH-CCGCCUUGCCAGUAUUGGCUUAGGCUGGAAGUUUGGCGG-idT; where G is 2'F, and G, A, C and U are 2'OMe modified RNA, C6SH represents a six-carbon thiol linker, and idT represents a 3' inverted deoxythymidine residue. |
| SEQ ID NO: 269 with modifications | Aptamer 1724 | RNA | C6SH-CCGCCUUGCCAGUAUUGGCUUAGGCUGGAAGUUUGGCGG-idT; where G is 2'F, and G, A, C and U are 2'OMe modified RNA, C6SH represents a six-carbon thiol linker, and idT represents a 3' inverted deoxythymidine residue. |

In some cases, an aptamer of the disclosure has a nucleic acid sequence that comprises SEQ ID NOs:13 or 269. In some cases, an aptamer having a nucleic acid sequence comprising SEQ ID NOs:13 or 269 inhibits a function associated with fD. In some cases, an aptamer having a nucleic acid sequence comprising SEQ ID NOs:13 or 269 binds to and/or blocks access to the active site of fD. In some cases, an aptamer having a nucleic acid sequence comprising SEQ ID NOs:13 or 269 binds to and/or blocks access to the exosite of fD. In some cases, an aptamer having a nucleic acid sequence comprising SEQ ID NOs:13 or 269 prevents or reduces binding of pre-formed C3bB complex to fD.

In some aspects, an aptamer of the disclosure has a nucleic acid sequence comprising any one of SEQ ID NOs:13, 165, 166, 244, 253, 256, 262, 269, 284, 285, 294, 303, 306, and 312, or having at least 80% sequence identity to any one of SEQ ID NOs:13, 165, 166, 244, 253, 256, 262, 269, 284, 285, 294, 303, 306, and 312. In some cases, the nucleic acid sequence comprises one or more modified nucleotides. In some cases, at least 50% of said nucleic acid sequence comprises the one or more modified nucleotides. In some cases, the one or more modified nucleotides comprises a 2'F-modified nucleotide, a 2'OMe-modified nucleotide, or a combination thereof. In some cases, the one or more modified nucleotides are selected from the group consisting of: 2'F-G, 2'OMe-G, 2'OMe-U, 2'OMe-A, 2'OMe-C, an inverted deoxythymidine at the 3' terminus, and any combination thereof. In some cases, aptamer is selected from the group consisting of: Aptamer 76 as described in Table 2, Aptamer 116 as described in Table 2, Aptamer 102 as described in Table 2, Aptamer 104 as described in Table 2, Aptamer 106 as described in Table 2, Aptamer 108 as described in Table 2, Aptamer 107 as described in Table 2, Aptamer 109 as described in Table 2, and Aptamer 99 as described in Table 2. In some cases, the aptamer is conjugated to a polyethylene glycol (PEG) molecule. In some cases, the PEG molecule has a molecular weight of 80 kDa or less (e.g., 40 kDa). In some cases, the PEG molecule is conjugated to the aptamer using a pegylation reagent. In some cases, the pegylation reagent comprises 2,3-Bis(methylpolyoxyethylene-oxy)-1-{3-[(1,5-dioxo-5-succinimidyloxy, pentyl)amino]propyloxy} propane.

In some cases, an aptamer of the disclosure does not comprise any one of SEQ ID NOs:1-3, 168-235 as described in Table 3. In some cases, an aptamer of the disclosure does not comprise any one of SEQ ID NOs:168-235 as described in Table 3. In some cases, an aptamer of the disclosure does not comprise any one of SEQ ID NOs:228-235 as described in Table 3.

TABLE 3 fD Aptamer Sequences

| SEQ ID NO. | Backbone | Sequence 5' to 3' |
|---|---|---|
| SEQ ID NO: 1 | RNA | GGGAGUGUGUACGAGGCAUUAGGCCG CCACCCAAACUGCAGUCCUCGUAAGUC UGCCUGGCGGCUUUGAUACUUGAUCG CCCUAGAAGC; where G is 2'F and A, C and U are 2'OMe modified RNA |
| SEQ ID NO: 2 | RNA | GGGAGUGUGUACGAGGCAUUAGUCCG CCGAAGUCUUUUGGCUCGGUUUUUUC AAGGUCGGCGGCUUUGAUACUUGAUC GCCCUAGAAGC; where G is 2'F and A, C and U are 2'OMe modified RNA |
| SEQ ID NO: 3 | RNA | GGGAGUGUGUACGAGGCAUUAGGCCG CCACCUCGUUUGAUUGCGGUUGUUCG GCCGCGGGCGGCUUUGAUACUUGAUC GCCCUAGAAGC; where G is 2'F and A, C and U are 2'OMe modified RNA |
| SEQ ID NO: 168 | DNA | GTGACGACTGACATATCTGCTCCGAGG TTATTGGGGTTGGGGCCTGGGCGATTG GGGCCTCGTAGTTGAGTCTGAGTGCT |
| SEQ ID NO: 169 | DNA | GTGACGACTGACATATCTGCGTTTGGG GTTGGGGCCTGGGAGTTTGGGGAGCAG AAAGGACGTAGTTGAGTCTGAGTGCT |
| SEQ ID NO: 170 | DNA | GTGACGACTGACATATCTGCTGTGGGT GTTGTGGGGGTGGGTGGTGGGCCCTTC GCCATGCGTAGTTGAGTCTGAGTGCT |
| SEQ ID NO: 171 | DNA | GTGACGACTGACATATCTGCGGCGGTT GGGGTCGAAGGGCGAGGGGTGGGAGG TCGCCGTAGTTGAGTCTGAGTGCT |
| SEQ ID NO: 172 | DNA | GTGACGACTGACATATCTGCTATTTTGG GGCCTGGGTGTTGGGGATTGGGGACTA TGTGTCGTAGTTGAGTCTGAGTGCT |
| SEQ ID NO: 173 | DNA | GTGACGACTGACATATCTGCTGTGGAT GGTGGGGGTGGTGTGGGAGGGCTGGT CGGTCGCGTAGTTGAGTCTGAGTGCT |
| SEQ ID NO: 174 | DNA | GTGACGACTGACATATCTGCCCTATAG GGGTGTGGGCGAGGGGTGGGTGGTAGG GCGGCTCGTAGTTGAGTCTGAGTGCT |
| SEQ ID NO: 175 | DNA | GTGACGACTGACATATCTGCGGAGGTG GGTGGGTGGGTGCGTGCGAGGGCGGTG TAGGTCCGTAGTTGAGTCTGAGTGCT |
| SEQ ID NO: 176 | DNA | GTGACGACTGACATATCTGCAAAAGTT AGATTGACATGGTATGCACCGTCTGAG GTTGGTCGTAGTTGAGTCTGAGTGCT |
| SEQ ID NO: 177 | DNA | GTGACGACTGACATATCTGCACCACGC TAGGGGTGAGGGCGAGGGGTGGGTAGC GCGTGGCGTAGTTGAGTCTGAGTGCT |

TABLE 3-continued fD Aptamer Sequences

| SEQ ID NO. | Backbone | Sequence 5' to 3' |
|---|---|---|
| SEQ ID NO: 178 | DNA | GTGACGACTGACATATCTGCTGTGGGT GTTGTGGGGCGGGTGGTGGGTGCGTC GGTGGTCGTAGTTGAGTCTGAGTGCT |
| SEQ ID NO: 179 | DNA | GTGACGACTGACATATCTGCTGCTTCCA GCGGTCATGATATGCACTGTCTGAAGC TCGGTCGTAGTTGAGTCTGAGTGCT |
| SEQ ID NO: 180 | DNA | GTGACGACTGACATATCTGCTCTGTTAT GATATGCACCGTCTGAGGGTAGTCGCG GGGTGCGTAGTTGAGTCTGAGTGCT |
| SEQ ID NO: 181 | DNA | GTGACGACTGACATATCTGCTGCTTGTT TAGTGGGTGGGTGGGTGGTGTGGTGGT GATGCGTAGTTGAGTCTGAGTGCT |
| SEQ ID NO: 182 | DNA | GTGACGACTGACATATCTGCCTTGGGG TTGGGGCCTGGGTGTTTGGGGTGGCCT AGAAGTCGTAGTTGAGTCTGAGTGCT |
| SEQ ID NO: 183 | DNA | GTGACGACTGACATATCTGCGCTAGGG GTGGGTTGGGGTTGGTGGTGTGCGTGT GGGTTGCGTAGTTGAGTCTGAGTGCT |
| SEQ ID NO: 184 | DNA | GTGACGACTGACATATCTGCTGTTGAG GTTGGTGGGGGTGGGCGGTGGGATGG TTGTGCCGTAGTTGAGTCTGAGTGCT |
| SEQ ID NO: 185 | DNA | GTGACGACTGACATATCTGCTTGACAG TCTGCTTTGCAGGGGCCGAGAGCGCCA TTGCGTCGTAGTTGAGTCTGAGTGCT |
| SEQ ID NO: 186 | DNA | GTGACGACTGACATATCTGCTGTGGTTG GTGGGGGTGGAGGGTGGGAGGCCGTG TGTCCCGTAGTTGAGTCTGAGTGCT |
| SEQ ID NO: 187 | DNA | GTGACGACTGACATATCTGCTGTGGTG GTGGGGGAGGGTGGTGGGGTGGCCGGC GCTCGTCGTAGTTGAGTCTGAGTGCT |
| SEQ ID NO: 188 | DNA | GTGACGACTGACATATCTGCTGGGTTA CGTGGTTCGGGGCTAGGGGGTGGGGT GTGTTTCGTAGTTGAGTCTGAGTGCT |
| SEQ ID NO: 189 | DNA | GTGACGACTGACATATCTGCTGGTGGT GTGCGGTGGGTTCTTGGGTGGGATGGG TGGTACCGTAGTTGAGTCTGAGTGCT |
| SEQ ID NO: 190 | DNA | GTGACGACTGACATATCTGCTATTAGAT CCTCGGTGGGTGGGTGGGTGTGTGGTG GTGTGCGTAGTTGAGTCTGAGTGCT |
| SEQ ID NO: 191 | DNA | GTGACGACTGACATATCTGCGGGCGTC TGAGCGCATGGATGACCCACCGACAGA TTGCGGCGTAGTTGAGTCTGAGTGCT |
| SEQ ID NO: 192 | DNA | GTGACGACTGACATATCTGCGCTTTGG GTGGGCTCGGTGTGCGGTGTGCGGGTG GGTTTGCGTAGTTGAGTCTGAGTGCT |
| SEQ ID NO: 193 | DNA | GTGACGACTGACATATCTGCGTTTGGG GTTGGGGCCTGGGAGTTTGGGGAGCAG AAAGGGCGTAGTTGAGTCTGAGTGCT |
| SEQ ID NO: 194 | DNA | GTGACGACTGACATATCTGCGGGTGGG TTGGGTTGGGTTTGGTGGTGGTGCCTGT TAGTTCGTAGTTGAGTCTGAGTGCT |
| SEQ ID NO: 195 | DNA | GTGACGACTGACATATCTGCAGGTGGG TGGGTGGGTGTGTGCGGTGGTGTGA TTTGGCCGTAGTTGAGTCTGGAGTGCT |
| SEQ ID NO: 196 | DNA | GTGACGACTGACATATCTGCTGTGGTTG GTGGGGGCGGCGGGTGGGAGCCTGG TGTTCCGTAGTTGAGTCTGAGTGCT |

TABLE 3-continued fD Aptamer Sequences

| SEQ ID NO. | Backbone | Sequence 5' to 3' |
|---|---|---|
| SEQ ID NO: 197 | DNA | GTGACGACTGACATATCTGCTCCCGTTT GAGGGCTTGTCGGACAGATTGCTGGCA CGTCACGTAGTTGAGTCTGAGTGCT |
| SEQ ID NO: 198 | DNA | GTGACGACTGACATATCTGCTCTTGGTG GTGGTGGTGGGTTGGGATGGGTCTTGG GCTGCCGTAGTTGAGTCTGAGTGCT |
| SEQ ID NO: 199 | DNA | GTGACGACTGACATATCTGCCTGTGAG GGGAGGGAGGGTGGGTTTGGCGGTGGC GCAGGCCGTAGTTGAGTCTGAGTGCT |
| SEQ ID NO: 200 | DNA | GTGACGACTGACATATCTGCGTGGTGG TGCGTGGGTGGTGGGGGGGGAGCTGG GTGCCCCGTAGTTGAGTCTGAGTGCT |
| SEQ ID NO: 201 | DNA | GTGACGACTGACATATCTGCTGTGGGT GTTGTGGGGGTGGGTGGTGGGCCCTTC GCCGTGCGTAGTTGAGTCTGAGTGCT |
| SEQ ID NO: 202 | DNA | GTGACGACTGACATATCTGCTTCCGGTA TGTGTGGGTGGGTGGTGGTGTGGTGG TGTTGCGTAGTTGAGTCTGAGTGCT |
| SEQ ID NO: 203 | DNA | GTGACGACTGACATATCTGCTCTCTTCT GTTGTGGGTGGGTGGGTGGTGTGGTGC GTGTGCGTAGTTGAGTCTGAGTGCT |
| SEQ ID NO: 204 | DNA | GTGACGACTGACATATCTGCGGCTGGG TGGGTTGGGTTAGGGTGGTGTGCGGTG GGTTGCCGTAGTTGAGTCTGAGTGCT |
| SEQ ID NO: 205 | DNA | GTGACGACTGACATATCTGCGTTTAGGT GGGCGGGTGGGTGTGCGGTGGGCGGTG TTGAACGTAGTTGAGTCTGAGTGCT |
| SEQ ID NO: 206 | DNA | GTGACGACTGACATATCTGCGGTGATT GGGGTTGGGGCCTGGGCGTTTGGGGAC CGCATGCGTAGTTGAGTCTGAGTGCT |
| SEQ ID NO: 207 | DNA | GTGACGACTGACATATCTGCGTTTGGG GTTGGGGCCTGGGAGTTTGGGGAGCAG AGAGGACGTAGTTGAGTCTGAGTGCT |
| SEQ ID NO: 208 | DNA | GTGACGACTGACATATCTGCTAACTTGT TGGGGTTTGGGGCCTGGGTGTTGGGGT TGTTTCGTAGTTGAGTCTGAGTGCT |
| SEQ ID NO: 209 | DNA | GTGACGACTGACATATCTGCTGGGGTT GGTGGGGGGAGGTGGGTGGGTTATGTG CGCTGGCGTAGTTGAGTCTGAGTGCT |
| SEQ ID NO: 210 | DNA | GTGACGACTGACATATCTGCTGTGGGT GTTGTGGGGGTGGGTTGGTGGGCATTG CGTGTGCGTAGTTGAGTCTGAGTGCT |
| SEQ ID NO: 211 | DNA | GTGACGACTGACATATCTGCGAGTGGG TTCGGTGGTGGTGTGTGGGAGGGTTGG GTACGTCGTAGTTGAGTCTGAGTGCT |
| SEQ ID NO: 212 | DNA | GTGACGACTGACATATCTGCTGGACAT GATTGCACCGTATGAGGTTTAGTCGTTA ATGTGCGTAGTTGAGTCTGAGTGCT |
| SEQ ID NO: 213 | DNA | GTGACGACTGACATATCTGCAGTGGGG CCTGGGCGTTGGGGTTTGGGGTGCCTC GTCAGTCGTAGTTGAGTCTGAGTGCT |
| SEQ ID NO: 214 | DNA | GTGACGACTGACATATCTGCATGGATTT TCGGTGGGTGGGTGGTTGGTGTGGTG GTGTGCGTAGTTGAGTCTGAGTGCT |
| SEQ ID NO: 215 | DNA | GTGACGACTGACATATCTGCTGTGGTTG GTGGGGGGTGGGTGGTGGGAAGGTTCC GGTGCCGTAGTTGAGTCTGAGTGCT |

TABLE 3-continued fD Aptamer Sequences

| SEQ ID NO. | Backbone | Sequence 5' to 3' |
|---|---|---|
| SEQ ID NO: 216 | DNA | GTGACGACTGACATATCTGCGGTTGGG GTTGGGGCCTGGGTGTTGGGGAGCAGG TAGCACCGTAGTTGAGTCTGAGTGCT |
| SEQ ID NO: 217 | DNA | GTGACGACTGACATATCTGCGGCCTGG GAGGGTTCGGTGGTGGTGCGAGGGTGG GCAAGCCGTAGTTGAGTCTGAGTGCT |
| SEQ ID NO: 218 | DNA | ACCTAGTTTGGCTTGCAXAAGTAACYA GCACGTGGGCTAG, where X = 5-(amino-1-propenyl)-2'-deoxyuridine; and Y = 5-(4-pivaloylbenzamido-1-propenyl)-2'-deoxyuridine. |
| SEQ ID NO: 219 | DNA | ACGATCGCCCCYGTCTWTAAGAXCGAA TACTATGGGCTAG, where W = 5-(indole-3-acetamido-1-propenyl)-2'-deoxyuridine; X = 5-(amino-1-propenyl)-2'-deoxyuridine; and Y = 5-(4-pivaloylbenzamido-1-propenyl)-2'-deoxyuridine. |
| SEQ ID NO: 220 | DNA | ACCTAGAAAGGCTTAGTGAAGTAAWG ATCAGGGCGGGATC, where W = 5-(indole-3-acetamido-1-propenyl)-2'-deoxyuridine. |
| SEQ ID NO: 221 | DNA | ACCTAGTTCCCYGTCTAXYAGAXCCGA GXGTATGCCGATC, where X = 5-(amino-1-propenyl)-2'-deoxyuridine; and Y = 5-(4-pivaloylbenzamido-1-propenyl)-2'-deoxyuridine. |
| SEQ ID NO: 222 | DNA | ACCTAGGCAGTCTTGCCGAATTTACGA GXGGGGAGGGATC, where X = 5-(amino-1-propenyl)-2'-deoxyuridine. |
| SEQ ID NO: 223 | DNA | ACGATCACTGCYCAGCWTYATTAACYA GCYTCGACCCTAG, where W = 5-(indole-3-acetamido-1-propenyl)-2'-deoxyuridine; and Y = 5-(4-pivaloylbenzamido-1-propenyl)-2'-deoxyuridine. |
| SEQ ID NO: 224 | DNA | ACGATCTTCCGCCAGCTGYATTXCGAA GXGCGTGAGGATC, where X = 5-(amino-1-propenyl)-2'-deoxyuridine: and Y = 5-(4-pivaloylbenzamido-1-propenyl)-2'-deoxyuridine |
| SEQ ID NO: 225 | DNA | ACCTAGGCGGTCTTXCCGTCGTTACGTC CYCGGCCCCTAG, where X = 5-(amino-1-propenyl)-2'-deoxyuridine; and Y = 5-(4-pivaloylbenzamido-1-propenyl)-2'-deoxyuridine. |
| SEQ ID NO: 226 | DNA | ACCTAGTTTGGCGTAGCGYATTAAWGG GXGCGGCAGCTAG, where W = 5-(indole-3-acetamido-1-propenyl)-2'-deoxyuridine; X = 5-(amino-1-propenyl)-2'-deoxyuridine; and Y = 5-(4-pivaloylbenzamido-1-propenyl)-2'-deoxyuridine. |
| SEQ ID NO: 227 | DNA | ACGATCGCTGACGTXCAXYAGTATGAG GCACGTGGGCTAG, where X = 5-(amino-1-propenyl)-2'-deoxyuridine; and Y = 5-(4-pivaloylbenzamido-1-propenyl)-2'-deoxyuridine. |

TABLE 3-continued fD Aptamer Sequences

| SEQ ID NO. | Backbone | Sequence 5' to 3' |
|---|---|---|
| SEQ ID NO: 228 | DNA | ACGGAGAAAGAGAGAGTGTAATTGCTA GCATAACCGCTGC |
| SEQ ID NO: 229 | DNA | GTAACCACGTTGCCAGACCGAGTCTAC CAGCGATCCTCAG |
| SEQ ID NO: 230 | DNA | TATGCCCAAATCCCTCAAGTCGGCCAG GATACACCACCGT |
| SEQ ID NO: 231 | DNA | AATCAAAAGGCTCACGCGCGGATTGGT CAACCTTACAACC |
| SEQ ID NO: 232 | DNA | TCGGCCTTCCCAGACCACCGCAATCCCC AGGGAACAGGCA |
| SEQ ID NO: 233 | DNA | CATCACACTGTCAACATACCCAGCCTG GGGAAAGACGAAC |
| SEQ ID NO: 234 | DNA | AACCCGCATGCCGATCGATGTCGTGCC TCGCTCCACGCTC |
| SEQ ID NO: 235 | DNA | ACCAGGCACCCGACGGACTAACTCATC ACTCAGGCGAGGG |

In some cases, an aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described herein. For example, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described in Table 1 or Table 2. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:13 or 269. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:165 or 284. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:166 or 285. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:244 or 294. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:253 or 303. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:256 or 306. In some cases, an anti-fD aptamer of the disclosure may have at least 80%, 81%, 82%, 83%, 84%, 85%, 86%, 87%, 88%, 89%, 90%, 91%, 92%, 93%, 94%, 95%, 96%, 97%, 98%, or 99% sequence identity with SEQ ID NOs:262 or 312.

In some cases, an anti-fD aptamer of the disclosure has at least 70% sequence identity with any one of SEQ ID NOs:13, 165, 166, 244, 253, 256, 262, 269, 284, 285, 294, 303, 306, and 312. In some cases, an anti-fD aptamer of the disclosure has at least 75% sequence identity with any one of SEQ ID NOs:13, 165, 166, 244, 253, 256, 262, 269, 284, 285, 294, 303, 306, and 312. In some cases, an anti-fD aptamer of the disclosure has at least 80% sequence identity with any one of SEQ ID NOs:13, 165, 166, 244, 253, 256, 262, 269, 284, 285, 294, 303, 306, and 312. In some cases, an anti-fD aptamer of the disclosure has at least 85% sequence identity with any one of SEQ ID NOs:13, 165, 166, 244, 253, 256, 262, 269, 284, 285, 294, 303, 306, and 312. In some cases, an anti-fD aptamer of the disclosure has at least 90% sequence identity with any one of SEQ ID NOs:13, 165, 166, 244, 253, 256, 262, 269, 284, 285, 294, 303, 306, and 312. In some cases, an anti-fD aptamer of the disclosure has at least 95% sequence identity with any one of SEQ ID NOs:13, 165, 166, 244, 253, 256, 262, 269, 284, 285, 294, 303, 306, and 312.

In some cases, an aptamer of the disclosure may have a primary nucleotide sequence that has at least 86%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described herein. For example, an anti-fD aptamer of the disclosure may have a primary nucleotide sequence that has at least 80%, 81%, 82%, 83%, 84%, 85%, 86%, 87%, 88%, 89%, 90%, 91%, 92%, 93%, 94%, 95%, 96%, 97%, 98%, or 99% sequence homology with any aptamer described in Table 1 or Table 2. In some cases, an aptamer of the disclosure may have a primary nucleotide sequence that has at least 80%, 81%, 82%, 83%, 84%, 85%, 86%, 87%, 88%, 89%, 90%, 91%, 92%, 93%, 94%, 95%, 96%, 97%, 98%, or 99% sequence homology with SEQ ID NOs:13 or 269.

In some cases, an aptamer of the disclosure may have a primary nucleotide sequence that shares at least 10, at least 11, at least 12, at least 13, at least 14, at least 15, at least 16, at least 17; at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides with a nucleotide sequence described in Table 1 or Table 2. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:13 or 269. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:165 or 284. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:166 or 285. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:244 or 294. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:253 or 303. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:256 or 306. In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, or at least 39 contiguous nucleotides with SEQ ID NOs:262 or 312.

In such cases where specific nucleotide modifications have been recited, it should be understood that any number and type of nucleotide modifications may be substituted. For example, 2'OMeG may be substituted for 2'FG. Non-limiting examples of nucleotide modifications have been provided herein. In some instances, all of the nucleotides of an aptamer are modified. In some instances, at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the nucleotides of an aptamer of the disclosure may be modified.

Aptamers of the disclosure may have a stem-loop secondary structure comprising at least one stem and at least one loop. FIG. 1 depicts an exemplary consensus nucleotide sequence of aptamers in relation to the structural elements of the aptamer. Although particular sequences and structural elements are described in FIG. 1, it should be understood that FIG. 1 is meant only as an example of a graphical representation of a family of anti-fD aptamers. Other structurally-related families of anti-fD aptamers are described herein. In some cases, aptamers of the disclosure may be structurally related to an aptamer of FIG. 1, but may tolerate some variation in size or nucleic acid sequence while still retaining anti-fD activity.

In various aspects, an aptamer of the disclosure may comprise a nucleic acid sequence that selectively blocks or occludes the active site of fD. The anti-fD aptamer may have a stem-loop secondary structure comprising at least one stem and at least one loop. In some cases, the anti-fD aptamer has a nucleic acid sequence comprising from 30 to 90 nucleotides. For example, the anti-fD aptamer may have a nucleic acid sequence comprising 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 nucleotides.

In various aspects, an aptamer of the disclosure may comprise a nucleic acid sequence that selectively binds to fD. The anti-fD aptamer may have a stem-loop secondary structure comprising at least one stem and at least one loop. In some cases, the anti-fD aptamer comprises at least one modified nucleotide.

In various aspects, an aptamer of the disclosure may comprise a nucleic acid sequence that selectively binds to fD. The anti-fD aptamer may have a stem-loop secondary structure comprising at least one stem and at least one loop. In some cases, the anti-fD aptamer does not include a nucleic acid sequence of any one of SEQ ID NOs:228-235. In some instances, the anti-fD aptamer does not include a nucleic acid sequence of any one of SEQ ID NOs:1-3, 168-227. In some cases, the anti-fD aptamer does not include a nucleic acid sequence of any one of SEQ ID NOs:168-227.

In various aspects, an aptamer of the disclosure may comprise a nucleic acid sequence that selectively blocks an active site of fD. The anti-fD aptamer may have a secondary structure having exactly three loops. In some instances, the anti-fD aptamer may have exactly two stems.

In various aspects, an aptamer of the disclosure may comprise a nucleic acid sequence that selectively blocks an activity of fD. The anti-fD aptamer may have a secondary structure having less than four loops. For example, the anti-fD aptamer may have three loops, two loops, or one loop. In some cases, a secondary structure of the anti-fD aptamer as predicted by M-fold contains less than a total of 15 unpaired residues at either terminus. For example, a secondary structure of the anti-fD aptamer as predicted by M-fold contains 15, 14, 13, 12, 11, 10, 9, 8, 7, 6, 5, 4, 3, 2, 1, or 0 total unpaired residues at either terminus. In some cases, a secondary structure of the anti-fD aptamer as predicted by M-fold has less 4 loops.

In some cases, a secondary structure of the anti-fD aptamer as defined by comparative sequence analysis and multiple sequence alignment contains less than a total of 15 unpaired residues at the 5' terminus. For example, a secondary structure of the anti-fD aptamer as defined by comparative sequence analysis and multiple sequence alignment may contain 15, 14, 13, 12, 11, 10, 9, 8, 7, 6, 5, 4, 3, 2, 1 or 0 unpaired nucleotide residues at the 5' terminus. In some cases, a secondary structure of the anti-fD aptamer as defined by comparative sequence analysis and multiple sequence alignment contains less than 15 unpaired residues at the 3' terminus. For example, a secondary structure of the anti-fD aptamer as defined by comparative sequence analysis and multiple sequence alignment may contain 15, 14, 13, 12, 11, 10, 9, 8, 7, 6, 5, 4, 3, 2, 1, or 0 unpaired nucleotide residues at the 3' terminus. In some cases, a secondary structure of the anti-fD aptamer as defined by comparative sequence analysis and multiple sequence alignment contains less than 30 total unpaired nucleotide residues at the 5' and 3' termini. For example, a secondary structure of the anti-fD aptamer as defined by comparative sequence analysis and multiple sequence alignment may contain 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 total unpaired nucleotide residues at the 5' and 3' termini. In some cases, a secondary structure of the anti-fD aptamer as defined by comparative sequence analysis and multiple sequence alignment has less 4 loops.

In various aspects, an aptamer of the disclosure may comprise a nucleic acid sequence that selectively binds to fD. The anti-fD aptamer may have a stem-loop secondary structure that comprises at least one stem and at least one loop. In some cases, the aptamer is an RNA aptamer or a modified RNA aptamer. In various aspects, an aptamer of the disclosure may be single-stranded, for example, may have no more than one nucleic acid strand. In other aspects, an aptamer of the disclosure may have more than one nucleic strands, for example, may have two or more nucleic strands.

In some cases, the anti-fD aptamer may have up to two stems, for example, the anti-fD aptamer may have one stem, or two stems. In some cases, each of the stems may have 1, 2, 3, 4, 5, 6, 7, 8, 9, 10, 11, 12, 13, 14, 15, 16, 17, 18, 19, 20 or greater than 20 base pairs. In some cases, each of the stems may have less than 20, less than 19, less than 18, less than 17, less than 16, less than 15, less than 14, less than 13, less than 12, less than 11, less than 10, less than 9, less than 8, less than 7, less than 6, less than 5, less than 4, less than 3, or less than 2 base pairs. In some instances, no more than one of the stems has more than 20 base pairs. In some cases, one or more of the stems may have one or more mismatched base pairs.

In some cases, the anti-fD aptamer may have up to three loops, for example, the anti-fD aptamer may have three loops, two loops, or one loop. In some cases, each of the loops may have up to 25 nucleotides. For example, each loop may have 1, 2, 3, 4, 5, 6, 7, 8, 9, 10, 11, 12, 13, 14, 15, 16, 17, 18, 19, 20, 21, 22, 23, 24 or 25 nucleotides. In some cases, at least one loop may have more than 1, more than 2, more than 3, more than 4, more than 5, more than 6, more than 7, more than 8, more than 9, or more than 10 nucleotides.

In particular aspects, aptamers of the disclosure may have a stem-loop secondary structure that includes, in a 5' to 3' direction, a first stem (S1), a first loop (L1), a second stem (S2), a second loop (L2), and a third loop (L3). As demonstrated in FIG. 1, the first loop (L1) may be connected to the 3' terminal end of the first stem (S1) and the 5' terminal end of the second stem (S2). The second stem (S2) may be connected to the 3' terminal end of the first loop (L1) and the 5' terminal end of the second loop (L2). The second loop (L2) may be connected to the 3' terminal end of the second stem (S2) and the 5' terminal end of the complementary region of the second stem (S2). The complementary region of the second stem (S2) may be connected to the 3' terminal end of the second loop (L2) and the 5' terminal end of the third loop (L3). The third loop (L3) may be connected to the 3' terminal end of the complementary region of the second stem (S2) and the 5' terminal end of the complementary region of the first stem (S1). In some cases, the first loop (L1) may comprise fewer nucleotides than the second loop (L2). In some cases, the third loop (L3) is connected to the first stem (S1) (e.g., connected to the 5' terminal end of the complementary region of the first stem (S1)).

In some aspects, the first loop (also referred to as L1) may have from 1 to 10 nucleotides. For example, the first loop (L1) may have 1, 2, 3, 4, 5, 6, 7, 8, 9, or 10 nucleotides. In particular aspects, the first loop (L1) may have from 3 to 5 nucleotides. For example, the first loop (L1) may have 3, 4 or 5 nucleotides. In some cases, the first loop (L1) has 3 or less nucleotides. For example, the first loop (L1) may have 1, 2, or 3 nucleotides. In some cases, the first loop (L1) has 3 or more nucleotides. For example, the first loop (L1) may have 3, 4, 5, 6, 7, 8, 9, or 10 nucleotides. In some cases, the first loop (L1) has greater than 4 nucleotides. In some cases, the first loop (L1) has greater than 5 nucleotides. In some cases, the first loop (L1) has greater than 6 nucleotides. In some cases, the first loop (L1) has greater than 7 nucleotides. In some cases, the first loop can contain one or more non-nucleotidyl spacers in place of nucleotides (e.g., a 3-carbon spacer, a 6-carbon spacer, a 9-carbon spacer, or an 18-atom spacer (such as a hexaethylene glycol spacer). In a non-limiting example, the first loop (L1) may comprise a nucleic acid sequence of 5'-DUG-3', where D is A, G, or U.

In some aspects, the second loop (L2) may have from 2 to 15 nucleotides. For example, the second loop (L2) may have 2, 3, 4, 5, 6, 7, 8, 9, 10, 11, 12, 13, 14, or 15 nucleotides. In a particular example, the second loop (L2) may have at least 6 nucleotides. In another particular example, the second loop (L2) may have at least 8 nucleotides. In another particular example, the second loop (L2) may have exactly 10 nucleotides. In yet another particular example, the second loop (L2) may have 10 or 11 nucleotides. In some cases, the second loop (L2) has 7 or more nucleotides. For example, the second loop (L2) may have 7, 8, 9, 10, 11, 12, 13, 14, or 15 nucleotides. In some cases, the second loop (L2) has 10 or more nucleotides. For example, the second loop (L2) may have 10, 11, 12, 13, 14, or 15 nucleotides. In some cases, the second loop (L2) has 10 or less nucleotides. For example, the second loop (L2) may have 10, 9, 8, 7, 6, 5, 4, 3, or 2 nucleotides. In some cases, the second loop (L2) has greater than 4 nucleotides. In some cases, the second loop (L2) has greater than 5 nucleotides. In some cases, the second loop (L2) has greater than 6 nucleotides. In some cases, the second loop (L2) has greater than 7 nucleotides. In some cases, the second loop can contain one or more non-nucleotidyl spacers in place of nucleotides (e.g., a 3-carbon spacer, a 6-carbon spacer, a 9-carbon spacer, or an 18-atom spacer (such as a hexaethylene glycol spacer). In a non-limiting example, the second loop (L2) may comprise a nucleic acid sequence of 5'-DWWVGCBHWG-3' (SEQ ID NO:319), where D is A, G, or U; W is A or U; V is A, C, or G; B is C, G, or U; and H is A, C, or U. In some cases, the second loop (L2) comprises a nucleic acid sequence having a U at nucleotide position 2 of the second loop (L2), at nucleotide position 3 of the second loop (L2), or both. In some cases, the first loop (L1) has fewer nucleotides than the second loop (L2).

In some aspects, the third loop (L3) may have from 2 to 10 nucleotides. For example, the third loop (L3) may have 2, 3, 4, 5, 6, 7, 8, 9, or 10 nucleotides. In a particular example, the third loop (L3) may have at least 6 nucleotides. In some cases, the third loop (L3) has exactly 6 nucleotides. In other cases, the third loop (L3) may have from 6 to 8 nucleotides, for example, 6, 7, or 8 nucleotides. In some cases, the third loop (L3) has 6 or more nucleotides, for example, 6, 7, 8, 9, or 10 nucleotides. In some cases, the third loop (L3) has 6 or less nucleotides, for example, 6, 5, 4, 3, or 2 nucleotides. In some cases, the third loop (L3) has greater than 4 nucleotides. In some cases, the third loop (L3) has greater than 5 nucleotides. In some cases, the third loop (L3) has greater than 6 nucleotides. In some cases, the third loop (L3) has greater than 7 nucleotides. In some cases, the third loop can contain one or more non-nucleotidyl spacers in place of nucleotides (e.g., a 3-carbon spacer, a 6-carbon spacer, a 9-carbon spacer, or an 18-atom spacer (such as a hexaethylene glycol spacer). In some examples, the third loop (L3) has a nucleic acid sequence comprising 5'-AAGUKN-3', where K is G or U; and N is A, G, C, or U. In some cases, the third loop (L3) is connected to the first stem (S1). In some cases, the third loop (L3) has at least 4 nucleotides and up to 2 non-nucleotidyl spacers.

In some aspects, the first stem (S1) may have from 2 to 10 base pairs. For example, the first stem (S1) may have 2, 3, 4, 5, 6, 7, 8, 9, or 10 base pairs. In a particular example, the first stem (S1) may have from 3 to 8 base pairs, for example, 3, 4, 5, 6, 7, or 8 base pairs. In some cases, the first stem (S1) has 10 or less base pairs, for example, 10, 9, 8, 7, 6, 5, 4, 3, or 2 nucleotides. In some cases, the first stem (S1) has 5 or less base pairs, for example, 5, 4, 3, or 2 base pairs. In some cases, the first stem (S1) may include one or more mismatched base pairs.

In some aspects, the second stem (S2) may have from 2 to 10 base pairs. For example, the second stem (S2) may have 2, 3, 4, 5, 6, 7, 8, 9, or 10 base pairs. In a particular example, the second stem (S2) may have 4 or 5 base pairs. In some cases, the second stem (S2) has 10 or less base pairs, for example, 10, 9, 8, 7, 6, 5, 4, 3, or 2 base pairs. In some cases, the second stem (S2) has 5 or less base pairs, for example, 5, 4, 3, or 2 base pairs. In some cases, the second stem (S2) may comprise a terminal U-G base pair, adjacent to the second loop (L2).

In various aspects, an aptamer of the disclosure is conjugated to a polyethylene glycol (PEG) molecule at the 5' end of the aptamer. Various non-limiting examples of PEG molecules suitable for use with an aptamer of the disclosure are provided throughout. In some cases, an aptamer of the disclosure is conjugated to a PEG molecule having a molecular weight of 80 kDa or less (e.g., 40 kDa).

In some cases, an aptamer of this disclosure may include: (1) a terminal stem (S1); (2) an asymmetric internal loop containing a 5' side (L1) and a 3' side (L3); (3) a second stem (S2); and (4) a terminal loop (L2). In some cases, an aptamer of this disclosure may contain any of the following: (1) a terminal stem (S1) having 3-8 base pairs; (2) an asymmetric internal loop, the 5' side of which (L1) ranging from 3-5 nucleotides; (3) a second stem (S2) having 4-5 base pairs; (4) a terminal loop (L2) that is 10 to 11 nucleotides in length; and (5) a 3' side of the asymmetric internal loop (L3) having 6-8 nucleotides.

In some cases, an aptamer of the disclosure comprises a nucleic acid sequence that selectively binds to complement factor D (fD) and has a stem-loop secondary structure comprising, in a 5' to 3' direction, a first base-paired stem, a first loop, a second base-paired stem, a second loop, and a third loop. In one aspect, the third loop may comprise 6 or more nucleotides, non-nucleotidyl spacers, or a combination thereof, and the first loop may have fewer nucleotides than said second loop. In another aspect, the third loop may comprise 6 or more nucleotides, non-nucleotidyl spacers, or a combination thereof, and the second loop may comprise more than 5 nucleotides, non-nucleotidyl spacers, or a combination thereof. In another aspect, the third loop may comprise 6 or more nucleotides, non-nucleotidyl spacers, or a combination thereof, and the third loop may be adjacent to the first stem. In yet another aspect, the third loop may comprise 6 or more nucleotides, non-nucleotidyl spacers, or a combination thereof, and the first base-paired stem may have no more than 5 base pairs. In yet another aspect, the second loop may comprise 7 or more nucleotides, non-nucleotidyl spacers, or a combination thereof, the first base-paired stem may have no more than 5 base pairs, and the second base-paired stem may comprise more than 2 base pairs. In another aspect, the second base-paired stem may comprise a terminal U-G base pair adjacent to the second loop. In another aspect, the first loop may comprise a nucleic acid sequence of 5'-DUG-3', where D is A, G, or U. In another aspect, the third loop may comprise a nucleic acid sequence comprising 5'-AAGUKN-3', where K is G or U; and N is A, G, C, or U. In yet another aspect, the second loop may comprise a nucleic acid sequence of 5'-DWWVGCB-HWG-3' (SEQ ID NO:319), where D is A, G, or U; W is A or U; V is A, C, or G; B is C, G, or U; and H is A, C, or U. In another aspect, the second loop may comprise a nucleic acid sequence having a U at nucleotide position 2, nucleotide position 3, or both. In another aspect, the second base-paired stem may comprise a terminal C-G base pair adjacent to the second loop. In some cases, the first base-paired stem is adjacent to the first loop. In some cases, the second base-paired stem is adjacent to the first loop, the second loop, and the third loop. In some cases, the first base-paired stem is adjacent to the first loop and the second base-paired stem is adjacent to the first loop, the second loop, and the third loop.

In some cases, an aptamer of the disclosure comprises a nucleic acid sequence that selectively binds to complement factor D (fD) and has a stem-loop secondary structure comprising a base-paired terminal stem; an asymmetric internal loop; an internal base-paired stem; and exactly one terminal loop. In some aspects, the terminal loop may comprise more than 4 nucleotides, non-nucleotidyl spacers, or a combination thereof, and the asymmetric internal loop may be adjacent to exactly 2 base-paired stems.

In some cases, an aptamer of the disclosure comprises a nucleic acid sequence that selectively binds to complement factor D (ID) and has a stem-loop secondary structure comprising exactly one terminal base-paired stem; exactly one asymmetric internal loop comprising, from a 5' to 3' direction, a first loop and a second loop; exactly one internal base-paired stem; and exactly one terminal loop. In some aspects, the first loop of the asymmetric internal loop may have fewer nucleotides than the terminal loop. In another aspect, the exactly one terminal loop may comprise more than 4 nucleotides, non-nucleotidyl spacers, or a combination thereof. In another aspect, the second loop may comprise 6 or more nucleotides, non-nucleotidyl spacers, or a combination thereof. In yet another aspect, the exactly one terminal loop may comprise 7 or more nucleotides, non-nucleotidyl spacers, or a combination thereof.

Anti-fD Compositions fD is a component of the alternative complement pathway and is believed to be involved in the pathogenesis of AMD and other ocular disorders. fD is unique among serine proteases in that it does not require cleavage of a zymogen for expression of proteolytic activity. Rather, fD requires a conformational change that is believed to be induced by the complex C3bB resulting in a reversible reorientation of the catalytic center and substrate binding site of fD. fD is primarily produced by adipocytes and is systemically available in serum at low levels. fD contains a self-inhibitory loop that prevents catalytic activity of fD. Binding of the C3bB complex to fD displaces the self-inhibitory loop and fD cleaves C3bB to form the C3 convertase C3bBb. The catalytic activity of fD only occurs in the context of complexed fB; fD does not cleave uncomplexed fB. The complex of fD, fB, and C3b forms an amplification loop of the alternative complement pathway of which fD is the rate-limited enzyme.

In some aspects, the methods and compositions described herein involve inhibition of fD, resulting in inhibition of the amplification step of the alternative complement pathway. The anti-fD compositions herein may involve the use of one or more anti-fD aptamers for the treatment of ocular diseases. In some cases, the ocular disease is macular degeneration. In some cases, macular degeneration is age-related macular degeneration. In some cases, age-related macular degeneration is dry age-related macular degeneration. In some cases, dry age-related macular degeneration is advanced dry age-related macular degeneration (i.e., geographic atrophy). In some cases, age-related macular degeneration is wet age-related macular degeneration. In some cases, macular degeneration is Stargardt disease or Stargardt-like disease.

Anti-fD Inhibitors

The anti-fD compositions disclosed herein may be designed to bind to specific regions of fD with high specificity and affinity. The compositions may bind to fD in such a way as to inhibit, either directly or indirectly, the catalytic activity of the enzyme. In some cases, the anti-fD aptamers can bind to the active site (e.g., the catalytic cleft) of fD and directly inhibit the catalytic activity of fD. In this example, the aptamer may be designed to target the active site (e.g., the catalytic cleft) of fD. In other cases, the anti-fD aptamers can bind to a region at or near the active site, such that binding of the aptamer occludes or blocks the substrate from accessing the active site. When the aptamer is bound to the active site of fD, it can prevent the substrate (e.g., C3bB) from accessing the active site. In some cases, the anti-fD aptamer can bind to an exosite of fD and indirectly inhibit the catalytic activity of fD by e.g., preventing the binding of C3bB. In some cases, the exosite may be remote from the catalytic site. In other cases, there may be some overlap with the catalytic site. In some cases the anti-fD aptamer can bind to the self-inhibitory loop of fD to prevent displacement of the self-inhibitory loop and thus, prevent activation of fD.

Amino acid residues of fD may be referenced according to the chymotrypsin numbering scheme and this numbering system is used throughout the disclosure to refer to specific amino acid residues of fD. Chymotrypsin numbering scheme for fD may be as depicted in FIG. 6 (SEQ ID NO:9)(chymotrypsin numbering displayed above amino acid sequence and fD numbering scheme below amino acid sequence).

Anti-fD aptamers as described herein can modulate or inhibit the activity of fD or a fD variant thereof. A fD variant as used herein encompasses variants that perform essentially the same function as fD. A fD variant includes essentially the same structure as fD and in some cases includes at least 80%, 85%, 86%, 87%, 88%, 89%, 90%, 91%, 92%, 93%, 94%, 95%, 96%, 97%, 98%, 99%, 99.5%, or 99.9% sequence identity to the amino acid sequence (shown above) of the fD protein.

In certain embodiments of the disclosure, methods are provided for the identification of fD aptamers that specifically bind to epitopes of fD. These methods may be utilized, for example, to determine the binding site and/or the mechanism of action of the aptamer.

In one instance, methods are provided for testing a fD aptamer in alternative complement dependent hemolysis of red blood cells. Human serum that is rendered deficient in the classical complement pathway by depleting C1q may be dependent on alternative complement activity to lyse rabbit red blood cells, an activity that may be dependent on fD (Katschke, W u, Ganesan, et al. (2012) Inhibiting alternative pathway complement activation by targeting the Factor D exosite. J. Biol. Chem. 287, 12886-12892). In some cases, the fD aptamers disclosed herein may inhibit alternative complement dependent hemolysis of red blood cells (see Example 2).

In another instance, methods are provided for testing a fD aptamer in fD esterase activity assays (see Example 3). Cleavage of a modified peptide substrate of fD, Z-lys-S-Bzl, may be monitored by the cleaved product reducing 5,5'-Dithiobis(2-nitrobenzoic acid). FD may have a lower catalytic rate than other complement proteases when using peptide thioester substrates, and one such substrate Z-lys-SBzl was found to be cleaved by fD and useful as a synthetic substrate (fD is called protein D in Kam, McRae et al. (1987) Human complement proteins D, C2, and B. J. Biol. Chem. 262, 3444-3451). In some cases, a molecule that binds fD may block catalytic activity by binding in the catalytic cleft to sterically prevent access of the peptide substrate to the catalytic residues of fD (Katschke, W u, Ganesan, et al. (2012) Inhibiting alternative pathway complement activation by targeting the Factor D exosite. J. Biol. Chem. 287, 12886-12892). In other cases, a molecule that binds fD may block catalytic activity by occluding access of the substrate to the active site. In yet other cases, a molecule that binds fD may block catalytic activity by an allosteric mechanism that induces structural changes in the enzyme. In yet other cases, a molecule that binds fD may bind to the fD exosite region to sterically inhibit binding of the physiologic substrate protein C3bB, but not of the synthetic modified peptide substrate Z-Lys-SBzl (Katschke, Wu, Ganesan, et al. (2012) Inhibiting alternative pathway complement activation by targeting the Factor D exosite. J. Biol. Chem. 287, 12886-12892). In some instances, where a molecule inhibits fD binding and proteolytic cleavage of fB but not Z-Lys-SBzl, the binding may be similar to how anti-factor D FAb antibody fragment binds to the exosite and induces a subtle conformational change that increases fD cleaving Z-Lys-S-Bzl (Katschke, Wu, Ganesan, et al. (2012) Inhibiting alternative pathway complement activation by targeting the Factor D exosite. J. Biol. Chem. 287, 12886-12892).

In another instance, methods are provided for testing a fD aptamer in a reconstituted biochemical fD activity assay which is composed of purified proteins fD, fB, and C3b (see Example 4). When fD binds to the complex of fB and C3b (C3bB), fB is cleaved by fD into fragments Ba and Bb (Katschke, Wu, Ganesan, et al. (2012) Inhibiting alternative pathway complement activation by targeting the Factor D exosite. J. Biol. Chem. 287, 12886-12892). The activity of fD can be monitored by the rate of fB cleavage and Ba fragment production using an ELISA that uses an antibody that specifically binds Ba (Quidel, A033), or by other means known in the art to measure Ba levels. In some cases, the concentrations of fB and C3b are equal so they form a 1:1 complex which can then bind fD and allow enzymatically active fD to cleave fB to fragments Ba and Bb. In some cases, the fB:C3b complex is present in 4-fold excess of fD. In other cases, the concentrations of fD and/or C3bB are varied in such a manner as to measure enzymatic constants, including, but not limited to $k_{cat}$, $K_m$ and $k_{cat}/K_m$.

In yet another instance, methods are provided for the identification of fD binding to C3bB in complex (see Example 5). FD is the rate-limiting enzyme in the alternative complement pathway, and converts the proconvertases C3bB and C3b$_2$B to form the active C3 convertase C3bBb or the active C5 convertase C3b$_2$Bb (Katschke et al 2012). For surface plasmon resonance (SPR) to detect fD in a stable complex with fB, catalytically inactive fD (S195A) may be used so that it does not cleave the fB upon binding to the fB:C3b complex (Katschke, Wu, Ganesan, et al. (2012) Inhibiting alternative pathway complement activation by targeting the Factor D exosite. J. Biol. Chem. 287, 12886-12892). When C3b is amine-coupled to a CM5 chip, SPR may detect binding of fB as increased mass, and binding of fD to the C3b:fB complex as a further increase in mass. In one aspect, the fD binding compounds are aptamers that bind fD and prevent fD binding to fB:C3b as determined by a reduced mass detected by SPR.

In some cases, a cell model of Stargardt disease may be used to detect activity of anti-fD aptamers (see Example 6). Retinal pigment epithelial (RPE) cells may undergo cell death early during the progress of Stargardt disease, and evidence points toward the involvement of the alternative complement pathway (AP) in RPE cell death (Berchuck, Yang, et al (2013) All-trans-retinal (atRal) sensitizes human RPE cells to alternative complement pathway-induced cell death. Invest Ophthalmol Vis Sci 54, 2669-2677). ARPE-19 cells are a spontaneously arising RPE cell line derived from the normal eyes of a 19-year-old male. The ARPE-19 cell line, established using the cuboidal basal cell layer cultured in specific culture media, expresses the RPE-specific markers cellular retinaldehyde binding protein and RPE-65. Stargardt disease is a hereditary juvenile macular degeneration that occurs in patients with homozygous mutations in the ABCA4 genes, which encode a protein that is responsible for removal of bisretinoid fluorophores, which can include N-retinylidene-N-retinyethanolamine (A2E), all-trans-retinal and related photo-oxidation products of vitamin A aldehyde which together constitute lipofuscin from photoreceptor cells (Molday (2007) ATP-binding cassette transporter ABCA4: molecular properties and role in vision and macular degeneration. J. Bioenerg Biomembr 39, 507-517). An ABCA4 and RDH8 mouse model of Stargardt disease presents with retinal pathology caused by accumulated atRal, and ABCA4 mutations are present in 16% of AMD patients, suggesting that elevated atRal may contribute to Stargardt disease and AMD disease progression (Berchuck et al 2013). Mechanistically, atRal decreased expression of CD46 and CD59 on RPE cells in vitro, which increased susceptibility to cell lysis mediated by alternative complement in response to anti-RPE antibody binding to the RPE cell membranes (Berchuck et al 2013). In some cases, the disclosure provides for the identification of fD inhibitors that inhibit alternative complement-mediated lysis of human retinal pigmented epithelial cells.

The anti-fD aptamers as disclosed herein, in some cases, may bind to the region of fD that includes the active site cleft. Upon activation by binding to C3bB, fD exhibits serine protease activity towards fB. Activation of fD by substrate binding is a two-step process: first, fD binds to fB in the open C3bB configuration at the Von Willebrand factor type-A (VWA)-serine protease (SP) interface of fB, interacting mainly via its exosite residues within loops 145-149, 169-173, 185-188 and 220-224. Binding of fD to C3bB causes the self-inhibitory loop of fD to be displaced from the active site cleft. The global architecture of fD is comprised of two anti-parallel beta barrel domains, each composed of six or seven beta strands that have the same topology in both domains. The beta-strands are connected by 14 turns/loops and three short alpha helices. The active site cleft is located within the loop formed between the two beta barrels, and encompasses structural elements including helix 1, loop 7 and beta-strand 7, loop 11 and beta-strand 11, beta-strand 12, loop 13 and beta-strand 13 (Jing et. al. 1998). Aptamers which bind the active site cleft could recognize any portion of the alpha helices, loops and beta strands which comprise the portion of fD within which the active site cleft resides, and by binding to this region, may prevent access to the active site cleft. Such residues include the catalytic triad, His57, Asp102 and Ser195, the oxyanion hole including the backbone amine of residue 193 and Ser195, the residues linking the catalytic triad to the oxyanion hole via a salt bridge including residue 16, 194 and Ser195, the S1 pocket, including residues 189-192, 214-216, and 224-228, as well as other elements of the specificity pocket including those residues comprising the S2, S3, S4 and Sn pockets. In particular, such aptamers would prevent interaction of P2-Pn residues of fB with specificity pockets S2-Sn of fD. In some cases, the aptamers as described herein specifically bind to the active site cleft or a region comprising the active site cleft of fD. Aptamers that are said to bind to the active site cleft or a region comprising the active site cleft may include any aptamers that bind to one or more of the regions including the catalytic triad (His57, Asp102 and Ser195); the oxyanion hole including the backbone amine of residue 193 and Ser195; the residues linking the catalytic triad to the oxyanion hole via a salt bridge including residue 16, 194 and Ser195; the S1 pocket, including residues 189-192, 214-216, and 224-228; as well as other elements of the specificity pocket including those residues comprising the S2, S3, S4 and Sn pockets.

Such fD inhibitors may inhibit alternative complement dependent hemolysis of red blood cells, may inhibit esterase activity of fD against thioester substrates of fD such as Z-Lys-S-Bzl, and may inhibit fB cleavage in the C3bB complex by fD. In esterase assays, such inhibitors may reduce $k_{cat}$ and increase $K_m$ of fD, with the primary effect decreasing $k_{cat}$ and decreasing $k_{cat}/K_m$ (Hedstrom). In complete biochemical assays, such inhibitors may decrease $k_{cat}$ and increase $K_m$, with a primary effect decreasing $k_{cat}$ and decreasing $k_{cat}/K_m$. Such inhibitors may not prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar E-S assembly assays assessed by ELISA or similar assays. Alternatively, such inhibitors may additionally prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar E-S assembly assays assessed by ELISA or similar assays.

In some cases, an anti-fD aptamer as disclosed herein may bind to fD with a $K_d$ of less than about 50 nM and may inhibit at least 85% of fD activity in an alternative complement dependent hemolysis assay. In some cases, an anti-fD aptamer as disclosed herein may bind to fD with a $K_d$ of less than about 25 nM and may inhibit at least 85% of fD activity in an alternative complement dependent hemolysis assay. In some cases, an anti-fD aptamer as disclosed herein may bind to fD with a $K_d$ of less than about 10 nM and may inhibit at least 85% of fD activity in an alternative complement dependent hemolysis assay. In some cases, an anti-fD aptamer as disclosed herein may bind to fD with a $K_d$ of less than about 5 nM and may inhibit at least 85% of fD activity in an alternative complement dependent hemolysis assay. In some cases, an anti-fD aptamer as disclosed herein may bind to fD with a $K_d$ of less than about 1 nM and may inhibit at least 85% of fD activity in an alternative complement dependent hemolysis assay. In some cases, an anti-fD aptamer as disclosed herein may bind to fD with a $K_d$ of less than about 500 pM and may inhibit at least 85% of fD activity in an alternative complement dependent hemolysis assay. In some cases, an anti-fD aptamer as disclosed herein may bind to fD with a $K_d$ of less than about 50 pM and may inhibit at least 85% of fD activity in an alternative complement dependent hemolysis assay. In some cases, an anti-fD aptamer as disclosed herein may bind to fD with a $K_d$ of less than about 5 pM and may inhibit at least 85% of fD activity in an alternative complement dependent hemolysis assay.

In some cases, an anti-fD aptamer as disclosed herein may bind to fD with a $K_d$ of less than about 50 nM and may inhibit at least 85% of fD activity in a fD convertase assay. In some cases, an anti-fD aptamer as disclosed herein may bind to fD with a $K_d$ of less than about 25 nM and may inhibit at least 85% of fD activity in a fD convertase assay. In some cases, an anti-fD aptamer as disclosed herein may bind to fD with a $K_d$ of less than about 10 nM and may inhibit at least 85% of fD activity in a fD convertase assay. In some cases, an anti-fD aptamer as disclosed herein may bind to fD with a $K_d$ of less than about 5 nM and may inhibit at least 85% of fD activity in a fD convertase assay. In some cases, an anti-fD aptamer as disclosed herein may bind to fD with a $K_d$ of less than about 1 nM and may inhibit at least 85% of fD activity in a fD convertase assay. In some cases, an anti-fD aptamer as disclosed herein may bind to fD with a $K_d$ of less than about 500 pM and may inhibit at least 85% of fD activity in a fD convertase assay. In some cases, an anti-fD aptamer as disclosed herein may bind to fD with a $K_d$ of less than about 50 pM and may inhibit at least 85% of fD activity in a fD convertase assay. In some cases, an anti-fD aptamer as disclosed herein may bind to fD with a $K_d$ of less than about 5 pM and may inhibit at least 85% of fD activity in a fD convertase assay.

In some cases, an anti-fD aptamer as disclosed herein may bind to fD with a $K_d$ of less than about 50 nM and inhibit fD activity in an esterase activity assay. In some cases, an anti-fD aptamer as disclosed herein may bind to fD with a $K_d$ of less than about 25 nM and may inhibit fD activity in an esterase activity assay. In some cases, an anti-fD aptamer as disclosed herein may bind to fD with a $K_d$ of less than about 10 nM and may inhibit fD activity in an esterase activity assay. In some cases, an anti-fD aptamer as disclosed herein may bind to fD with a $K_d$ of less than about 5 nM and may inhibit fD activity in an esterase activity assay. In some cases, an anti-fD aptamer as disclosed herein may bind to fD with a $K_d$ of less than about 1 nM and may inhibit fD activity in an esterase activity assay. In some cases, an anti-fD aptamer as disclosed herein may bind to fD with a $K_d$ of less than about 500 pM and may inhibit fD activity in an esterase activity assay. In some cases, an anti-fD aptamer as disclosed herein may bind to fD with a $K_d$ of less than about 50 pM and may inhibit fD activity in an esterase activity assay. In some cases, an anti-fD aptamer as disclosed herein may bind to fD with a $K_d$ of less than about 5 pM and may inhibit fD activity in an esterase activity assay.

The anti-fD aptamers as disclosed herein, in some cases, may bind to the region of fD that includes the self-inhibitory loop (residues 212-218) and regions adjacent to the self-inhibitory loop, so as to stabilize the self-inhibited state of fD. Mature fD maintains a self-inhibited state through a set of conformations in the free fD state including the conformation of residues 212-218, which may be referred to as the self-inhibitory loop of fD. These residues may comprise portions of the polypeptide binding site as well as the S1 specificity pocket of fD. In the inactive state of fD, this loop is in an elevated conformation and forms specific bonds with key components of the catalytic triad and S1 specificity pocket, rendering fD inactive. In some cases, the anti-fD compounds of the disclosure are designed to target the self-inhibitory loop of fD to prevent the activation of fD. For example, the anti-fD compounds may bind to the self-inhibitory loop or to regions around the self-inhibitory loop to prevent displacement of the self-inhibitory loop from the active site cleft. In some cases, the anti-fD compounds may be designed to target residues 212-218 of fD. In cases where anti-fD aptamers bind to a region comprising one or more of amino acid residues 212-218 of fD, it may be said that such anti-fD aptamers bind to the self-inhibitory loop or a portion thereof of fD.

Such fD inhibitors may inhibit alternative complement dependent hemolysis of red blood cells, may inhibit esterase activity of fD against thioester substrates of fD such as Z-Lys-S-Bzl, and may inhibit fB cleavage in the C3bB complex by fD. In esterase assays, such inhibitors may reduce $k_{cat}$ and increase $K_m$ of fD, with the primary effect decreasing $k_{cat}$ and decreasing $k_{cat}/K_m$. In complete biochemical assays, such inhibitors may decrease $k_w$ and increase $K_m$, with a primary effect decreasing $k_{cat}$ and decreasing $k_{cat}/K_m$. Such inhibitors may not prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar E-S assembly assays assessed by ELISA or similar assays. Alternatively, such inhibitors may also prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar E-S assembly assays assessed by ELISA or similar assays.

The anti-fD aptamers as disclosed herein, in some cases, may bind to the exosite of fD so as to prevent formation of the ES complex. Without wishing to be bound by theory, the high specificity of fD for fB may be due to protein-protein interactions between the exosites of fD and fB. The exosite of fD is approximately 25 Å from the catalytic center and consists of 4 loops comprised by residues 145-149, 169-173, 185-188 and 220-224. In some cases, the anti-fD compounds of the disclosure may target the exosite of fD and prevent the interaction of fD with fB. Anti-fD compounds of this nature may target one or more of the 4 loops of the fD exosite, for example, the anti-fD compounds may be designed to target one or more of amino acid residues 145-149, 169-173, 185-188 and 220-224 of fD. In cases where an anti-fD aptamer binds to one or more of amino acid residues 145-149, 169-173, 185-188, and 220-224, it may be said that such aptamers bind to the exosite of fD.

Aptamer inhibitors that block binding of the C3bB substrate to fD may inhibit alternative complement dependent hemolysis of red blood cells. Such inhibitors may enhance the esterase activity of fD against thioester substrates of fD such as Z-Lys-S-Bzl, as observed for the anti-fD Fab's when bound to human fD (Katschke et. al.). Alternatively, aptamers which bind to the exosite of fD may not impact the esterase activity of fD, as for example, when the anti-fD Fab in Katschke et. al. binds fD from cynomolgus monkeys, it neither inhibits nor enhances fD esterase activity. Exosite binding aptamers would inhibit fB cleavage in the C3bB complex by fD. In esterase assays, such inhibitors may increase $k_{cat}$ and have no or minimal impact on $K_m$ of fD, with the primary effect increasing $k_{cat}$ and increasing $k_{cat}/K_m$, or such inhibitors would neither impact $k_{cat}$ or $K_m$ or $k_{cat}/K_m$. In complete biochemical assays, such inhibitors would primarily increase $K_m$ and decrease $k_{cat}/K_m$. Such inhibitors may prevent formation of the enzyme-substrate complex (fD-C3bB complex) as assessed in enzymatic assays or enzyme-substrate assembly assays, such as surface plasmon resonance (SPR) assays described in Forneris et. al. or Katschke et. al., or similar ES assembly assays assessed by ELISA or similar assays.

Catalytic turn-over of fD activation of fB requires dissociation of the ES complex if bound in a non-productive state or the EP (fD-C3bBb) complex upon fB cleavage. The anti-fD aptamers as disclosed herein, in some cases, may bind to fD in such a way as to prevent dissociation of fD from C3bB or C3bBb. As envisioned, such aptamers may bind near the exosite of fD and bind to fD in such a manner as to increase the affinity of fD for C3bB or C3bBb by decreasing the off-rate of this interaction. Such aptamers could be generated by selection against the fD-C3bB complex, by for example using a catalytically inactivated form of fD such as a mutant form in which Ser195 is mutated to Ala195 (Forneris et. al.), to provide a stable, non-reactive ES complex as a target for selection. Aptamers possessing such a mechanism of action would inhibit alternative complement dependent hemolysis of red blood cells. Such inhibitors may inhibit the esterase activity of fD against thioester substrates of fD such as Z-Lys-S-Bzl, or may not impact the esterase activity of fD. Such binding aptamers would inhibit the turn-over of fB cleavage in the C3bB complex by fD. In esterase assays, such inhibitors may decrease the $k_{cat}$ and have no or minimal impact on $K_m$ of fD, with the primary effect decreasing $k_{cat}$ and decreasing $k_{cat}/K_m$, or such inhibitors would neither impact $k_{cat}$ or $K_m$ or $k_{cat}/K_m$. In complete biochemical assays, such inhibitors would primarily decrease $K_{cat}$ and decrease $k_{cat}/K_m$. Such inhibitors would enhance formation of the enzyme-substrate complex (fD-C3bB complex) as assessed in enzymatic assays or enzyme-substrate assembly assays, such as surface plasmon resonance (SPR) assays described in Forneris et. al., and may increase the apparent affinity of fD for C3bB or C3bBb.

In some cases, an aptamer as described herein may bind the same epitope as an anti-fD antibody or antibody fragment thereof. In some cases, an aptamer as described herein may bind to the same epitope as an anti-fD therapeutic antibody. For example, the anti-fD aptamer may bind to the same or similar region of fD to that which an anti-fD therapeutic antibody such as an anti-fD Fab with an amino acid sequence of heavy chain variable region according to SEQ ID NO:7 and an amino acid sequence of light chain variable region according to SEQ ID NO:8; Mab 166-3 or LS-C135735 bind. For example, an anti-fD Fab with an amino acid sequence of heavy chain variable region according to SEQ ID NO:7 and light chain variable region according to SEQ ID NO:8 may bind residues 129-132, residues 164-178, Arg223 and Lys224, with the bulk of the interaction involving the loop encompassing amino acid 170 (the "170 loop"). In some cases, an aptamer that binds to the same or similar region of fD to that which an anti-fD Fab with an amino acid sequence of heavy chain variable region according to SEQ ID NO:7 and light chain variable region according to SEQ ID NO:8 binds (e.g., a region comprising one or more of amino acid residues 129-132, 164-178, Arg223 and Lys224) may be said to be binding to the exosite of fD.

In some cases, an anti-fD aptamer for the modulation of fD is provided. In some cases, an anti-fD aptamer for the inhibition of a function associated with fD is provided. In some cases, the anti-fD aptamer inhibits the catalytic activity of fD. In some cases, an anti-fD aptamer for the treatment of dry AMD or geographic atrophy is provided. In some cases, an anti-fD aptamer for the treatment of wet AMD is provided. In some cases, an anti-fD aptamer for the treatment of Stargardt disease is provided.

The dissociation constant ($K_d$) can be used to describe the affinity of an aptamer for a target (or to describe how tightly the aptamer binds to the target) or to describe the affinity of an aptamer for a specific epitope of a target (e.g., exosite, catalytic cleft, etc.). The dissociation constant is defined as the molar concentration at which half of the binding sites of a target are occupied by the aptamer. Thus, the smaller the $K_d$, the tighter the binding of the aptamer to its target. In some cases, an anti-fD aptamer has a dissociation constant ($K_d$) for fD protein of less than 1 mM, less than 100 µM, less than 10 µM, less than 1 µM, less than 100 nM, less than 10 nM, less than 1 nM, less than 500 pM, or less than 100 pM. In some cases, an anti-fD aptamer has a dissociation constant ($K_d$) for fD protein of less than 50 nM. In some cases, an anti-fD aptamer has a dissociation constant ($K_d$) for fD protein of less than 25 nM. In some cases, an anti-fD aptamer has a dissociation constant ($K_d$) for fD protein of less than 10 nM. In some cases, an anti-fD aptamer has a dissociation constant ($K_d$) for fD protein of less than 5 nM. In some cases, an anti-fD aptamer has a dissociation constant ($K_d$) for fD protein of less than 500 pM. In some cases, an anti-fD aptamer has a dissociation constant ($K_d$) for fD protein of less than 50 pM. In some cases, an anti-fD aptamer has a dissociation constant ($K_d$) for fD protein of less than 5 pM. In some cases, the aptamer binds to the catalytic cleft, the active site, the exosite, and/or the self-inhibitory loop of fD with a $K_d$ of less than about 1 mM, 100 µM, 10 µM, 100 nM, 50 nM, 25 nM, 10 nM, 5 nM, 500 pM, 50 pM, or 5 pM. In some cases, the anti-fD aptamer binds to the catalytic cleft, the active site, and/or the self-inhibitory loop of fD with a $K_d$ from about 500 pM to about 1 nM. In some cases, the anti-fD aptamer binds to the catalytic cleft, the active site, and/or the self-inhibitory loop of fD with a $K_d$ from about 1 nM to about 10 nM. In some cases, the $K_d$ is determined by a flow cytometry assay as described herein.

The aptamers disclosed herein may bind to the catalytic cleft of fD with a $K_d$ of less than about 50 nM and have an $IC_{50}$ of less than about 50 nM as measured by an alternative complement dependent hemolysis assay. The aptamers disclosed herein may bind to the catalytic cleft of fD with a $K_d$ of less than about 50 nM and have an $IC_{50}$ of less than about 10 nM as measured by an alternative complement dependent hemolysis assay. The aptamers disclosed herein may bind to the catalytic cleft of fD with a $K_d$ of less than about 50 nM and have an $IC_{50}$ of less than about 5 nM as measured by an alternative complement dependent hemolysis assay. The aptamers disclosed herein may bind to the catalytic cleft of fD with a $K_d$ of less than about 10 nM and have an $IC_{50}$ of less than about 50 nM as measured by an alternative complement dependent hemolysis assay. The aptamers disclosed herein may bind to the catalytic cleft of fD with a $K_d$ of less than about 10 nM and have an $IC_{50}$ of less than about 10 nM as measured by an alternative complement dependent hemolysis assay. The aptamers disclosed herein may bind to the catalytic cleft of fD with a $K_d$ of less than about 10 nM and have an $IC_{50}$ of less than about 5 nM as measured by an alternative complement dependent hemolysis assay. The aptamers disclosed herein may bind to the catalytic cleft of fD with a $K_d$ of less than about 5 nM and have an $IC_{50}$ of less than about 50 nM as measured by an alternative complement dependent hemolysis assay. The aptamers disclosed herein may bind to the catalytic cleft of fD with a $K_d$ of less than about 5 nM and have an $IC_{50}$ of less than about 10 nM as measured by an alternative complement dependent hemolysis assay. The aptamers disclosed herein may bind to the catalytic cleft of fD with a $K_d$ of less than about 5 nM and have an $IC_{50}$ of less than about 5 nM as measured by an alternative complement dependent hemolysis assay. The aptamers disclosed herein may bind to the catalytic cleft of fD with a $K_d$ of less than about 1 nM and have an $IC_{50}$ of less than about 50 nM as measured by an alternative complement dependent hemolysis assay. The aptamers disclosed herein may bind to the catalytic cleft of fD with a $K_d$ of less than about 1 nM and have an $IC_{50}$ of less than about 10 nM as measured by an alternative complement dependent hemolysis assay. The aptamers disclosed herein may bind to the catalytic cleft of fD with a $K_d$ of less than about 1 nM and have an $IC_{50}$ of less than about 5 nM as measured by an alternative complement dependent hemolysis assay. The aptamers disclosed herein may bind to the catalytic cleft of fD with a $K_d$ of about 500 pM or greater and have an $IC_{50}$ of less than about 50 nM as measured by an alternative complement dependent hemolysis assay. The aptamers disclosed herein may bind to the catalytic cleft of fD with a $K_d$ of about 500 pM or greater and have an $IC_{50}$ of less than about 10 nM as measured by an alternative complement dependent hemolysis assay. The aptamers disclosed herein may bind to the catalytic cleft of fD with a $K_d$ of about 500 pM or greater and have an $IC_{50}$ of less than about 5 nM as measured by an alternative complement dependent hemolysis assay.

The aptamers disclosed herein may bind to the active site of fD with a $K_d$ of less than about 50 nM and have an $IC_{50}$ of less than about 50 nM as measured by an alternative complement dependent hemolysis assay. The aptamers disclosed herein may bind to the active site of fD with a $K_d$ of less than about 50 nM and have an $IC_{50}$ of less than about 10 nM as measured by an alternative complement dependent hemolysis assay. The aptamers disclosed herein may bind to the active site of fD with a $K_d$ of less than about 50 nM and have an $IC_{50}$ of less than about 5 nM as measured by an alternative complement dependent hemolysis assay. The aptamers disclosed herein may bind to the active site of fD with a $K_d$ of less than about 10 nM and have an $IC_{50}$ of less than about 50 nM as measured by an alternative complement dependent hemolysis assay. The aptamers disclosed herein may bind to the active site of fD with a $K_d$ of less than about 10 nM and have an $IC_{50}$ of less than about 10 nM as measured by an alternative complement dependent hemolysis assay. The aptamers disclosed herein may bind to the active site of fD with a $K_d$ of less than about 10 nM and have an $IC_{50}$ of less than about 5 nM as measured by an alternative complement dependent hemolysis assay. The aptamers disclosed herein may bind to the active site of fD with a $K_d$ of less than about 5 nM and have an $IC_{50}$ of less than about 50 nM as measured by an alternative complement dependent hemolysis assay. The aptamers disclosed herein may bind to the active site of fD with a $K_d$ of less than about 5 nM and have an $IC_{50}$ of less than about 10 nM as measured by an alternative complement dependent hemolysis assay. The aptamers disclosed herein may bind to the active site of fD with a $K_d$ of less than about 5 nM and have an $IC_{50}$ of less than about 5 nM as measured by an alternative complement dependent hemolysis assay. The aptamers disclosed herein may bind to the active site of fD with a $K_d$ of less than about 1 nM and have an $IC_{50}$ of less than about 50 nM as measured by an alternative complement dependent hemolysis assay. The aptamers disclosed herein may bind to the active site of fD with a $K_d$ of less than about 1 nM and have an $IC_{50}$ of less than about 10 nM as measured by an alternative complement dependent hemolysis assay. The aptamers disclosed herein may bind to the active site of fD with a $K_d$ of less than about 1 nM and have an $IC_{50}$ of less than about 5 nM as measured by an alternative complement dependent hemolysis assay. The aptamers disclosed herein may bind to the active site of fD with a $K_d$ of about 500 pM or greater and have an $IC_{50}$ of less than about 50 nM as measured by an alternative complement dependent hemolysis assay. The aptamers disclosed herein may bind to the active site of fD with a $K_d$ of about 500 pM or greater and have an $IC_{50}$ of less than about 10 nM as measured by an alternative complement dependent hemolysis assay. The aptamers disclosed herein may bind to the active site of fD with a $K_d$ of about 500 pM or greater and have an $IC_{50}$ of less than about 5 nM as measured by an alternative complement dependent hemolysis assay.

The aptamers disclosed herein may bind to a region of fD such that the aptamers block or occlude access to the active site of fD, thereby preventing a natural substrate of fD from accessing the active site. The aptamers disclosed herein may bind to such a region of fD with a $K_d$ of less than about 50 nM and have an $IC_{50}$ of less than about 50 nM as measured by an alternative complement dependent hemolysis assay. The aptamers disclosed herein may bind to such a region of fD with a $K_d$ of less than about 50 nM and have an $IC_{50}$ of less than about 10 nM as measured by an alternative complement dependent hemolysis assay. The aptamers disclosed herein may bind to such a region of fD with a $K_d$ of less than about 50 nM and have an $IC_{50}$ of less than about 5 nM as measured by an alternative complement dependent hemolysis assay. The aptamers disclosed herein may bind to such a region of fD with a $K_d$ of less than about 10 nM and have an $IC_{50}$ of less than about 50 nM as measured by an alternative complement dependent hemolysis assay. The aptamers disclosed herein may bind to such a region of fD with a $K_d$ of less than about 10 nM and have an $IC_{50}$ of less than about 10 nM as measured by an alternative complement dependent hemolysis assay. The aptamers disclosed herein may bind to such a region of fD with a $K_d$ of less than about 10 nM and have an $IC_{50}$ of less than about 5 nM as measured by an alternative complement dependent hemolysis assay. The aptamers disclosed herein may bind to such a region of fD with a $K_d$ of less than about 5 nM and have an $IC_{50}$ of less than about 50 nM as measured by an alternative complement dependent hemolysis assay. The aptamers disclosed herein may bind to such a region of fD with a $K_d$ of less than about 5 nM and have an $IC_{50}$ of less than about 10 nM as measured by an alternative complement dependent hemolysis assay. The aptamers disclosed herein may bind to such a region of fD with a $K_d$ of less than about 5 nM and have an $IC_{50}$ of less than about 5 nM as measured by an alternative complement dependent hemolysis assay. The aptamers disclosed herein may bind to such a region of fD with a $K_d$ of less than about 1 nM and have an $IC_{50}$ of less than about 50 nM as measured by an alternative complement dependent hemolysis assay. The aptamers disclosed herein may bind to such a region of fD with a $K_d$ of less than about 1 nM and have an $IC_{50}$ of less than about 10 nM as measured by an alternative complement dependent hemolysis assay. The aptamers disclosed herein may bind to such a region of fD with a $K_d$ of less than about 1 nM and have an $IC_{50}$ of less than about 5 nM as measured by an alternative complement dependent hemolysis assay. The aptamers disclosed herein may bind to such a region of fD with a $K_d$ of about 500 pM or greater and have an $IC_{50}$ of less than about 50 nM as measured by an alternative complement dependent hemolysis assay. The aptamers disclosed herein may bind to such a region of fD with a $K_d$ of about 500 pM or greater and have an $IC_{50}$ of less than about 10 nM as measured by an alternative complement dependent hemolysis assay. The aptamers disclosed herein may bind to such a region of fD with a $K_d$ of about 500 pM or greater and have an $IC_{50}$ of less than about 5 nM as measured by an alternative complement dependent hemolysis assay.

The aptamers disclosed herein may bind to the exosite of fD with a $K_d$ of less than about 50 nM and have an $IC_{50}$ of less than about 50 nM as measured by an alternative complement dependent hemolysis assay. The aptamers disclosed herein may bind to the exosite of fD with a $K_d$ of less than about 50 nM and have an $IC_{50}$ of less than about 10 nM as measured by an alternative complement dependent hemolysis assay. The aptamers disclosed herein may bind to the exosite of fD with a $K_d$ of less than about 50 nM and have an $IC_{50}$ of less than about 5 nM as measured by an alternative complement dependent hemolysis assay. The aptamers disclosed herein may bind to the exosite of fD with a $K_d$ of less than about 10 nM and have an $IC_{50}$ of less than about 50 nM as measured by an alternative complement dependent hemolysis assay. The aptamers disclosed herein may bind to the exosite of fD with a $K_d$ of less than about 10 nM and have an $IC_{50}$ of less than about 10 nM as measured by an alternative complement dependent hemolysis assay. The aptamers disclosed herein may bind to the exosite of fD with a $K_d$ of less than about 10 nM and have an $IC_{50}$ of less than about 5 nM as measured by an alternative complement dependent hemolysis assay. The aptamers disclosed herein may bind to the exosite of fD with a $K_d$ of less than about 5 nM and have an $IC_{50}$ of less than about 50 nM as measured by an alternative complement dependent hemolysis assay. The aptamers disclosed herein may bind to the exosite of fD with a $K_d$ of less than about 5 nM and have an $IC_{50}$ of less than about 10 nM as measured by an alternative complement dependent hemolysis assay. The aptamers disclosed herein may bind to the exosite of fD with a $K_d$ of less than about 5 nM and have an $IC_{50}$ of less than about 5 nM as measured by an alternative complement dependent hemolysis assay. The aptamers disclosed herein may bind to the exosite of fD with a $K_d$ of less than about 1 nM and have an $IC_{50}$ of less than about 50 nM as measured by an alternative complement dependent hemolysis assay. The aptamers disclosed herein may bind to the exosite of fD with a $K_d$ of less than about 1 nM and have an $IC_{50}$ of less than about 10 nM as measured by an alternative complement dependent hemolysis assay. The aptamers disclosed herein may bind to the exosite of fD with a $K_d$ of less than about 1 nM and have an $IC_{50}$ of less than about 5 nM as measured by an alternative complement dependent hemolysis assay. The aptamers disclosed herein may bind to the exosite of fD with a $K_d$ of about 500 pM or greater and have an $IC_{50}$ of less than about 50 nM as measured by an alternative complement dependent hemolysis assay. The aptamers disclosed herein may bind to the exosite of fD with a $K_d$ of about 500 pM or greater and have an $IC_{50}$ of less than about 10 nM as measured by an alternative complement dependent hemolysis assay. The aptamers disclosed herein may bind to the exosite of fD with a $K_d$ of about 500 pM or greater and have an $IC_{50}$ of less than about 5 nM as measured by an alternative complement dependent hemolysis assay.

The aptamers disclosed herein may bind to a region of fD such that the aptamers block or occlude access to the substrate-binding exosite of fD. The aptamers disclosed herein may bind to such a region of fD with a $K_d$ of less than about 50 nM and have an $IC_{50}$ of less than about 50 nM as measured by an alternative complement dependent hemolysis assay. The aptamers disclosed herein may bind to such a region of fD with a $K_d$ of less than about 50 nM and have an $IC_{50}$ of less than about 10 nM as measured by an alternative complement dependent hemolysis assay. The aptamers disclosed herein may bind to such a region of fD with a $K_d$ of less than about 50 nM and have an $IC_{50}$ of less than about 5 nM as measured by an alternative complement dependent hemolysis assay. The aptamers disclosed herein may bind to such a region of fD with a $K_d$ of less than about 10 nM and have an $IC_{50}$ of less than about 50 nM as measured by an alternative complement dependent hemolysis assay. The aptamers disclosed herein may bind to such a region of fD with a $K_d$ of less than about 10 nM and have an $IC_{50}$ of less than about 10 nM as measured by an alternative complement dependent hemolysis assay. The aptamers disclosed herein may bind to such a region of fD with a $K_d$ of less than about 10 nM and have an $IC_{50}$ of less than about 5 nM as measured by an alternative complement dependent hemolysis assay. The aptamers disclosed herein may bind to such a region of fD with a $K_d$ of less than about 5 nM and have an $IC_{50}$ of less than about 50 nM as measured by an alternative complement dependent hemolysis assay. The aptamers disclosed herein may bind to such a region of fD with a $K_d$ of less than about 5 nM and have an $IC_{50}$ of less than about 10 nM as measured by an alternative complement dependent hemolysis assay. The aptamers disclosed herein may bind to such a region of fD with a $K_d$ of less than about 5 nM and have an $IC_{50}$ of less than about 5 nM as measured by an alternative complement dependent hemolysis assay. The aptamers disclosed herein may bind to such a region of fD with a $K_d$ of less than about 1 nM and have an $IC_{50}$ of less than about 50 nM as measured by an alternative complement dependent hemolysis assay. The aptamers disclosed herein may bind to such a region of fD with a $K_d$ of less than about 1 nM and have an $IC_{50}$ of less than about 10 nM as measured by an alternative complement dependent hemolysis assay. The aptamers disclosed herein may bind to such a region of fD with a $K_d$ of less than about 1 nM and have an $IC_{50}$ of less than about 5 nM as measured by an alternative complement dependent hemolysis assay. The aptamers disclosed herein may bind to such a region of fD with a $K_d$ of about 500 pM or greater and have an $IC_{50}$ of less than about 50 nM as measured by an alternative complement dependent hemolysis assay. The aptamers disclosed herein may bind to such a region of fD with a $K_d$ of about 500 pM or greater and have an $IC_{50}$ of less than about 10 nM as measured by an alternative complement dependent hemolysis assay. The aptamers disclosed herein may bind to such a region of fD with a $K_d$ of about 500 pM or greater and have an $IC_{50}$ of less than about 5 nM as measured by an alternative complement dependent hemolysis assay.

The aptamers disclosed herein may bind to a region of fD such that the aptamers block or occlude access to both the active site and the substrate-binding exosite of fD. The aptamers disclosed herein may bind to such a region of fD with a $K_d$ of less than about 50 nM and have an $IC_{50}$ of less than about 50 nM as measured by an alternative complement dependent hemolysis assay. The aptamers disclosed herein may bind to such a region of fD with a $K_d$ of less than about 50 nM and have an $IC_{50}$ of less than about 10 nM as measured by an alternative complement dependent hemolysis assay. The aptamers disclosed herein may bind to such a region of fD with a $K_d$ of less than about 50 nM and have an $IC_{50}$ of less than about 5 nM as measured by an alternative complement dependent hemolysis assay. The aptamers disclosed herein may bind to such a region of fD with a $K_d$ of less than about 10 nM and have an $IC_{50}$ of less than about 50 nM as measured by an alternative complement dependent hemolysis assay. The aptamers disclosed herein may bind to such a region of fD with a $K_d$ of less than about 10 nM and have an $IC_{50}$ of less than about 10 nM as measured by an alternative complement dependent hemolysis assay. The aptamers disclosed herein may bind to such a region of fD with a $K_d$ of less than about 10 nM and have an $IC_{50}$ of less than about 5 nM as measured by an alternative complement dependent hemolysis assay. The aptamers disclosed herein may bind to such a region of fD with a $K_d$ of less than about 5 nM and have an $IC_{50}$ of less than about 50 nM as measured by an alternative complement dependent hemolysis assay. The aptamers disclosed herein may bind to such a region of fD with a $K_d$ of less than about 5 nM and have an $IC_{50}$ of less than about 10 nM as measured by an alternative complement dependent hemolysis assay. The aptamers disclosed herein may bind to such a region of fD with a $K_d$ of less than about 5 nM and have an $IC_{50}$ of less than about 5 nM as measured by an alternative complement dependent hemolysis assay. The aptamers disclosed herein may bind to such a region of fD with a $K_d$ of less than about 1 nM and have an $IC_{50}$ of less than about 50 nM as measured by an alternative complement dependent hemolysis assay. The aptamers disclosed herein may bind to such a region of fD with a $K_d$ of less than about 1 nM and have an $IC_{50}$ of less than about 10 nM as measured by an alternative complement dependent hemolysis assay. The aptamers disclosed herein may bind to such a region of fD with a $K_d$ of less than about 1 nM and have an $IC_{50}$ of less than about 5 nM as measured by an alternative complement dependent hemolysis assay. The aptamers disclosed herein may bind to such a region of fD with a $K_d$ of about 500 pM or greater and have an $IC_{50}$ of less than about 50 nM as measured by an alternative complement dependent hemolysis assay. The aptamers disclosed herein may bind to such a region of fD with a $K_d$ of about 500 pM or greater and have an $IC_{50}$ of less than about 10 nM as measured by an alternative complement dependent hemolysis assay. The aptamers disclosed herein may bind to such a region of fD with a $K_d$ of about 500 pM or greater and have an $IC_{50}$ of less than about 5 nM as measured by an alternative complement dependent hemolysis assay.

The aptamers disclosed herein may bind to the self-inhibitory loop of fD with a $K_d$ of less than about 50 nM and have an $IC_{50}$ of less than about 50 nM as measured by an alternative complement dependent hemolysis assay. The aptamers disclosed herein may bind to the self-inhibitory loop of fD with a $K_d$ of less than about 50 nM and have an $IC_{50}$ of less than about 10 nM as measured by an alternative complement dependent hemolysis assay. The aptamers disclosed herein may bind to the self-inhibitory loop of fD with a $K_d$ of less than about 50 nM and have an $IC_{50}$ of less than about 5 nM as measured by an alternative complement dependent hemolysis assay. The aptamers disclosed herein may bind to the self-inhibitory loop of fD with a $K_d$ of less than about 10 nM and have an $IC_{50}$ of less than about 50 nM as measured by an alternative complement dependent hemolysis assay. The aptamers disclosed herein may bind to the self-inhibitory loop of fD with a $K_d$ of less than about 10 nM and have an $IC_{50}$ of less than about 10 nM as measured by an alternative complement dependent hemolysis assay. The aptamers disclosed herein may bind to the self-inhibitory loop of fD with a $K_d$ of less than about 10 nM and have an $IC_{50}$ of less than about 5 nM as measured by an alternative complement dependent hemolysis assay. The aptamers disclosed herein may bind to the self-inhibitory loop of fD with a $K_d$ of less than about 5 nM and have an $IC_{50}$ of less than about 50 nM as measured by an alternative complement dependent hemolysis assay. The aptamers disclosed herein may bind to the self-inhibitory loop of fD with a $K_d$ of less than about 5 nM and have an $IC_{50}$ of less than about 10 nM as measured by an alternative complement dependent hemolysis assay. The aptamers disclosed herein may bind to the self-inhibitory loop of fD with a $K_d$ of less than about 5 nM and have an $IC_{50}$ of less than about 5 nM as measured by an alternative complement dependent hemolysis assay. The aptamers disclosed herein may bind to the self-inhibitory loop of fD with a $K_d$ of less than about 1 nM and have an $IC_{50}$ of less than about 50 nM as measured by an alternative complement dependent hemolysis assay. The aptamers disclosed herein may bind to the self-inhibitory loop of fD with a $K_d$ of less than about 1 nM and have an $IC_{50}$ of less than about 10 nM as measured by an alternative complement dependent hemolysis assay. The aptamers disclosed herein may bind to the self-inhibitory loop of fD with a $K_d$ of less than about 1 nM and have an $IC_{50}$ of less than about 5 nM as measured by an alternative complement dependent hemolysis assay. The aptamers disclosed herein may bind to the self-inhibitory loop of fD with a $K_d$ of about 500 pM or greater and have an $IC_{50}$ of less than about 50 nM as measured by an alternative complement dependent hemolysis assay. The aptamers disclosed herein may bind to the self-inhibitory loop of fD with a $K_d$ of about 500 pM or greater and have an $IC_{50}$ of less than about 10 nM as measured by an alternative complement dependent hemolysis assay. The aptamers disclosed herein may bind to the self-inhibitory loop of fD with a $K_d$ of about 500 pM or greater and have an $IC_{50}$ of less than about 5 nM as measured by an alternative complement dependent hemolysis assay.

In some aspects, the aptamers disclosed herein have an improved half-life as compared to other therapeutics, including antibodies. In some cases, the aptamers have an improved half-life in a biological fluid or solution as compared to an antibody. In some cases, the aptamers have an improved half-life in vivo as compared to an antibody. In one example, the aptamers have an improved half-life when injected into the eye (intraocular half-life) as compared to an antibody. In some cases, the aptamers may have an improved intraocular half-life when injected into the eye of a human. In some cases, the aptamers may demonstrate improved stability over antibodies, under physiological conditions.

In some cases, the aptamers described herein have an intraocular half-life of at least 7 days in a human. In some cases, the aptamers described herein have an intraocular half-life of at least 8 days, at least 9 days, at least 10 days, at least 11 days, at least 12 days, at least 13 days, at least 14 days, at least 15 days, at least 20 days or greater in a human.

In some cases, the aptamers described herein have an intraocular half-life of at least 1 day in a non-human animal (e.g., rodent/rabbit/monkey). In some cases, the aptamers described herein have an intraocular half-life of at least 1 day, at least 2 days, at least 3 days, at least 4 days, at least 5 days, at least 6 days, at least 7 days, at least 8 days, at least 9 days, at least 10 days or greater in a non-human animal such as a rodent, rabbit or monkey.

In some aspects, the aptamers described herein may have a shorter half-life as compared to other therapeutics. For example, an unmodified or unconjugated aptamer may have a lower half-life as compared to a modified or conjugated aptamer, however, the low molecular weight of the unmodified or unconjugated forms may allow for orders of magnitude greater initial concentrations, thereby achieving greater duration/efficacy. In some examples, the aptamer may have an intraocular half-life of less than about 7 days in a human. In some examples, the aptamers described herein have an intraocular half-life of less than about 6 days, less than about 5 days or even less than about 4 days in a human.

The aptamers disclosed herein may demonstrate high specificity for fD versus other complement pathway components. Generally, the aptamer may be selected such that the aptamer has high affinity for fD, but with little to no affinity for other complement pathway components or serine proteases. In some cases, the aptamers bind to fD with a specificity of at least 5-fold, at least 10-fold, at least 15-fold, at least 20-fold, or greater than 20-fold greater than the aptamers bind to any of C3, CS, Factor B, Factor H or Factor I (or any of their related dimeric, trimeric, or multimeric complexes, units or subunits) at relative serum concentrations. For example, in some cases the aptamers bind to fD with a specificity of at least 50-fold greater than the aptamers bind to any of C3, C5, Factor B, Factor H or Factor I (or any of their related dimeric, trimeric, or multimeric complexes, units or subunits) at relative serum concentrations. For example, in some cases the aptamers bind to FD with a specificity of at least 100-fold greater than the aptamers bind to any of C3, C5, Factor B, Factor H or Factor I (or any of their related dimeric, trimeric, or multimeric complexes, units or subunits) at relative serum concentrations.

The activity of a therapeutic agent can be characterized by the half maximal inhibitory concentration ($IC_{50}$). The $IC_{50}$ is calculated as the concentration of therapeutic agent in nM at which half of the maximum inhibitory effect of the therapeutic agent is achieved. The $IC_{50}$ is dependent upon the assay utilized to calculate the value. In some examples, the $IC_{50}$ of an aptamer described herein is less than 100 nM, less than 50 nM, less than 25 nM, less than 10 nM, less than 5 nM, less than 1 nM, less than 0.5 nM, less than 0.1 nM or less than 0.01 nM as measured by an alternative complement dependent hemolysis assay (Pangburn, 1988, *Methods in Enzymology*; and Katschke, 2009, *Journal of Biological Chemistry*).

In some examples, the aptamers described herein increase the activity of fD as measured by a fD esterase activity assay as compared to a control, and inhibit activity of fD as measured by an alternative complement dependent hemolysis assay. In other examples, the aptamers described herein inhibit activity of fD as measured by a fD esterase activity assay as compared to a control, and inhibit activity of fD as measured by an alternative complement dependent hemolysis assay. In yet other cases, the aptamer does not inhibit activity of fD as measured by a fD esterase activity assay as compared to a control, and does inhibit activity of fD as measured by an alternative complement dependent hemolysis assay.

Aptamers generally have high stability at ambient temperatures for extended periods of time. The aptamers described herein demonstrate greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, greater than 99%, greater than 99.5%, or greater than 99.9% activity in solution under physiological conditions at 30 days or later.

In some cases, a composition of the disclosure comprises anti-fD aptamers, wherein essentially 100% of the anti-fD aptamers comprise nucleotides having ribose in the β-D-ribofuranose configuration. In other examples, a composition of the disclosure may comprise anti-fD aptamers, wherein at least 50%, at least 60%, at least 70%, at least 80%, at least 90%, or greater than 90% of the anti-fD aptamers have ribose in the β-D-ribofuranose configuration.

Indications

In some aspects, the methods and compositions provided herein are used for the treatment of ocular diseases or disorders. Ocular diseases or disorders can include, without limitation, any complement-mediated ocular disorders such as inflammatory conjunctivitis, including allergic and giant papillary conjunctivitis, macular edema, uveitis, endophthalmitis, scleritis, corneal ulcers, dry eye syndrome, glaucoma, ischemic retinal disease, corneal transplant rejection, complications related to intraocular surgery such intraocular lens implantation and inflammation associated with cataract surgery, Behcet's disease, Stargardt disease, immune complex vasculitis, Fuch's disease, Vogt-Koyanagi-Harada disease, subretinal fibrosis, keratitis, vitreoretinal inflammation, ocular parasitic infestation/migration, retinitis pigmentosa, cytomeglavirus retinitis and choroidal inflammation.

Other examples of ocular diseases or disorders that may be amendable to treatment by the methods and compositions provided herein may include, without limitation, ectropion, lagophthalmos, blepharochalasis, ptosis, xanthelasma of the eyelid, parasitic infestation of the eyelid, dermatitis of the eyelid, dacryoadenitis, epiphora, dysthyroid exophthalmos, conjunctivitis, scleritis, keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis, uveitis, sympathetic ophthalmia, cataracts, chorioretinal inflammation, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated retinochoroiditis, exudative retinopathy, posterior cyclitis, pars planitis, Harada's disease, chorioretinal scars, macula scars of posterior pole, solar retinopathy, choroidal degeneration, choroidal atrophy, choroidal sclerosis, angioid streaks, hereditary choroidal dystrophy, choroideremia, choroidal dystrophy (central arealor), gyrate atrophy (choroid), ornithinaemia, choroidal haemorrhage and rupture, choroidal haemorrhage (not otherwise specified), choroidal haemorrhage (expulsive), choroidal detachment, retinoschisis, retinal artery occlusion, retinal vein occlusion, hypertensive retinopathy, diabetic retinopathy, retinopathy, retinopathy of prematurity, macular degeneration, Bull's Eye maculopathy, epiretinal membrane, peripheral retinal degeneration, hereditary retinal dystrophy, retinitis pigmentosa, retinal haemorrhage, separation of retinal layers, central serous retinopathy, retinal detachment, macular edema, glaucoma—optic neuropathy, glaucoma suspect—ocular hypertension, primary open-angle glaucoma, primary angle-closure glaucoma, floaters, Leber's hereditary optic neuropathy, optic disc drusen, strabismus, ophthalmoparesis, progressive external ophthaloplegia, esotropia, exotropia, disorders of refraction and accommodation, hypermetropia, myopia, astigmastism, anisometropia, presbyopia, internal ophthalmoplegia, amblyopia, Leber's congenital amaurosis, scotoma, anopsia, color blindness, achromatopsia, maskun, nyctalopia, blindness, River blindness, micropthalmia, coloboma, red eye, Argyll Robertson pupil, keratomycosis, xerophthalmia, aniridia, sickle cell retinopathy, ocular neovascularization, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, proliferative vitreoretinopathy, and neovascularization due to penetration of the eye or ocular injury.

In some aspects, the methods and compositions provided herein are suitable for the treatment of macular degeneration. In some cases, macular degeneration is age-related macular degeneration. In some cases, the methods and compositions can be utilized to treat neovascular or exudative ("wet") age-related macular degeneration. In other cases, the methods and compositions can be utilized to treat non-exudative ("dry") age-related macular degeneration. In some cases, advanced forms of dry age-related macular degeneration can be treated, including geographic atrophy. In some cases, the methods and compositions herein can be utilized to prevent age-related macular degeneration and associated diseases thereof. In other cases, the methods and compositions herein can be utilized to slow or halt the progression of age-related macular degeneration and associated diseases thereof.

In some aspects, the methods and compositions provided herein are suitable for the treatment of Stargardt disease. In some cases, the methods and compositions herein can be utilized to prevent age-related Stargardt disease. In other cases, the methods and compositions herein can be utilized to slow or halt the progression of Stargardt disease.

In some aspects, the methods and compositions provided herein are suitable for the treatment of diseases causing ocular symptoms. Examples of symptoms which may be amenable to treatment with the methods disclosed herein include: increased drusen volume, reduced reading speed, reduced color vision, retinal thickening, increase in central retinal volume and/or, macular sensitivity, loss of retinal cells, increase in area of retinal atrophy, reduced best corrected visual acuity such as measured by Snellen or ETDRS scales, Best Corrected Visual Acuity under low luminance conditions, impaired night vision, impaired light sensitivity, impaired dark adaptation, contrast sensitivity, and patient reported outcomes.

In some cases, the methods and compositions provided herein may alleviate or reduce a symptom of a disease. In some cases, treatment with an aptamer provided herein may result in a reduction in the severity of any of the symptoms described herein. In some cases, treatment with an aptamer described herein may slow, halt or reverse the progression of any of the symptoms described herein. In some cases, treatment with an aptamer described herein may prevent the development of any of the symptoms described herein. In some cases, treatment with an aptamer described herein may slow, halt or reverse the progression of a disease, as measured by the number and severity of symptoms experienced. Examples of symptoms and relevant endpoints where the aptamer may have a therapeutic effect include increased drusen volume, reduced reading speed, reduced color vision, retinal thickening, increase in central retinal volume and/or, macular sensitivity, loss of retinal cells, increase in area of retinal atrophy, reduced best corrected visual acuity such as measured by Snellen or ETDRS scales, Best Corrected Visual Acuity under low luminance conditions, impaired night vision, impaired light sensitivity, impaired dark adaptation, contrast sensitivity, and patient reported outcomes. In some instances, treatment with an aptamer described herein may have beneficial effects as measured by clinical endpoints including drusen volume, reading speed, retinal thickness as measured by Optical Coherence Tomography or other techniques, central retinal volume, number and density of retinal cells, area of retinal atrophy as measured by Fundus Photography or Fundus Autofluoresence or other techniques, best corrected visual acuity such as measured by Snellen or ETDRS scales, Best Corrected Visual Acuity under low luminance conditions, light sensitivity, dark adaptation, contrast sensitivity, and patient reported outcomes as measured by such tools as the National Eye Institute Visual Function Questionnaire and Health Related Quality of Life Questionnaires.

Subjects

The terms "subject" and "patient" are used interchangeably herein to refer to a vertebrate, preferably a mammal, more preferably a human. Mammals include, but are not limited to, murines, simians, humans, research animals, farm animals, sport animals, and pets. In some cases, the methods described herein may be used on tissues or cells derived from a subject and the progeny of such tissues or cells. For example, aptamers described herein may be used to effect some function (e.g., inhibit or block fD) in tissues or cells of a subject. The tissues or cells may be obtained from a subject in vivo. In some cases, the tissues or cells are cultured in vitro and contacted with a composition provided herein (e.g., an aptamer).

In some aspects, the methods and compositions provided herein are used to treat a subject in need thereof. In some cases, the subject suffers from an ocular disease or disorder. In some cases, the subject is a human. In some cases, the human is a patient at a hospital or a clinic. In some cases, the subject is a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal.

In cases where the subject is a human, the subject may be of any age. In some cases, the subject has an age-related ocular disease or disorder (e.g., age-related macular degeneration, Stargardt disease). In some cases, the subject is about 50 years or older. In some cases, the subject is about 55 years or older. In some cases, the subject is about 60 years or older. In some cases, the subject is about 65 years or older. In some cases, the subject is about 70 years or older. In some cases, the subject is about 75 years or older. In some cases, the subject is about 80 years or older. In some cases, the subject is about 85 years or older. In some cases, the subject is about 90 years or older. In some cases, the subject is about 95 years or older. In some cases, the subject is about 100 years or older. In some cases, the subject is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject is about 1, 2, 3, 4, 5, 6, 7, 8, 9, 10, 11, 12, 13, 14, 15, 16, 17, 18, 19, 20 or greater than 20 years old.

In cases where the subject is a human, the subject may have any genetic profile. In some cases, the subject may have mutations in complement Factor H (CFH), complement component 3 (C3), complement component 2 (C2), complement Factor B, complement Factor I (CFI), ABC4A, ELOVL4, or any combination thereof.

In some aspects, the methods and compositions provided herein are utilized to treat a subject suffering from ocular symptoms as described herein. In some aspects, the methods and compositions provided herein are utilized to treat a subject suffering from an ocular disease as provided herein. In some cases, the methods and compositions provided herein are utilized to treat a subject suffering from wet AMD. In some cases, the methods and compositions provided herein are utilized to treat a subject suffering from dry AMD or geographic atrophy. In some cases, the methods and compositions provided herein are utilized to treat a subject suffering from Stargardt disease.

In some aspects, the methods and compositions provided herein may be utilized to treat a subject with a highly active immune system. In some cases, the methods and compositions provided herein may be used to treat a subject with an autoimmune disease. In some cases, the methods and compositions provided herein may be used to treat a subject with an inflammatory disease. In some cases, the methods and compositions provided herein may be used to treat a subject undergoing an inflammatory reaction to a disease such as an infectious disease. For example, the aptamers described herein may be used to treat a subject with a fever. In some cases, the aptamers described herein may be used to treat a subject with an allergy. In some cases, the aptamers described herein may be used to treat a subject suffering from an allergic response. In some cases, the aptamers described herein may be particularly useful for treating a subject who has experienced an allergic reaction to an antibody treatment, and/or who has developed neutralizing antibodies against an antibody treatment.

Pharmaceutical Compositions or Medicaments

Disclosed herein are pharmaceutical compositions or medicaments, used interchangeably, for use in a method of therapy, or for use in a method of medical treatment. Such use may be for the treatment of ocular diseases. In some cases, the pharmaceutical compositions can be used to treat AMD. In some cases, the pharmaceutical compositions can be used to treat non-exudative (dry) AMD. In some cases, the pharmaceutical compositions can be used to treat geographic atrophy (advanced dry AMD). In some cases, the pharmaceutical compositions can be used to treat wet AMD. In some cases, the pharmaceutical compositions can be used to treat Stargardt disease. Pharmaceutical compositions described herein may include one or more aptamers for the treatment of dry AMD. Pharmaceutical compositions described herein may include one or more aptamers for the treatment of wet AMD. Pharmaceutical compositions described herein may include one or more aptamers for the treatment of Stargardt disease. In some cases, the one or more aptamers bind to and inhibit a component of the alternative complement pathway. In some cases, the one or more aptamers bind to one or more targets of fD as described herein. In some cases, the one or more aptamers inhibit fD as described herein. In some cases, the compositions include, e.g., an effective amount of the aptamer, alone or in combination, with one or more vehicles (e.g., pharmaceutically acceptable compositions or e.g., pharmaceutically acceptable carriers). In some cases, the compositions described herein are administered with one or more additional pharmaceutical treatments (e.g., co-administered, sequentially administered or co-formulated). In some examples, the compositions described herein are co-administered with one or more of an anti-vascular endothelial growth factor (VEGF) therapy, an anti-Factor P therapy, an anti-complement component 5 (C5) therapy, an anti-complement component 3 (C3) therapy, an anti-platelet-derived growth factor (PDGF) therapy, an anti-hypoxia-inducible factor 1-alpha (HIF1a) therapy, an anti-FAS therapy, an anti-integrin therapy or an anti-angiopoietin-2 (Ang2) therapy.

Formulations

Compositions as described herein may comprise a liquid formulation, a solid formulation or a combination thereof. Non-limiting examples of formulations may include a tablet, a capsule, a gel, a paste, a liquid solution and a cream. The compositions of the present disclosure may further comprise any number of excipients. Excipients may include any and all solvents, coatings, flavorings, colorings, lubricants, disintegrants, preservatives, sweeteners, binders, diluents, and vehicles (or carriers). Generally, the excipient is compatible with the therapeutic compositions of the present disclosure. The pharmaceutical composition may also contain minor amounts of non-toxic auxiliary substances such as wetting or emulsifying agents, pH buffering agents, and other substances such as, for example, sodium acetate, and triethanolamine oleate.

Dosage and Routes of Administration

Therapeutic doses of formulations of the disclosure can be administered to a subject in need thereof. In some cases, a formulation is administered to the eye of a subject to treat, for example, dry AMD, geographic atrophy, wet AMD or Stargardt disease. Administration to the eye can be a) topical; b) local ocular delivery; or c) systemic. A topical formulation can be applied directly to the eye (e.g., eye drops, contact lens loaded with the formulation) or to the eyelid (e.g., cream, lotion, gel). In some cases, topical administration can be to a site remote from the eye, for example, to the skin of an extremity. This form of administration may be suitable for targets that are not produced directly by the eye. In one non-limiting example, fD is thought to be produced primarily by adipose cells, and thus an anti-fD aptamer may be administered topically to a non-ocular region of the body. In some cases, a formulation of the disclosure is administered by local ocular delivery. Non-limiting examples of local ocular delivery include intravitreal (IVT), intracamarel, subconjunctival, subtenon, retrobulbar, posterior juxtascleral, and peribulbar. In some cases, a formulation of the disclosure is delivered by intravitreal administration (IVT). Local ocular delivery may generally involve injection of a liquid formulation. In other cases, a formulation of the disclosure is administered systemically. Systemic administration can involve oral administration. In some cases, systemic administration can be intravenous administration, subcutaneous administration, infusion, implantation, and the like.

Other formulations suitable for delivery of the pharmaceutical compositions described herein may include a sustained release gel or polymer formulations by surgical implantation of a biodegradable microsize polymer system, e.g., microdevice, microparticle, or sponge, or other slow release transscleral devices, implanted during the treatment of an ophthalmic disease, or by an ocular delivery device, e.g. polymer contact lens sustained delivery device. In some cases, the formulation is a polymer gel, a self assembling gel, a durable implant, an eluting implant, a biodegradable matrix or biodegradable polymers. In some cases, the formulation may be administered by iontophoresis using electric current to drive the composition from the surface to the posterior of the eye. In some cases, the formulation may be administered by a surgically implanted port with an intravitreal reservoir, an extra-vitreal reservoir or a combination thereof. Examples of implantable ocular devices can include, without limitation, the Durasert™ technology developed by Bausch & Lomb, the ODTx device developed by On Demand Therapeutics, the Port Delivery System developed by ForSight VISION4 and the Replenish Micro-Pump™ System developed by Replenish, Inc.

In some cases, nanotechnologies can be used to deliver the pharmaceutical compositions including nanospheres, nanoparticles, nanocapsules, liposomes, nanomicelles and dendrimers.

A composition of the disclosure can be administered once or more than once each day. In some cases, the composition is administered as a single dose (i.e., one-time use). In this example, the single dose may be curative. In other cases, the composition may be administered serially (e.g., taken every day without a break for the duration of the treatment regimen). In some cases, the treatment regime can be less than a week, a week, two weeks, three weeks, a month, or greater than a month. In some cases, the composition is administered over a period of at least 12 weeks. In other cases, the composition is administered for a day, at least two consecutive days, at least three consecutive days, at least four consecutive days, at least five consecutive days, at least six consecutive days, at least seven consecutive days, at least eight consecutive days, at least nine consecutive days, at least ten consecutive days, or at least greater than ten consecutive days. In some cases, a therapeutically effective amount can be administered one time per week, two times per week, three times per week, four times per week, five times per week, six times per week, seven times per week, eight times per week, nine times per week, 10 times per week, 11 times per week, 12 times per week, 13 times per week, 14 times per week, 15 times per week, 16 times per week, 17 times per week, 18 times per week, 19 times per week, 20 times per week, 25 times per week, 30 times per week, 35 times per week, 40 times per, week, or greater than 40 times per week. In some cases, a therapeutically effective amount can be administered one time per day, two times per day, three times per day, four times per day, five times per day, six times per day, seven times per day, eight times per day, nine times per day, 10 times per day, or greater than 10 times per day. In some cases, the composition is administered at least twice a day. In further cases, the composition is administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day.

Aptamers as described herein may be particularly advantageous over antibodies as they may sustain therapeutic intravitreal concentrations of drug for longer periods of time, thus requiring less frequent administration. For example, an anti-fD Fab having an amino acid sequence of heavy chain variable region according to SEQ ID NO:7 and a light chain variable region according to SEQ ID NO:8, may show clinical efficacy for the treatment of geographic atrophy at 10 mg when dosed every 4 weeks (q4w) but not every 8 weeks (q8w). The aptamers described herein have a longer intraocular half-life, and/or sustain therapeutic intravitreal concentrations of drug for longer periods of time, than an anti-fD Fab with an amino acid sequence of heavy chain variable region according to SEQ ID NO:7 and light chain variable region according to SEQ ID NO:8 and other antibody therapies and thus, can be dosed less frequently. In some cases, the aptamers are dosed at least every 4 weeks (q4w), every 5 weeks (q5w), every 6 weeks (q6w), every 7 weeks (q7w), every 8 weeks (q8w), every 9 weeks (q9w), every 10 weeks (g10w), every 12 weeks (q12w) or greater than q12w.

In some aspects, a therapeutically effective amount of the aptamer is administered. A "therapeutically effective amount" or "therapeutically effective dose" are used interchangeably herein and refer to an amount of a therapeutic agent (e.g., an aptamer) that provokes a therapeutic or desired response in a subject. The therapeutically effective amount of the composition may be dependent on the route of administration. In the case of systemic administration, a therapeutically effective amount may be about 10 mg/kg to about 100 mg/kg. In some cases, a therapeutically effective amount may be about 10 µg/kg to about 1000 µg/kg for systemic administration. For intravitreal administration, a therapeutically effective amount can be about 0.01 mg to about 150 mg in about 25 µl to about 100 µl volume per eye.

Methods

Disclosed herein are methods for the treatment of ocular diseases. In some cases, the ocular disease is dry age-related macular degeneration or geographic atrophy. In some cases, the method involves administering a therapeutically effective amount of a composition to a subject to treat the disease. In some cases, the composition includes one or more aptamers as described herein. The aptamers may inhibit a function associated with fD as described herein. The methods can be performed at a hospital or a clinic, for example, the pharmaceutical compositions can be administered by a healthcare professional. In other cases, the pharmaceutical compositions can be self-administered by the subject. Treatment may commence with the diagnosis of a subject with an ocular disease (e.g., AMD). In the event that further treatments are necessary, follow-up appointments may be scheduled for the administration of subsequence doses of the composition, for example, administration every 8 weeks.

Methods of Generating Aptamers

The SELEX™ Method

The aptamers described herein can be generated by any method suitable for generating aptamers. In some cases, the aptamers described herein are generated by a process known as Systematic Evolution of Ligands by Exponential Enrichment" ("SELEX™"). The SELEX™ process is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands", each of which are herein incorporated by reference. By performing iterative cycles of selection and amplification, SELEX™ may be used to obtain aptamers with any desired level of target binding affinity.

The SELEX™ method relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA polymerases (e.g., T3, T4, T7, and SP6), sequences to form stems to present the randomized region of the library within a defined terminal stem structure, restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool can include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in some cases, random oligonucleotides comprise entirely random sequences; however, in other cases, random oligonucleotides can comprise stretches of nonrandom or partially random sequences. Partially random sequences can be created by adding the four nucleotides in different molar ratios at each addition step.

The starting library of oligonucleotides may be RNA, DNA, substituted RNA or DNA or combinations thereof. In those instances where an RNA library is to be used as the starting library it is typically generated by synthesizing a DNA library, optionally PCR amplifying, then transcribing the DNA library in vitro using T7 RNA polymerase or modified T7 RNA polymerases, and purifying the transcribed library. The nucleic acid library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX' method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested as ligands or aptamers for 1) target binding affinity; and 2) ability to effect target function.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure.

In some cases, the aptamers of the disclosure are generated using the SELEX™ method as described above. In other cases, the aptamers of the disclosure are generated using any modification or variant of the SELEX™ method.

In some cases, the aptamers described herein have been generated using methodologies to select for specific sites related to activity or function of a target protein. In some cases, the aptamers described herein may be selected using methods that improve the chances of selecting an aptamer with a desired function or desired binding site. In some cases, the aptamers described herein are generated using methods that increase the chances of selecting an aptamer that binds to a region of fD that serves as an epitope for an anti-fD therapeutic antibody, which anti-fD therapeutic antibody inhibits a function associated with fD.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Identification of Modified RNA Aptamers to fD

A. Selection of Anti-Factor D Aptamers

Figure 7C:
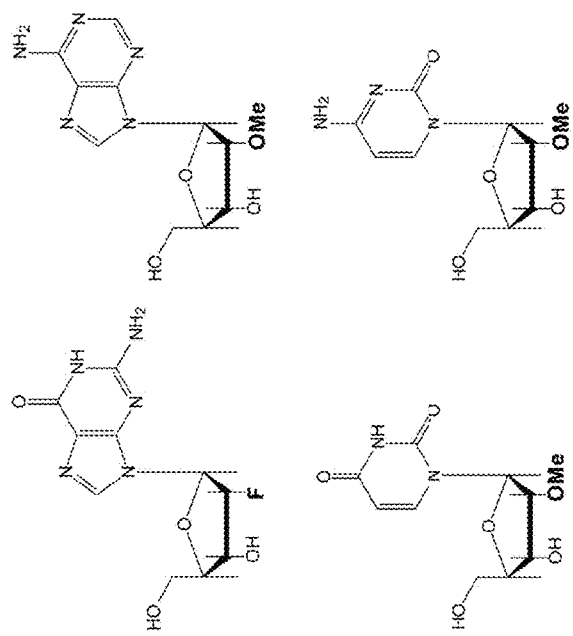
Figure 7B:
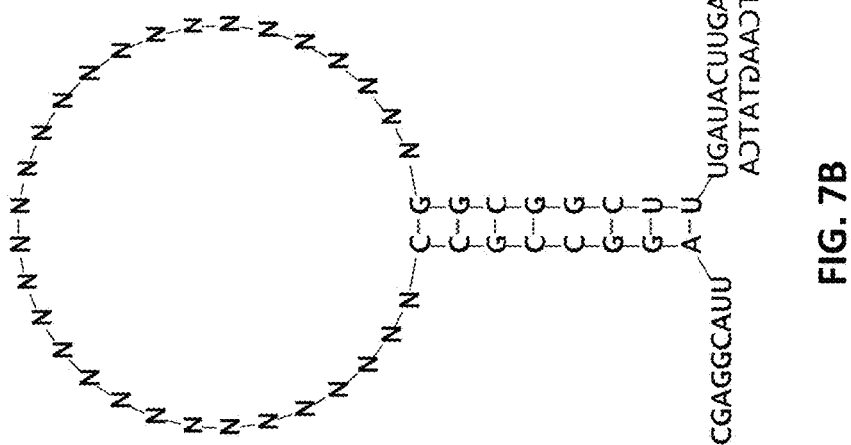

Anti-factor D (fD) aptamers were identified using an N30 library (N30S) comprised of a 30-nucleotide random region flanked by constant regions containing a built-in stem region as depicted in FIG. 7A. The sequence in italics represents the forward and reverse primer binding sites. The built-in stem region is underlined. FIG. 7B depicts a representation of the N30S library with the reverse oligo hybridized. For nuclease stability, the library was composed of 2'-fluoro-G (2'F GTP) and 2'-O-methyl (2'OMe) A/C/U. FIG. 7C depicts structures of modified nucleotides used to generate the N30S library for selection against target fD. For simplicity, the nucleosides, and not the nucleotide triphosphates are shown.

The library sequence (underlined sequences represent the built-in stem) and the sequence of oligos used to amplify the library are described in Table 4.

TABLE 4

Library sequence and sequence of oligos used to amplify the library

| SEQ ID NO. | Sequence (5' to 3') |
|---|---|
| SEQ ID NO: 4 Library sequence (Total library length: 89 bases) | GGGAGTGTGTACGAGGCATT<u>AGGCCGCC</u>-N30-<u>GGCGGCTTT</u>GATACTTGATCGCCCTAGAAGC |
| SEQ ID NO: 5 N30S.F | TCTTAATACGACTCACTATAGGGAGTGTGTACGAGGCATTA |
| SEQ ID NO: 6 N30S.R | GCTTCTAGGGCGATCAAGTATCA |

The starting library was transcribed from a pool of ~$10^{14}$ double-stranded DNA (dsDNA) molecules. The dsDNA library was generated by primer extension using Klenow exo (−) DNA polymerase, the pool forward primer (N30S.F) and synthetic single-stranded DNA (ssDNA) molecule encoding the library. The dsDNA was subsequently converted to 100% backbone modified RNA via transcription using a mixture of 2'F GTP, 2'OMe ATP/CTP/UTP and a variant of T7 RNA polymerase in buffer optimized to facilitate efficient transcription. Following transcription, RNAs were treated with DNAse to remove the template dsDNA and purified.

The selection targeting fD was facilitated by the use of a His-tagged recombinant human complement Factor D protein and magnetic His capture beads. Briefly, beads (the amount varied with the amount of target protein coupled) were washed three times with immobilization buffer (50 mM sodium phosphate, pH 8.0, 300 mM NaCl, 0.01% Tween-20) and were resuspended in 50 μL of immobilization buffer. His-tagged recombinant fD, in immobilization buffer, was then added to the beads and incubated at room temperature for 30 minutes. The amount of target protein varied with the rounds (Table 5). The beads were washed three times with binding buffer SB1T (40 mM HEPES, pH 7.5, 125 mM NaCl, 5 mM KCl, 1 mM $MgCl_2$, 1 mM $CaCl_2$, 0.05% Tween-20) to remove any unbound protein and then re-suspended in 50 μL SB1T buffer containing 1 μg/μl ssDNA and 0.1% BSA.

For the first round of selection, ~3 nanomoles of the Round 0 RNA pool, ~$10^{14}$ sequences, was used. Prior to each round, the library was thermally equilibrated by heating at 80° C. for 5 minutes and cooled at room temperature for 15 minutes in the presence of a 1.5-fold molar excess of reverse primer (N30S.R) to allow the library to refold and simultaneously block the 3' end of the pool. Following renaturation, the final volume of the reaction was adjusted to 50 μL in SB1T supplemented with 1 μg/ml ssDNA and 0.1% BSA.

For the first round, the library was added to the fD immobilized on beads and incubated at 37° C. for 1 hour with intermittent mixing. After one hour, the beads were washed using 3×1 ml SB1T buffer to remove unbound aptamers. For round 0, each wash step was incubated for 5 minutes. After washing, fD-bound aptamers were eluted using 200 μL elution buffer (2M Guanidine-HCl in SB buffer) two times (total volume 400 μL). The eluted aptamers, in 400 μL of elution buffer, were precipitated by adding 40 μL 3M NaOAc, pH 5.2, 1 ml ethanol and 2 μl glycogen and incubating at −80° C. for 15 minutes. The recovered library was converted to DNA by reverse transcription using Super Script IV reverse transcriptase, and the ssDNA was subsequently amplified by PCR. The resulting dsDNA library was subsequently converted back into modified RNA via transcription as described above. DNased, purified RNA was used for subsequent rounds.

For subsequent rounds, the washing time and number of washes was varied as the selection progressed, the input RNA was kept fixed at 25 picomoles, and the protein input varied (Table 5). After the first round, a negative selection step was included in all the subsequent rounds. For the negative selection, the pool was prepared as described before and first incubated with non-labelled beads for 1 hour at 37° C. in SB1T buffer. The beads were then spun down and the supernatant containing molecules that did not bind to the unlabeled beads was incubated with fD-labeled beads for an additional 1 hour at 37° C.

B. Assessing the Progress of Selection

Figure 8:
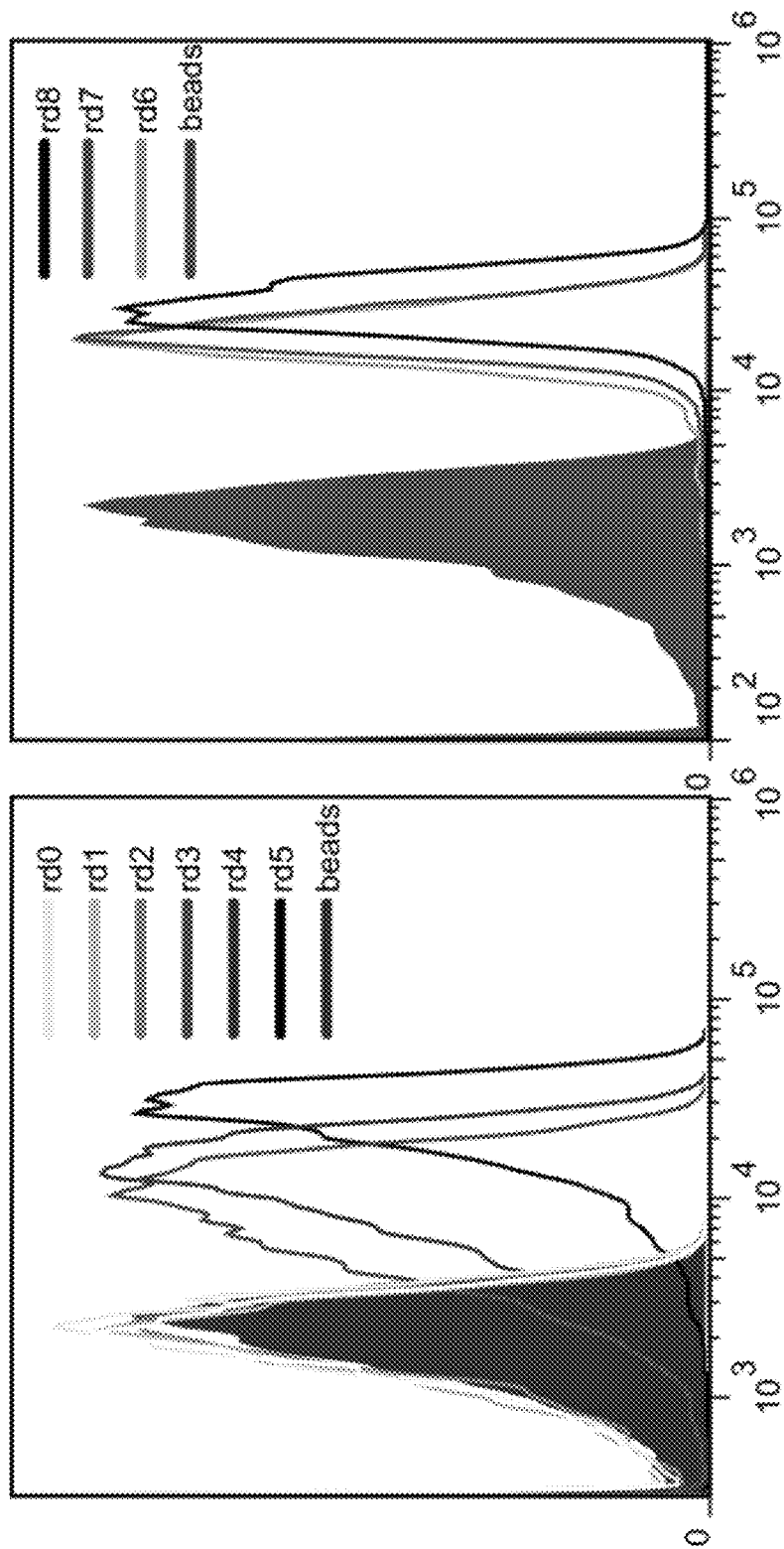
FIG. 8 depicts binding analysis of libraries enriched in anti-Factor D aptamers by flow cytometry according to an embodiment of the disclosure.
Figure 9:
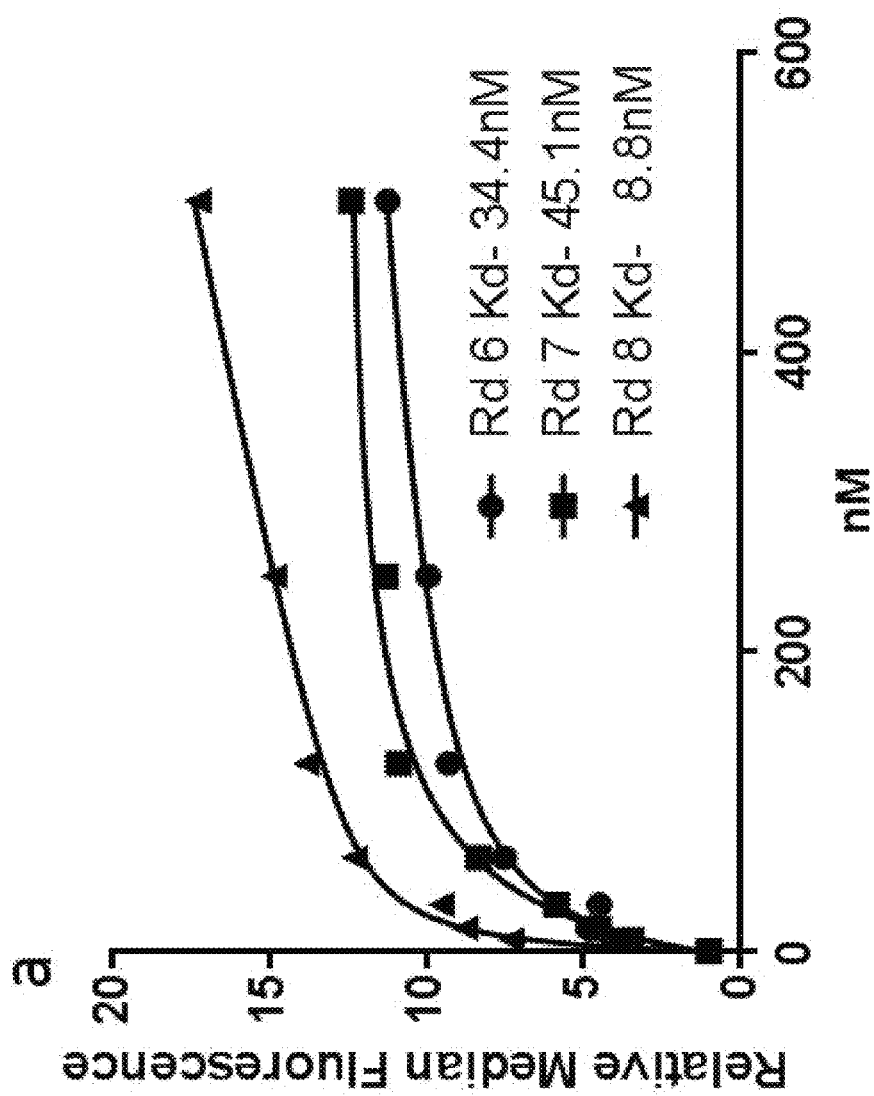
FIG. 9 depicts measurement of $K_d$ values of libraries enriched in anti-Factor D aptamers according to an embodiment of the disclosure.

Flow cytometry was used to assess the progress of the selection. For these assays, RNA from each round was first hybridized with reverse complement oligonucleotide composed of 2'OMe RNA labeled with Dylight® 650 (Dy650-N30S.R.OMe). Briefly, the library was combined with 1.5-fold molar excess of Dy650-N30S.R.OMe, heated at 80° C. for 6 minutes and allowed to cool at room temperature for 15 min. after which it was incubated with beads labelled with fD, in SB1T buffer containing 0.1% BSA and 1 μg/μssDNA. Following incubation for 1 hour at 37° C., the beads were washed 3 times with SB1T, re-suspended in SB1T buffer and analyzed by flow cytometry. As shown in FIG. 8, an improvement in fluorescent signal with the progressing rounds was seen as early as Round 3. After Round 6, there was little change in the binding signal through Round 8. "Beads" refers to the signal of fD-labelled beads in the absence of labeled RNA. The apparent affinity of rounds 6, 7, and 8 for fD was also measured using flow cytometry-based assays and revealed $K_d$s in the range of 8-45 nM (FIG. 9, Table 7).

C. Selection, Purification and Characterization of Clones

The enriched aptamer populations recovered from rounds 6, 7, and 8 of the selection were sequenced to identify individual functional clones. The sequences were grouped in families based on sequence similarity. From an analysis of Rounds 6, 7 and 8, 7 individual clones were selected for testing. Individual bacterial colonies corresponding to these clones were picked and plasmid isolated using QIAGEN Mini Prep Kit. The sequences for each clone were PCR amplified using the F and R oligo of the library. Each full length clone was transcribed from the PCR product using the protocol described before. The clones were gel purified and used for further analysis.

A summary of the clones tested is shown in Table 6. For simplicity, the constant regions have been omitted from sequences C1 though C3.

D. Assaying Individual Clones for Binding

Individual clones were assayed by flow cytometry in a manner similar to that described above for individual rounds of selection. In the case of clones C1 through C3, fluorescent labeling of each aptamer was achieved via hybridization to Dy650-N30S.R.OMe as described above.

Figure 10:
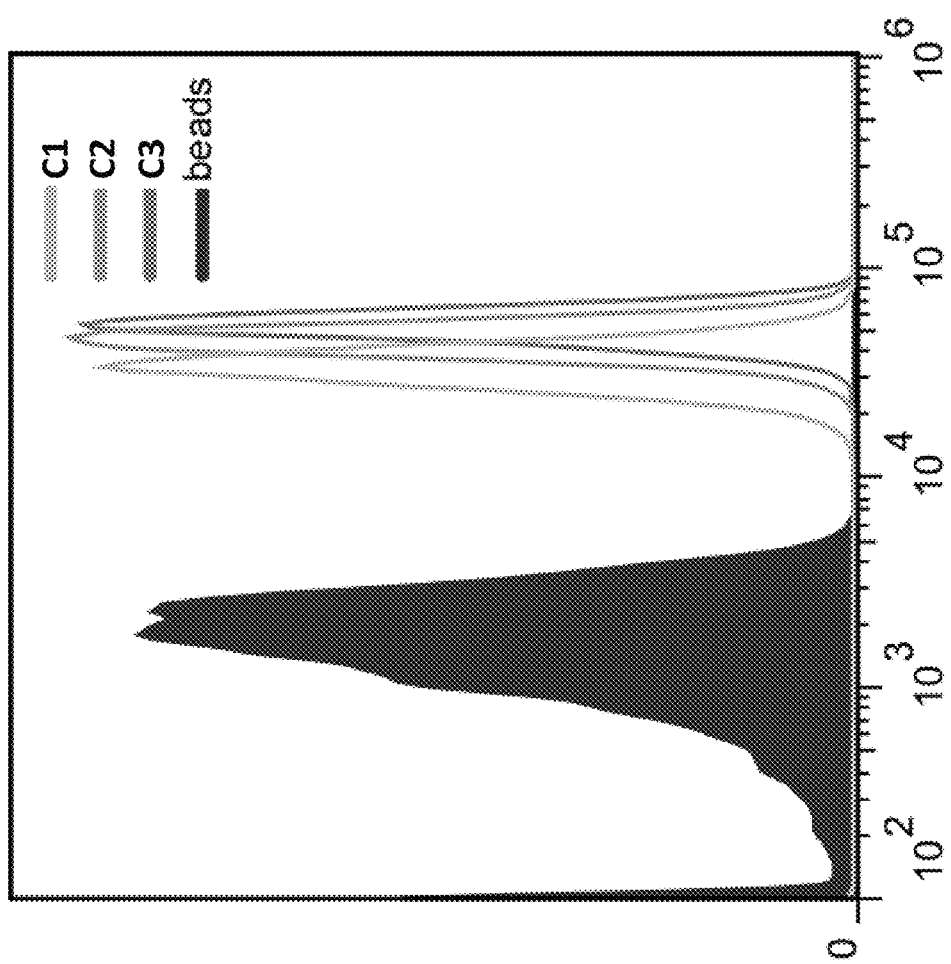
FIG. 10 depicts direct binding analysis of anti-Factor D aptamers by flow cytometry according to an embodiment of the disclosure.

As an initial assay, the binding of each aptamer to fD was assessed using bead-immobilized fD when incubated at 100 nM for 1 hour at 37° C. As shown in FIG. 10, clones C1-C3 displayed significant levels of binding to fD beads. No binding was observed when similar experiments were performed using beads bearing no target or a non-specific target, human growth factor.

E. Measurement of Apparent $K_d$ on Beads

Figure 11:
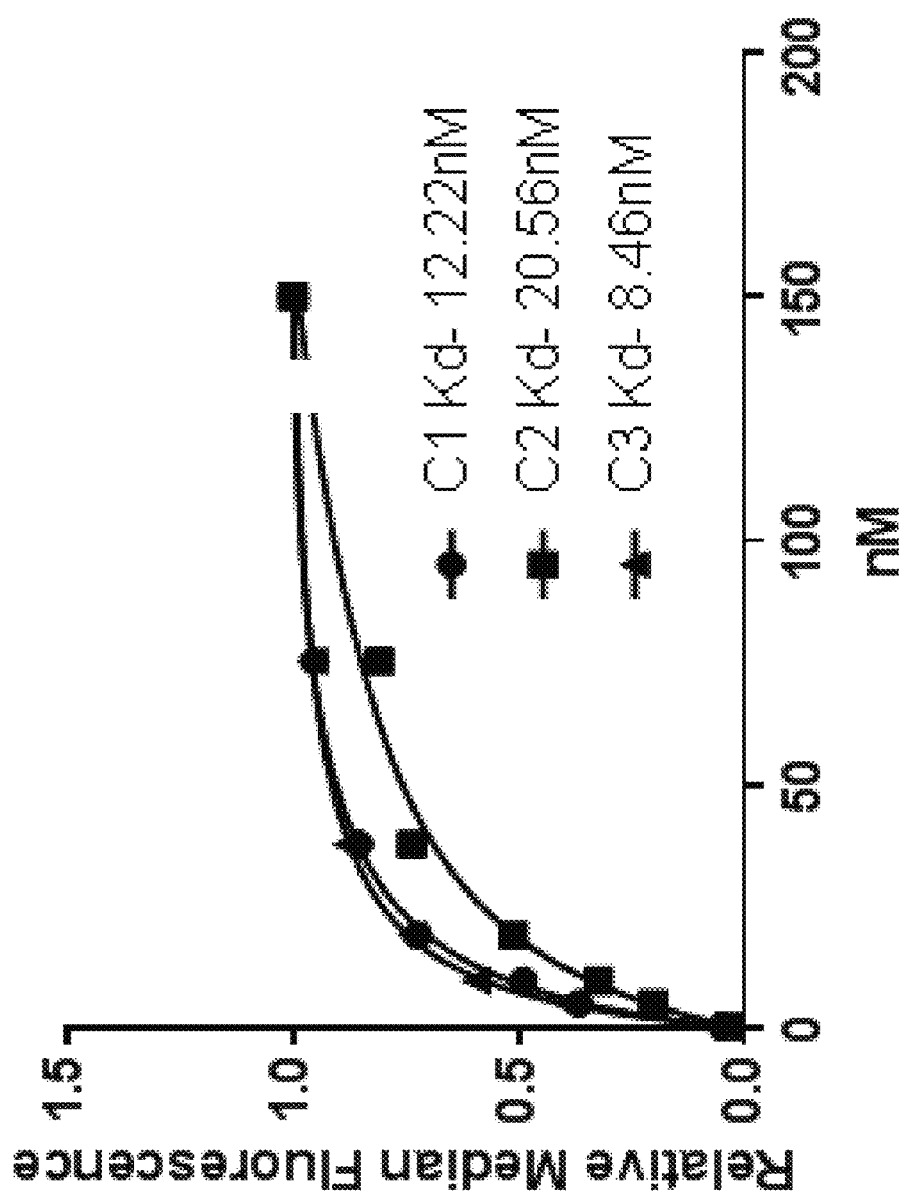
FIG. 11 depicts measurement of $K_d$ values of anti-Factor D aptamers according to an embodiment of the disclosure.

Flow cytometry was used to measure the binding affinity of each individual aptamer to fD. Assays were again performed as described before but using serially diluted solutions of each aptamer. Following incubation for 1 hour at 37° C., the beads were washed and fluorescence was measured using flow cytometry and a plot of median fluorescent intensity versus aptamer concentration (FIG. 11) was used to determine the apparent binding constant for each clone. Apparent $K_d$ values were obtained using the equation Y=Bmax*X/(KD+X). The apparent binding constant for each clone is also reported in Table 7. The apparent affinity of aptamers to fD ranged from approximately 8 to 20 nM.

F. Competition Assays with Rounds or Individual Clones

Figure 12:
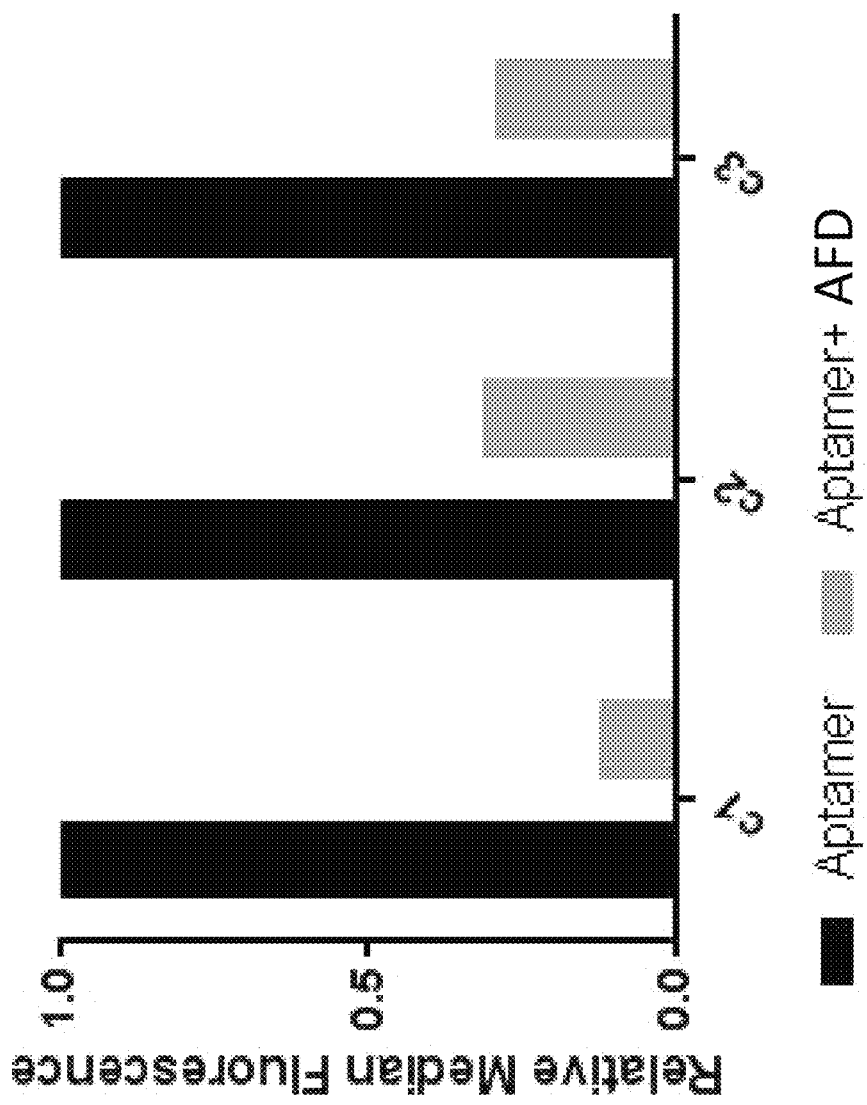
FIG. 12 depicts a competition assay according to an embodiment of the disclosure.

Competition binding assays were performed using a clone of an anti-fD Fab with an amino acid sequence of heavy chain variable region according to SEQ ID NO:7 and light chain variable region according to SEQ ID NO:8 (hereinafter, "AFD") to further assess binding. For the competition assays, beads labelled with fD were first incubated with 50 nM round or individual aptamer, in 50 µl SB1T (with ssDNA and BSA), for 30 minutes at 37° C. The beads were then washed with SB1T to remove unbound aptamers and incubated with or without 100 nM AFD for 30 minutes at 37° C. Following incubation, the beads were washed three times with SB1T, and assayed by flow cytometry (FIG. 12). These assays revealed that binding of AFD reduced the aptamer signal by ~75%-~90%, for both the Round 7 and 8 populations as well all selected aptamers. In cases where aptamers are sufficiently outcompeted by AFD as described above, such aptamers were presumed to be binding to the exosite or the self-inhibitory loop of fD.

TABLE 5

Selection details

| Round | Input library pmoles/conc | Target protein pmoles/conc | Binding buffer | Washing buffer | washes | #cycles | NGS |
|---|---|---|---|---|---|---|---|
| 0 | 1000 pm/40 µM | 40 pm/0.4 µM | SB1T | SB1T | 3 × 5 min | 22 | yes |
| 1 | 25 pm/1 µM | 40 pm/0.4 µM | SB1T | SB1T | 3 × 5 min | 22 | yes |
| 2 | 25 pm/1 µM | 40 pm/0.4 µM | SB1T | SB1T | 3 × 5 min | 20 | yes |
| 3 | 25 pm/1 µM | 4 pm/0.04 µM | SB1T | SB1T | 3 × 5 min | 18 | yes |
| 4 | 25 pm/1 µM | 8 pm/0.08 µM | SB1T | SB1T | 3 × 10 min | 18 | yes |
| 5 | 25 pm/1 µM | 8 pm/0.08 µM | SB1T | SB1T | 3 × 10 min | 16 | yes |
| 6 | 25 pm/1 µM | 4 pm/0.04 µM | HBSS | SB1T | 4 × 15 min | 14 | yes |
| 7 | 25 pm/1 µM | 4 pm/0.04 µM | HBSS | HBSS + SB1T | 4 × 15 min | 14 | yes |
| 8 | 25 pm/1 µM | 4 pm/0.04 µM | SB1T | SB1T | 4 × 15 min | 12 | yes |

TABLE 6

Sequences of random region-derived sequences of select fD aptamers

| SEQ ID NO. | Compound Name | Sequence (5' to 3') |
|---|---|---|
| SEQ ID NO: 1 with modifications | C1 | GGGAGUGUGUACGAGGCAUUAGGCCGCCA CCCAAACUGCAGUCCUCGUAAGUCUGCCUG GCGGCUUUGAUACUUGAUCGCCCUAGAAGC where G is 2'F and A, C and U are 2'OMe modified RNA |
| SEQ ID NO: 2 with modifications | C2 | GGGAGUGUGUACGAGGCAUUAGUCCGCCG AAGUCUUUUGGCUCGGUUUUUUCAAGGUC GGCGGCUUUGAUACUUGAUCGCCCUAGAAGC where G is 2'F and A, C and U are 2'OMe modified RNA |

TABLE 6-continued

Sequences of random region-derived sequences of select fD aptamers

| SEQ ID NO. | Compound Name | Sequence (5' to 3') |
|---|---|---|
| SEQ ID NO: 3 with modifications | C3 | GGGAGUGUGUACGAGGCAUUAGGCCGCCA CCUCGUUUGAUUGCGGUUGUUCGGCCGCG GGCGGCUUUGAUACUUGAUCGCCCUAGAAGC where G is 2'F and A, C and U are 2'OMe modified RNA |

TABLE 7

Affinity constant of selected rounds and aptamers generated in selection to fD

| Round/Clone | $K_d$ (nM) |
|---|---|
| Rd 6 | 34.4 |
| Rd 7 | 45.1 |
| Rd 8 | 8.8 |
| C1 | 12.2 |
| C2 | 20.6 |
| C3 | 8.5 |

Example 2

Identification of fD Inhibitors in Hemolysis Assays

In some cases, the disclosure provides for the identification of aptamers that inhibit a function associated with fD. In some cases, the identification of aptamers that that inhibit a function associated with fD may involve performing an alternative complement-dependent hemolysis assay. Human serum that is rendered deficient in the classical complement pathway by depleting C1q may be dependent on alternative complement activity to lyse rabbit red blood cells, an activity that may be dependent on fD. (Katschke, Wu, Ganesan, et al. (2012) Inhibiting alternative pathway complement activation by targeting the Factor D exosite. J. Biol. Chem. 287, 12886-12892).

Briefly, citrated rabbit blood was centrifuged at 500×g for 5 minutes at room temperature. The top plasma fraction was removed and the volume was replaced with 1× Veronal buffer containing 0.1% gelatin (prepared from 5× Veronal buffer, Lonza #12-624E and 2% gelatin solution, Sigma-Aldrich, G1393). The red blood cells were washed two more times. The washed rabbit red blood cells were diluted in 1× Veronal buffer to a concentration of $2 \times 10^9$ cells/mL (RBCs).

In V-bottom 96-well plates the following reagents were added to a final volume of 250 µL: appropriate volume of 1× Veronal buffer with 0.1% gelatin, 100 µL aptamer, 30 µL of C1q-depleted human serum and 20 µl RBCs. This mixture was incubated for 25 minutes at room temperature, then the reaction was stopped by the addition of 5 µL of 500 mM EDTA. The plate was centrifuged for 5 minutes at 500×g at room temperature, then 100 µL of supernatant was removed and the extent of RBC lysis was determined by measuring absorbance at 405 nm. Controls for the assay were provided by complete RBC lysis with water in the absence of C1q-depleted serum, and by inhibition of lysis caused by C1q-depleted serum by 100 µM small molecule fD inhibitor 3,4-dichloroisocoumarin.

Figure 13:
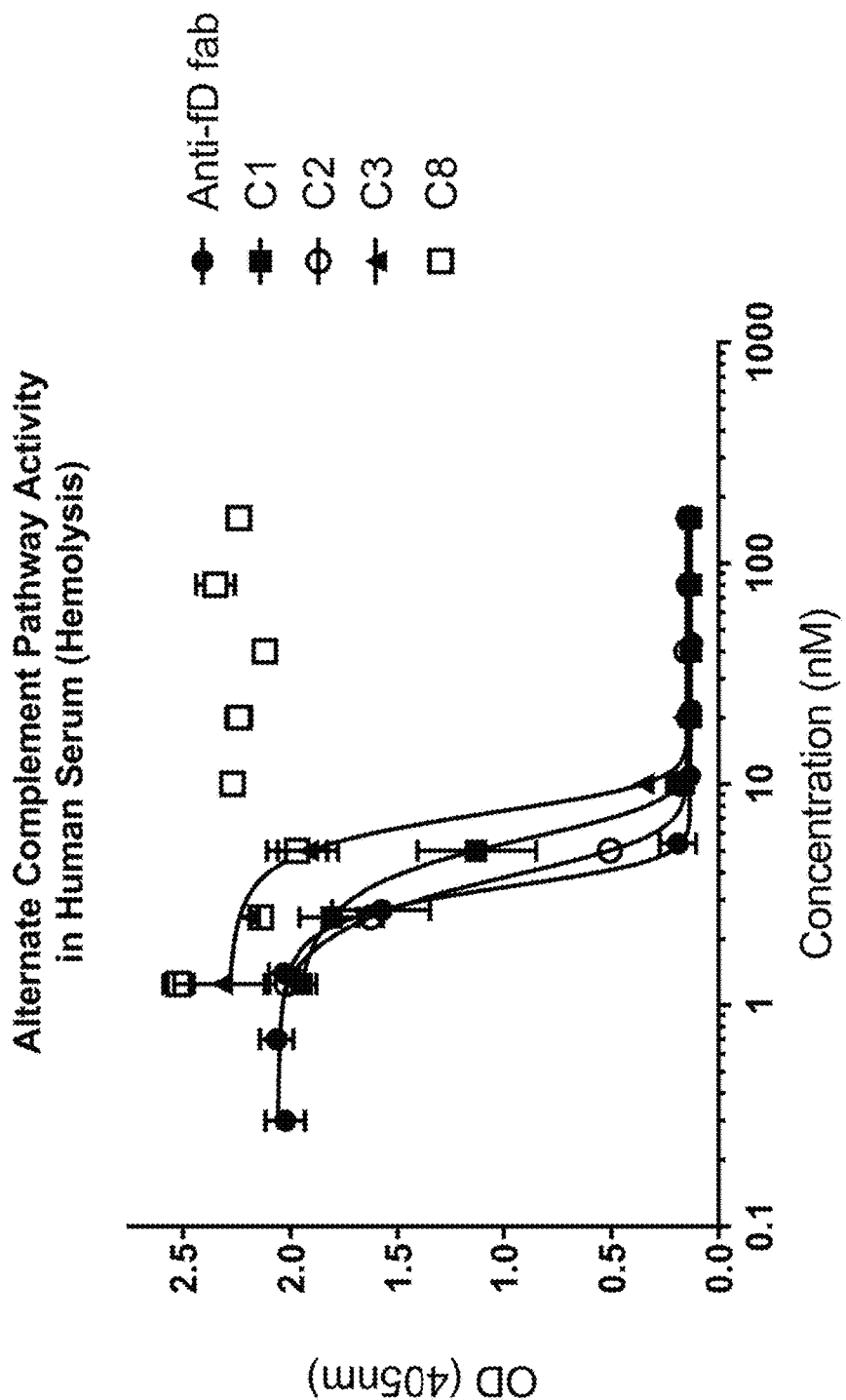
FIG. 13 depicts examples of data obtained from an alternative complement dependent hemolysis assay according to an embodiment of the disclosure.

C1-C3 identified in Example 1, a non-specific control oligo (C8), and one anti-fD Fab antibody fragment as described in Example 1 (AFD) were incubated with C1q-depleted human serum to allow binding to fD present in the serum, then assayed for the ability to inhibit fD-dependent lysis of rabbit red blood cells (FIG. 13). The endogenous concentration of fD was expected to be about 9.6 nM in 10% C1q-depleted human serum (Loyet, Good, Davancaze et al. (2014) Complement inhibition in cynomolgus monkeys by anti-factor D antigen-binding fragment for the treatment of an advanced form of dry age-related macular degeneration. J. Pharm. Exp. Ther. 351, 527-537), so compounds that bound fD with significantly better affinity, such as less than 1 nM, were expected to bind nearly stoichiometrically to the fD present in the assay. This appeared to be the case for AFD (FIG. 13; Table 8), which was reported to have a low pM affinity for fD (20 pM, Loyet et al. 2014). $IC_{50}$ values for C1-C3, C8 and AFD are depicted in Table 8.

TABLE 8

$IC_{50}$ values for C1-C3, C8 and AFD inhibiting alternative complement in human serum

| Aptamer | AFD | C1 | C2 | C3 | C8 |
|---|---|---|---|---|---|
| $IC_{50}$ (nM) | 3.3 | 5.1 | 3.3 | 7.0 | >160 |

Example 3

Factor D Esterase Activity Assay

In some cases, a fD esterase activity assay may be used to test the activity of putative anti-fD aptamers. In some cases, inhibition of esterase activity may suggest that the anti-fD aptamer is binding to the catalytic cleft, the associated substrate binding specificity pockets, or sterically occluding access to the active site. In some cases, an enhancement of esterase activity may suggest that the anti-fD aptamer is binding to the exosite in a manner which causes allosteric activation, such as observed for an anti-fD Fab having an amino acid sequence of heavy chain variable region according to SEQ ID NO:7 and a light chain variable region according to SEQ ID NO:8. In yet other cases, no effect on esterase activity in combination with inhibition of hemolysis may suggest that the anti-fD aptamer is binding the exosite in manner that does not cause allosteric activation, or is binding to neither the exosite or catalytic cleft. Cleavage of a modified peptide substrate of fD, such as Z-lys-S-Bzl, may be monitored by measuring the amount of reduced 5,5'-Dithiobis(2-nitrobenzoic acid) (DTNB). FD may have a lower catalytic rate than other complement proteases when using peptide thioester substrates, and one such substrate Z-lys-SBzl was found to be cleaved by fD and useful as a synthetic substrate (fD is called protein D in Kam, McRae et al. (1987) Human complement proteins D, C2, and B. J. Biol. Chem. 262, 3444-3451).

In one aspect a molecule that binds fD could block catalytic activity by binding in the catalytic cleft to sterically prevent access of the peptide substrate to the catalytic residues of fD (Katschke, Wu, Ganesan, et al. (2012) Inhibiting alternative pathway complement activation by targeting the Factor D exosite. J. Biol. Chem. 287, 12886-12892). In another aspect a molecule that binds fD could block catalytic activity by an allosteric mechanism that induces structural changes in the enzyme. In a further aspect, a molecule that binds fD could bind to the fD exosite region to sterically inhibit binding of the physiologic substrate protein fB, but not of the synthetic modified peptide substrate Z-Lys-SBzl (Katschke, Wu, Ganesan, et al. (2012) Inhibiting alternative pathway complement activation by targeting the Factor D exosite. J. Biol. Chem. 287, 12886-12892).

In a further aspect where a molecule inhibits fD binding and proteolytic cleavage of fB but not Z-Lys-SBzl, the binding could be similar to how anti-factor D FAb antibody fragment binds to the exosite and induces a subtle conformational change that increases fD cleaving Z-Lys-S-Bzl (Katschke, Wu, Ganesan, et al. (2012) Inhibiting alternative pathway complement activation by targeting the Factor D exosite. J. Biol. Chem. 287, 12886-12892).

Briefly, in flat bottom 96-well plates, the following reagents were added to a final volume of 200 µL: 1× Veronal buffer with 0.1% gelatin and 10 mM $MgCl_2$; anti-fD antibody (AFD), aptamers (C1-C3, see Example 1) or a non-specific oligo control (C8); and a final concentration of fD at or within 5% of 10 nM, 20 nM, 40 nM, 80 nM, or 160 nM. After incubating for 10 min. at room temperature, Z-Lys-SBzl was added at or within 5% of 94 µM, 188 µM, 375 µM, or 750 µM and DTNB at or within 5% of 5 µM, 20 µM, or 40 µM. In some cases, fD was added at 41.7 nM, Z-Lys-SBzl at 375 µM, and DTNB at 20.0 µM. The absorbance was immediately read in a plate reader at 405 nm for 1.5 hours with a read every 30 seconds and a 3 second plate shaking before each read.

Figure 14:
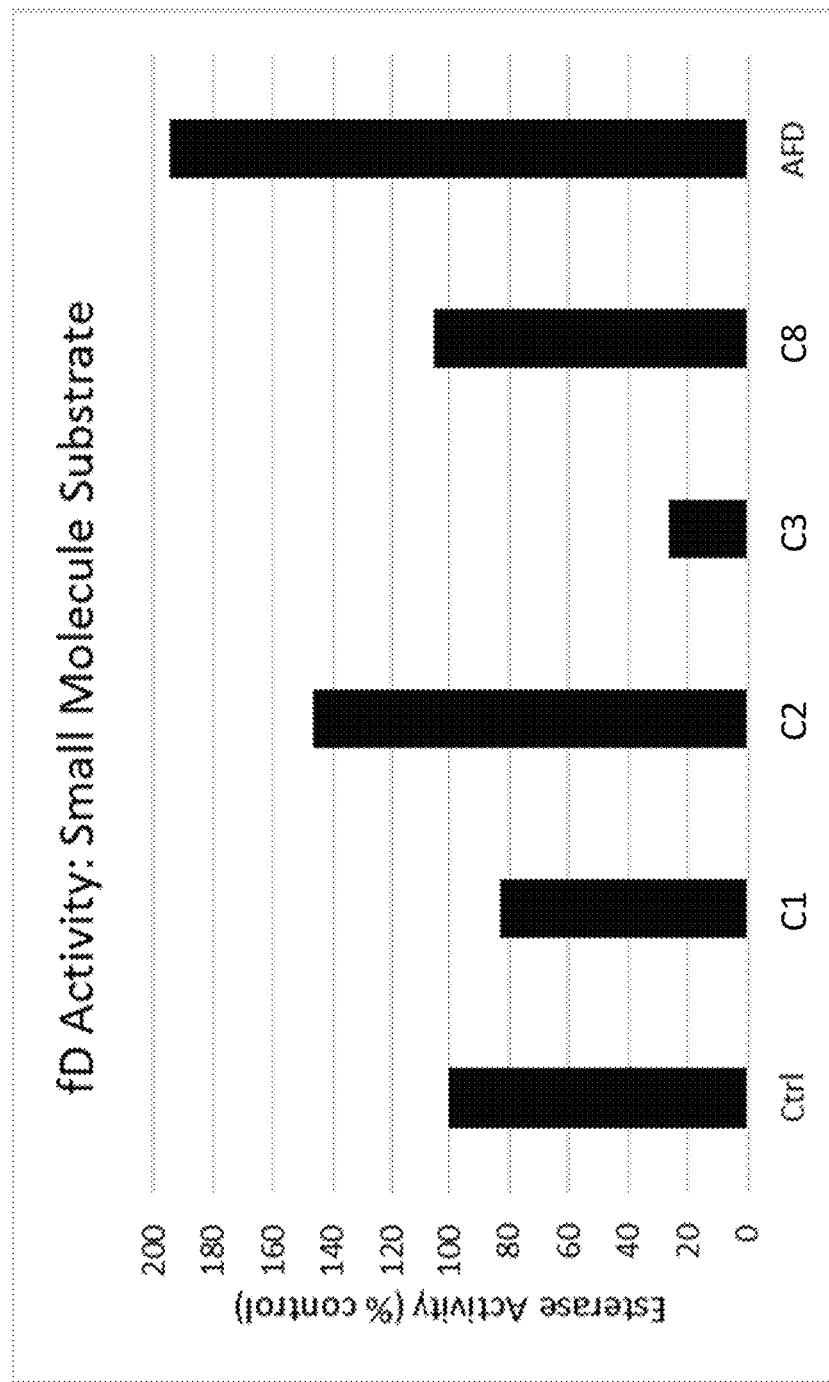
FIG. 14 depicts examples of data obtained from a fD esterase activity assay according to an embodiment of the disclosure.

Results of the assay are depicted in Table 9 and FIG. 14. Briefly, C3 was determined to be an active site inhibitor based on having inhibitory activity comparable to a known active site inhibitor of fD, dichloroisocoumarin (DIC). When run in this assay under these conditions, fD activity in this assay was reduced to 29±15.8% (mean±SD), which established that C3 was a potent fD inhibitor, operating via the catalytic or active site cleft. The data further established that C2 bound the exosite in a manner similar to that of AFD. The data also established that C1 either worked by a different mechanism of action than C2 and C3, or it functioned like C2 via the exosite, but did not affect fD in exactly the same way to cause allosteric activation of fD.

TABLE 9

Impact of C1, C2, C3, C8 and AFD on fD Esterase activity.

| Aptamer | AFD | C1 | C2 | C3 | C8 |
|---|---|---|---|---|---|
| Activity (%) | 195 | 83 | 147 | 26 | 105 |

Example 4

Identification of fD Inhibitors in Reconstituted Enzymatic fD Assay

In some cases, the disclosure provides for the identification of fD inhibitors in a reconstituted biochemical fD activity assay which is composed of purified proteins fD, fB, and C3b. When fD binds to the complex of fB and C3b (C3bB), fB is cleaved by fD into fragments Ba and Bb (Katschke, Wu, Ganesan, et al. (2012) Inhibiting alternative pathway complement activation by targeting the Factor D exosite. J. Biol. Chem. 287, 12886-12892). The activity of fD can be monitored by the rate of fB cleavage and Ba fragment production using an ELISA that uses an antibody that specifically binds Ba (Quidel, A033).

The fB convertase assay mixture is 0.1% gelatin Veronal buffer and 10 mM $MgCl_2$ with complement proteins fD at or within 5% of 7.5 nM, 15 nM, 30 nM, 60 nM, 120 nM, 240 nM (0.125 µM), factor B (fB) at 125 nM, 250 nM, 500 nM, or 1 µM and C3b at 125 nM, 250 nM, 500 nM, or 1 µM and antibodies or aptamers.

In one example, the concentrations of fB and C3b are equal so they form a 1:1 complex which can then bind fD and allow enzymatically active fD to cleave fB to fragments Ba and Bb. In another example, the fB:C3b complex is present in 4-fold excess of fD. For example, final reaction concentrations of fD of 125 nM and 0.5 µM aptamer (or a concentration range) are mixed for 15 minutes, then 0.5 µM fB and 0.5 µM of C3b are added to the FD/inhibitor mixture and incubated for 30 minutes at 37° C., then 10 mM EDTA in 0.1% gelatin Veronal buffer is added to stop the reaction.

Example 5

Identification of Inhibitors of fD Binding to C3bB

In some aspects, the disclosure provides for the identification of inhibitors of fD binding to fB in complex with C3b. FD is the rate-limiting enzyme in the alternative complement pathway, and converts the proconvertases C3bB and $C3b_2B$ to form the active C3 convertase C3bBb or the active C5 convertase $C3b_2Bb$ (Katschke et al 2012). For surface plasmon resonance (SPR) to detect fD in a stable complex with fB, in some cases, catalytically inactive fD (S195A) can be used so that it does not cleave the fB upon binding to the fB:C3b complex (Katschke, Wu, Ganesan, et al. (2012) Inhibiting alternative pathway complement activation by targeting the Factor D exosite. J. Biol. Chem. 287, 12886-12892). In other cases wild type fD can be catalytically inactivated by the covalent inhibitor 3,4-dichloroisocoumarin (DIC) (Harper, Hemmi, Powers (1985) Reaction of serine proteases with substituted isocoumarins: discovery of 3,4-dichloroisocoumarin, a new general mechanism based serine protease inhibitor. Biochemistry 24, 1831-1841).

When C3b is amine-coupled to a CM5 chip, SPR detects binding of fB to C3b as increased mass, and binding of fD to the resultant C3b:fB complex as a further increase in mass. fB, 3,4-dichloroisocoumarin (DIC) inactivated S195A fD, and fD binding compounds in assay buffer (Veronal buffer, 1 mM $NiCl_2$, and 0.05% surfactant P-20) are flowed over the SPR chip at a flow rate of 10, 20, 30, 40, 50, or 60 µL/min, 90 µL. fB is flowed over the immobilized C3b at 0.25, 0.5, 1, 2, or 4 µM, then fB and fD are co-injected at 0.25, 0.5, 1, 2, or 4 µM fB and DIC-inactivated fD at 2-fold dilutions concentration range of 7.8 nM to 8 µM. In some cases, the flow rate is 30 µL/min and the fB concentration is 1 µM, and complexes formed are allowed to dissociate in assay buffer for 5 minutes.

In one example, fD binding compounds are co-injected with a mixture of fB and fD. For example, 1 µM fB and 1 µM 3,4-dichloroisocoumarin (DIC)-inactivated fD are co-injected with aptamers at a 2-fold dilution range of 1 µM to 128 µM. In one aspect, the fD binding compounds are aptamers that bind fD and prevent fD binding to fB:C3b as determined by a reduced mass detected by SPR.

Example 6

Inhibition of fD in Cell-Based Model Complement Pathology in Stargardt Disease

Retinal pigment epithelial (RPE) cells undergo cell death early during the progress of Stargardt disease, and evidence points toward the involvement of the alternative complement pathway (AP) in RPE cell death (Berchuck, Yang, et al (2013) All-trans-retinal (atRal) sensitizes human RPE cells to alternative complement pathway-induced cell death. Invest Ophthalmol Vis Sci 54, 2669-2677). ARPE-19 cells are a spontaneously arising RPE cell line derived from the normal eyes of a 19-year-old male. The ARPE-19 cell line, established using the cuboidal basal cell layer cultured in specific culture media, expresses the RPE-specific markers cellular retinaldehyde binding protein and RPE-65.

Stargardt disease is a hereditary juvenile macular degeneration that occurs in patients with homozygous mutations in the ABCA4 genes, which encode a protein that is responsible for removal of bisretinoid fluorophores, which can include N-retinylidene-N-retinyethanolamine (A2E), all-trans-retinal and related photo-oxidation products of vitamin A aldehyde which together constitute lipofuscin from photoreceptor cells (Molday (2007) ATP-binding cassette transporter ABCA4: molecular properties and role in vision and macular degeneration. J. Bioenerg Biomembr 39, 507-517). An ABCA4 and RDH8 mouse model of Stargardt disease presents with retinal pathology caused by accumulated atRal, and ABCA4 mutations are present in 16% of AMD patients, suggesting that elevated atRal may contribute to Stargardt disease and AMD disease progression (Berchuck et al 2013).

Mechanistically, atRal decreased expression of CD46 and CD59 on RPE cells in vitro, which increased susceptibility to cell lysis mediated by alternative complement in response to anti-RPE antibody binding to the RPE cell membranes (Berchuck et al 2013).

In some cases, the disclosure provides for the identification of fD inhibitors that inhibit alternative complement-mediated lysis of human retinal pigmented epithelial cells. Briefly, human RPE cells (ARPE-19 cells, ATCC, Manassas, Va., USA) are grown in 1:1 mixture (vol/vol) of Dulbecco's modified Eagle's and Ham's nutrient mixture F-12; (Invitrogen-Gibco, Carlsbad, Calif., USA), non-essential amino acids 10 mM, 0.37% sodium bicarbonate, 0.058% L-glutamine, 10% fetal bovine serum, and antibiotics (penicillin G 100 U/mL, streptomycin sulfate 0.1 mg/mL, gentamicin 10 µg/mL, amphotericin-B 2.5 µg/mL). Cells are incubated at 37° C. in 5% CO2 and 95% relative humidity.

ARPE-19 cells are plated on six-well plates for determining cell viability in an in vitro model of Stargardt disease. 5×105 cells in 2 mL of culture media per well are plated and incubated in standard conditions for 24 hours. To sensitize cells to complement mediated lysis by atRal, ARPE-19 cells are treated with atRal for 90 minutes or 24 hours. To activate the fD-dependent alternative complement pathway, cells are incubated with 24% sheep anti-RPE antibody for 30 minutes and then treated with 6% C1q-depleted human serum. After 90 minutes at 37° C., the supernatant is collected in a 96-well plate and replaced with fresh medium. LDH release is measured in the supernatant using a Cytotoxicity Detection Kit. The effect of fD-neutralizing aptamers is determined in the AP-induced cytotoxicity assay using defined doses (control—no drug, ½×, 1×, 2× and 10×) of all drugs.

Example 7

Treatment of Geographic Atrophy with Anti-fD Aptamer

In this example, a patient is diagnosed with geographic atrophy secondary to AMD. The patient is treated with a therapeutically effective dose of a PEGylated-anti-fD aptamer by intravitreal administration. The aptamer targets the exosite of fD and prevents binding and cleavage of the C3bB complex. The patient is treated once every 4 weeks or once every 8 weeks. After six months of treatment, one year of treatment, and every six months thereafter, the patient is assessed for stabilization of geographic atrophy. The patient shows significantly greater stabilization when compared to an untreated patient and comparable or greater stabilization when compared to a patient who has been treated with an anti-fD antibody fragment therapy once every 4 weeks.

Example 8

Isolation of Active-Site Directed Aptamer Inhibitors of fD

In order to preferentially skew enrichment for sequences that utilized the library's engineered stem (FIG. 7B), we continued the selection described above in Example 1, and performed the thermal equilibration step in the presence of a 1.5 molar excess of the reverse primer (N30S.R; SEQ ID NO:6) and a forward blocking primer, complementary to the 5' end of the library (N30S.F-block; AATGCCTCGTACA-CACTCCC; SEQ ID NO:236). Two rounds of selection using this strategy were conducted (denoted 9FR and 10FR), and conditions are indicated in Table 10.

TABLE 10

Selection details

| Round | Input library pmoles/conc. | Target protein pmoles/conc. | Binding buffer | Washing buffer | washes | #cycles | NGS |
|---|---|---|---|---|---|---|---|
| 9FR | 25 pm/1 µM | 4 pm/0.04 µM | SB1T | SB1T | 4 × 15 min | 20 | no |
| 10FR | 25 pm/1 µM | 4 pm/0.04 µM | SB1T | SB1T | 4 × 20 min | 18 | yes |

Analysis of the sequence data obtained from round 9FR and 10FR identified an additional unique sequence, 10FR-14 (Table 11). Subsequently, truncates of 10FR-14 based on formation of the engineered stem of the library as designed yielded S31, and a further truncate of S31 termed S32 (Table 11). These aptamers were synthesized chemically on an inverted dT CPG column bearing a 5' six-carbon disulfide containing linker. A sequence related to S32, Aptamer 15, containing a 5' six-carbon amino containing linker was also synthesized.

percentage difference in the amount of fBa produced by fD and the amount of fBa produced by fD in the presence of S32 at each concentration.

TABLE 11

Sequences of aptamers obtained from selection method

| SEQ ID NO: | Compound Name | Sequence (5' to 3') |
|---|---|---|
| SEQ ID NO: 10 with modifications | 10FR-14 | GGGAGUGUGUACGAGGCAUUAGGCCGCCUUG CCAGUAUUGGCUUAGGCUGGAAGUUUGGCGG CUUUGAUACUUGAUCGCCCUAGAAGC; where G is 2'F and A, C and U are 2'OMe modified RNA. |
| SEQ ID NO: 267 with modifications | S31 | C6S-AGGCCGCCUUGCCAGUAUUGGCUUAGGCUGG AAGUUUGGCGGCUU-idT; where G is 2'F and A, C and U are 2'OMe modified RNA; idT represents a 3' inverted deoxythymidine residue; C6S represents a 6-carbon disulfide containing linker. |
| SEQ ID NO: 268 with modifications | S32 | C6S-CCGCCUUGCCAGUAUUGGCUUAGGCUGGAAG UUUGGCGG-idT; where G is 2'F and A, C and U are 2'OMe modified RNA; idT represents a 3' inverted deoxythymidine residue; C6S represents a 6-carbon disulfide containing linker. |
| SEQ ID NO: 269 with modifications | Aptamer 15 | C6NH$_2$-CCGCCUUGCCAGUAUUGGCUUAGGCUGGAAG UUUGGCGG-idT; where G is 2'F and A, C and U are 2'OMe modified RNA; idT represents a 3' inverted deoxythymidine residue; C6NH$_2$ represents a 6-carbon amino containing linker. |

Example 9

Characterization of the Mechanism of Action of Stem-Loop Aptamers

Figure 15A:
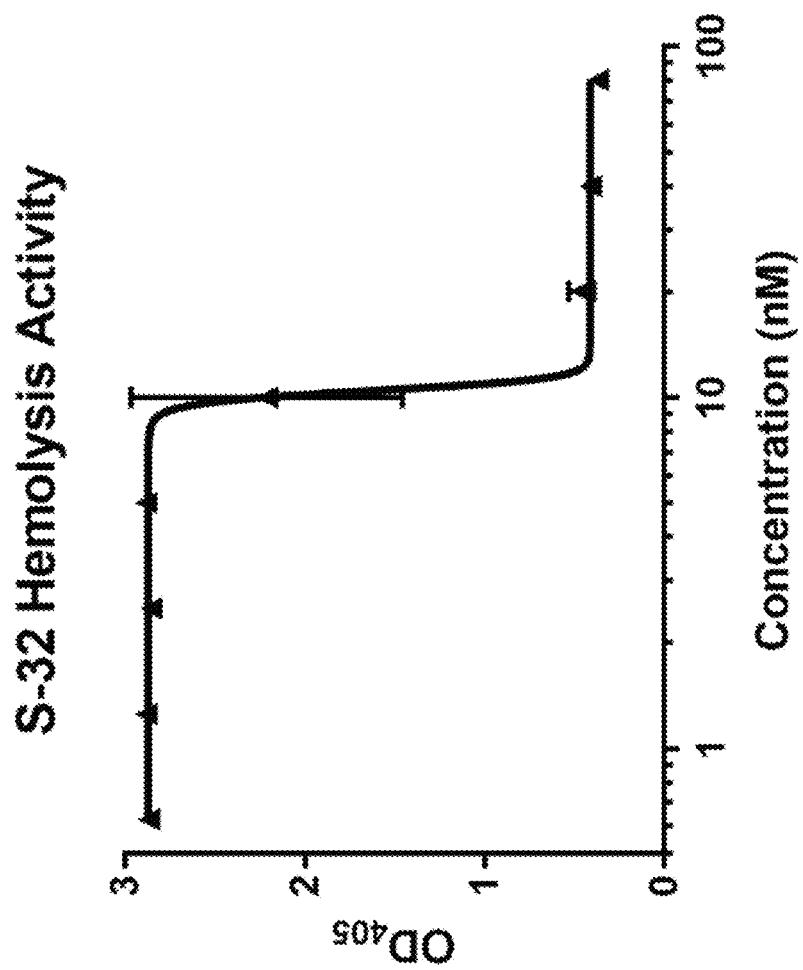
FIG. 15A depicts examples of data obtained from an alternative complement dependent hemolysis assay according to an embodiment of the disclosure.
Figure 15B:
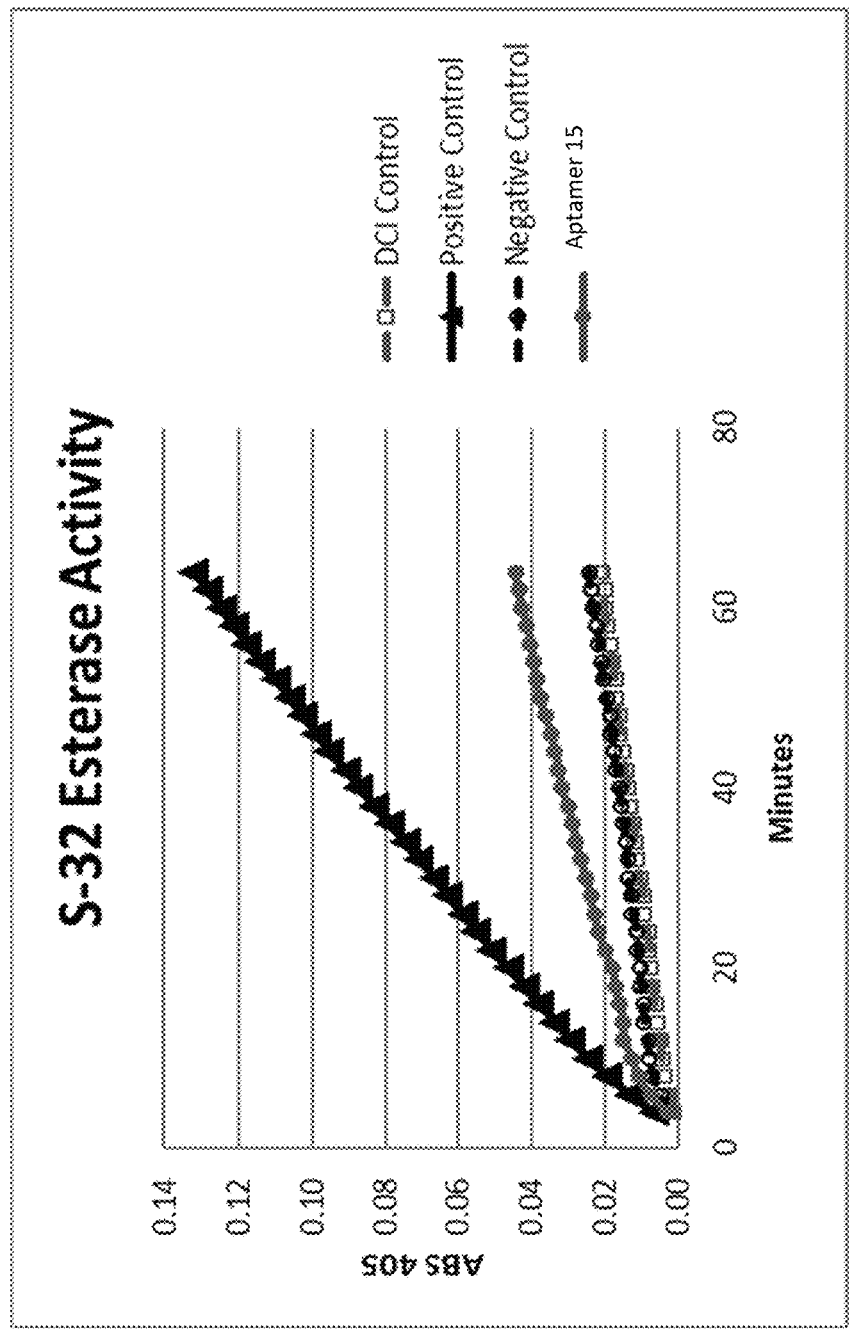
FIG. 15B depicts examples of data obtained from a fD esterase activity assay according to an embodiment of the disclosure.
Figure 15C:
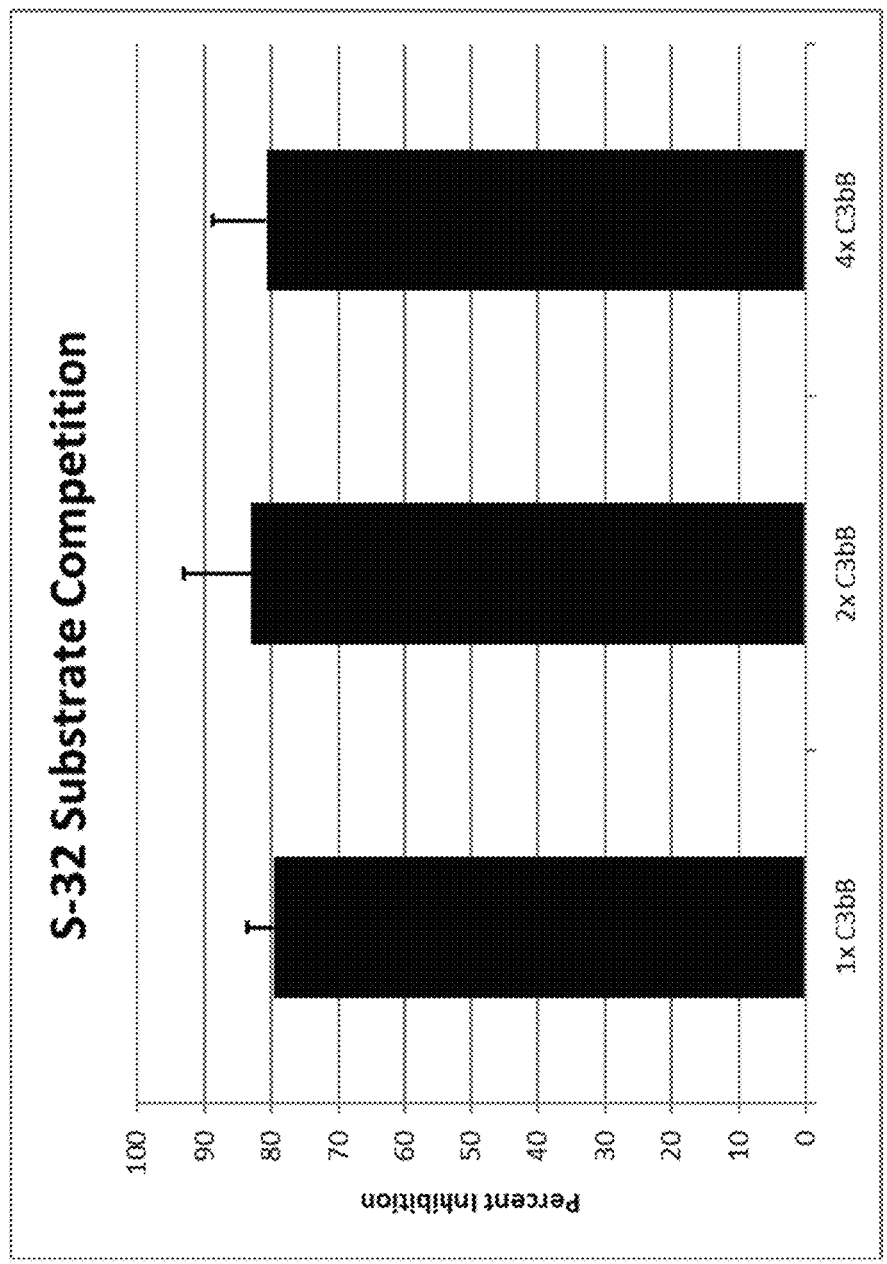
FIG. 15C depicts examples of data obtained from a competition assay according to an embodiment of the disclosure.

The inhibition profile of S31, S32 and Aptamer 15 was characterized in fD dependent assays, including the alternative complement pathway dependent hemolysis of red blood cells, the fD esterase assay, and the fully reconstituted biochemical fD convertase assay as detailed above in Examples 2-4, respectively. As shown in FIG. 15A, FIG. 15B, and FIG. 15C, these aptamers (as exemplified by S32 in these figures) are quite potent inhibitors of fD, with $IC_{50}$'s in the approximate 4-15 nM range in the hemolysis assay, and further, possess a mechanism of action that both directly inhibits the active site of fD and inhibits substrate binding to fD. This conclusion is based on (1) their potent inhibition of red-blood cell hemolysis mediated by the alternative complement pathway; (2) their ability to potently inhibit cleavage of the synthetic modified peptide substrate Z-Lys-SBzl; (3) their ability to block cleavage of C3bB to C3bBb+Ba in the convertase assay; (4) their ability to inhibit convertase activity even in the presence of excess substrate; and (5) their ability to inhibit substrate binding to fD in the SPR assay. For the substrate competition assay (see FIG. 15C), an approximately $IC_{30}$ concentration of S32 (150 nM) was added to fD (62.5 nM) and the fD substrate complex C3b:fB 1:1 (1×=250 nM C3b and 250 nM fB; 2×=500 nM C3b and 500 nM fB; 4×=1 μM C3b and 1 μM C3b). The enzymatic reaction proceeded for 8 minutes, at which time the fB cleavage product fBa fragment was quantified by a specific ELISA. Inhibition of fD activity is expressed as the Example 10

Structure Activity Relationship of Aptamers

Visual analysis of the sequences presented in Table 11 suggested this family of aptamers formed a secondary structure comprising the engineered stem incorporated into the library, an asymmetric internal loop, a second stem, and a terminal loop. To better define the secondary structure of this class of aptamers, as well as to potentially identify fD aptamers with increased potency, a secondary selection was performed utilizing a partially randomized library consisting of 70% S32 parental sequence+10% of the other 3 nucleotides at each position within S32, flanked by 5' and 3' constant regions. Four rounds of selection against fD were conducted using this library, after which the library possessed a greater binding activity than S32 using the flow cytometry binding assay described in Example 1, above. Clones from rounds 3 and 4 of the secondary selection were sequenced, and the sequences obtained were manually incorporated into the multiple sequence alignment shown in Table 12. The alignment of these sequences provides strong covariation support for a secondary structure consisting of a terminal first stem (S1), a first loop forming the 5' side of an asymmetric internal loop (L1), a second stem (S2), a terminal second loop (L2), and a third loop forming the 3' side of an asymmetric internal loop (L3), which joins the structure to the terminal first stem (S1).

TABLE 12

Multiple sequence alignment of active-site directed aptamer inhibitors of fD

| | S1 | L1 | S2 | L2 | S2 | L3 | S1 | |
|---|---|---|---|---|---|---|---|---|
| S32/015 | CCGCC | UUG | CCAGU | AUUGGCUUAG | GCUGG | AAGUUU | GGCGG | SEQ ID NO: 13 |
| S31 | AGGCCGCC | UUG | CCAGU | AUUGGCUUAG | GCUGG | AAGUUU | GGCGGCUU | SEQ ID NO: 11 |
| rd3-06 | -CGCC | UUG | CAAGU | AUUGGCUUUG | GCUUG | AAGUUU | GGCGG | SEQ ID NO: 14 |
| rd4-28 | CCGCC | UUG | CAAGU | AUUGGCUUAG | GCUUG | AAGUUU | GGCGG | SEQ ID NO: 15 |
| rd3-11 | CUGCC | UUG | CGGGU | AUUGGCGUUG | GCCCG | AAGUUU | GGCUG | SEQ ID NO: 16 |
| rd3-10 | CAGUC | UUG | CGAG- | UUUGGCUAAGC | -UUCG | AAGUUU | GGCUG | SEQ ID NO: 17 |
| rd4-42 | CCGCC | UUG | CGAGU | AAUGGCGUAG | GCUCG | AAGUUG | GGCGG | SEQ ID NO: 18 |
| rd3-18 | CCGCC | UUG | CGAGU | AUUGGCUUAG | GCUCG | AAGUUU | GGCGG | SEQ ID NO: 19 |
| rd4-02 | CCGGC | UUG | CGAGU | AUUGGCUUAG | GCUCG | AAGUUU | GCCGG | SEQ ID NO: 20 |
| rd4-46 | CCGCC | UUG | CGAGU | AUUGGCUUUG | GCUCG | AAGUUU | GUCUG | SEQ ID NO: 21 |
| rd3-21 | CCG--CCUUG | | CGAGU | AUUGGCGUUG | GCUCG | AAGUUUU-CGG | | SEQ ID NO: 22 |
| rd3-08 | UCACC | UUG | CCAUU | AUUGGCUUAG | GAUGG | AAGUUU | GGUGG | SEQ ID NO: 23 |
| rd3-22 | CCACC | UUG | CCAGU | AUUGGCUUUG | GCCGG | AAGUUU | GGUGG | SEQ ID NO: 24 |
| rd4-29 | CCACC | UUG | CCAGU | AUUGGCUUAG | GCUGG | AAGUUU | GGUGG | SEQ ID NO: 25 |
| rd3-35 | CCGCC | UUG | CCAGU | AUUGGGUUUG | GCUGG | AAGUUU | GGCGG | SEQ ID NO: 26 |
| rd3-24 | CCG--CAUUG | | CCAGU | AUUGGCUUCG | GCUGG | AAGUUUGC-CGG | | SEQ ID NO: 27 |
| rd3-01 | CCGCA | UUG | CCAGU | AUAGGCUUAU | GCUGG | AAGUUU | UGCGG | SEQ ID NO: 28 |
| rd4-07 | CCGCG | UUG | CCAGU | AUAGGCUUAG | GCUGG | AAGUUU | CGCGG | SEQ ID NO: 29 |
| rd3-47 | -CGCA | UUG | CUAGU | AUUGGCUUAG | GCUAG | AAGUGU | UGCG- | SEQ ID NO: 30 |
| rd3-31 | CUGC- | CUUG | CCAGU | AUUGGCUUAG | GCUGG | AAGUUUU | -GCGG | SEQ ID NO: 31 |
| rd4-18 | CCGGG | UUG | CCAGU | AUUGGCUUAG | GCUGG | AAGUUU | CGCGG | SEQ ID NO: 32 |
| rd4-03 | CCGAC | UUG | CCAGU | AUUGGCGUAG | GCUGG | AAGUUU | GUCGG | SEQ ID NO: 33 |
| rd3-23 | CCGAC | UUG | CCAGU | AUUGGCGUAG | GCUGG | AAGUUU | GCCGG | SEQ ID NO: 34 |
| rd4-24 | CCGAC | UUG | CCAGU | AUUGGCCUAG | GCUGG | AAGUUU | GUCGG | SEQ ID NO: 35 |
| rd4-32 | UCGAC | UUG | CCAGU | AUUGGCUUAG | GCUGG | AAGUUU | GUCGG | SEQ ID NO: 36 |
| rd3-39 | -CGAC | UUG | CCAG-UAUUGGCUUAGU | | -CUGG | AAGUUU | GUCG- | SEQ ID NO: 37 |
| rd4-20 | CCGAC | UUG | CCAGU | GUUGGCUUUG | GCUGG | AAGUUU | GUCGG | SEQ ID NO: 38 |
| rd4-38 | CCGAC | UUG | CCAGU | AUUGGCUUUG | GCUGG | AAGUUU | GCCGG | SEQ ID NO: 39 |
| rd4-13 | CCGAC | UUG | CCAGU | AUUGGCUUAG | GCUGG | AAGUUU | GCCGG | SEQ ID NO: 40 |
| rd4-37 | CGGCC | UUG | CCAGU | AUUGGCUUUG | GCUGG | AAGUUU | GGCCG | SEQ ID NO: 41 |
| rd3-03 | CGGCC | UUG | CAUGU | AUUGGCUCAG | GCAUG | AAGUUU | GUCCG | SEQ ID NO: 42 |
| rd4-25 | CGUGC | UUG | UCAGU | AUUGGCGUUG | GCUGA | AAGUUU | GCACG | SEQ ID NO: 43 |
| rd3-27 | CGUAC | UUG | CCAGU | AUUGGCGUAG | GCUGG | AAGUUU | GUGCG | SEQ ID NO: 44 |
| rd4-47 | CGGGC | UUG | CCAGU | AUUAGGUAG | GCUGG | AAGUUU | GGCCG | SEQ ID NO: 45 |
| rd4-12 | CGGGC | UUG | CCAGU | AUUGGCUUAG | GCUGG | AAGUUU | GUCCG | SEQ ID NO: 46 |
| rd3-33 | GAGAC | UCG | CCAGU | AUAGGCUAAG | GCUGG | AAGUAU | GUCUG | SEQ ID NO: 47 |
| rd4-39 | CUGAC | UUG | CCAGU | AUUGGCUUAG | GCUGG | AAGUUU | GUCGG | SEQ ID NO: 48 |
| rd4-10 | CUGAC | UUG | CCAGU | AUUGGCUUAG | GCUGG | AAGUUU | GUCAG | SEQ ID NO: 49 |

TABLE 12-continued

Multiple sequence alignment of active-site directed aptamer inhibitors of fD

|  | S1 | L1 | S2 | L2 | S2 | L3 | S1 | |
|---|---|---|---|---|---|---|---|---|
| rd3-25 | CUGAC | UUG | CCAGU | AUUAGCUUAG | GCUGG | AAGUUU | GGCGG | SEQ ID NO: 50 |
| rd4-16 | CCGGC | UUG | CCAGU | AUUGGCUUAG | GCUGG | AAGUUU | GCCGG | SEQ ID NO: 51 |
| rd4-21 | CCGCC | UUG | CCAGU | AUUGGCUUAG | GCUGG | AAGUUU | GUCGG | SEQ ID NO: 52 |
| rd3-20 | CCGGC | UUG | CCAGU | AUUGGCUCAG | GCUGG | AAGUUU | GCCGG | SEQ ID NO: 53 |
| rd3-41 | CCGGC | UUG | CCAGU | AUAGGCUCAG | GCUGG | AAGUUU | GCCGG | SEQ ID NO: 54 |
| rd3-40 | UCGGC | UUG | CCAGU | AUUGGCUUAG | GCUGG | AAGUUU | GCCGG | SEQ ID NO: 55 |
| rd3-02 | CCGGC | UUG | CCAGU | AUUGGCUUUG | GCUGG | AAGUUU | GCCGG | SEQ ID NO: 56 |
| rd4-43 | CCGGC | UUG | CCAGU | AUUGGCGUAG | GCUGG | AAGUUU | GCCGG | SEQ ID NO: 57 |
| rd4-34 | CCGAC | UUG | CCAGU | AUUCGCUUAG | GCGGG | AAGUUU | GCCGG | SEQ ID NO: 58 |
| rd4-04 | CCGAC | UUG | CCAGU | AUUGGCUUAG | GCUGG | AAGUUU | GUCGG | SEQ ID NO: 59 |
| rd3-36 | -CGAC | UUG | CCAGU | AUUGGCUUAG | GCUGG | AAGUUU | GUCG- | SEQ ID NO: 60 |
| rd4-06 | CCGAC | UUG | CCAGU | AAUGGCUUAG | GCUGG | AAGUUU | GUCGG | SEQ ID NO: 61 |
| rd3-13 | CCGAC | UUG | CCAGU | AUUGGCGAUG | GCUGG | AAGUUU | GUCGG | SEQ ID NO: 62 |
| rd4-15 | CCGAC | UUG | CCAGU | AUUGGCUUUG | GCUGG | AAGUUU | GUCGG | SEQ ID NO: 63 |
| rd3-16 | CCGCC | UUG | CCAGU | AUUGGCUUAG | GCUGG | AAGUAU | GGCGG | SEQ ID NO: 64 |
| rd4-01 | CCACC | UUG | CCAGU | AUUGGCUUAG | GCUGG | AAGUGU | GGUGG | SEQ ID NO: 65 |
| rd3-26 | ACACC | UUG | CGAGU | AUUGGCUUAG | GCUCG | AAGUUU | GGCGU | SEQ ID NO: 66 |
| rd3-07 | ACGC | -UUUG | CCAGU | AUUGGCUUAG | GCUGG | AAGUUUC | -GCGU | SEQ ID NO: 67 |
| rd4-23 | CCGCG | UUG | CCAGU | AUUGGCUUUG | GCUGG | AAGUUU | CGCGG | SEQ ID NO: 68 |
| rd4-26 | CCGC | -CUUG | CCAGU | AUUGGCUUAG | GCUGG | AAGUUUU | -GCGG | SEQ ID NO: 69 |
| rd4-30 | CCGCC | UUG | CCAGU | AUUGGCUCAG | GCUGG | AAGUUU | GGCGG | SEQ ID NO: 70 |
| rd4-41 | CCGCC | UUG | CCAGU | AUUAGCGUAG | GCUGG | AAGUUU | GGCGG | SEQ ID NO: 71 |
| rd4-11 | CCGCC | UUG | CAAGU | AUUGGCGUUG | GCUUG | AAGUUU | GGCGG | SEQ ID NO: 72 |
| rd3-43 | UCGCC | UUG | CAUGU | AUUGGGUUUG | GCAUG | AAGUUU | GGCGG | SEQ ID NO: 73 |
| rd3-28 | CCGCC | UUGC-AAGU |  | AUAGGCUUAG | GCUU- | AAGUUU | GGGGG | SEQ ID NO: 74 |
| rd3-34 | CAGCC | AUG | CAAGU | AUUGGCUUAG | GCUUG | AAGUUC | GGCUG | SEQ ID NO: 75 |
| rd4-19 | CAGCC | GUG | CUAGU | AUUGGCAUUG | GCUAG | AAGUUA | GGCUG | SEQ ID NO: 76 |
| rd3-44 | CGGGC | UUG | CCAGU | AUUGGCGUUG | GCUGG | AAGUUU | GCCCG | SEQ ID NO: 77 |
| rd3-14 | UGGGC | UUG | CCAGU | AUUGGCUUAG | GCUGG | AAGUUU | GCCCG | SEQ ID NO: 78 |
| rd3-15 | -GGGC | UUG | CCAGU | AUUGGCUUAG | GCUGG | AAGUUU | GUCC- | SEQ ID NO: 79 |

This multiple sequence alignment may define key features of these active site-directed inhibitors of fD. For example, the fD inhibitor may include: (1) a terminal stem (S1). The terminal stem may have 3-8 base pairs. The fD inhibitor may further include: (2) an asymmetric internal loop, the 5' side of which (L1) may range from 3-5 nucleotides. In some cases, the first loop may have a minimal consensus sequence of 5'DUG 3', where D is A, G, or U. The fD inhibitor may further include: (3) a second stem (S2). The second stem may have 4-5 base pairs. In some cases, the second stem is not highly conserved in sequence but may have a terminal U-G base pair adjacent to L2. In other cases, the second stem may have a terminal C-G base pair adjacent to L2. In yet other cases, the base pair at the terminus of the second stem adjacent to L2 may be any base pair. The fD inhibitor may further include: (4) a terminal loop (L2). In some cases, L2 may be 10 to 11 nucleotides in length. In some cases, L2 may have a minimal consensus sequence of 5' DWWVGCB-HWG 3' (SEQ ID NO:319), where D is A, G, or U; W is A or U, V is A, C, or G, B is C, G or U and H is A, C or U. In some examples, L2 may have a U at nucleotide position 2 of L2, a U at nucleotide position 3 of L2, or both. The fD inhibitor may further include: (5) the 3' side of the asymmetric internal loop (L3). In some cases, L3 has 6-8 nucleotides. In some cases, L3 has a consensus sequence of 5' AAGUKN 3', where K is G or U and N is any nucleotide. The consensus secondary structure of this family of active-site directed inhibitors of fD is presented in FIG. 1.

Figure 16:
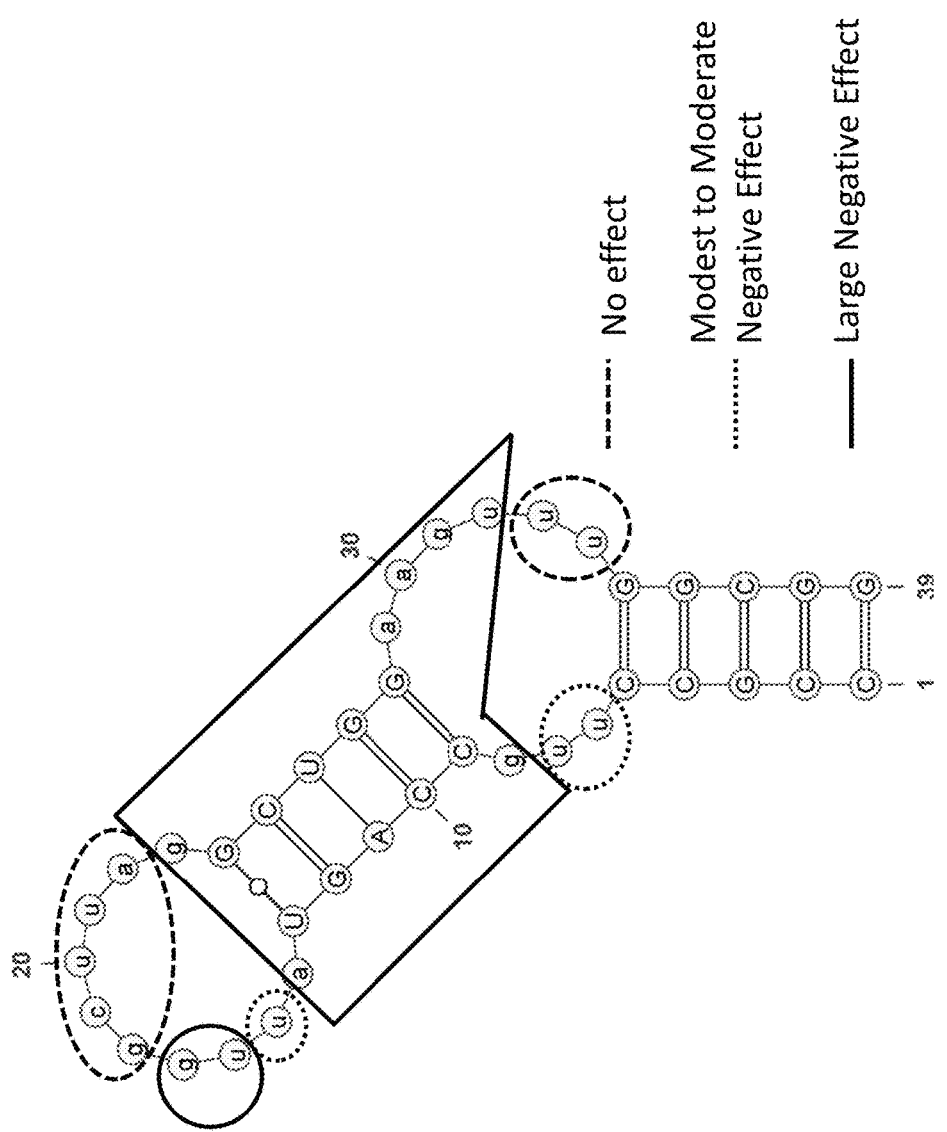
FIG. 16 depicts examples of data obtained from selective substitution of 3-carbon spacers for each nucleotide of a fD aptamer according to an embodiment of the disclosure (SEQ ID NO:12).

The structure activity relationship for this family of active-site directed fD inhibitors was further probed by selective substitution of 3-carbon spacers (C3) for each nucleotide in Aptamer 15, beginning with the U residue at the first position of loop 1 (position 6 excluding the hexylamino linker) and proceeding to the U residue at the 3' end of loop 3 (position 34 excluding the hexylamino linker). These single C3 linker substituted molecules were assayed in the hemolysis assay to interrogate the importance of the sugar and base identity at each substituted position. As can be seen in FIG. 16, substitution at U6 and U7 with C3 led to a modest to moderate reduction in activity, whereas substitution of G8 with C3 resulted in large loss of fD inhibitory activity. This data is consistent with the sequence alignment presented above, in which the identity of the sequence within loop 1 is an important feature of the aptamer structure. Substitution of nucleotides within stem 2 with C3 linkers, which are not capable of forming base-pairing interactions, led to a complete to near complete loss of activity for each such aptamer, confirming the formation of stem 2 as a base-paired region within the aptamer structure. Substitution of positions within loop 2 with C3 linkers demonstrated the importance of the nucleotide residues at positions 14-17 (first 4 nucleotides of loop 2) and 23, whereas nucleotides at position 18-22 could be replaced with a C3 linker without loss of activity, indicating the presence of nucleotides at these positions is non-essential for fD inhibition. Substitution of nucleotides at 29-32 with C3 linkers led to a complete loss of activity, demonstrating the importance of nucleotides at these residues, whereas the C3 substitution at positions 33 and 34 was well tolerated.

Alignment of the sequences obtained from the secondary selection, combined with the results of the C3 scanning study, provide very strong evidence for the formation of the proposed secondary structure as well as key specific sequence elements required for fD inhibition. To further refine our understanding of the sequence activity relationship of this aptamer class for fD inhibition, a series of terminal sequence truncations, internal deletions and linker substitutions as shown in Table 13 were designed and tested for fD inhibitory activity in the alternative complement pathway dependent hemolysis assay.

TABLE 13 fD Aptamer Sequences

| SEQ ID NO: | Aptamer Number | Sequence (5' to 3') |
|---|---|---|
| SEQ ID NO: 270 with modifications | Aptamer 16 | C6NH$_2$-CGCCUUGCCAGUAUUGGCUUAGGCUGGAAGUUUGGCG-idT |
| SEQ ID NO: 271 with modifications | Aptamer 17 | C6NH$_2$-GCCUUGCCAGUAUUGGCUUAGGCUGGAAGUUUGGC-idT |
| SEQ ID NO: 272 with modifications | Aptamer 18 | C6NH$_2$-CCGCCUUGCAGUAUUGGCUUAGGCUGAAGUUUGGCGG-idT |
| SEQ ID NO: 273 with modifications | Aptamer 19 | C6NH$_2$-CCGCCUUGCCAGAUUGGCUUAGCUGGAAGUUUGGCGG-idT |
| SEQ ID NO: 274 with modifications | Aptamer 20 | C6NH$_2$-CCGCCUUGAAGUAUUGGCUUAGGCUUAAGUUUGGCGG-idT |
| SEQ ID NO: 275 with modifications | Aptamer 21 | C6NH$_2$-CCGCCUUGCCAGUAUUGGGCUGGAAGUUUGGCGG-idT |
| SEQ ID NO: 276 with modifications | Aptamer 22 | C6NH$_2$-CCGCCUUGCCAGUAUUGGCGGCUGGAAGUUUGGCGG-idT |
| SEQ ID NOs: 154 and 318 with modifications | Aptamer 23 | C6NH$_2$-CCGCCUUGCCAGUAUUG[I-18]GGCUGGAAGUUUGGCGG-idT |
| SEQ ID NOs: 155 and 318 with modifications | Aptamer 24 | C6NH$_2$-CCGCCUUGCCAGUAUUG[I-9]GGCUGGAAGUUUGGCGG-idT |
| SEQ ID NOs: 156 and 318 with modifications | Aptamer 25 | C6NH$_2$-CCGCCUUGCCAGUAUUGGC[I-9]GGCUGGAAGUUUGGCGG-idT |
| SEQ ID NO: 277 with modifications | Aptamer 26 | C6NH$_2$-CCGCCUUGCCAGUAUUGGCUUAGGCUGGAAGUGGCGG-idT |
| SEQ ID NO: 278 with modifications | Aptamer 27 | C6NH$_2$-CCGCCUUGCCAGUAUUGGCUUAGGCUGGAAGUUGGCGG-idT |

TABLE 13-continued fD Aptamer Sequences

| SEQ ID NO: | Aptamer Number | Sequence (5' to 3') |
|---|---|---|
| SEQ ID NO: 159 with modifications | Aptamer 28 | C6NH$_2$-CCGCCUUGCCAGUAUUGGCUUAGGC UGGAAGU[I-6]GGCGG-idT | where G is 2'F and A, C and U are 2'OMe modified RNA; idT represents a 3' inverted deoxythymidine residue; [I-18] represents a hexaethylene glycol spacer; [I-9] represents a 9-carbon spacer; and [I-6] represents a 6-carbon spacer.

Figure 17:
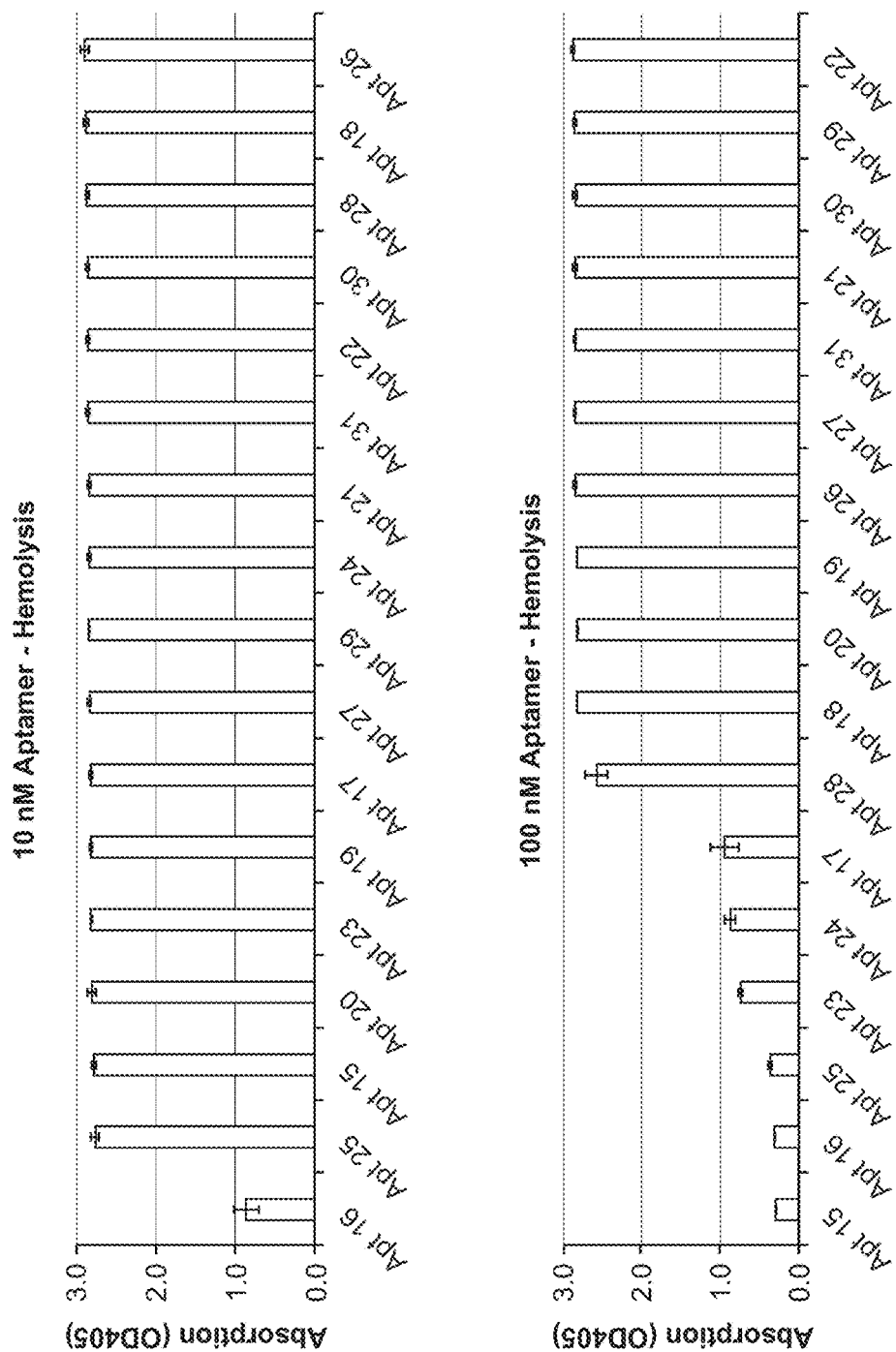
FIG. 17 depicts examples of data obtained from an alternative complement dependent hemolysis assay according to an embodiment of the disclosure.

Aptamers 16-28 were evaluated for fD inhibitory activity at 100 and 10 nM using the alternative complement dependent hemolysis assay. The data presented in FIG. 17 demonstrate that stem 1 tolerates reduction in size to a 3 or 4 base pair stem. Further, loop 2 tolerates reduction in size to 5 or 7 nucleotides when non-nucleotidyl spacers are used to substitute for deleted residues, but does not tolerate a reduction in size to 5 or 7 nucleotides in the absence of additional spacer substitutions. Reduction of stem 2 from 5 to 4 base pairs does not appear to be tolerated, although the sequencing results from the secondary selection indicate a stem 2 of 4 base pairs is expected to be functional in certain sequence contexts. While loop 3 tolerates substitution of C3 linkers for U33 or U34, reduction of this loop to 4 or 5 nucleotides is not tolerated, nor is substitution of both U33 and U34 with a 6-carbon spacer.

In parallel to designing aptamers based on the C3 linker substitution and multiple sequence alignment data, variant sequences isolated in the secondary selection were chosen to probe the importance of primary and secondary structural features for inhibition of fD activity (Table 14).

TABLE 14 fD Aptamer Sequences

| SEQ ID NO. | Aptamer Number | Sequence (5' to 3') |
|---|---|---|
| SEQ ID NO: 279 with modifications | Aptamer 33 | C6NH$_2$-CAGCCAUGCAAGUAUUGGC UUAGGCUUGAAGUUCGGCU G-idT |
| SEQ ID NO: 280 with modifications | Aptamer 34 | C6NH$_2$-CAGCCGUGCUAGUAUUGGC AUUGGCUAGAAGUUAGGCU G-idT |
| SEQ ID NO: 281 with modifications | Aptamer 35 | C6NH$_2$-CCGCCUUGCGAGUAAUGGC GUAGGCUCGAAGUUGGGCG G-idT |
| SEQ ID NO: 282 with modifications | Aptamer 36 | C6NH$_2$-CCGACUUGCCAGUGUUGGC UUUGGCUGGAAGUUUGUCG G-idT |
| SEQ ID NO: 283 with modifications | Aptamer 37 | C6NH$_2$-CAGUCUUGCGAGUUUGGCU AAGCUUCGAAGUUUGGCU G-idT |
| SEQ ID NO: 284 with modifications | Aptamer 38 | C6NH$_2$-CUGCCUUGCGGGUAUUGGC GUUGGCCCGAAGUUUGGCU G-idT |

TABLE 14-continued fD Aptamer Sequences

| SEQ ID NO. | Aptamer Number | Sequence (5' to 3') |
|---|---|---|
| SEQ ID NO: 285 with modifications | Aptamer 39 | C6NH$_2$-CCGACUUGCCAGUAUUGGC GAUGGCUGGAAGUUUGUCG G-idT |
| SEQ ID NO: 286 with modifications | Aptamer 40 | C6NH$_2$-CGCAUUGCUAGUAUUGGCU UAGGCUAGAAGUGUUGCG-idT | where G is 2'F and A, C and U are 2'OMe modified RNA, and idT represents a 3' inverted deoxythymidine residue.

Figure 18:
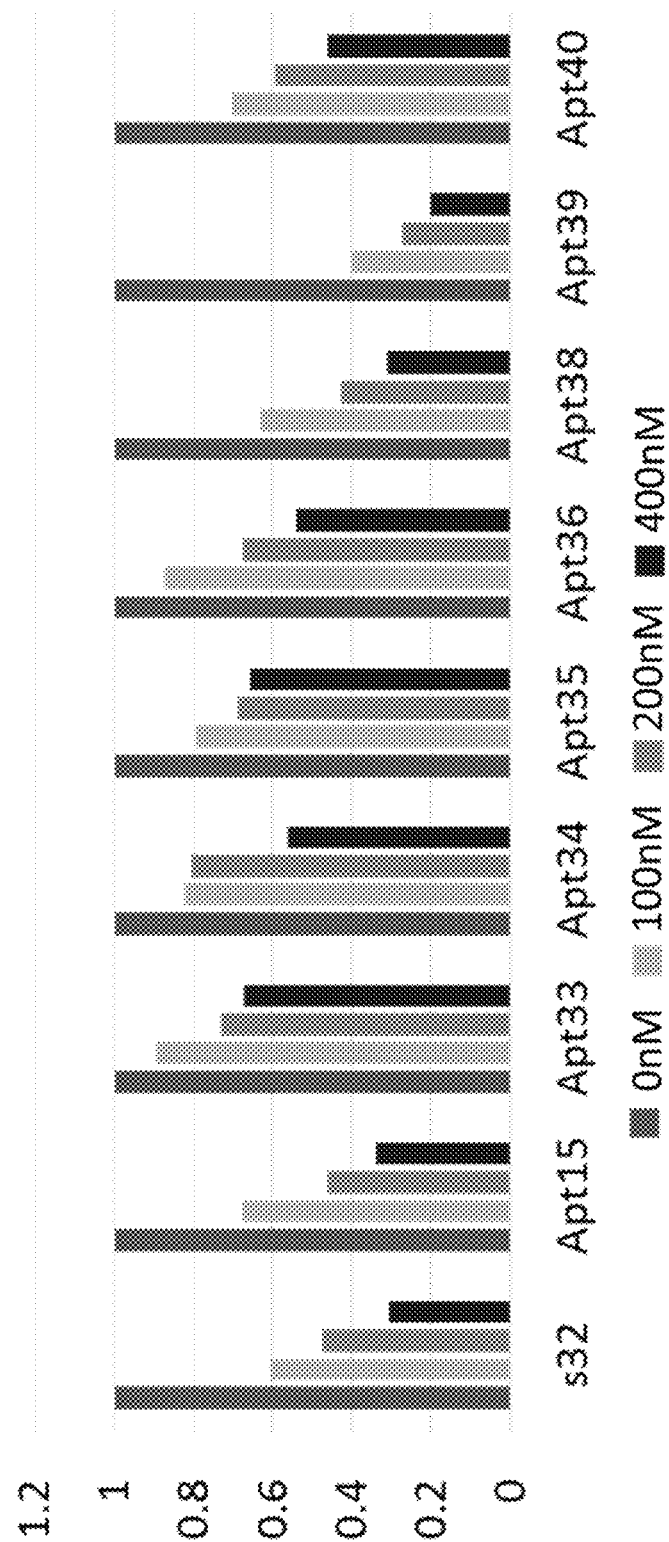
FIG. 18 depicts examples of data obtained from a competition binding assay according to an embodiment of the disclosure.
Figure 19A:
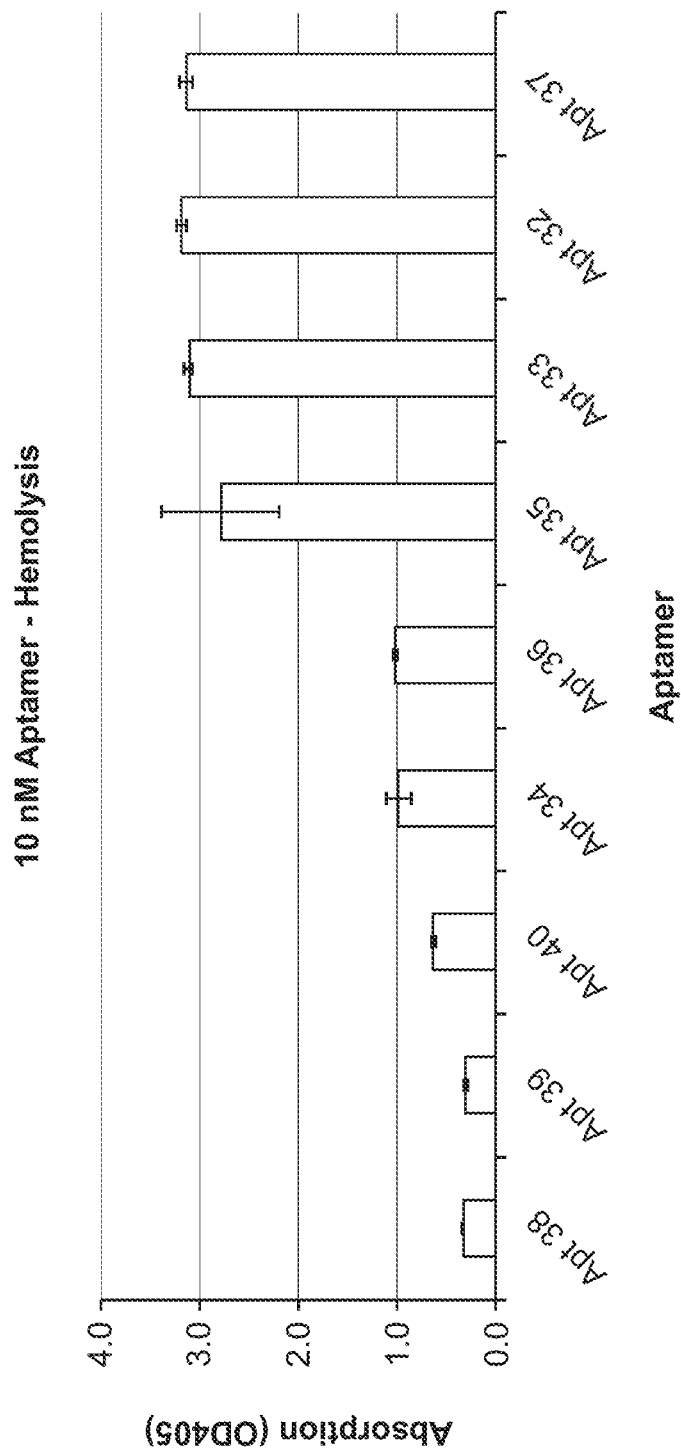
FIG. 19A and FIG. 19B depict examples of data obtained from an alternative complement dependent hemolysis assay according to an embodiment of the disclosure.
Figure 19B:
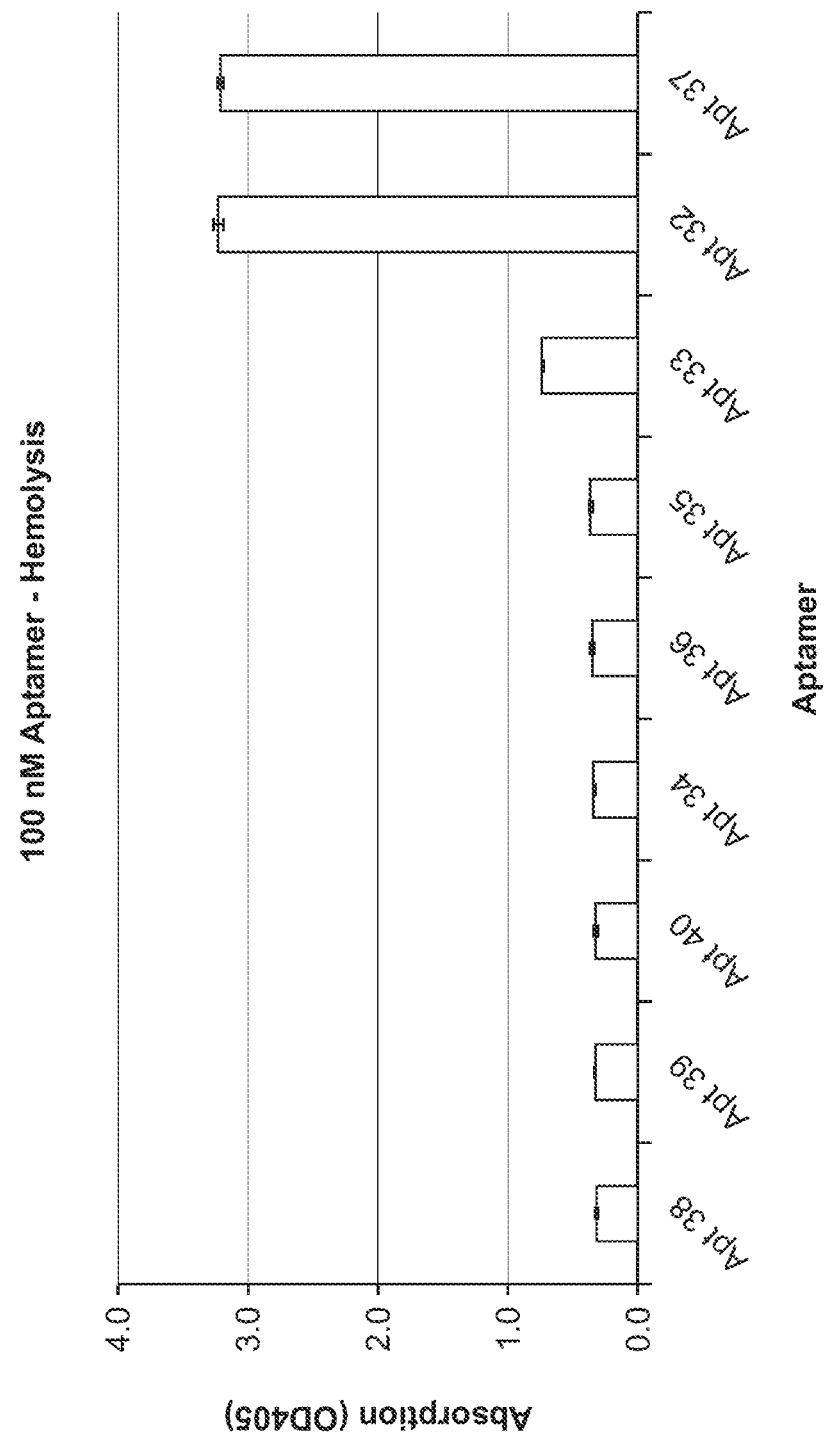
Figure 20B:
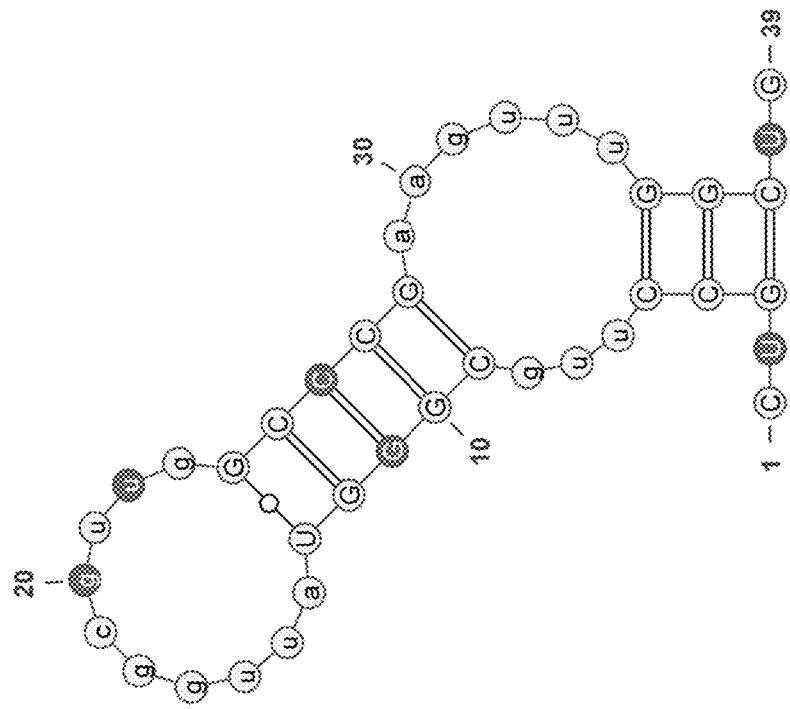
Figure 20A:
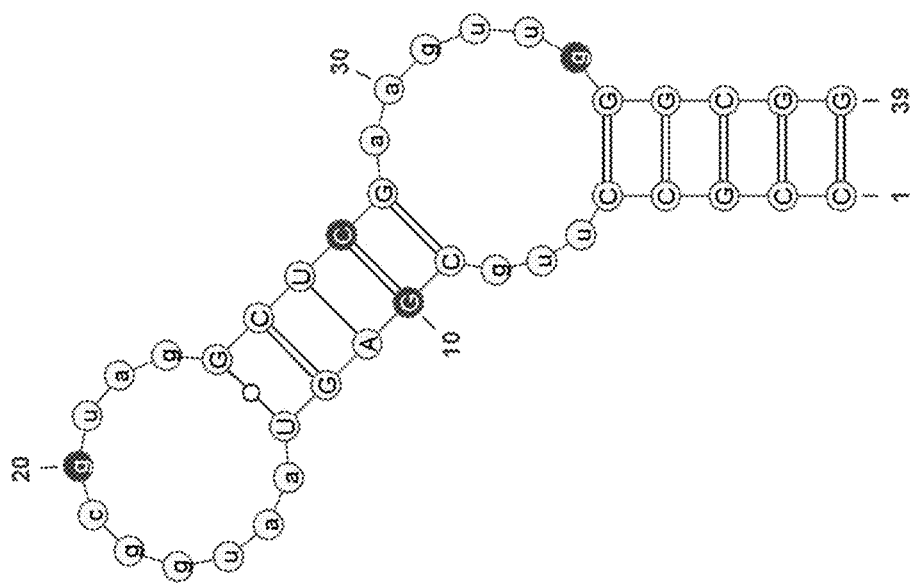
Figure 21:
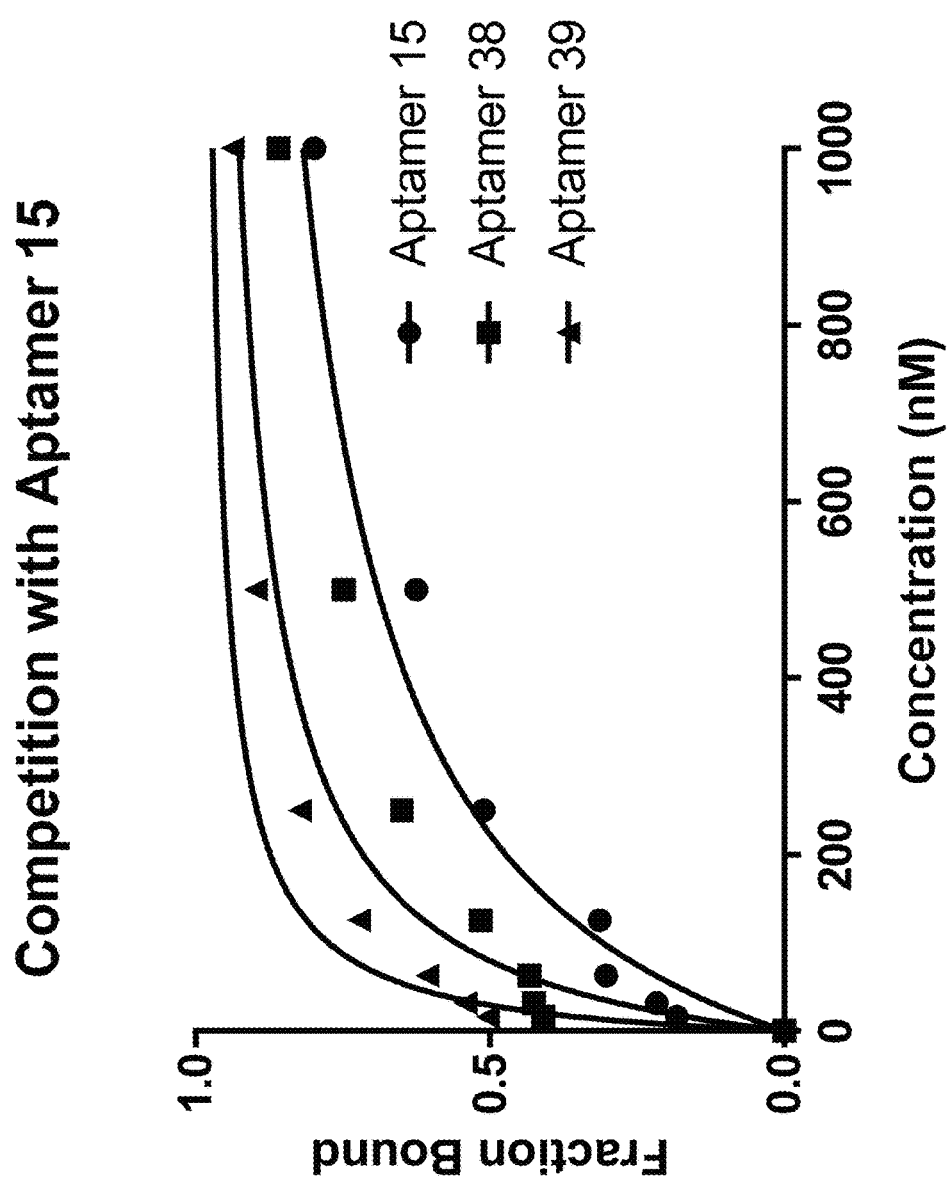
FIG. 21 depicts examples of relative binding affinity of several active-site directed inhibitors of fD using a flow cytometry based competition binding assay according to an embodiment of the disclosure.

Aptamers 33-40 were evaluated for affinity to fD using the flow cytometric bead-immobilized fD binding assay (see Example 1) in competition format using S32 as the fluorescently labeled aptamer. Briefly, fluorescently labeled (Dylight® 650) S32 at 200 nM was combined with 0, 100, 200 or 400 nM unlabeled aptamer competitor and subsequently incubated with bead immobilized fD. Aptamers 33-40 were also evaluated for fD inhibitory activity at 100 nM and 10 nM using the alternative complement dependent hemolysis assay. The data in FIG. 18, FIG. 19A, and FIG. 19B demonstrate that the identity of the base pairs within stem 1 is not critical to fD inhibitory activity, as Aptamers 33, 34, 36, 38 and 40, each of which contains base pair substitutions within stem 1, retain fD inhibitory activity. Further, the data reinforces that the length of stem 1 can vary, as aptamers such as Aptamer 38, which has a 3 base pair stem 1 (note the U-U mispair within this stem yields a 3 base pair stem) retains potent fD inhibitory activity, as does Aptamer 40, which has a 4 base pair stem 1. The data in FIG. 18, FIG. 19A, and FIG. 19B further demonstrate that the identity of the first nucleotide of loop 1 is not critical to fD inhibitor activity, as Aptamer 33 (5'-AUG-3') and Aptamer 34 (5'-GUG-3') both retain fD inhibitory activity, consistent with the proposed consensus sequence for this loop. The data in FIG. 18, FIG. 19A, and FIG. 19B also demonstrate that the identity of base pairs within stem 2 is not critical to fD inhibitory activity. Aptamers 33, 34, 36, 38, and 40, each of which contains base pair substitutions within stem 2, retain fD inhibitory activity. The data in FIG. 18, FIG. 19A and FIG. 19B further confirm the tolerance for variability in the sequence of loop 2, consistent with the proposed consensus structure. Of the sequences tested, only Aptamer 37 appeared to be fully inactive, which could be due to the number of changes present in this molecule, including the length of stem 2, the sequence of stem 1, and the length and identity of residues in loop 2. The data in FIG. 18, FIG. 19A, and FIG. 19B also demonstrate that loop 3, particularly at the 5$^{th}$ and 6$^{th}$ position of this loop, can be variable, as Aptamer 33 (5'-AAGUUC-3'), Aptamer 34 (5'-AAGUUA-3') and Aptamer 35 (5'-AAGUUG-3') all retain fD inhibitory activity, as does Aptamer 40 (5.'-AAGUGU-3'), consistent with the proposed secondary structure. The IC$_{50}$ of select aptamers was determined in the alternative complement dependent hemolysis assay, and is shown in Table 15. Several of these aptamers, in particular Aptamers 35, 38, 39, and 40 (see FIG. 20A, FIG. 20B, FIG. 20C, and FIG. 20D), appear to be more potent inhibitors of fD than Aptamer 15, indicating the set of nucleotide substitutions within these aptamers may improve their function. Aptamer 38 has about 80% sequence identity to Aptamer 15, and Aptamer 39 has about 77% sequence identity to Aptamer 15. To better assess this, a more thorough competition binding analysis was performed on two of these clones. For these assays, fluorescently labeled (Alexa Fluor® 647) Aptamer 15 at 200 nM was incubated with bead-immobilized fD in the presence of unlabeled Aptamers 15, 38 and 39. The data in FIG. 21 demonstrate that Aptamer 38 and Aptamer 39 possess between a 2.5 and 7.7 fold improvement in binding affinity when compared to Aptamer 15 in a competition binding assay. Together these data further support the assertion that the set of nucleotide substitutions within Aptamer 38 and Aptamer 39 may improve their function.

TABLE 15

IC$_{50}$ values for various fD aptamers

| Aptamer Number | IC$_{50}$ (nM) |
| --- | --- |
| Aptamer 33 | 11 |
| Aptamer 34 | 6.9 |
| Aptamer 35 | 5.4 |
| Aptamer 36 | 8.2 |
| Aptamer 38 | 5.5 |
| Aptamer 39 | 3.1 |
| Aptamer 40 | 5.8 |

Example 11

Refinement of Structure Activity Relationship of Aptamers

To further refine and interrogate the secondary structure determined in Example 10, two initial approaches were taken. First, structural motif swaps amongst the sequences identified in the secondary selection were designed to assess the robustness of the secondary structure. Second, libraries obtained in the secondary selection were subjected to deep sequencing to obtain a greater number of sequences to test and interrogate the robustness of the consensus sequences described in Example 10.

If the stem-loop secondary structure proposed for the active-site directed fD aptamers is accurate, aptamers composed of secondary structure elements such as stems or loops from one aptamer should generally be able to be substituted with equivalent sequences comprising the secondary structure elements from other aptamers of this family. Further, secondary structure elements of a given aptamer sequence should be able to be modified per the consensus and retain fD inhibitory activity. Therefore, new aptamers composed of secondary structure elements from various aptamers described in this application were designed and their activity assessed in the alternative complement dependent hemolysis assay described in Example 2. The following stem and loop swaps were constructed and tested, with sequences and activity data provided in Table 16: Aptamer 53 composed of Aptamer 39 with a 4 base pair Stem 1 (S1); Aptamer 54 composed of Aptamer 39 with Stem 2 (S2) of Aptamer 38; Aptamer 55 composed of Aptamer 39 with a 4 base pair Stem 1 (S1), and Stem 2 (S2) of Aptamer 38; Aptamer 56 composed of Aptamer 39 with Stem 1 (S1) of Aptamer 38; Aptamer 57 composed of Aptamer 38 with Loop 2 (L2) of Aptamer 39; Aptamer 58 composed of Aptamer 39 with Stem 1 (S1) from Aptamer 17; Aptamer 59 composed of Aptamer 38 with Stem 1 (S1) from Aptamer 39; and Aptamer 60 composed of Aptamer 39 with Stem 1 (S1) from Aptamer 16. As provided in Table 16, each of these aptamers, with the exception of Aptamer 58, possessed fD inhibitory activity, providing strong support for the secondary structure of this class of aptamers. As described in Example 12, for Aptamer 58, it is likely that the sequence of this 3 base pair stem is sub-optimal in the context of the Aptamer 39 Loop 1 (L1) sequence. Nonetheless, the inhibitory activity of Aptamers 53, 55, 56, and 60 support that Stem 1 (S1) can range from 3 to 5 base pairs.

The highest frequency sequence identified from deep sequencing of the secondary selection is Aptamer 88. As provided in Table 16, Aptamer 88 provides potent fD inhibitory activity supporting sequence variation within Stem 1 (S1).

Sequences obtained from the deep sequencing analysis of the secondary selection provided a number of variants to interrogate the Loop 2 (L2) consensus of 5' DWWVGCBHWG 3' (SEQ ID NO:319), where D is A, G, or U; W is A or U, V is A, C, or G, B is C, G or U and H is A, C or U. The following Loop 2 (L2) sequence variants identified via deep sequencing were constructed, and their activity was assessed in the alternative complement dependent hemolysis assay described in Example 2 (Nucleotide numbering refers to the nucleotide position within Loop 2 (L2) of the consensus secondary structure): Aptamer 64 where V at position 4 is present as A; Aptamer 66 where B at position 7 is present as C; Aptamer 67 where W at position 3 is present as A and position 10 is U and not present as G as in the consensus; Aptamer 68 where B at position 7 is present as G, H at position 8 is present as C, and W at position 9 is present as U; Aptamer 69 where B at position 7 is present as G, and H at position 8 is present as C; Aptamer 71 where B at position 7 is present as G, and H at position 8 is present as A; Aptamer 72 where position H at position 8 is present as C, and W at position 9 is present as U. As provided in Table 16, substitutions at Loop 2 (L2) positions 3, 4, 7, 8, 9 which fall within the consensus 5' DWWVGCBHWG 3' (SEQ ID NO:319) possess anti-fD activity, confirming the consensus primary sequence proposed for loop 2 (L2). Further, the lack of anti-fD inhibitory activity for Aptamer 67 provides additional support that position 10 does not tolerate nucleotides other than G.

TABLE 16 fD Aptamer Sequences

| SEQ ID NO: | Aptamer Number | Sequence (5' to 3') | Activity |
| --- | --- | --- | --- |
| SEQ ID NO: 287 with modifications | Aptamer 53 | C6NH$_2$-CGACUUGCCAGUAUUGGCGAUGGCUG GAAGUUUGUCG-idT | ++++ |

TABLE 16-continued fD Aptamer Sequences

| SEQ ID NO: | Aptamer Number | Sequence (5' to 3') | Activity |
|---|---|---|---|
| SEQ ID NO: 288 with modifications | Aptamer 54 | C6NH$_2$-CCGACUUGCGGGUAUUGGCGAUGGCC CGAAGUUUGUCGG-idT | +++ |
| SEQ ID NO: 289 with modifications | Aptamer 55 | C6NH$_2$-CGACUUGCGGGUAUUGGCGAUGGCCC GAAGUUUGUCG-idT | +++ |
| SEQ ID NO: 290 with modifications | Aptamer 56 | C6NH$_2$-CUGCCUUGCCAGUAUUGGCGAUGGCU GGAAGUUUGGCUG-idT | ++ |
| SEQ ID NO: 291 with modifications | Aptamer 57 | C6NH$_2$-CUGCCUUGCGGGUAUUGGCGAUGGCC CGAAGUUUGGCUG-idT | +++ |
| SEQ ID NO: 292 with modifications | Aptamer 58 | C6NH$_2$-GCCUUGCCAGUAUUGGCGAUGGCUGG AAGUUUGGC-idT | − |
| SEQ ID NO: 293 with modifications | Aptamer 59 | C6NH$_2$-CCGACUUGCGGGUAUUGGCGUUGCC CGAAGUUUGUCGG-idT | ++++ |
| SEQ ID NO: 294 with modifications | Aptamer 60 | C6NH$_2$-CGCCUUGCCAGUAUUGGCGAUGGCUG GAAGUUUGGCG-idT | ++++ |
| SEQ ID NO: 295 with modifications | Aptamer 62 | C6NH$_2$-CCGACUUGCCAGUAUAGGCUCAGGCU GGAAGUUUGUCGG-idT | +++ |
| SEQ ID NO: 296 with modifications | Aptamer 64 | C6NH$_2$-CCGACUUGCCAGUAUUAGCUUAGGCU GGAAGUUUGUCGG-idT | + |
| SEQ ID NO: 297 with modifications | Aptamer 66 | C6NH$_2$-CCGACUUGCCAGUAUUGGCCUAGGCU GGAAGUUUGUCGG-idT | + |
| SEQ ID NO: 298 with modifications | Aptamer 67 | C6NH$_2$-CCGACUUGCCAGUAUAGGCUUAUGCU GGAAGUUUGUCGG-idT | − |
| SEQ ID NO: 299 with modifications | Aptamer 68 | C6NH$_2$-CCGACUUGCCAGUAUUGGCGCUGGCU GGAAGUUUGUCGG-idT | +++ |
| SEQ ID NO: 300 with modifications | Aptamer 69 | C6NH$_2$-CCGACUUGCCAGUAUUGGCGCAGGCU GGAAGUUUGUCGG-idT | ++++ |
| SEQ ID NO: 301 with modifications | Aptamer 71 | C6NH$_2$-CCGACUUGCCAGUAUUGGCGAAGGCU GGAAGUUUGUCGG-idT | ++++ |
| SEQ ID NO: 302 with modifications | Aptamer 72 | C6NH$_2$-CCGACUUGCCAGUAUUGGCUCUGGCU GGAAGUUUGUCGG-idT | + |
| SEQ ID NO: 303 with modifications | Aptamer 88 | C6NH$_2$-CCGACUUGCCAGUAUUGGCUUAGGCU GGAAGUUUGUCGG-idT | ++++ | where G is 2'F and A, C and U are 2'OMe modified RNA; C6NH$_2$ represents a hexylamine linker; and idT represents a 3' inverted deoxythymidine residue.
where ++++ = IC$_{50}$ <10 nM; +++ = IC$_{50}$ ~10 nM; ++ = IC$_{50}$ between 10 and 100 nM; + = IC$_{50}$ of ~100 nM; − = IC$_{50}$ >100 nM

Example 12

Refinement of Structure Activity Relationship of Aptamers—Rational Stem Design If the stem loop secondary structure proposed for the active-site directed fD aptamers is accurate, it is possible that the identity of the nucleotide in both stem S1 and stem S2 of the aptamer could be changed without significant loss of aptamer function.

To this end, series of aptamer variants were designed based on the loop L2 sequences for Aptamers 15, 39, and 38 in which the sequence of S1 and S2 were altered while maintaining pairing (Table 17). These included Aptamers 90, and 94-98. Additionally, a truncate of Aptamer 38 (Aptamer 91) was designed with 3 base pairs in stem S1. The stem elements (S1 and S2) from this molecule were also used to generate Aptamer 92, which contained L2 from Aptamer 39. As shown in Table 17, even though the sequence identity of stem S1 and S2 were significantly altered from that of the parental sequence, anti-fD activity was maintained. The ability to design new active sequences based upon the consensus secondary structure by altering sequence while maintaining pairing within stems S1 and S2 further supports the accuracy of the model for this genus of aptamer.

TABLE 17 fD Aptamer Sequences

| SEQ ID NO: | Aptamer Number | Design based on | Sequence (5' to 3') | Activity |
|---|---|---|---|---|
| SEQ ID NO: 269 with modifications | Aptamer 15 | | C6NH$_2$-CCGCCUUGCCAGUAUUGG*CUUA*GGCUGGAAGUUUGGCGG-idT | ++++ |
| SEQ ID NO: 270 with modifications | Aptamer 16 | Aptamer 15 | C6NH$_2$-CGCCUUGCCAGUAUUGG*CUUA*GGCUGGAAGUUUGGCG-idT | ++++ |
| SEQ ID NO: 271 with modifications | Aptamer 17 | Aptamer 15 | C6NH$_2$-GCCUUGCCAGUAUUGG*CUUA*GGCUGGAAGUUUGGC-idT | ++ |
| SEQ ID NO: 285 with modifications | Aptamer 39 | | C6NH$_2$-CCGACUUGCCAGUAUUGG*CGAU*GGCUGGAAGUUUGUCGG-idT | ++++ |
| SEQ ID NO: 287 with modifications | Aptamer 53 | Aptamer 39 | C6NH$_2$-CGACUUGCCAGUAUUGG*CGAU*GGCUGGAAGUUUGUCG-idT | +++ |
| SEQ ID NO: 308 with modifications | Aptamer 94 | Aptamer 15 | C6NH$_2$-GCCCUUGUCCGUAUUGG*CUUA*GGCCGGAAAGUUUGGGC-idT | ++ |
| SEQ ID NO: 311 with modifications | Aptamer 97 | Aptamer 15 | C6NH$_2$-GGCCUUGCCCGUAUUGG*CUUA*GGCCGGAAGUUUGGCC-idT | ++ |
| SEQ ID NO: 309 with modifications | Aptamer 95 | Aptamer 39 | C6NH$_2$-GCGGUUGCGGGUAUUGG*CGAU*GGCCCGAAGUUUCCGC-idT | ++ |
| SEQ ID NO: 312 with modifications | Aptamer 98 | Aptamer 39 | C6NH$_2$-GGCCUUGCCCGUAUUGG*CGAU*GGCGGGAAGUUUGGCC-idT | ++++ |
| SEQ ID NO: 304 with modifications | Aptamer 90 | Aptamer 15 | C6NH$_2$-CCGUUGUGGGUAUUGG*CUUA*GGCCCAAAGUUUCGG-idT | – |
| SEQ ID NO: 310 with modifications | Aptamer 96 | Aptamer 15 | C6NH$_2$-CCCUUGCCCGUAUUGG*CUUA*GGCGGGAAGUUUGGG-idT | ++ |

TABLE 17-continued fD Aptamer Sequences

| SEQ ID NO: | Aptamer Number | Design based on | Sequence (5' to 3') | Activity |
|---|---|---|---|---|
| SEQ ID NO: 307 with modifications | Aptamer 93 | Aptamer 39 | C6NH$_2$-<br>GCCUUGAGGGUAUUG<br>G*CGAU*GGCCCUAAGU<br>UUGGC-idT | + |
| SEQ ID NO: 306 with modifications | Aptamer 92 | Aptamer 39 | C6NH$_2$-<br>GCCUUGCGGGUAUUG<br>G*CGAU*GGCCCGAAGU<br>UUGGC-idT | +++ |
| SEQ ID NO: 305 with modifications | Aptamer 91 | Aptamer 38 | C6NH$_2$-<br>GCCUUGCGGGUAUUG<br>G*CGUU*GGCCCGAAGU<br>UUGGC-idT | ++ | where G is 2'F and A, C and U are 2'OMe modified RNA; C6NH$_2$ represents a hexylamine linker; and idT represents a 3' inverted deoxythymidine residue.
Bolded, italicized nucleotides indicate differences in L2 between the sequences.
Bolded, underlined nucleotides indicate differences between designed stems and parental molecule
Activity Key: ++++ = IC$_{50}$ <10 nM; +++ = IC$_{50}$ ~10 nM; ++ = IC$_{50}$ between 10 and 100 nM; + = IC$_{50}$ of ~100 nM; − = IC$_{50}$ >100 nM

Example 13

Optimization of fD Aptamers by 2'Ome Sugar Substitutions

2'OMe modifications are known to impart higher duplex stability and have greater coupling efficiency during synthesis compared to 2'F-containing nucleotides. The use of these nucleotides also avoids the potential loss of the 2'F group which can happen during deprotection and exposure to heat. To probe the effect of 2'F-G to 2'OMe-G substitution on target binding, variants of Aptamer 15 were synthesized where 2'F-G at certain positions was selectively substituted with 2'OMe-G (Table 18). 5 variants of Aptamer 15 were synthesized—Aptamer 74 with 2'OMe-G at positions 3, 39, 38, 36, and 35 in Stem 1 (S1); Aptamer 1721 with 2'OMe-G at positions 3, 39, 38, 36, and 35 in Stem 1 (S1) and at positions 12 and 27 in Stem 2 (S2); Aptamer 1722 with 2'OMe-G at positions 3, 39, 38, 36, and 35 in Stem 1 (S1) and at positions 12, 27, and 28 in Stem 2 (S2); Aptamer 1723 with 2'OMe-G at positions 3, 39, 38, 36, and 35 in Stem 1 (S1) and at positions 12, 24, 27, and 28 in Stem 2 (S2); Aptamer 1724 with 2'OMe-G at positions 3, 39, 38, 36, and 35 in Stem 1 (S1), at positions 12, 24, 27, and 28 in Stem 2 (S2), at position 8 in Loop 1 (L1), at positions 17, 18, and 23 in Loop 2 (L2) and position 31 in Loop 3 (L3). These variants were assayed to determine their binding affinity to fD using the bead-based direct binding assay described in Example 1. As shown in Table 18, 2'F-G to 2'OMe-G substitutions were well tolerated in Stem 1 (S1) which was evident from the higher affinity of Aptamer 74 as compared to the parent Aptamer 15 and other 2'OMe-G variants. This could be due to increased stability in the Stem 1 (S1) architecture resulting from the inclusion of 2'OMe-Gs, which may improve the overall structural stability of the aptamer. Interestingly, 2'OMe-G substitutions in Stem 2 (S2) (Aptamers 1721 to 1723) are tolerated, but do affect the affinity as determined by flow cytometry, suggesting a role for the 2'F-G residues within this stem. 2'OMe-G substitutions were not tolerated in Loop 1, 2 or 3 regions when all of the 2'F-G residues were modified (Aptamer 1724), clearly indicating that 2'F-G residues in the loop regions are either crucial in maintaining the loop structure required for binding fD or are making direct contacts with fD. Together these data clearly support that 2'OMe-G substitutions in Stem 1 (S1) of Aptamer 15 enhance its affinity to fD and improve its fD inhibitory function.

TABLE 18 fD Aptamer Sequences with 2'OMe-G Substitutions

| SEQ ID NO | Aptamer number | Sequence | K$_d$ |
|---|---|---|---|
| SEQ ID NO: 269 with modifications | Aptamer 15 | RNA C6NH$_2$-<br>CCGCCUUGCCAGUAUUGGCUU<br>AGGCUGGAAGUUUGGCGG-idT | 7-10 nM |
| SEQ ID NO: 269 with modifications | Aptamer 74 | RNA C6NH$_2$-<br>CC<u>G</u>CCUUGCCAGUAUUGGCUU<br>AGGCUGGAAGUUU<u>GG</u>C<u>GG</u>-idT | 2.7 nM |
| SEQ ID NO: 269 with modifications | Aptamer 1721 | RNA C6SH-<br>CC<u>G</u>CCUUGCCA<u>G</u>UAUUGGCUU<br>AGGCU<u>G</u>GAAGUUU<u>GG</u>C<u>GG</u>-idT | 4.5 nM |

TABLE 18-continued fD Aptamer Sequences with 2'OMe-G Substitutions

| SEQ ID NO | Aptamer number | Sequence | K$_d$ |
|---|---|---|---|
| SEQ ID NO: 269 with modifications | Aptamer 1722 | RNA C6SH-CC<u>G</u>CCUUGCCA<u>G</u>UAUUGGCUU AGGCU<u>GG</u>AAGUUU<u>GG</u>C<u>GG</u>-idT | 11.0 nM |
| SEQ ID NO: 269 with modifications | Aptamer 1723 | RNA C6SH-CC<u>G</u>CCUUGCCA<u>G</u>UAUUGGCUU AGGCU<u>GG</u>AAGUUU<u>GG</u>C<u>GG</u>-idT | 45 nM |
| SEQ ID NO: 269 with modifications | Aptamer 1724 | RNA C6SH-CC<u>G</u>CCUUG<u>C</u>CA<u>G</u>UAUU<u>GG</u>CUU AG<u>G</u>CU<u>GG</u>AA<u>G</u>UUU<u>GG</u>C<u>GG</u>-idT | <1000 nM | where G is 2'F, and <u>G</u>, A, C and U are 2'OMe modified RNA, C6NH$_2$ represents a six-carbon amino containing linker, C6SH represents a six-carbon thiol linker, and idT represents a 3' inverted deoxythymidine residue.

Due to the synthetic and stability advantages of 2'OMe-Gs over 2'F-Gs and that 2'OMe-G substitutions in Stem 1 (S1) improved affinity of Aptamer 74, similar substitutions were constructed in Stem 1 (S1) of other potent fD aptamers and their activity was assessed in the alternative complement dependent hemolysis assay. The following nine aptamers with 2'OMe-Gs in Stem 1 (S1) were synthesized: Aptamer 76 (2'OMe-Gs substituted in Stem 1 (S1) of Aptamer 39), Aptamer 116 (Aptamer comprising loop 2 (L2) of Aptamer 39 and Stem 1 (S1) of Aptamer 15 with 2'OMe-Gs in Stem 1 (S1)), Aptamer 102 (4 base pair 2'OMe-G Stem 1 (S1) variant of Aptamer 76), Aptamer 104 (4 base pair 2'OMe-G Stem 1 (S1) variant of Aptamer 74), Aptamer 106 (Aptamer 88 with 2'OMe-G Stem 1 (S1)), Aptamer 107 (4 base pair 2'OMe-G Stem 1 (S1) variant of Aptamer 88), Aptamer 108 (3 base pair 2'OMe-G Stem 1 (S1) variant of Aptamer 92), Aptamer 109 (4 base pair 2'OMe-G Stem 1 (S1) variant of Aptamer 98) and, Aptamer 99 (4 base pair 2'OMe-G Stem 1 (S1) variant of Aptamer 60). All of these aptamers demonstrated very high potency with IC$_{50}$<10 nM in alternative complement dependent hemolysis assay as shown in Table 19. This data demonstrates that 2'OMe-G substitutions in Stem 1 (S1) may be preferred and improve the fD inhibitory activity and fD affinity of the stem-loop aptamers.

TABLE 19 fD Aptamer Sequences with 2'OMe-G Substitutions

| SEQ ID NO | Aptamer number | Sequence | Activity |
|---|---|---|---|
| SEQ ID NO: 269 with modifications | Aptamer 74 | RNA C6NH$_2$-CC<u>G</u>CCUUGCCAGUAUUGGCU UAGGCUGGAAGUUU<u>GG</u>C<u>GG</u>-idT | ++++ |
| SEQ ID NO: 285 with modifications | Aptamer 76 | RNA C6NH$_2$-CC<u>GA</u>CUUGCCAGUAUUGGC GAUGGCUGGAAGUUU<u>G</u>UC<u>G</u> <u>G</u>-idT | ++++ |
| SEQ ID NO: 316 with modifications | Aptamer 116 | RNA C6NH$_2$-CC<u>G</u>CCUUGCCAGUAUUGGCG AUGGCUGGAAGUUU<u>GG</u>C<u>GG</u>-idT | ++++ |
| SEQ ID NO: 313 with modifications | Aptamer 102 | RNA C6NH$_2$-C<u>GA</u>CUUGCCAGUAUUGGCG AUGGCUGGAAGUUU<u>G</u>UC<u>G</u>-idT | ++++ |
| SEQ ID NO: 314 with modifications | Aptamer 104 | RNA C6NH$_2$-C<u>G</u>CCUUGCCAGUAUUGGCU UAGGCUGGAAGUUU<u>GG</u>C<u>G</u>-idT | ++++ |
| SEQ ID NO: 303 with modifications | Aptamer 106 | RNA C6NH$_2$-CC<u>GA</u>CUUGCCAGUAUUGGC UUAGGCUGGAAGUUU<u>G</u>UC<u>G</u> <u>G</u>-idT | ++++ |
| SEQ ID NO: 315 with modifications | Aptamer 107 | RNA C6NH$_2$-C<u>GA</u>CUUGCCAGUAUUGGCU UAGGCUGGAAGUUU<u>G</u>UC<u>G</u>-idT | ++++ |

TABLE 19-continued fD Aptamer Sequences with 2'OMe-G Substitutions

| SEQ ID NO | Aptamer number | Sequence | Activity |
|---|---|---|---|
| SEQ ID NO: 306 with modifications | Aptamer 108 | RNA C6NH$_2$-<u>G</u>CCUUGCGGGUAUUGGCGAUGGCCCGAAGUUU<u>GG</u>C-idT | ++++ |
| SEQ ID NO: 312 with modifications | Aptamer 109 | RNA C6NH$_2$-<u>GG</u>CCUUGCCCGUAUUGGCGAUGGCGGGAAGUUU<u>GG</u>CC-idT | ++++ |
| SEQ ID NO: 294 with modifications | Aptamer 99 | RNA C6NH$_2$-C<u>G</u>CCUUGCCAGUAUUGGCGAUGGCUGGAAGUUU<u>GG</u>C<u>G</u>-idT | ++++ | where G is 2'F, and <u>G</u>, A, C and U are 2'OMe modified RNA, C6NH$_2$ represents a six-carbon amino containing linker, C6SH represents a six-carbon thiol linker, and idT represents a 3' inverted deoxythymidine residue.

Example 14

Affinity Measures for fD Aptamers

The binding affinity of aptamers for fD was determined by surface plasmon resonance (SPR) on a Reichert4 SPR System, where either aptamer or fD was immobilized as ligand on a solid surface and the interactant analyte was flowed in solution over the immobilized ligand (Table 20). In brief, 14-30 μg/mL human fD in 10 mM sodium acetate pH 5.2 or pH 5.7 was amine coupled to an EDC/NHS activated dextran chip surface, then blocked with 1 M ethanolamine pH 8.5, resulting in 835 RIU immobilized fD. 9 point, 2-fold aptamer dose response curves with 125 nM top concentration were then generated, and $K_D$ affinity values were calculated as the ratio of the dissociation and association rate constants ($K_D=K_d/K_a$) and are presented in Table 20. Affinities were similar sub- to low-nM, ranging from 0.6 nM to 4.2 nM (Table 20).

TABLE 20 fD Aptamer Sequences with 2'OMe-G Substitutions

| SEQ ID NO. | Aptamer number | Sequence | SPR Affinity (nM) |
|---|---|---|---|
| SEQ ID NO: 269 with modifications | 74 | RNA C6NH$_2$-CC<u>G</u>CCUUGCCAGUAUUGGCUUAGGCUGGAAGUUU<u>GGCG</u>G-idT | 3.7 |
| SEQ ID NO: 285 with modifications | 76 | RNA C6NH$_2$-CC<u>G</u>ACUUGCCAGUAUUGGCGAUGGCUGGAAGUUU<u>G</u>UC<u>GG</u>-idT | 1.6 |
| SEQ ID NO: 313 with modifications | 102 | RNA C6NH$_2$-C<u>G</u>ACUUGCCAGUAUUGGCGAUGGCUGGAAGUUU<u>G</u>UC<u>G</u>-idT | 2.5 |
| SEQ ID NO: 314 with modifications | 104 | RNA C6NH$_2$-C<u>G</u>CCUUGCCAGUAUUGGCUUAGGCUGGAAGUUU<u>GG</u>C<u>G</u>-idT | 3.9 |
| SEQ ID NO: 303 with modifications | 106 | RNA C6NH$_2$-CC<u>G</u>ACUUGCCAGUAUUGGCUUAGGCUGGAAGUUU<u>G</u>UC<u>GG</u>-idT | 1.7 |
| SEQ ID NO: 315 with modifications | 107 | RNA C6NH$_2$-C<u>G</u>ACUUGCCAGUAUUGGCUUAGGCUGGAAGUUU<u>G</u>UC<u>G</u>-idT | 4.2 |
| SEQ ID NO: 306 with modifications | 108 | RNA C6NH$_2$-<u>G</u>CCUUGCGGGUAUUGGCGAUGGCCCGAAGUUU<u>GG</u>C-idT | 2.7 |

TABLE 20-continued fD Aptamer Sequences with 2'OMe-G Substitutions

| SEQ ID NO. | Aptamer number | Sequence | SPR Affinity (nM) |
|---|---|---|---|
| SEQ ID NO: 312 with modifications | 109 | RNA C6NH$_2$-GGCCUUGCCCGUAUUGGCGAUGGCGGGAAGUUUGGCC-idT | 0.6-1.9 |
| SEQ ID NO: 294 with modifications | 99 | RNA C6NH$_2$-CGCCUUGCCAGUAUUGGCGAUGGCUGGAAGUUUGGCG-idT | 3.1-3.6 | where G is 2'F, and G, A C and U are 2'OMe modified RNA, C6NH$_2$ represents a six-carbon amino containing linker, C6SH represents a six-carbon thiol linker, and idT represents a 3' inverted deoxythymidine residue.

The binding affinity of aptamers for fD was determined in solution using a homogenous time-resolved fluorescence resonance energy transfer (TR-FRET) assay (Table 21). In brief, 2.5 nM recombinant human Factor D with a hexahistidine tag (SEQ ID NO:324) (His), 2.5 nM anti-His Europium, and varied concentrations of Dylight® 650-labeled aptamer was added to half-well black 96-well plates in TR-FRET buffer (50 mM MOPS, pH 7.4, 125 mM NaCl, 5 mM KCl, 0.1 mg/mL BSA, 50 µM CHAPS, 1 mM CaCl$_2$ and 1 mM MgCl$_2$). After 1 hour incubation at 25° C., binding activity was assessed using a BioTek® Cytation™ 5 plate reader. Affinity binding constants were calculated as the concentration at which 50% of aptamer is bound using a single site binding model, with values ranging from 0.66 nM to 2.5 nM (Table 21).

TABLE 21 fD Aptamer Sequences with 2'OMe-G Substitutions

| SEQ ID NO. | Aptamer number | Sequence | TR-FRET Affinity (nM) |
|---|---|---|---|
| SEQ ID NO: 269 with modifications | 74 | RNA C6NH$_2$-CCGCCUUGCCAGUAUUGGCUUAGGCUGGAAGUUUGGCGG-idT | 2.5 |
| SEQ ID NO: 285 with modifications | 76 | RNA C6NH$_2$-CCGACUUGCCAGUAUUGGCGAUGGCUGGAAGUUUGUCGG-idT | 0.8 |
| SEQ ID NO: 313 with modifications | 102 | RNA C6NH$_2$-CGACUUGCCAGUAUUGGCGAUGGCUGGAAGUUUGUCG-idT | 1.6 |
| SEQ ID NO: 303 with modifications | 106 | RNA C6NH$_2$-CCGACUUGCCAGUAUUGGCUUAGGCUGGAAGUUUGUCGG-idT | 0.66 | where G is 2'F, and G, A, C and U are 2'OMe modified RNA, C6NH$_2$ represents a six-carbon amino containing linker, C6SH represents a six-carbon thiol linker, and idT represents a 3' inverted deoxythymidine residue.

Example 15

SPR Complex Assembly Data

In some cases, surface plasmon resonance (SPR) may be used to assemble fD in complex with the natural substrate fB when fB is in complex with C3b (C3bB), where C3b is immobilized to a solid surface, incubated with fB to allow the C3bB complex to form, and then further incubated with enzymatically inactivated fD (*fD) to allow *fD to bind to the C3bB substrate without proteolytically cleaving fB. This assay may be used to test whether putative anti-fD aptamers compete for binding to fD with C3bB. In some cases, an anti-fD aptamer may bind and inhibit fD enzyme activity by binding at or near the active site without interfering with C3bB substrate binding. In some cases, an anti-fD aptamer may bind fD and inhibit C3bB substrate binding. In some cases, an anti-fD aptamer may bind at or near the active site and inhibit enzyme activity, while also binding in such a manner as to inhibit C3bB substrate binding.

In one aspect, lack of inhibition of fD binding to C3bB may suggest that the anti-fD aptamer is binding to fD at the catalytic site without interfering, or competing, with C3bB binding to fD. In one aspect, inhibition of fD binding to C3bB may suggest that the anti-fD aptamer is binding to fD on a shared portion of the interface between fD and C3bB such that the aptamer interferes, or competes, with C3bB binding to fD in a substrate competitive mechanism. Given the relative proximity of the active site and the substrate binding exosite of fD, it is also possible that anti-fD aptamer is binding on a shared portion of the interface between fD and C3bB such that the aptamer interferes, or competes, with C3bB binding to fD in a substrate competitive mechanism, and also blocks access to the active site of fD.

Briefly, human fD was pre-incubated with 50 µM of the covalent fD inhibitor, 3,4-dichloroisocoumarin (DIC) for 1 hour, which completely inactivated fD esterase activity (referred to hereinafter as *fD) so that it could form a complex with C3bB without enzymatically cleaving the fB substrate. 25 µg/mL human C3b in 10 mM sodium acetate pH 4.0 was amine coupled to an EDC/NHS activated dextran chip surface for 0.5-10 minutes, then blocked with 1 M ethanolamine pH 8.5, resulting in 800-2,242 RIU immobilized, then *fD was injected as a negative control. 1 µM fB was injected for 3 minutes to allow the C3bB complex to form, then 1 µM fB preincubated with 1 µM*fD plus up to 2 µM aptamer was injected for 3 minutes to allow the C3bB:fD complex to form. Following each injection of fB/*fD/aptamer, the complexes were dissociated from the bound C3b with 2×60 seconds injections of 3M NaCl in 50 mM sodium acetate pH 5.0.

Figure 22:
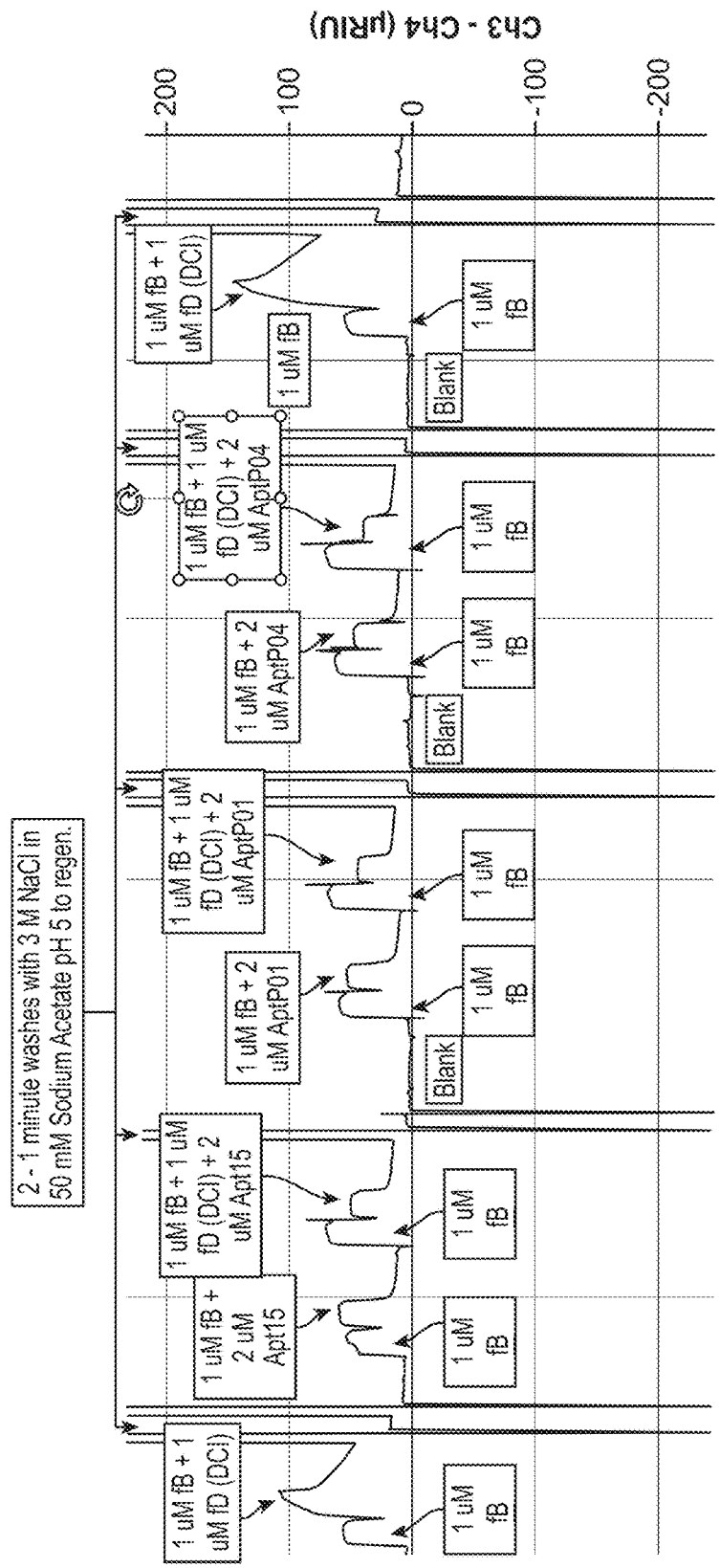
FIG. 22 depicts a non-limiting example of SPR complex assembly data according to an embodiment of the disclosure.

Results of the assay are depicted in FIG. 22, which has the results presented as non-ligand channel subtracted from the C3b-ligand channel. fB was bound to immobilized C3b to form C3bB, which was further bound by *fD (fD (DCI)) as indicated by an increase in signal to form the complex C3bB:*fD. In contrast, when the experiment was repeated in the presence of Aptamer 15, the immobilized C3b still bound fB to form C3bB, but addition of *fD did not further increase the signal, indicating that Aptamer 15 inhibited *fD binding to the C3bB substrate. When fB plus Aptamer 15 was added, there was also no increase in signal above fB alone, confirming Aptamer 15 specificity for *fD. Thus, under all conditions, fB bound to the immobilized C3b, which could then bind *fD, but the *fD binding to C3bB was inhibited by Aptamer 15, consistent with Aptamer 15 binding *fD and inhibiting *fD binding to substrate C3bB. Similar results as for Aptamer 15 were observed for the other aptamers P01 and P04 (described in Example 16) (FIG. 22). Throughout the sample runs, the immobilized C3b retained the ability to bind fB and *fD, as the final sample injection of fB and *fD had fB and *fD both binding to the immobilized C3b similarly to the beginning of the sample runs (FIG. 22).

Figure 23:
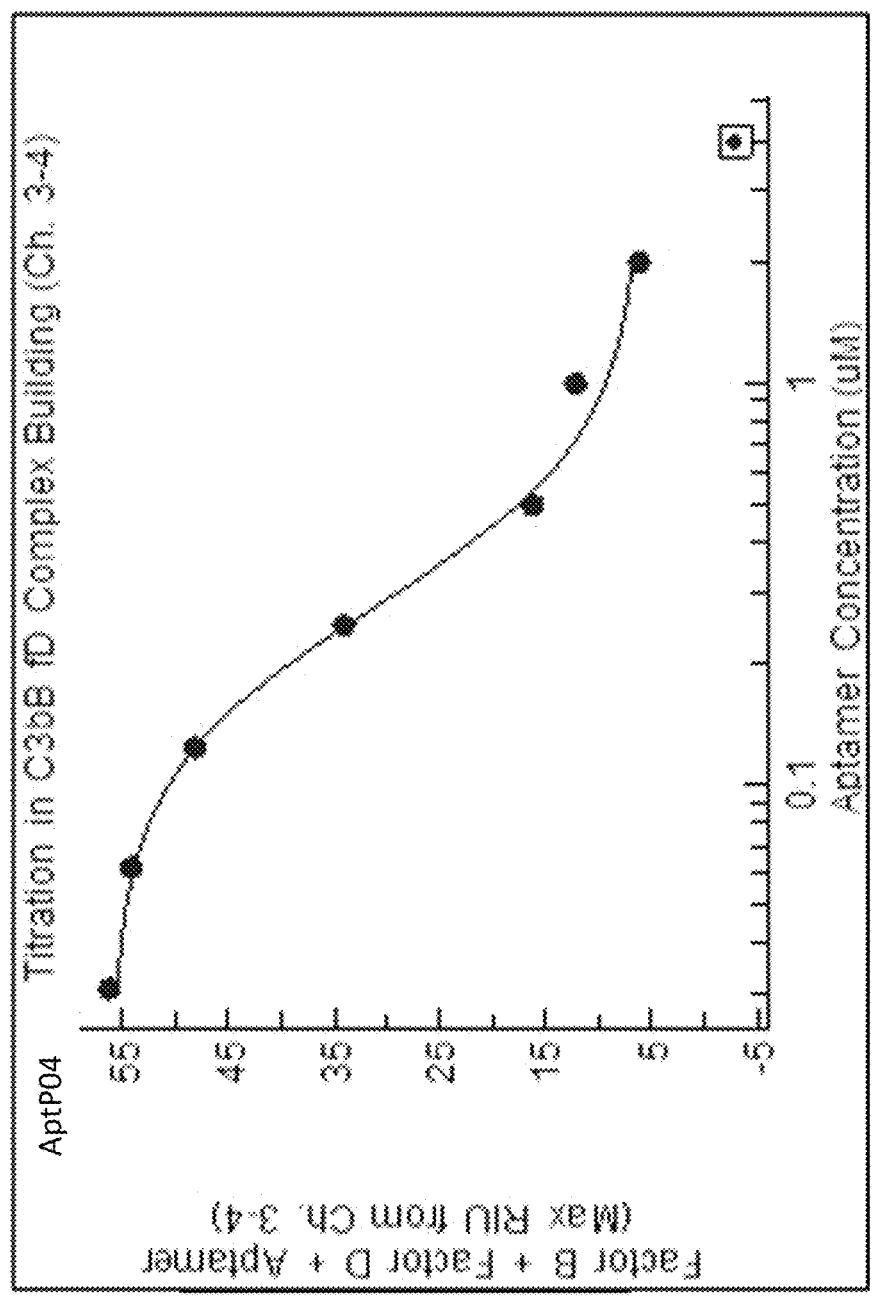
FIG. 23 depicts a non-limiting example of dose-dependent inhibition of C3bB:inactivated fD complex assembly with a fD aptamer according to an embodiment of the disclosure.

Aptamer inhibition of C3bB:*fD complex assembly was further demonstrated by titrating 2-fold Aptamer P04 (PEGylated Aptamer 74, described in Example 16) from 4 µM down to 31.3 nM (FIG. 23). A dose-dependent inhibition of C3bB:*fD complex assembly was observed throughout the dose-response curve, consistent with Aptamer P04 binding *fD and inhibiting *fD binding to substrate C3bB (FIG. 23). This data, in combination with the inhibition of fD esterase activity against small synthetic substrates (Example 9), demonstrate that this stem-loop class of anti-fD aptamer, represented by Aptamer 15, inhibits fD by at least two mechanisms of action. First, this class of aptamer possesses an active-site directed mechanism which blocks access to the active site and/or directly inhibits fD catalytic activity, and second, it prevents association of its biologic substrate, C3bB, with fD.

Example 16

Pegylation of Aptamers

Potent fD inhibiting Aptamers 15, 74, 76, 102 and 106 were conjugated to a 40 kDa branched PEG to evaluate their tolerance for pegylation. Briefly, a concentrated feed solution consisting of aptamer in DMSO, 16 to 25 mM borate and water was combined with a solution consisting of several equivalents 2,3-Bis(methylpolyoxyethylene-oxy)-1-{3-[(1,5-dioxo-5-succinimidyloxy, pentyl)amino]propyloxy} propane (for example SUNBRIGHT® GL2-400GS2) in acetonitrile, and incubated at approximately 35° C. for approximately 1 hour with mixing to effect conjugation of the PEG to the amine moiety of the hexyl amine linker present on the 5' terminus of the aptamer. Following the pegylation reaction, each PEG-aptamer was purified by anion exchange chromatography to collect the pegylated aptamer and remove unreacted PEG and unreacted aptamer. Anion exchange purified PEG-aptamers were desalted by ultrafiltration into water prior to functional characterization. The pegylated versions of aptamers 15, 74, 76, 102 and 106 are termed aptamers P01, P04, P06, P07 and P08, respectively.

Example 17

In Vitro Characterization of Pegylated Aptamers

The potency of the PEG-aptamers P01, P04, P06, P07 and P08 compared to their non-pegylated counterparts was determined in the alternative complement-dependent hemolysis assay as described in Example 2. As shown in Table 22, this class of aptamer tolerates pegylation well, with each PEG-aptamer exhibiting a modest increase in potency compared to its non-pegylated counterpart as determined by their respective $IC_{50}$ values in this assay.

TABLE 22

$IC_{50}$ values for select PEG and non-PEG aptamers

| Aptamer | $IC_{50}$ nM (mean ± sd) |
| --- | --- |
| 15 | 9.4 ± 4.4 |
| P01 | 6.1 ± 1.5 |
| 74 | 7.0 ± 1.4 |
| P04 | 3.2 ± 0.8 |
| 76 | 4.2 ± 0.8 |
| P06 | 4.1 ± 0.9 |
| 102 | 6.3 ± 0.1 |
| P07 | 4.4 ± 0.6 |
| 106 | 5.2 ± 0.4 |
| P08 | 4.1 ± 0.5 |

Example 18

In Vivo Characterization of PEG-Aptamer P01

Aptamer P01 was selected as a representative pegylated form of an active site directed inhibitor of fD with a stem loop secondary structure to characterize the duration of action of this class of aptamer following intravitreal administration to rabbits. Sixteen New Zealand White rabbits, two rabbits per timepoint, were treated with 1.5 mg/eye of aptamer P01 administered by intravitreal injection. Vitreous and plasma samples were taken at 1, 8, 24, 48, 96, 168, 240 and 336 hours post aptamer P01 administration with individual samples being obtained from the left and right eye of each animal at each timepoint. Vitreous and plasma samples were also obtained from 2 placebo treated animals to serve as controls for sample analysis. The duration of action of aptamer P01 was determined by measuring the anti-fD activity retained in the vitreous over time following administration using the alternative complement-dependent hemolysis assay. Additionally, the terminal concentration of aptamer P01 was measured using a dual hybridization ELISA assay.

For ex vivo measurement of the retained anti-fD activity of aptamer P01 following intravitreal administration, a small volume of vitreous obtained from each eye was added to normal human serum and tested in the alternative complement-dependent hemolysis assay as described in Example 2. Absorbance readings obtained from treated samples in the hemolysis assay were normalized to those obtained when vitreous from control animals was tested in parallel in this assay to determine the percent of fD inhibition observed. As shown in Table 23, inhibition of fD activity by aptamer P01 was consistent from 1 to 336 hours post administration, with essentially complete fD inhibition observed at each time point. Therefore, aptamer P01 maintains complete inhibition of fD activity in rabbits for at least 14 days following a single intravitreal administration of 1.5 mg/eye.

TABLE 23

Percent inhibition of fD activity ex vivo following intravitreal administration of aptamer P01

| | Timepoint (hr post administration) | | | | | | |
|---|---|---|---|---|---|---|---|
| 1 | 8 | 24 | 48 | 96 | 168 | 240 | 336 |
| % fD Inhibition 96.4 | 96.4 | 95.9 | 96.2 | 96.3 | 96.6 | 96.4 | 96 |

To further characterize the duration of action of aptamer P01, the terminal concentration was determined by measuring the concentration of P01 in the vitreous 336 hours post intravitreal administration. The concentration of aptamer P01 in the vitreous at the 336 hour timepoint was approximately 4,600 nM. This concentration is approximately 760-fold greater than the $IC_{50}$ of aptamer P01 in the alternative complement-dependent hemolysis assay and 270-fold greater than the concentration of complement fD in the human vitreous, which is approximately 17 nM (Loyet, DeForge, Katschke Jr., et al. (2012) Activation of the alternative complement pathway in vitreous is controlled by genetics in age-related macular degeneration. Invest. Ophthalmol: Vis. Sci. 53:6628-6637). The pegylated aptamer Macugen® which has been well-studied following intravitreal administration in animals and humans contains similar sugar modifications to aptamer P01 and is conjugated to similar 2-arm branched 40 kDa PEG, and provides a good analog from which to extrapolate the expected performance of aptamer P01 in humans. Assuming that aptamer P01 has a half-life in rabbits of at least 80 hours, similar to Macugen® (The EyeTech Study Group (2002) Preclinical and phase 1A clinical evaluation of an anti-VEGF pegylated aptamer (EYE001) for the treatment of exudative age-related macular degeneration. Retina 22(2): 143-152), and that complete inhibition of fD will be achieved when the aptamer concentration is two-fold or greater than the vitreous fD concentration, aptamer P01 administered at 1.5 mg/eye would be anticipated to provide complete inhibition of fD following intravitreal administration in rabbits for at least 30 days, the time at which the vitreous concentration of aptamer P01 is extrapolated to be, under these assumptions, approximately 40 nM. Macugen® has a half-life in humans following intravitreal administration of approximately 10 days ("MACUGEN®, Drugs at FDA; https://www.accessdata.fda.gov/drugsatfda_docs/label/2011/021756s0181b1.pdf). If the in vivo performance of aptamer P01 performs like Macugen® and exhibits a similar approximately 3-fold increase in half-life in humans as compared to rabbits, one would anticipate a duration of action of approximately 90 days or greater for aptamer P01 following intravitreal administration of 1.5 mg/eye. Minimally, one would anticipate intravitreal administration of 1.5 mg/eye of P01 to provide a therapeutic effect for at least 60 days, and potentially up to 120 days.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An aptamer comprising a nucleic acid sequence that selectively binds to complement factor D (fD) and having a stem-loop secondary structure comprising, in a 5' to 3' direction, a first base-paired stem, a first loop, a second base-paired stem, a second loop, and a third loop, wherein said third loop comprises 6 or more nucleotides, non-nucleotidyl spacers, or a combination thereof, and wherein said third loop is adjacent to said first base-paired stem.

2. The aptamer of claim 1, wherein said first loop has fewer nucleotides than said second loop.

3. The aptamer of claim 1, wherein said first loop has from 1 to 10 nucleotides, non-nucleotidyl spacers, or a combination thereof.

4. The aptamer of claim 1, wherein said second loop comprises at least 6 nucleotides, non-nucleotidyl spacers, or a combination thereof.

5. The aptamer of claim 1, wherein said third loop has from 6 to 8 nucleotides, non-nucleotidyl spacers, or a combination thereof.

6. The aptamer of claim 1, wherein said first base-paired stem has from 2 to 10 base pairs.

7. The aptamer of claim 1, wherein said second base-paired stem has from 2 to 10 base pairs.

8. The aptamer of claim 1, wherein said third loop comprises at least 4 nucleotides and up to 2 non-nucleotidyl spacers.

9. The aptamer of claim 1, wherein said third loop comprises at least 6 nucleotides.

10. The aptamer of claim 1, wherein:
    a) said first base-paired stem is adjacent to said first loop;
    b) said second base-paired stem is adjacent to said first loop, said second loop, and said third loop; or
    c) said first base-paired stem is adjacent to said first loop and said second base-paired stem is adjacent to said first loop, said second loop, and said third loop.

11. The aptamer of claim 1, wherein said aptamer is an RNA aptamer or a modified RNA aptamer.

12. The aptamer of claim 1, wherein said aptamer is a DNA aptamer or a modified DNA aptamer.

13. The aptamer of claim 1, wherein said aptamer comprises one or more modified nucleotides.

14. The aptamer of claim 13, wherein said one or more modified nucleotides comprises a 2'F-modified nucleotide, a 2'OMe-modified nucleotide, or a combination thereof.

15. The aptamer of claim 1, wherein said stem-loop structure has exactly two base-paired stems.

16. The aptamer of claim 1, wherein said aptamer is an RNA aptamer comprising nucleotides having ribose in a β-D-ribofuranose configuration.

17. The aptamer of claim 1, wherein said aptamer blocks an active site of fD.

18. The aptamer of claim 1, wherein said aptamer inhibits a function associated with fD.

19. The aptamer of claim 1, wherein said nucleic acid sequence comprises from 30 to 90 nucleotides, non-nucleotidyl spacers, or a combination thereof.

20. The aptamer of claim 1, wherein: said aptamer is conjugated to a polyethylene glycol (PEG) molecule.

21. The aptamer of claim 1, wherein said second loop comprises more than 5 nucleotides, non-nucleotidyl spacers, or a combination thereof.

22. The aptamer of claim 1, wherein said first base-paired stem has no more than 5 base pairs.

23. The aptamer of claim 1, wherein said first loop comprises a nucleic acid sequence of 5'-DUG-3', where D is A, G, or U.

24. The aptamer of claim 1, wherein said second loop comprises a nucleic acid sequence of 5'-DWWVGCBHWG-3', where D is A, G, or U; W is A or U; V is A, C, or G; B is C, G, or U; and H is A, C, or U.

25. The aptamer of claim 1, wherein said second loop comprises a nucleic acid sequence having a U at nucleotide position 2, a U at nucleotide position 3, or both.

26. The aptamer of claim 1, wherein said third loop comprises a nucleic acid sequence comprising 5'-AAGUKN-3', where K is G or U; and N is A, G, C, or U.

27. The aptamer of claim 1, wherein said second base-paired stem comprises a terminal U-G base pair adjacent to said second loop.

28. The aptamer of claim 1, wherein said second base-paired stem comprises a terminal C-G base pair adjacent to said second loop.

* * * * *